(12) United States Patent
Domon et al.

(10) Patent No.: US 9,332,754 B2
(45) Date of Patent: May 10, 2016

(54) ALKYL PHENYL SULFIDE DERIVATIVE AND PEST CONTROL AGENT

(71) Applicants: KUMIAI CHEMICAL INDUSTRY CO., LTD., Tokyo (JP); IHARA CHEMICAL INDUSTRY CO., LTD., Tokyo (JP)

(72) Inventors: Kei Domon, Shizuoka (JP); Keiji Toriyabe, Shizuoka (JP); Yutaka Ogawa, Shizuoka (JP); Junichiro Bessho, Shizuoka (JP); Kei Kawamoto, Shizuoka (JP); Akira Watanabe, Shizuoka (JP); Masaaki Komatsu, Tokyo (JP); Takeshi Matsuda, Tokyo (JP); Seisuke Ito, Tokyo (JP)

(73) Assignees: KUMIAI CHEMICAL INDUSTRY CO., LTD., Tokyo (JP); IHARA CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/394,438

(22) PCT Filed: Apr. 11, 2013

(86) PCT No.: PCT/JP2013/002459
§ 371 (c)(1),
(2) Date: Oct. 14, 2014

(87) PCT Pub. No.: WO2013/157229
PCT Pub. Date: Oct. 24, 2013

(65) Prior Publication Data
US 2015/0087833 A1    Mar. 26, 2015

(30) Foreign Application Priority Data
Apr. 20, 2012  (JP) .................. 2012-096356

(51) Int. Cl.
*C07C 331/10*  (2006.01)
*C07C 323/62*  (2006.01)
*C07C 323/20*  (2006.01)
(Continued)

(52) U.S. Cl.
CPC ............... *A01N 31/16* (2013.01); *A01N 33/20* (2013.01); *A01N 37/10* (2013.01); *A01N 37/32* (2013.01); *A01N 37/34* (2013.01); *A01N 37/38* (2013.01); *A01N 39/00* (2013.01); *A01N 41/10* (2013.01); *A01N 43/08* (2013.01); *A01N 43/40* (2013.01); *A01N 43/50* (2013.01); *A01N 43/54* (2013.01); *A01N 43/56* (2013.01); *A01N 43/653* (2013.01); *A01N 43/78* (2013.01); *A01N 47/02* (2013.01); *A01N 47/48* (2013.01); *A01N 55/00* (2013.01); *C07C 317/22* (2013.01); *C07C 317/32* (2013.01); *C07C 317/46* (2013.01); *C07C 323/12* (2013.01); *C07C 323/18* (2013.01); *C07C 323/20* (2013.01); *C07C 323/25* (2013.01); *C07C 323/62* (2013.01); *C07C 331/10* (2013.01); *C07D 213/34* (2013.01); *C07D 231/12* (2013.01);
(Continued)

(58) Field of Classification Search
CPC .. C07C 331/10; C07C 323/62; C07C 323/20; C07C 317/46; A01N 37/32; A01N 43/08; A01N 47/02; A01N 41/10; A01N 33/20; A01N 55/00; A01N 47/48; A01N 39/00
See application file for complete search history.

(56) References Cited

U.S. PATENT DOCUMENTS 3,388,167 A  6/1968  Ishida et al.
3,962,345 A  6/1976  Yukio et al.
(Continued)

FOREIGN PATENT DOCUMENTS

CN    1456549 A     11/2003
CN    1456552 A  *  11/2003
(Continued)

OTHER PUBLICATIONS

Trachsel, D.,"Synthesis of Novel (Phenylalkyl)amines for the Investigation of Structure—Activity Relationships", Helvetica Chimica Acta 2003, 86: 2610-2619.*
(Continued)

*Primary Examiner* — Samantha Shterengarts
*Assistant Examiner* — Matt Mauro
(74) *Attorney, Agent, or Firm* — Bacon & Thomas, PLLC

(57) ABSTRACT

An alkyl phenyl sulfide derivative represented by the general formula [I] or an agriculturally acceptable salt thereof, and a pest control agent containing the derivative or the salt as an active ingredient.

[Formula 1]

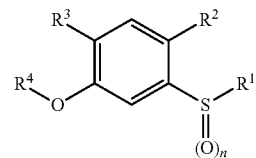

[I]

[in the above formula, $R^1$ is, for example, a $C_1\text{–}C_6$ alkyl group which is mono- or poly-substituted with halogen atom; $R^2$ is, for example, a halogen atom or a $C_1\text{–}C_6$ alkyl group; $R^3$ is, for example, a hydrogen atom or a halogen atom; and $R^4$ is, for example, a hydrogen atom or a $C_1\text{–}C_{12}$ alkyl group.] The derivative or the salt has an excellent pest control effect.

12 Claims, No Drawings

(51) Int. Cl.

| | |
|---|---|
| C07C 317/46 | (2006.01) |
| A01N 37/32 | (2006.01) |
| A01N 43/08 | (2006.01) |
| A01N 47/02 | (2006.01) |
| A01N 41/10 | (2006.01) |
| A01N 33/20 | (2006.01) |
| A01N 55/00 | (2006.01) |
| A01N 47/48 | (2006.01) |
| A01N 39/00 | (2006.01) |
| A01N 31/16 | (2006.01) |
| A01N 37/34 | (2006.01) |
| A01N 43/40 | (2006.01) |
| A01N 43/54 | (2006.01) |
| A01N 43/56 | (2006.01) |
| A01N 43/653 | (2006.01) |
| A01N 43/78 | (2006.01) |
| C07C 317/22 | (2006.01) |
| A01N 37/10 | (2006.01) |
| A01N 37/38 | (2006.01) |
| A01N 43/50 | (2006.01) |
| C07C 317/32 | (2006.01) |
| C07C 323/12 | (2006.01) |
| C07C 323/18 | (2006.01) |
| C07C 323/25 | (2006.01) |
| C07D 213/34 | (2006.01) |
| C07D 231/12 | (2006.01) |
| C07D 233/64 | (2006.01) |
| C07D 239/26 | (2006.01) |
| C07D 249/08 | (2006.01) |
| C07D 277/26 | (2006.01) |

(52) U.S. Cl.
CPC ........... C07D 233/64 (2013.01); C07D 239/26 (2013.01); C07D 249/08 (2013.01); C07D 277/26 (2013.01)

(56) References Cited

U.S. PATENT DOCUMENTS

| | | | |
|---|---|---|---|
| 4,005,148 A | 1/1977 | Aoki et al. | |
| 4,931,474 A | 6/1990 | Kato et al. | |
| 2009/0143413 A1 | 6/2009 | Adams | |

FOREIGN PATENT DOCUMENTS

| | | |
|---|---|---|
| EP | 255935 A1 | 2/1988 |
| JP | 50-29744 A | 3/1975 |
| JP | 51-19121 A | 2/1976 |
| JP | 1975-029744 A | 9/1976 |
| JP | 1976-019121 A | 8/1977 |
| JP | 57-35162 A | 7/1982 |
| JP | 1982-035162 A | 9/1983 |
| JP | S60-158162 A | 8/1985 |
| JP | 63-41451 A | 2/1988 |
| JP | S63-41451 A | 2/1988 |
| JP | 1988-041451 A | 8/1989 |
| JP | 4-312566 A | 4/1992 |
| JP | 1992-312566 A | 7/1995 |
| WO | 2007/034755 A1 | 3/2007 |
| WO | 2007/064553 A2 | 6/2007 |
| WO | 2012/176856 A2 | 12/2012 |

OTHER PUBLICATIONS

International Preliminary Report on Patentability dated Oct. 21, 2014, for PCT/JP2013/002459, and English translation thereof.
Hartwell, J. L., "O-Chlorobromobenzene," Organic Synthesis Coll., vol. 3, p. 185 (1955).
Allen, C.F.H., et al., "Thiosalicylic Acid," Organic Synthesis, Coll. vol. 2, p. 580 (1943).
Bogert, M. T., et al., "A Further Study of the Interaction of Sulfer and Para-Toluidine in the Presence of Litharge: Thio-Para-Toluidine and Related Compounds," J. Am. Chem. Soc., 60, 428 (1928).
Djerassi, C., et al., "Studies in Organic Sulfer Compounds," J. Am. Chem. Soc., 79, 2553 (1957).
D'Amico, J. J., "Derivatives of 2-Benzothiazolesulfenanides," J. Org. Chem., 26, 3436 (1961).
Overman, L.E., et al., "Nucleophilic Cleavage of the Sulfur-Sulfur Bond by Phosphorus Nucleophiles," J. Am. Chem. Soc., 96, 6081 (1974).
International Search Report (ISR) dated May 14, 2013, for PCT/JP2013/002459, and English translation thereof.
Helvetica Chimica Acta, 2003, vol. 86, No. 7, pp. 2610-2619.
Zhurnal Organicheskoi Khimii, 1971, vol. 7, No. 7, pp. 1466-1469 (pp. 1518-1520).
Tetrahedron: Asymmetry, 2011, vol. 22, No. 5, pp. 575-579.
Organic Letters, 2009, vol. 11, No. 10, pp. 2109-2112.
Synthetic Communications, 1981, vol. 11, No. 12, pp. 957-968.
Zhurnal Organicheskoi Khimii, 1969, vol. 5, No. 10, pp. 1813-1815 (pp. 1760-1762).
Journal of the Chemical Society, 1945, pp. 14-18.
Registry (STN) [online], Nov. 16, 1984, CAS registration No. 85292-33-7.

* cited by examiner

ALKYL PHENYL SULFIDE DERIVATIVE AND PEST CONTROL AGENT

TECHNICAL FIELD

The present invention relates to a novel alkyl phenyl sulfide derivative or an agriculturally acceptable salt thereof, as well as to a pest control agent containing the derivative or the salt thereof as an active ingredient.

BACKGROUND ART

Alkyl phenyl sulfide derivatives having a pest control effect are described in patent literatures 1, 2, 3, 4, 5 and 6. However, the compounds described in the patent literatures 1, 2, 3 and 4 are restricted to alkyl phenyl sulfide derivatives having no substituent group on the alkylthio group; the compounds described in the patent literature 5 are restricted to alkyl phenyl sulfide derivatives having certain substituents on the phenyl ring; and the compounds described in the patent literature 6 are restricted to alkyl phenyl sulfide derivatives having a 2-bromoethylthio group as a substituent group. Thus, these patent literatures make no mention of an alkyl phenyl sulfide derivative having a substituent group other than bromine atom on the alkylthio group.

The follow-up experiment made on the compounds described in the above patent literatures revealed that, despite the description made therein, the compounds have an insufficient effect to spider mites, have no effect to spider mites which have acquired chemical resistance, and accordingly have no sufficient control effect.

Patent literature 1: JP-A-1975-29744
Patent literature 2: JP-A-1976-19121
Patent literature 3: JP-B-1982-35162
Patent literature 4: JP-A-1988-41451
Patent literature 5: JP-A-1992-312566
Patent literature 6: U.S. Pat. No. 3,388,167

SUMMARY OF THE INVENTION

Pest control agent applied to useful crops is desired to be a chemical agent which exhibits a sufficient pest control effect at a low dose when applied to soil or stem and leaf. Also, development of safer pest control agent is desired because requirements for safety of chemical substance and its influence to environment are becoming stronger. Further, in recent years, the use of pest control agents such as insecticide, miticide and the like over many years have invited the appearance of pests which have acquired resistance to such pest control agents, and complete control of pests have become difficult. Furthermore, the use of pest control agents having high toxicity to humans and livestock has become a problem from the safety to workers and others.

Under such circumstances, the task of the present invention is to solve the above-mentioned problems of conventional pest control agents and provide a pest control agent superior in safety, control effect, residual effect, etc.

Means to Solve the Problems

In order to develop a pest control agent having the above-mentioned desirable properties, the present inventors synthesized various alkyl phenyl sulfide derivatives and investigated their physiological activities earnestly. As a result, it was found that an alkyl phenyl sulfide derivative represented by the following general formulas [I] or [I'] (the derivative is hereinafter referred to as the present compound) has an excellent effect on various pests, particularly on spider mites represented by *Tetranychus urticae, Tetranychus kanzawai, Panonychus citri*, etc. A further research has led to the completion of the present invention.

The present invention is as follows.

(1) An alkyl phenyl sulfide derivative represented by the general formula [I] or an agriculturally acceptable salt thereof

[formula 1]

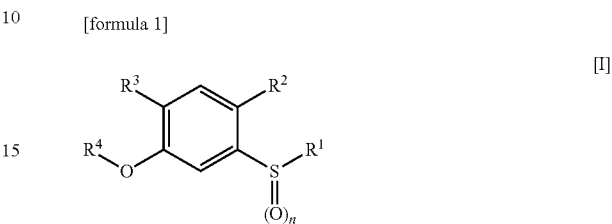

[I]

[in the formula [I],
n is an integer of 0, 1 or 2,
$R^1$ is a $C_1$~$C_6$ haloalkyl group (the group excludes 2-bromoethyl group), a $C_2$~$C_8$ alkenyl group (the group excludes allyl group), a $C_2$~$C_8$ haloalkenyl group, a $C_2$~$C_6$ alkynyl group, a $C_2$~$C_6$ haloalkynyl group, a branched $C_4$~$C_6$ alkyl group (the group excludes isobutyl group), a $C_3$~$C_6$ cycloalkyl $C_1$~$C_6$ alkyl group or a $C_3$~$C_6$ halocycloalkyl $C_1$~$C_6$ alkyl group,
$R^2$ is a halogen atom, a $C_1$~$C_6$ alkyl group, a $C_1$~$C_6$ haloalkyl group, a $C_3$~$C_6$ cycloalkyl group, a $C_3$~$C_6$ halocycloalkyl group, a $C_1$~$C_6$ alkoxy group, a $C_1$~$C_6$ haloalkoxy group, a cyano group or a nitro group,
$R^3$ is a hydrogen atom, a halogen atom, a $C_1$~$C_6$ alkyl group or a $C_1$~$C_6$ haloalkyl group,
$R_4$ is a $C_1$~$C_{12}$ alkyl group (the group may be mono- or poly-substituted with $R^5$), a $C_3$~$C_6$ cycloalkyl group (the group may be mono- or poly-substituted with $R^5$), a $C_2$~$C_8$ alkenyl group (the group may be mono- or poly-substituted with $R^5$), a $C_2$~$C_6$ alkynyl group (the group may be mono- or poly-substituted with $R^5$) or a benzoyl group (the group may be mono- or poly-substituted with $R^6$),
$R^5$ is a halogen atom, a $C_1$~$C_6$ alkyl group, a $C_1$~$C_6$ haloalkyl group, a $C_3$~$C_6$ cycloalkyl group (the group may be mono- or poly-substituted with $R^6$), a $C_3$~$C_6$ halocycloalkyl group, a hydroxyl group, a $C_1$~$C_6$ alkoxy group, a $C_1$~$C_6$ haloalkoxy group, a $C_3$~$C_6$ cycloalkoxy group, a $C_3$~$C_6$ halocycloalkoxy group, a $C_1$~$C_6$ alkoxy $C_1$~$C_6$ alkoxy group, a $C_1$~$C_6$ haloalkoxy $C_1$~$C_6$ alkoxy group, a $C_1$~$C_6$ haloalkoxy $C_1$~$C_6$ haloalkoxy group, a $C_1$~$C_6$ alkylsulfinyloxy group, a $C_1$~$C_6$ haloalkylsulfinyloxy group, a $C_3$~$C_6$ cycloalkylsulfinyloxy group, a $C_3$~$C_6$ halocycloalkylsulfinyloxy group, a $C_1$~$C_6$ alkylsulfonyloxy group, a $C_1$~$C_6$ haloalkylsulfonyloxy group, a $C_3$~$C_6$ cycloalkylsulfonyloxy group, a $C_3$~$C_6$ halocycloalkylsulfonyloxy group, a thiol group, a $C_1$~$C_6$ alkylthio group, a $C_1$~$C_6$ haloalkylthio group, a $C_2$~$C_6$ alkenylthio group, a $C_2$~$C_6$ haloalkenylthio group, a $C_3$~$C_6$ cycloalkylthio group, a $C_3$~$C_6$ halocycloalkylthio group, a $C_3$~$C_6$ cycloalkyl $C_1$~$C_6$ alkylthio group, a $C_3$~$C_6$ halocycloalkyl $C_1$~$C_6$ alkylthio group, a tri($C_1$~$C_6$ alkyl)silyl $C_1$~$C_6$ alkylthio group, a $C_1$~$C_6$ alkylsulfinyl group, a $C_1$~$C_6$ haloalkylsulfinyl group, a $C_3$~$C_6$ cycloalkylsulfinyl group, a $C_3$~$C_6$ halocycloalkylsulfinyl group, a $C_1$~$C_6$ alkylsulfonyl group, a $C_1$~$C_6$ haloalkylsulfonyl group, a $C_3$~$C_6$ cycloalkylsulfonyl group, a $C_3$~$C_6$ halocycloalkylsulfonyl group, a $C_1$~$C_6$ alkylcarbonyl group, a $C_1$~$C_6$ haloalkylcarbonyl group, a formyl group, a $C_1$~$C_6$ alkylcarbonyloxy group, a $C_1$~$C_6$ haloalkylcarbonyloxy group, a formyloxy group, an amino group, a $C_1$~$C_6$ alkylcarbonylamino group (the amino group may be substituted with $R^9$), a $C_1$~$C_6$ haloalkylcarbonylamino group (the amino group may be substituted with $R^9$), a phenylcarbonylamino group (the phenyl group may be mono- or poly-substituted with $R^6$, the amino group may be substituted with $R^9$), a $C_1$~$C_6$ alkoxycarbonylamino group (the amino group may be substituted with $R^9$), a $C_1$~$C_6$ haloalkoxycarbonylamino group (the amino group may be substituted with $R^9$), a $C_1$~$C_6$ alkylaminocarbonylamino group (the amino group may be substituted with $R^9$), a $C_1$~$C_6$ haloalkylaminocarbonylamino group (the amino group may be substituted with $R^9$), a $C_1$~$C_6$ alkylsulfonylamino group (the amino group may be substituted with $R^9$), a $C_1$~$C_6$ haloalkylsulfonylamino group (the amino group may be substituted with $R^9$), a phenylsulfonylamino group (the phenyl group may be substituted with $R^6$, the amino group may be substituted with $R^9$), a $C_1$~$C_6$ alkylamino group (the amino group may be substituted with $R^9$), a $C_1$~$C_6$ haloalkylamino group (the amino group may be substituted with $R^9$), a $C_1$~$C_6$ alkylaminocarbonylthio group (the amino group may be substituted with $R^9$), a $C_1$~$C_6$ haloalkylaminocarbonylthio group (the amino group may be substituted with $R^9$), a $C_1$~$C_6$ alkylaminocarbonyl group (the amino group may be substituted with $R^9$), a $C_1$~$C_6$ haloalkylaminocarbonyl group (the amino group may be substituted with $R^9$), a $C_1$~$C_6$ alkoxycarbonyl group, a $C_1$~$C_6$ haloalkoxycarbonyl group, a tri($C_1$~$C_6$ alkyl)silyl group, a phenyl group (the group may be mono- or poly-substituted with $R^6$), a pyridyloxyphenyl group (the pyridyl group may be mono- or poly-substituted with $R^6$), a phenoxy group (the group may be mono- or poly-substituted with $R^6$), a phenyl $C_1$~$C_6$ alkoxy group (the phenyl group may be mono- or poly-substituted with $R^6$), a phenylcarbonyloxy group (the phenyl group may be mono- or poly-substituted with $R^6$), a phenylcarbonyl group (the phenyl group may be mono- or poly-substituted with $R^6$), a benzoyl group (the group may be mono- or poly-substituted with $R^6$), a benzoyloxy group (the group may be mono- or poly-substituted with $R^6$), a phenylthio group (the group may be mono- or poly-substituted with $R^6$), a phenylsulfonyl group (the group may be mono- or poly-substituted with $R^6$), a phenylsulfinyl group (the group may be mono- or poly-substituted with $R^6$), a phenyl $C_1$~$C_6$ alkylthio group (the phenyl group may be mono- or poly-substituted with $R^6$), a phenyl $C_1$~$C_6$ alkylsulfinyl group (the phenyl group may be mono- or poly-substituted with $R^6$), a phenyl $C_1$~$C_6$ alkylsulfonyl group (the phenyl group may be mono- or poly-substituted with $R^6$), a —O—N=C($R^7$)($R^8$) group, an adamantyl group, a pyrrolyl group (the group may be mono- or poly-substituted with $R^6$), a pyrazolyl group (the group may be mono- or poly-substituted with $R^6$), an imidazolyl group (the group may be mono- or poly-substituted with $R^6$), a triazolyl group (the group may be mono- or poly-substituted with $R^6$), an oxazolyl group (the group may be mono- or poly-substituted with $R^6$), an isoxazolyl group (the group may be mono- or poly-substituted with $R^6$), a thiazolyl group (the group may be mono- or poly-substituted with $R^6$), an isothiazolyl group (the group may be mono- or poly-substituted with $R^6$), a pyridyl group (the group may be mono- or poly-substituted with $R^6$ and the nitrogen atom of the group may be oxidized to form N-oxide), a pyrimidinyl group (the group may be mono- or poly-substituted with $R^6$), a pyridyloxy group (the group may be mono- or poly-substituted with $R^6$), a tetrahydrofuranyl group (the group may be mono- or poly-substituted with $R^6$), 1,3-dioxoisoindolinyl group (the group may be mono- or poly-substituted with $R^6$), a cyano group, a nitro group, a carboxyl group, a thiocyanato group or an aminoxy group, $R^6$ is a halogen atom, a $C_1$~$C_6$ alkyl group, a $C_1$~$C_6$ haloalkyl group, a $C_3$~$C_6$ cycloalkyl group, a $C_3$~$C_6$ halocycloalkyl group, a $C_3$~$C_6$ cycloalkyl $C_1$~$C_6$ alkyl group, a $C_3$~$C_6$ halocycloalkyl $C_1$~$C_6$ alkyl group, a $C_1$~$C_6$ alkoxy group, a $C_1$~$C_6$ haloalkoxy group, a $C_1$~$C_6$ alkylthio group, a $C_1$~$C_6$ haloalkylthio group, a $C_1$~$C_6$ alkylsulfinyl group, a $C_1$~$C_6$ haloalkylsulfinyl group, a $C_1$~$C_6$ alkylsulfonyl group, a $C_1$~$C_6$ haloalkylsulfonyl group, a $C_1$~$C_6$ alkylthio $C_1$~$C_6$ alkyl group, a $C_1$~$C_6$ haloalkylthio $C_1$~$C_6$ alkyl group, a $C_1$~$C_6$ alkylsulfonyloxy group, a $C_1$~$C_6$ haloalkylsulfonyloxy group, a phenyl group (the group may be mono- or poly-substituted with halogen atom, alkyl group or haloalkyl group), a phenyl $C_1$~$C_6$ alkyl group, a phenyl $C_1$~$C_6$ alkoxy group, a cyano group or a nitro group, $R^7$ and $R^8$ may be the same or different, are each a hydrogen atom, a $C_1$~$C_6$ alkyl group, a $C_1$~$C_6$ haloalkyl group, a $C_3$~$C_6$ cycloalkyl group, a $C_3$~$C_6$ halocycloalkyl group or a phenyl group (the group may be mono- or poly-substituted with $R^6$), and may form a 3- to 6-membered ring together with the carbon atom to which they bond, and $R^9$ is a $C_1$~$C_6$ alkyl group, a $C_1$~$C_6$ haloalkyl group, a $C_3$~$C_6$ cycloalkyl group, a $C_3$~$C_6$ halocycloalkyl group, a $C_1$~$C_6$ alkylcarbonyl group, a $C_1$~$C_6$ haloalkylcarbonyl group, a $C_1$~$C_6$ alkoxycarbonyl group, a $C_1$~$C_6$ haloalkoxycarbonyl group, a $C_1$~$C_6$ alkylaminocarbonyl group, a $C_1$~$C_6$ haloalkylaminocarbonyl group or benzoyl group (the group may be mono- or poly-substituted with $R^6$].

(2) An alkyl phenyl sulfide derivative or an agriculturally acceptable salt thereof, set forth in (1), wherein $R^1$ in the general formula [I] is a 2,2-difluoroethyl group, a 2,2,2-trifluoroethyl group, a 3,3,3-trifluoropropyl group, a pentafluoroethyl group, 1,2,2,2-tetrafluoroethyl group, 2-chloro-2,2-difluoroethyl group, a 2,2,3,3-tetrafluoropropyl group, a 2,2,3,3,3-pentafluoropropyl group, a 3,3-dichloroallyl group, a propargyl group, a cyclopropylmethyl group or a (2,2-difluorocyclopropyl)methyl group.

(3) An alkyl phenyl sulfide derivative or an agriculturally acceptable salt thereof, set forth in (1) or (2), wherein $R^2$ in the general formula [I] is a halogen atom, a $C_1$~$C_6$ alkyl group, a $C_1$~$C_6$ haloalkyl group or a cyano group.

(4) An alkyl phenyl sulfide derivative or an agriculturally acceptable salt thereof, set forth in any of (1) to (3), wherein $R^3$ in the general formula [I] is a hydrogen atom, a halogen atom or a $C_1$~$C_6$ alkyl group.

(5) A pest control agent which contains, as an active ingredient, an alkyl phenyl sulfide derivative or an agriculturally acceptable salt thereof, set forth in any of (1) to (4).

(6) An alkyl phenyl sulfide derivative represented by the general formula [I'] or an agriculturally acceptable salt thereof

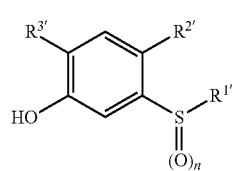

[I']

wherein n is an integer of 0, 1 or 2, $R^{1'}$ is a $C_1$~$C_6$ haloalkyl group (the group excludes 2-bromoethyl group), a $C_2$~$C_8$ alkenyl group (the group excludes allyl group), a $C_2$~$C_8$ haloalkenyl group, a $C_2$~$C_6$ alkynyl group, a $C_2$~$C_6$ haloalkynyl group, a branched $C_4$~$C_6$ alkyl group (the group excludes isobutyl group), a $C_3$~$C_6$ cycloalkyl $C_1$~$C_6$ alkyl group or a $C_3$~$C_6$ halocycloalkyl $C_1$~$C_6$ alkyl group, $R^{2'}$ is a halogen atom, a $C_1$~$C_6$ alkyl group, a $C_1$~$C_6$ haloalkyl group, a $C_3$~$C_6$ cycloalkyl group, a $C_3$~$C_6$ halocycloalkyl group, a $C_1$~$C_6$ alkoxy group, a $C_1$~$C_6$ haloalkoxy group, a cyano group or a nitro group, $R^{3'}$ is a hydrogen atom, a halogen atom, a $C_1$~$C_6$ alkyl group or a $C_1$~$C_6$ haloalkyl group.

(7) An alkyl phenyl sulfide derivative or an agriculturally acceptable salt thereof, set forth in (6), wherein $R^{1'}$ in the general formula [I'] is a 2,2-difluoroethyl group, a 2,2,2-trifluoroethyl group, a 3,3,3-trifluoropropyl group, a pentafluoroethyl group, a 1,2,2,2-tetrafluoroethyl group, a 2-chloro-2,2-difluoroethyl group, a 2,2,3,3-tetrafluoropropyl group a 2,2,3,3,3-pentafluoropropyl group, a 3,3-dichloroallyl group, a propargyl group, a cyclopropylmethyl group or a (2,2-difluorocyclopropyl)methyl group.

(8) An alkyl phenyl sulfide derivative represented by the general formula [I'] or an agriculturally acceptable salt thereof, set forth in (6) or (7), wherein $R^{2'}$ in the general formula [I'] is a halogen atom, a $C_1$~$C_6$ alkyl group, a $C_1$~$C_6$ haloalkyl group or a cyano group.

(9) An alkyl phenyl sulfide derivative represented by the general formula [I'] or an agriculturally acceptable salt thereof, set forth in any of (6) to (8), wherein $R^{3'}$ in the general formula [I'] is a hydrogen atom, a halogen atom or a $C_1$~$C_6$ alkyl group.

Advantages of the Invention

The pest control agent containing the present compound has an excellent effect to a wide range of pests such as Hemiptera, Lepidoptera, Coleoptera, Diptera, Hymenoptera, Orthoptera, Order Isoptera, Thysanoptera, spider mites, plant parasitic nematodes and the like and can control even pests which have acquired chemical resistance.

In particular, the pest control agent containing the present compound has an excellent effect to spider mites as pest, represented by *Tetranychus urticae, Tetranychus kanzawai, Panonychus citri*, etc., and has a sufficient effect even to spider mites which have acquired chemical resistance.

The symbols and terms used in this Specification are explained.

In the present invention, pest control agent means insecticide, miticide, nematicide, etc., used in agricultural and horticultural field, animals (e.g. livestock and pets), household, or infectious disease control.

In the present invention, halogen atom indicates fluorine atom, chlorine atom, bromine atom or iodine atom.

In the present invention, expression such as $C_1$~$C_6$ indicates that the substituent group after the expression has 1 to 6 carbon atoms in this case.

In the present invention, $C_1$~$C_6$ alkyl group indicates a straight chain or branched chain alkyl group having 1 to 6 carbon atoms, unless otherwise specified. There can be mentioned, for example, groups such as methyl, ethyl, n-propyl, isopropyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl and 1-ethyl-2-methylpropyl.

In the present invention, $C_1$~$C_6$ haloalkyl group indicates a straight chain or branched chain haloalkyl group having 1 to 6 carbon atoms, substituted with 1 to 13 same or different halogen atoms, unless otherwise specified. There can be mentioned, for example, fluoromethyl, difluoromethyl, trifluoromethyl, chloromethyl, dichloromethyl, trichloromethyl, bromomethyl, dibromomethyl, tribromomethyl, iodomethyl, chlorodifluoromethyl, dichlorofluoromethyl, 1-fluoroethyl, 2-fluoroethyl, 1,1-difluoroethyl, 2,2-difluoroethyl, 2,2,2-trifluoroethyl, 1,1,2,2-tetrafluoroethyl, pentafluoroethyl, 1-chloroethyl, 2-chloroethyl, 1,1-dichloroethyl, 2,2-dichloroethyl, 2,2,2-trichloroethyl, 1,1,2,2-tetrachloroethyl, pentachloroethyl, 1-bromoethyl, 2-bromoethyl, 2,2,2-tribromoethyl, 1-iodoethyl, 2-iodoethyl, 2-chloro-2,2-difluoroethyl, 2,2-dichloro-2-fluoroethyl, 2-trichloroethyl, 1-fluoropropyl, 2-fluoropropyl, 3-fluoropropyl, 1,1-difluoropropyl, 2,2-difluoropropyl, 3,3-difluoropropyl, 3,3,3-trifluoropropyl, 2,2,3,3-pentafluoropropyl, heptafluoropropyl, 1-fluoropropane-2-yl, 2-fluoropropane-2-yl, 1,1-difluoropropane-2-yl, 1,2-difluoropropane-2-yl, 1,3-difluoropropane-2-yl, 1,2,3-trifluoropropane-2-yl, 1,1,3,3-tetrafluoropropane-2-yl, 1,1,1,3,3,3-hexafluoropropane-2-yl, heptafluoropropane-2-yl, 1-chloropropyl, 2-chloropropyl, 3-chloropropyl, 1,1-dichloropropyl, 2,2-dichloropropyl, 3,3-dichloropropyl, 3,3,3-trichloropropyl, 2,2,3,3,3-pentachloropropyl, heptachloropropyl, 1-chloropropane-2-yl, 2-chloropropane-2-yl, 1,1-dichloropropane-2-yl, 1,2-dichloropropane-2-yl, 1,3-dichloropropane-2-yl, 1,2,3-trichloropropane-2-yl, 1,1,3,3-tetrachloropropane-2-yl, 1,1,1,3,3-hexachloropropane-2-yl, heptachloropropane-2-yl, 1-bromopropyl, 2-bromopropyl, 3-bromopropyl, 1-bromopropane-2-yl, 2-bromopropane-2-yl, 1-iodopropyl, 2-iodopropyl, 3-iodopropyl, 1-iodopropane-2-yl, 2-iodopropane-2-yl, 1-fluorobutyl, 2-fluorobutyl, 3-fluorobutyl, 4-fluorobutyl, 4,4-difluorobutyl, 4,4,4-trifluorobutyl, 3,3,4,4,4-pentafluorobutyl, 2,2,3,3,4,4,4-heptafluorobutyl, nonafluorobutyl, 1,1,1-trifluorobutane-2-yl 4,4,4-trifluorobutane-2-yl, 3,3,4,4,4-pentafluorobutane-2-yl, nonafluorobutane-2-yl, 1,1,1,3,3,3-hexafluoro-2-(trifluoromethyl)propane-2-yl, 1-chlorobutyl, 2-chlorobutyl, 3-chlorobutyl, 4-chlorobutyl, 4,4-dichlorobutyl, 4,4,4-trichlorobutyl, nonachlorobutyl, 1,1,1-trichlorobutane-2-yl 4,4,4-trichlorobutane-2-yl, nonachlorobutane-2-yl, 1-bromobutyl, 2-bromobutyl, 3-bromobutyl, 4-bromobutyl, 1-iodobutyl, 2-iodobutyl, 3-iodobutyl, 4-iodobutyl, 4-chloro-1,1,2,2,3,3,4,4-octafluorobutyl, 4-bromo-1,1,2,2,3,3,4,4-octafluorobutyl, 1-fluoropentyl, 2-fluoropentyl, 3-fluoropentyl, 4-fluoropentyl, 5-fluoropentyl, 5,5,5-trifluoropentyl, 4,4,5,5,5-pentafluoropentyl, 3,3,4,4,5,5,5-heptafluoropentyl, 2,2,3,3,4,4,5,5,5-nonafluoropentyl, undecafluoropentyl, 1-chloropentyl, 2-chloropentyl, 3-chloropentyl, 4-chloropentyl, 5-chloropentyl, 5,5,5-trichloropentyl, 4,4,5,5,5-pentachloropentyl, 3,3,4,4,5,5,5-heptachloropentyl, 2,2,3,3,4,4,5,5,5-nonachloropentyl, undecachloropentyl, 1-bromopentyl, 2-bromopentyl, 3-bromopentyl, 4-bromopentyl, 5-bromopentyl, 5-iodopentyl, 1-fluorohexyl, 2-fluorohexyl, 3-fluorohexyl, 4-fluorohexyl, 5-fluorohexyl, 6-fluorohexyl, 6,6,6-trifluorohexyl, 5,5,6,6,6-pentafluorohexyl, 4,4,5,5,6,6,6-heptafluorohexyl, 3,3,4,4,5,5,6,6,6-nonafluorohexyl, 2,2,3,3,4,4,5,5,6,6,6-undecafluorohexyl, tridecafluorohexyl, 1-chlorohexyl, 2-chlorohexyl, 3-chlorohexyl, 4-chlorohexyl, 5-chlorohexyl, 6-chlorohexyl, 5-bromohexyl, 6-bromohexyl, 5-iodohexyl and 6-iodohexyl.

In the present invention, $C_1$~$C_{12}$ alkyl group indicates a straight chain or branched chain alkyl group having 1 to 12 carbon atoms, unless otherwise specified. There can be mentioned, in addition to the above-mentioned $C_1$~$C_6$ carbon atoms, for example, n-heptyl, n-octyl, n-nonyl, n-decyl, nundecyl, n-dodecyl, 4,4-dimethylpentyl, 5-methylhexyl, 5,5-dimethylhexyl, 3,5,5-trimethylhexyl, 6-methylheptyl, 6,6-dimethylheptyl, 3,6,6-trimethylheptyl, 7-methyloctyl, 7,7- dimethyloctyl, 8-methylnonyl, 8,8-dimethylnonyl, 9-methyldecyl, 9,9-dimethyldecyl and 10-methylundecyl.

In the present invention, branched chain $C_4$~$C_6$ alkyl group indicates a branched chain alkyl group having 4 to 6 carbon atoms, unless otherwise specified. There can be mentioned, for example, groups such as sec-butyl, isobutyl, tert-butyl, 1-methylbutyl, 2-methylbutyl, 3-methylbutyl, 1-ethylpropyl, 1,1-dimethylpropyl, 1,2-dimethylpropyl, neopentyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl and 1-ethyl-2-methylpropyl.

In the present invention, $C_3$~$C_6$ cycloalkyl group indicates a cycloalkyl group having 3 to 6 carbon atoms, unless otherwise specified. There can be mentioned, for example, groups such as cyclopropyl, cyclobutyl, cyclopentyl and cyclohexyl.

In the present invention, $C_3$~$C_6$ halocycloalkyl group indicates a cycloalkyl group having 3 to 6 carbon atoms, substituted with 1 to 11 same or different halogen atoms, unless otherwise specified. There can be mentioned, for example, groups such as 1-fluorocyclopropyl, 2-fluorocyclopropyl, 2,2-difluorocyclopropyl, 2,2,3,3-tetrafluorocyclopropyl, 1-chlorocyclopropyl, 2-chlorocyclopropyl, 2,2-dichlorocyclopropyl, 2,2,3,3-tetrachlorocyclopropyl, 2,2-dibromocyclopropyl, 2,2-diiodocyclopropyl, 1-fluorocyclobutyl, 2-fluorocyclobutyl, 3-fluorocyclobutyl, 3,3-difluorocyclobutyl, heptafluorocyclobutyl, 2-chlorocyclobutyl, 3-chlorocyclobutyl, 3,3-dichlorocyclobutyl, 3,3-dibromocyclobutyl, 3,3-diiodocyclobutyl, 1-fluorocyclopentyl, 2-fluorocyclopentyl, 3-fluorocyclopentyl, 2,2-difluorocyclopentyl, 3,3-difluorocyclopentyl, nonafluorocyclopentyl, 2,2-dichlorocyclopentyl, 3,3-dichlorocyclopentyl, 2,2-dibromocyclopentyl, 3,3-dibromocyclopentyl, 2,2-diiodocyclopentyl, 3,3-diiodocyclopentyl, 1-fluorocyclohexyl, 2-fluorocyclohexyl, 3-fluorocyclohexyl, 4-fluorocyclohexyl, 2,2-difluorocyclohexyl, 3,3-difluorocyclohexyl, 4,4-difluorocyclohexyl, 1-chlorocyclohexyl, 2-chlorocyclohexyl, 3-chlorocyclohexyl, 4-chlorocyclohexyl, 2,2-dichlorocyclohexyl, 3,3-dichlorocyclohexyl, 4,4-dichlorocyclohexyl, 3,3-dibromocyclohexyl, 4,4-dibromocyclohexyl, 3,3-diiodocyclohexyl and 4,4-diiodocyclohexyl.

In the present invention, $C_2$~$C_8$ alkenyl group indicates a straight chain or branched chain alkenyl group having 2 to 8 carbon atoms, unless otherwise specified. There can be mentioned, for example, groups such as vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadieneyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 2,3-butadien-1-yl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-methyl-2-propenyl, 1-ethyl-2-methyl-2-propenyl, 1-(isopropyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl, 2,4-hexadienyl, 2-octenyl and 3,7-dimethyl-6-octenyl.

In the present invention, $C_2$~$C_8$ haloalkenyl group indicates a haloalkenyl group having 2 to 8 carbon atoms, substituted with 1 to 15 same or different halogen atoms, unless otherwise specified. There can be mentioned, for example, groups such as 1-fluorovinyl, 2-fluorovinyl, 1,2-difluorovinyl, 2,2-difluorovinyl, trifluorovinyl, 1-chlorovinyl, 2-chlorovinyl, dichlorovinyl, trichlorovinyl, dibromovinyl, diiodovinyl, 1-fluoro-2-propenyl, 2-fluoro-2-propenyl, 3-fluoro-2-propenyl, 2,3-difluoro-2-propenyl, 3,3-difluoro-2-propenyl, 3,3-difluoro-1-propenyl, 2,3,3-trifluoro-2-propenyl, 3,3,3-trifluoro-1-propenyl, 1,2,3,3,3-pentafluoro-1-propenyl, 1-chloro-2-propenyl, 2-chloro-2-propenyl, 3-chloro-2-propenyl, 2,3-dichloro-2-propenyl, 3,3-dichloro-2-propenyl, 3,3-dichloro-1-propenyl, 2,3,3-trichloro-2-propenyl, 3,3,3-trichloro-1-propenyl, 3-bromo-2-propenyl, 3,3-dibromo-2-propenyl, 3,3-diiodo-2-propenyl, 2,2-difluoro-1-propen-2-yl, 3,3,3-trifluoro-1-propen-2-yl, 3,3,3-trichloro-1-propen-2-yl, 4-fluoro-3-butenyl, 4,4-difluoro-3-butenyl, 4,4-difluoro-3-buten-2-yl, 4,4,4-trifluoro-2-butenyl, 3,4,4-trifluoro-3-butenyl, 2-trifluoromethyl-2-propenyl, 2-trifluoromethyl-3,3-difluoro-2-propenyl, 4,4,4-trifluoro-3-chloro-2-butenyl, 4,4-dichloro-3-butenyl, 4,4,4-trichloro-2-butenyl, 2-trichloromethyl-2-propenyl, 5,5-difluoro-4-pentenyl, 4,5,5-trifluoro-4-pentenyl, 5,5,5-trifluoro-3-pentenyl, 4,4,4-trifluoro-3-methyl-2-butenyl, 4,4,4-trifluoro-3-trifluoromethyl-2-butenyl, 5,5-dichloro-4-pentenyl, 4,4,4-trichloro-3-methyl-2-butenyl, 6,6-difluoro-5-hexenyl, 5,6,6-trifluoro-5-pentenyl, 6,6,6-trifluoro-4-pentenyl, 5,5,5-trifluoro-4-methyl-3-pentenyl, 5,5,5-trifluoro-4-trifluoromethyl-3-pentenyl, 6,6-dichloro-5-hexenyl and 5,5,5-trichloro-4-methyl-3-pentenyl.

In the present invention, $C_2$~$C_6$ alkynyl group indicates a straight chain or branched chain alkynyl group having 2 to 6 carbon atoms, unless otherwise specified. There can be mentioned, for example, groups such as ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-(isopropyl)-2-propynyl, 1,1-dimethyl-2-butynyl and 2,2-dimethyl-3-butynyl.

In the present invention, $C_2$~$C_6$ haloalkynyl group indicates a straight chain or branched chain haloalkynyl group having 2 to 6 carbon atoms, substituted with 1 to 9 same or different halogen atoms, unless otherwise specified. There can be mentioned, for example, groups such as fluoroethynyl, chloroethynyl, bromoethynyl, iodoethynyl, 3-fluoro-2-propynyl, 3-chloro-2-propynyl, 3-bromo-2-propynyl, 3-iodo-2-propynyl, 4-fluoro-3-butynyl, 4-chloro-3-butynyl, 4-bromo-3-butynyl, 4-iodo-3-butynyl, 4,4-difluoro-2-butynyl, 4,4-dichloro-2-butynyl, 4,4,4-trifluoro-2-butynyl, 4,4,4-trichloro-2-butynyl, 3-fluoro-1-methyl-2-propynyl, 3-chloro-1-methyl-2-propynyl, 5-fluoro-4-pentynyl, 5-chloro-4-pentynyl, 5,5,5-trifluoro-3-pentynyl, 5,5,5-trichloro-3-pentynyl, 4-fluoro-2-methyl-3-butynyl, 4-chloro-2-methyl-3-butynyl, 6-fluoro-5-hexynyl, 6-chloro-5-hexynyl, 6,6,6-trifluoro-4-hexynyl, 6,6,6-trichloro-4-hexynyl, 5-fluoro-3-methyl-4-pentynyl and 5-chloro-3-methyl-4-pentynyl.

In the present invention, $C_3$~$C_6$ cycloalkyl $C_1$~$C_6$ alkyl group indicates a ($C_3$~$C_6$ cycloalkyl)-($C_1$~$C_6$ alkyl) group wherein the cycloalkyl and alkyl has the above-mentioned meaning, unless otherwise specified. There can be mentioned, for example, groups such as cyclopropylmethyl, 2-cyclopropylethyl, 3-cyclopropylpropyl, 4-cyclopropylbutyl, 5-cyclopropylpentyl, 6-cyclopropylhexyl, cyclobutylmethyl, cyclopentylmethyl and cyclohexylmethyl.

In the present invention, $C_3\sim C_6$ halocycloalkyl $C_1\sim C_6$ alkyl group indicates a $(C_3\sim C_6$ halocycloalkyl)-$(C_1\sim C_6$ alkyl) group wherein the halocycloalkyl and alkyl has the above-mentioned meaning, unless otherwise specified. There can be mentioned, for example, groups such as 1-fluorocyclopropylmethyl, 2-fluorocyclopropylmethyl, 2,2-difluorocyclopropylmethyl, 2-chlorocyclopropylmethyl, 2,2-dichlorocyclopropylmethyl, 2,2-dibromocyclopropylmethyl, 2,2-diiodorocyclopropylmethyl, 2-(2,2-difluorocyclopropyl) ethyl, 2-(2,2-dichlorocyclopropyl)ethyl, 3-(2,2-difluorocyclopropyl)propyl, 4-(2,2-difluorocyclopropyl) butyl, 5-(2,2-dichlorocyclopropyl)pentyl, 5-(2,2-difluorocyclopropyl)pentyl, 6-(2,2-difluorocyclopropyl) hexyl, 2,2-difluorocyclobutylmethyl, 2,2-dichlorocyclobutylmethyl, 3,3-difluorocyclopentylmethyl, 3,3-dichlorocyclopentylmethyl, 4,4-difluorocyclohexylmethyl and 4,4-dichlorocyclohexylmethyl.

In the present invention, $C_1\sim C_6$ alkoxy group indicates a $(C_1\sim C_6$ alkyl)-O— group wherein the alkyl has the above-mentioned meaning, unless otherwise specified. There can be mentioned, for example, groups such as methoxy, ethoxy, n-propoxy, isopropxy, n-butoxy, isobutoxy, sec-butoxy, tert-butoxy, n-pentoxy, 1-methylbutoxy, 2-methylbutoxy, 3-methylbutoxy, 1-ethylpropoxy, 1,1-dimethylpropoxy, 1,2-dimethylpropoxy and n-hexyloxy.

In the present invention, $C_1\sim C_6$ haloalkoxy group indicates a $(C_1\sim C_6$ haloalkyl)-O— group wherein the haloalkyl has the above-mentioned meaning, unless otherwise specified. There can be mentioned, for example, groups such as difluoromethoxy, trifluoromethoxy, trichloromethoxy, tribromomethoxy, 2,2,2-trifluoroethoxy, 2,2,2-trichloroethoxy, pentafluoroethoxy, 3,3,3-trifluoropropoxy, heptafluoro-2-propoxy, tri(trifluoromethyl)methoxy, 3,3,3-trichloropropoxy and heptafluoropropoxy.

In the present invention, $C_3\sim C_6$ cycloalkoxy group indicates a $(C_3\sim C_6$ cycloalkyl)-O— group wherein the cycloalkyl has the above-mentioned meaning, unless otherwise specified. There can be mentioned, for example, groups such as cyclopropoxy, cyclobutoxy, cyclopentyloxy and cyclohexyloxy.

In the present invention, $C_3\sim C_6$ halocycloalkoxy group indicates a $(C_3\sim C_6$ halocycloalkyl)-O— group wherein the halocycloalkyl has the above-mentioned meaning, unless otherwise specified. There can be mentioned, for example, groups such as 2,2-difluorocyclopropoxy, 2,2-dichlorocyclopropoxy, 3,3-difluorocyclobutoxy, 3,3-dichlorocyclobutoxy, 3-fluorocyclopentyloxy, 3,3-difluorocyclopentyloxy, nonafluorocyclopentyloxy, 3,3-dichlorocyclopentyloxy, 4,4-difluorocyclohexyloxy, and 4,4-dichlorocyclohexyloxy.

In the present invention, $C_1\sim C_6$ alkoxy $C_1\sim C_6$ alkoxy group indicates a $(C_1\sim C_6$ alkoxy)-$(C_1\sim C_6$ alkoxy)-group wherein the alkoxy has the above-mentioned meaning, unless otherwise specified. There can be mentioned, for example, groups such as 2-methoxyethoxy, 3-methoxypropoxy, 2-ethoxyisopropoxy, 2-isopropoxybutoxy, 5-ethoxypentyloxy, 6-ethoxyhexyloxy, 2-(tert-butoxy)ethoxy, 2-methoxyisopentyloxy and 2-isopropoxyisobutoxy.

In the present invention, $C_1\sim C_6$ haloalkoxy $C_1\sim C_6$ alkoxy group indicates a $(C_1\sim C_6$ haloalkoxy)-$(C_1\sim C_6$ alkoxy) group wherein the haloalkoxy and alkoxy has the above-mentioned meaning, unless otherwise specified. There can be mentioned, for example, groups such as 2-difluoromethoxyethoxy, 2-trifluoromethoxyethoxy, 3-trifluoromethoxypropoxy and 2-(2,2,2-trifluoroethoxy)ethoxy.

In the present invention, $C_1\sim C_6$ haloalkoxy $C_1\sim C_6$ haloalkoxy group indicates a $(C_1\sim C_6$ haloalkoxy)-$(C_1\sim C_6$ haloalkoxy)-group wherein the haloalkoxy has the above-mentioned meaning, unless otherwise specified. There can be mentioned, for example, groups such as 2-(difluoromethoxy)-1,1,2,2-tetrafluoroethoxy, 2-(trifluoromethoxy)-1,1,2,2-tetrafluoroethoxy, 1,1,2,3,3,3-hexafluoro-2-(hexafluoropropoxy)propoxy, and 2-(2,2,2-trifluoroethoxy)-1,1,2,2-tetrafluoroethoxy.

In the present invention, $C_1\sim C_6$ alkylsulfinyloxy group indicates a $(C_1\sim C_6$ alkyl)-SO—O— group wherein the alkyl has the above-mentioned meaning, unless otherwise specified. There can be mentioned, for example, groups such as methylsulfinyloxy, ethylsulfinyloxy, n-propylsulfinyloxy and isopropylsulfinyloxy.

In the present invention, $C_1\sim C_6$ haloalkylsulfinyloxy group indicates a $(C_1\sim C_6$ haloalkyl)-SO—O— group wherein the haloalkyl has the above-mentioned meaning, unless otherwise specified. There can be mentioned, for example, groups such as difluoromethylsulfinyloxy, trifluoromethylsulfinyloxy, 2,2,2-trifluoroethylsulfinyloxy, pentafluoroethylsulfinyloxy, heptafluoropropylsulfinyloxy, trichloromethylsulfinyloxy and heptafluoro-2-propylsulfinyloxy.

In the present invention, $C_3\sim C_6$ cycloalkylsulfinyloxy group indicates a $(C_3\sim C_6$ cycloalkyl)-SO—O— group wherein the cycloalkyl has the above-mentioned meaning, unless otherwise specified. There can be mentioned, for example, groups such as cyclopropylsulfinyloxy, cyclobutylsulfinyloxy, cyclopentylsulfinyloxy and cyclohexylsulfinyloxy.

In the present invention, $C_3\sim C_6$ halocycloalkylsulfinyloxy group indicates a $(C_3\sim C_6$ halocycloalkyl)-SO—O— group wherein the halocycloalkyl has the above-mentioned meaning, unless otherwise specified. There can be mentioned, for example, groups such as 2,2-difluorocyclopropylsulfinyloxy, 2,2-dichlorocyclopropylsulfinyloxy, 3,3-difluorocyclobutylsulfinyloxy, 3,3-difluorocyclopentylsulfinyloxy and 4,4-difluorocyclohexylsulfinyloxy.

In the present invention, $C_1\sim C_6$ alkylsulfonyloxy group indicates a $(C_1\sim C_6$ alkyl)-SO$_2$—O— group wherein the alkyl has the above-mentioned meaning, unless otherwise specified. There can be mentioned, for example, groups such as methylsulfonyloxy, ethylsulfonyloxy, n-propylsulfonyloxy and isopropylsulfonyloxy.

In the present invention, $C_1\sim C_6$ haloalkylsulfonyloxy group indicates a $(C_1\sim C_6$ haloalkyl)-SO$_2$—O— group wherein the haloalkyl has the above-mentioned meaning, unless otherwise specified. There can be mentioned, for example, groups such as difluoromethylsulfonyloxy, trifluoromethylsulfonyloxy, trichloromethylsulfonyloxy, 2,2,2-trifluoroethylsulfonyloxy, 2,2,2-trichloroethylsulfonyloxy, 3,3,3-trifluoropropylsulfonyloxy, heptafluoro-2-propylsulfonyloxy and perfluorobutylsulfonyloxy.

In the present invention, $C_3\sim C_6$ cycloalkylsulfonyloxy group indicates a $(C_3\sim C_6$ cycloalkyl)-SO$_2$—O— group wherein the cycloalkyl has the above-mentioned meaning, unless otherwise specified. There can be mentioned, for example, groups such as cyclopropylsulfonyloxy, cyclobutylsulfonyloxy, cyclopentylsulfonyloxy and cyclohexylsulfonyloxy.

In the present invention, $C_3\sim C_6$ halocycloalkylsulfonyloxy group indicates a $(C_3\sim C_6$ halocycloalkyl)-SO$_2$—O— group wherein the halocycloalkyl has the above-mentioned meaning, unless otherwise specified. There can be mentioned, for example, groups such as 2,2-difluorocyclopropylsulfonyloxy, 2,2-dichlorocyclopropylsulfonyloxy, 3,3-difluorocyclobutylsulfonyloxy, 3,3-cyclopentylsulfonyloxy and 4,4-difluorocyclohexylsulfonyloxy.

In the present invention, $C_1\sim C_6$ alkylthio group indicates a $(C_1\sim C_6$ alkyl)-S-group wherein the alkyl has the above-mentioned meaning, unless otherwise specified. There can be mentioned, for example, groups such as methylthio, ethylthio, n-propylthio, isopropylthio, n-butylthio, isobutylthio, sec-butylthio, tert-butylthio and neo-pentylthio.

In the present invention, $C_1\sim C_6$ haloalkylthio group indicates a $(C_1\sim C_6$ haloalkyl)-S-group wherein the haloalkyl has the above-mentioned meaning, unless otherwise specified. There can be mentioned, for example, groups such as fluoromethylthio, difluoromethylthio, trifluoromethylthio, trichloromethylthio, 2,2,2-trifluoroethylthio, pentafluoroethylthio, 2,2,2-trichloroethylthio, 3,3,3-trifluoropropylthio, heptafluoropropylthio, 1,1,1,3,3,3-hexafluoropropane-2-yl-thio, heptafluoropropane-2-yl-thio, 4,4,4-trifluorobutylthio and 2,2,2-trichloroethylthio.

In the present invention, $C_2\sim C_6$ alkenylthio group indicates a $(C_2\sim C_6$ alkenyl)-S-group wherein the alkenyl has the above-mentioned meaning, unless otherwise specified. There can be mentioned, for example, groups such as vinylthio, 1-propenylthio, isopropenylthio, 2-propenylthio, 2-butenylthio, 3-butenylthio, 2-pentenylthio, 3-pentenylthio, 4-pentenylthio, 2-methyl-2-butenylthio, 2,4-pentadienylthio, 2-hexenylthio, 3-hexenylthio, 4-hexenylthio, 5-hexenylthio and 2,4-hexadienylthio.

In the present invention, $C_2\sim C_6$ haloalkenylthio group indicates a $(C_2\sim C_6$ haloalkenyl)-S-group wherein the haloalkenyl has the above-mentioned meaning, unless otherwise specified. There can be mentioned, for example, groups such as 2,2-difluorovinylthio, 2,2-dichlorovinylthio, 3,3-difluoro-2-propenylthio, 2,3,3-trifluoro-2-propenylthio, 3-chloro-2-propenylthio, 3,3-dichloro-2-propenylthio, 3-bromo-2-propenylthio, 4,4-difluoro-3-butenylthio, 4,4-difluoro-3-butene-2-ylthio, 3,4,4-trifluoro-3-butenylthio, 4,4,4-trifluoro-3-chloro-2-butenylthio, 4,4-dichloro-3-butenylthio, 4,5,5-trifluoro-4-pentenylthio, 5,5,5-trifluoro-3-pentenylthio, 4,4,4-trifluoro-3-trifluoromethyl-2-butenylthio, 6,6-difluoro-5-hexenylthio, 5,6,6-trifluoro-5-hexenylthio and 6,6-dichloro-5-hexenylthio.

In the present invention, $C_3\sim C_6$ cycloalkylthio group indicates a $(C_3\sim C_6$ cycloalkyl)-S-group wherein the cycloalkyl has the above-mentioned meaning, unless otherwise specified. There can be mentioned, for example, groups such as cyclopropylthio, cyclobutylthio, cyclopentylthio and cyclohexylthio.

In the present invention, $C_3\sim C_6$ halocycloalkylthio group indicates a $(C_3\sim C_6$ halocycloalkyl)-S-group wherein the halocycloalkyl has the above-mentioned meaning, unless otherwise specified. There can be mentioned, for example, groups such as 2,2-difluorocyclopropylthio, 2,2-dichlorocyclopropylthio, 3,3-difluorocyclobutylthio, 3,3-difluorocyclopentylthio and 4,4-difluorocyclohexylthio.

In the present invention, $C_3\sim C_6$ cycloalkyl $C_1\sim C_6$ alkylthio group indicates a $(C_3\sim C_6$ cycloalkyl)-$(C_1\sim C_6$ alkyl)-S-group wherein the cycloalkyl and alkyl has the above-mentioned meaning, unless otherwise specified. There can be mentioned, for example, groups such as cyclopropylmethylthio, 2-cyclopropylethylthio, 3-cyclopropylpropylthio, 4-cyclopropylbutylthio, 5-cyclopropylpentylthio, cyclobutylmethylthio, cyclopentylmethylthio and cyclohexylmethylthio.

In the present invention, $C_3\sim C_6$ halocycloalkyl $C_1\sim C_6$ alkylthio group indicates a $(C_3\sim C_6$ halocycloalkyl)-$(C_1\sim C_6$ alkyl)-S-group wherein the halocycloalkyl and alkyl has the above-mentioned meaning, unless otherwise specified. There can be mentioned, for example, groups such as 2,2-difluorocyclopropylmethylthio, 2,2-dichlorocyclopropylmethylthio, 2-(2,2-difluorocyclopropyl)ethylthio, 2-(2,2-dichlorocyclopropyl)ethylthio, 2,2-difluorocyclobutylmethylthio and 4,4-difluorocyclohexylmethylthio.

In the present invention, tri($C_1\sim C_6$ alkyl)silyl-$C_1\sim C_6$ alkylthio group indicates a $(C_1\sim C_6$ alkyl)$_3$-Si—$(C_1\sim C_6$ alkyl)-S— group wherein the alkyl has the above-mentioned meaning, unless otherwise specified. There can be mentioned, for example, groups such as trimethylsilylmethylthio, triethylsilylmethylthio, trimethylsilylethylthio, tertbutyldimethylsilylmethylthio, and trimethylsilylpropylthio.

In the present invention, $C_1\sim C_6$ alkylsulfinyl group indicates a $(C_1\sim C_6$ alkyl)-SO— group wherein the alkyl has the above-mentioned meaning, unless otherwise specified. There can be mentioned, for example, groups such as methylsulfinyl, ethylsulfinyl, n-propylsulfinyl, isopropylsulfinyl, n-butylsulfinyl, isobutylsulfinyl, sec-butylsulfinyl and tert-butylsulfinyl.

In the present invention, $C_1\sim C_6$ haloalkylsulfinyl group indicates a $(C_1\sim C_6$ haloalkyl)-SO— group wherein the haloalkyl has the above-mentioned meaning, unless otherwise specified. There can be mentioned, for example, groups such as difluoromethylsulfinyl, trifluoromethylsulfinyl, 2,2,2-trifluoroethylsulfinyl, 2,2,2-trichloroethylsulfinyl, pentafluoroethylsulfinyl, heptafluoropropylsulfinyl, trichloromethylsulfinyl and heptafluoro-2-propylsulfinyl.

In the present invention, $C_3\sim C_6$ cycloalkylsulfinyl group indicates a $(C_3\sim C_6$ cycloalkyl)-SO— group wherein the cycloalkyl has the above-mentioned meaning, unless otherwise specified. There can be mentioned, for example, groups such as cyclopropylsulfinyl, cyclobutylsulfinyl, cyclopentylsulfinyl and cyclohexylsulfinyl.

In the present invention, $C_3\sim C_6$ halocycloalkylsulfinyl group indicates a $(C_3\sim C_6$ halocycloalkyl)-SO— group wherein the halocycloalkyl has the above-mentioned meaning, unless otherwise specified. There can be mentioned, for example, groups such as 2,2-difluorocyclopropylsulfinyl, 2,2-dichlorocyclopropylsulfinyl, 3,3-difluorocyclobutylsulfinyl, 3,3-difluorocyclopentylsulfinyl and 4,4-difluorocyclohexylsulfinyl.

In the present invention, $C_1\sim C_6$ alkylsulfonyl group indicates a $(C_1\sim C_6$ alkyl)-SO$_2$— group wherein the alkyl has the above-mentioned meaning, unless otherwise specified. There can be mentioned, for example, groups such as methylsulfonyl, ethylsulfonyl, n-propylsulfonyl, isopropylsulfonyl, n-butylsulfonyl, isobutylsulfonyl, sec-butylsulfonyl and tert-butylsulfonyl.

In the present invention, $C_1\sim C_6$ haloalkylsulfonyl group indicates a $(C_1\sim C_6$ haloalkyl)-SO$_2$— group wherein the haloalkyl has the above-mentioned meaning, unless otherwise specified. There can be mentioned, for example, groups such as difluoromethylsulfonyl, trifluoromethylsulfonyl, trichloromethylsulfonyl, 2,2,2-trifluoroethylsulfonyl, 3,3,3-trifluoropropylsulfonyl and heptafluoro-2-propylsulfonyl.

In the present invention, $C_3\sim C_6$ cycloalkylsulfonyl group indicates a $(C_3\sim C_6$ cycloalkyl)-SO$_2$— group wherein the cycloalkyl has the above-mentioned meaning, unless otherwise specified. There can be mentioned, for example, groups such as cyclopropylsulfonyl, cyclobutylsulfonyl, cyclopentylsulfonyl and cyclohexylsulfonyl.

In the present invention, $C_3\sim C_6$ halocycloalkylsulfonyl group indicates a $(C_3\sim C_6$ halocycloalkyl)-SO$_2$— group wherein the halocycloalkyl has the above-mentioned meaning, unless otherwise specified. There can be mentioned, for example, groups such as 2,2-difluorocyclopropylsulfonyl, 2,2-dichlorocyclopropylsulfonyl, 3,3-difluorocyclobutylsulfonyl, 3,3-difluorocyclopentylsulfonyl and 4,4-difluorocyclohexylsulfonyl.

In the present invention, $C_1$~$C_6$ alkylthio $C_1$~$C_6$ alkyl group indicates a ($C_1$~$C_6$ alkyl)-S—($C_1$~$C_6$ alkyl) group wherein the alkyl has the above-mentioned meaning, unless otherwise specified. There can be mentioned, for example, groups such as methylthiomethyl, 2-(methylthio)ethyl, 3-(methylthio)propyl, 4-(methylthio)butyl, ethylthiomethyl, propylthiomethyl, butylthiomethyl and pentylthiomethyl.

In the present invention, $C_1$~$C_6$ haloalkylthio $C_1$~$C_6$ alkyl group indicates a ($C_1$~$C_6$ haloalkyl)-S—($C_1$~$C_6$ alkyl) group wherein the alkyl and haloalkyl have the above-mentioned meaning, unless otherwise specified. There can be mentioned, for example, groups such as trifluoromethylthiomethyl, difluoromethylthiomethyl, 2,2,2-trifluoroethylthiomethyl, 2,2,2-trichloroethylthiomethyl, 2-(trifluoromethylthio)ethyl, 2-(difluoromethylthio)ethyl, 2-(2,2,2-trifluoroethylthio)ethyl, 3-(trifluoromethylthio)propyl, 3-(difluoromethylthio)propyl and 3-(2,2,2-trifluoroethylthio)propyl.

In the present invention, $C_1$~$C_6$ alkylcarbonyl group indicates a ($C_1$~$C_6$ alkyl)-C(═O)— group wherein the alkyl has the above-mentioned meaning, unless otherwise specified. There can be mentioned, for example, groups such as acetyl, propionyl, isopropionyl and pivaloyl.

In the present invention, $C_1$~$C_6$ haloalkylcarbonyl group indicates a ($C_1$~$C_6$ haloalkyl)-C(═O)— group wherein the haloalkyl has the above-mentioned meaning, unless otherwise specified. There can be mentioned, for example, groups such as fluoroacetyl, difluoroacetyl, trifluoroacetyl, chloroacetyl, trichloroacetyl, tribromoacetyl, 3,3,3-trifluoropropionyl, 3,3-difluoropropionyl and 4,4,4-trifluorobutyryl.

In the present invention, $C_1$~$C_6$ alkylcarbonyloxy group indicates a ($C_1$~$C_6$ alkyl)-C(═O)—O— group wherein the alkyl has the above-mentioned meaning, unless otherwise specified. There can be mentioned, for example, groups such as acetoxy and propionyloxy.

In the present invention, $C_1$~$C_6$ haloalkylcarbonloxy group indicates a ($C_1$~$C_6$ haloalkyl)-C(═O)—O— group wherein the haloalkyl has the above-mentioned meaning, unless otherwise specified. There can be mentioned, for example, groups such as fluoroacetoxy, difluoroacetoxy, trifluoroacetoxy, chloroacetoxy, trichloroacetoxy, tribromoacetoxy, 3,3,3-trifluoropropionyloxy, 3,3-difluoropropionyloxy and 4,4,4-trifluorobutyryloxy.

In the present invention, $C_1$~$C_6$ alkoxycarbonyl group indicates a ($C_1$~$C_6$ alkoxy)-C(═O)— group wherein the alkoxy has the above-mentioned meaning, unless otherwise specified. There can be mentioned, for example, groups such as methoxycarbonyl, ethoxycarbonyl, n-propoxycarbonyl, isopropoxycarbonyl and tert-butoxycarbonyl.

In the present invention, $C_1$~$C_6$ haloalkoxycarbonyl group indicates a ($C_1$~$C_6$ haloalkoxy)-C(═O)— group wherein the haloalkoxy has the above-mentioned meaning, unless otherwise specified. There can be mentioned, for example, groups such as 2-fluoroethoxycarbonyl, 2,2,2-trifluoroethoxycarbonyl, 2,2,2-trichloroethoxycarbonyl, pentafluoroethoxycarbonyl, 3,3,3-trifluoropropoxycarbonyl and heptafluoro-2-propoxycarbonyl.

In the present invention, $C_1$~$C_6$ alkylamino group indicates a ($C_1$~$C_6$ alkyl)-NH— group wherein the alkyl has the above-mentioned meaning, unless otherwise specified. There can be mentioned, for example, groups such as methylamino, ethylamino and n-propylamino.

In the present invention, $C_1$~$C_6$ haloalkylamino group indicates a ($C_1$~$C_6$ haloalkyl)-NH— group wherein the haloalkyl has the above-mentioned meaning, unless otherwise specified. There can be mentioned, for example, groups such as 2-fluoroethylamino, 2,2-difluoroethylamino, 2,2,2-trifluoroethylamino, 2,2,2-trichloroethylamino, pentafluoroethylamino, 3,3,3-trifluoropropylamino and 1,1,1,3,3,3-hexafluoro-2-propylamino.

In the present invention, $C_1$~$C_6$ alkylcarbonylamino group indicates a ($C_1$~$C_6$ alkyl)-C(═O)—NH— group wherein the alkyl has the above-mentioned meaning, unless otherwise specified. There can be mentioned, for example, groups such as acetylamino, propionylamino, butyrylamino, isobutyrylamino and tert-butylcarbonylamino.

In the present invention, $C_1$~$C_6$ haloalkylcarbonylamino group indicates a ($C_1$~$C_6$ haloalkyl)-C(═O)—NH— group wherein the haloalkyl has the above-mentioned meaning, unless otherwise specified. There can be mentioned, for example, groups such as fluoroacetylamino, difluoroacetylamino, trifluoroacetylamino, chloroacetylamino, trichloroacetylamino, tribromoacetylamino, 3,3,3-trifluoropropionylamino, pentafluoropropionylamino, 3,3-difluoropropionylamino and 3,3,3-trifluoro-2-methyl-2-trifluoromethylpropionylamino.

In the present invention, $C_1$~$C_6$ alkoxycarbonylamino group indicates a ($C_1$~$C_6$ alkoxy)-C(═O)—NH— group wherein the alkoxy has the above-mentioned meaning, unless otherwise specified. There can be mentioned, for example, groups such as methoxycarbonylamino, ethoxycarbonylamino, n-propoxycarbonylamino and isopropoxycarbonylamino.

In the present invention, $C_1$~$C_6$ haloalkoxycarbonylamino group indicates a ($C_1$~$C_6$ haloalkoxy)-C(═O)—NH— group wherein the haloalkoxy has the above-mentioned meaning, unless otherwise specified. There can be mentioned, for example, groups such as 2-fluoroethoxycarbonylamino, 2,2,2-trifluoroethoxycarbonylamino, 2,2,2-trichloroethoxycarbonylamino, pentafluoroethoxycarbonylamino, 3,3,3-trifluoropropoxycarbonylamino, and heptafluoro-2-propoxycarbonylamino.

In the present invention, $C_1$~$C_6$ alkylaminocarbonylamino group indicates a ($C_1$~$C_6$ alkyl)-NH—C(═O)—NH— group wherein the alkyl has the above-mentioned meaning, unless otherwise specified. There can be mentioned, for example, groups such as methylaminocarbonylamino, ethylaminocarbonylamino, n-propylaminocarbonylamino, isopropylaminocarbonylamino, tert-butylaminocarbonylamino, and tert-pentylaminocarbonylamino.

In the present invention, $C_1$~$C_6$ haloalkylaminocarbonylamino group indicates a ($C_1$~$C_6$ haloalkyl)-NH—C(═O)—NH— group wherein the haloalkyl has the above-mentioned meaning, unless otherwise specified. There can be mentioned, for example, groups such as 2-fluoroethylaminocarbonylamino, 2,2,2-trifluoroethylaminocarbonylamino, 2,2,2-trichloroethylaminocarbonylamino, pentafluoroethylaminocarbonylamino and 1,1,1,3,3,3-hexafluoro-2-propylaminocarbonylamino.

In the present invention, $C_1$~$C_6$ alkylsulfonylamino group indicates a ($C_1$~$C_6$ alkyl)-SO$_2$—NH— group wherein the alkyl has the above-mentioned meaning, unless otherwise specified. There can be mentioned, for example, groups such as methylsulfonylamino, ethylsulfonylamino, n-propylsulfonylamino, isopropylsulfonylamino and tertbutylsulfonylamino.

In the present invention, $C_1$~$C_6$ haloalkylsulfonylamino group indicates a ($C_1$~$C_6$ haloalkyl)-SO$_2$—NH— group wherein the haloalkyl has the above-mentioned meaning, unless otherwise specified. There can be mentioned, for example, groups such as fluoromethylsulfonylamino, difluoromethylsulfonylamino, trifluoromethylsulfonylamino, chloromethylsulfonylamino, trichloromethylsulfonylamino, 2,2,2-trifluoroethylsulfonylamino, 2,2-difluoroethylsulfonylamino and 3,3,3-trifluoropropylsulfonylamino.

In the present invention, $C_1$–$C_6$ alkylaminocarbonylthio group indicates a ($C_1$–$C_6$ alkyl)-NH—C(O=)—S-group wherein the alkyl has the above-mentioned meaning, unless otherwise specified. There can be mentioned, for example, groups such as methylaminocarbonylthio, ethylaminocarbonylthio, propylaminocarbonylthio, isopropylaminocarbonylthio and dimethylaminocarbonylthio.

In the present invention, $C_1$–$C_6$ haloalkylaminocarbonylthio group indicates a ($C_1$–$C_6$ haloalkyl)-NH—C(O=)—S-group wherein the haloalkyl has the above-mentioned meaning, unless otherwise specified. There can be mentioned, for example, groups such as 2-fluoroethylaminocarbonylthio, 2,2,2-trifluoroethylaminocarbonylthio, 2,2,2-trichloroethylaminocarbonylthio, pentafluoroethylaminocarbonylthio and 1,1,1,3,3,3-hexafluoro-2-propylaminocarbonylthio.

In the present invention, $C_1$–$C_6$ alkylaminocarbonyl group indicates a ($C_1$–$C_6$ alkyl)-NH—C(=O)— group wherein the alkyl has the above-mentioned meaning, unless otherwise specified. There can be mentioned, for example, groups such as methylaminocarbonyl, ethylaminocarbonyl, propylaminocarbonyl and isopropylaminocarbonyl.

In the present invention, $C_1$–$C_6$ haloalkylaminocarbonyl group indicates a ($C_1$–$C_6$ haloalkyl)-NH—C(=O)— group wherein the haloalkyl has the above-mentioned meaning, unless otherwise specified. There can be mentioned, for example, groups such as 2-fluoroethylaminocarbonyl, 2,2,2-trifluoroethylaminocarbonyl, 2,2,2-trichloroethylaminocarbonyl, pentafluoroethylaminocarbonyl and 1,1,1,3,3,3-hexafluoro-2-propylaminocarbonyl.

In the present invention, tri($C_1$–$C_6$ alkyl)silyl group indicates a ($C_1$–$C_6$ alkyl)$_3$-Si— group wherein the alkyl has the above-mentioned meaning, unless otherwise specified. There can be mentioned, for example, groups such as trimethylsilyl, triethylsilyl, triisopropylsilyl, dimethylisopropylsilyl and tert-butyldimethylsilyl.

In the present invention, phenyl $C_1$–$C_6$ alkyl group indicates a phenyl-($C_1$–$C_6$ alkyl)-group wherein the alkyl has the above-mentioned meaning, unless otherwise specified. There can be mentioned, for example, groups such as benzyl, 1-phenylethyl, 2-phenylethyl, 1-phenylpropyl, 2-phenylbutyl and 1-phenylpentyl.

In the present invention, phenyl $C_1$–$C_6$ alkoxy group indicates a phenyl-($C_1$–$C_6$ alkoxy)-group wherein the alkoxy has the above-mentioned meaning, unless otherwise specified. There can be mentioned, for example, groups such as phenylmethoxy, 1-phenylethoxy, 2-phenylethoxy, 1-phenylpropoxy, 2-phenylbutoxy and 1-phenylpentoxy.

In the present invention, phenyl $C_1$–$C_6$ alkylthio group indicates a phenyl-($C_1$–$C_6$ alkyl)-S-group wherein the alkyl has the above-mentioned meaning, unless otherwise specified. There can be mentioned, for example, groups such as phenylmethylthio, 1-phenylethylthio, 2-phenylethylthio, 1-phenylpropylthio, 2-phenylbutylthio and 1-phenylpentylthio.

In the present invention, phenyl $C_1$–$C_6$ alkylsulfinyl group indicates a phenyl-($C_1$–$C_6$ alkyl)-SO— group wherein the alkyl has the above-mentioned meaning, unless otherwise specified. There can be mentioned, for example, groups such as phenylmethylsulfinyl, 1-phenylethylsulfinyl, 2-phenylethylsulfinyl, 1-phenylpropylsulfinyl, 2-phenylbutylsulfinyl and 1-phenylpentylsulfinyl.

In the present invention, phenyl $C_1$–$C_6$ alkylsulfonyl group indicates a phenyl-($C_1$–$C_6$ alkyl)-$SO_2$— group wherein the alkyl has the above-mentioned meaning, unless otherwise specified. There can be mentioned, for example, groups such as phenylmethylsulfonyl, 1-phenylethylsulfonyl, 2-phenylethylsulfonyl, 1-phenylpropylsulfonyl, 2-phenylbutylsulfonyl and 1-phenylpentylsulfonyl.

In the present invention, agriculturally acceptable salt refers, when the present compound represented by the general formula [I] and general formula [I'] contains, in its structure, hydroxyl group, carboxyl group, amino group, etc., to a salt of the present compound with a metal or an organic base, or with a mineral acid or an organic acid. As the metal, there can be mentioned an alkali metal such as sodium, potassium or the like, or an alkaline earth metal such as magnesium, calcium or the like. As the organic base, there can be mentioned triethylamine, diisopropylamine, etc. As the mineral acid, there can be mentioned hydrochloric acid, hydrobromic acid, sulfuric acid, etc. As the organic acid, there can be mentioned formic acid, acetic acid, methanesulfonic acid, 4-toluenesulfonic acid, trifluoromethanesulfonic acid, etc.

Next, representative examples of the compounds included in the alkyl phenyl sulfide derivative represented by the general formula [I] are shown in Table 1 to Table 41, and those represented by the general formula [I'] are shown in Table 42. However, the compounds included in the present derivative are not restricted thereto. Incidentally, the compound Nos. shown in Tables are used in later description.

Incidentally, the compounds included in the alkyl phenyl sulfide derivative of the present invention contain, in some cases, geometrical isomers of E form and Z form depending upon the kinds of substituent groups. The present invention includes the E forms, the Z forms and mixtures containing the E form and the Z form at any ratio. Also, the compounds included in the present invention contain, in some cases, optical isomers having 1 to 2 asymmetric carbon atoms or asymmetric sulfur atoms. The present invention includes all optical isomers, racemic modifications, and diastereomers.

The following expressions used in the Tables of the present specification indicate the following groups.

Me: methyl

Et: ethyl tBu: tert-butyl $CF_3$: trifluoromethyl

Ph(4-$CF_3$): 4-trifluoromethylphenyl

Ph(2,5-($CF_3$)): 2,5-bis(trifluoromethyl)phenyl

Ph(3-F,4-$CF_3$): 3-fluoro-4-trifluoromethylphenyl

Ac: acetyl nPropyl: n-propyl

Isopropyl: isopropyl nButyl: n-butyl nPentyl: n-pentyl nHexyl: n-hexyl nHeptyl: n-heptyl nOctyl: n-octyl nNonyl: n-nonyl nDecyl: n-decyl

TABLE 1

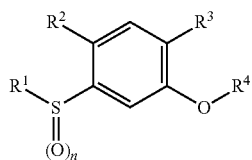

[I]

| Compound No. | R¹ | R² | R³ | n | R⁴ |
|---|---|---|---|---|---|
| A-0001 | CH₂CF₃ | Me | F | 0 | Me |
| A-0002 | CH₂CF₃ | Me | F | 1 | nPropyl |
| A-0003 | CH₂CF₃ | Cl | F | 1 | nPropyl |
| A-0004 | CH₂CF₃ | CN | F | 0 | isopropyl |
| A-0005 | CH₂CF₃ | CN | F | 1 | isopropyl |
| A-0006 | CH₂CF₃ | Me | F | 0 | isopropyl |
| A-0007 | CH₂CF₃ | Me | F | 1 | isopropyl |
| A-0008 | CH₂CF₃ | Me | F | 1 | nButyl |
| A-0009 | CH₂CF₃ | Cl | F | 1 | nButyl |
| A-0010 | CH₂CF₃ | CN | F | 0 | nButyl |
| A-0011 | CH₂CF₃ | CN | F | 1 | nButyl |
| A-0012 | CH₂CF₃ | CN | F | 0 | nPentyl |
| A-0013 | CH₂CF₃ | CN | F | 1 | nPentyl |
| A-0014 | CH₂CF₃ | Me | F | 0 | nHexyl |
| A-0015 | CH₂CF₃ | Me | F | 1 | nHexyl |
| A-0016 | CH₂CF₃ | Cl | F | 1 | nHexyl |
| A-0017 | CH₂CF₃ | CN | F | 0 | nHexyl |
| A-0018 | CH₂CF₃ | CN | F | 1 | nHexyl |
| A-0019 | CH₂CF₃ | Me | H | 1 | nHexyl |
| A-0020 | CH₂CF₃ | Me | Cl | 1 | nHexyl |
| A-0021 | CH₂CF₃ | Cl | Cl | 1 | nHexyl |
| A-0022 | CH₂CF₃ | Me | F | 0 | nHeptyl |
| A-0023 | CH₂CF₃ | Me | F | 1 | nHeptyl |
| A-0024 | CH₂CF₃ | CN | F | 0 | nHeptyl |
| A-0025 | CH₂CF₃ | CN | F | 1 | nHeptyl |
| A-0026 | CH₂CF₃ | Me | F | 1 | nOctyl |
| A-0027 | CH₂CF₃ | CN | F | 0 | nOctyl |
| A-0028 | CH₂CF₃ | CN | F | 1 | nOctyl |
| A-0029 | CH₂CF₃ | Me | F | 1 | nNonyl |
| A-0030 | CH₂CF₃ | Me | F | 0 | nDecyl |

TABLE 2

| Compound No. | R¹ | R² | R³ | n | R⁴ |
|---|---|---|---|---|---|
| A-0031 | CH₂CF₃ | Me | F | 1 | nDecyl |
| A-0032 | CH₂CF₃ | Me | F | 0 | CH₂CH(Me)CH₃ |
| A-0033 | CH₂CF₃ | Me | F | 1 | CH₂CH(Me)CH₃ |
| A-0034 | CH₂CF₃ | Cl | F | 1 | CH₂CH(Me)CH₃ |
| A-0035 | CH₂CF₃ | CN | F | 0 | CH₂CH(Me)CH₃ |
| A-0036 | CH₂CF₃ | CN | F | 1 | CH₂CH(Me)CH₃ |
| A-0037 | CH₂CF₃ | Me | F | 0 | CH₂CH₂CH(Me)CH₃ |
| A-0038 | CH₂CF₃ | Me | F | 1 | CH₂CH₂CH(Me)CH₃ |
| A-0039 | CH₂CF₃ | CN | F | 0 | CH₂CH₂CH(Me)CH₃ |
| A-0040 | CH₂CF₃ | CN | F | 1 | CH₂CH₂CH(Me)CH₃ |
| A-0041 | CH₂CF₃ | Me | F | 1 | CH₂CH(Me)CH₂CH₃ |
| A-0042 | CH₂CF₃ | Me | F | 1 | CH(Me)CH₂CH₂CH₃ |
| A-0043 | CH₂CF₃ | Me | F | 0 | CH₂CH₂CH₂CH(Me)CH₃ |
| A-0044 | CH₂CF₃ | Me | F | 1 | CH₂CH₂CH₂CH(Me)CH₃ |
| A-0045 | CH₂CF₃ | Me | H | 1 | CH₂CH₂CH₂CH(Me)CH₃ |
| A-0046 | CH₂CF₃ | CN | F | 0 | CH₂CH₂CH₂CH(Me)CH₃ |
| A-0047 | CH₂CF₃ | CN | F | 1 | CH₂CH₂CH₂CH(Me)CH₃ |
| A-0048 | CH₂CF₃ | Me | F | 1 | CH₂CH₂CH(Me)CH₂CH₃ |
| A-0049 | CH₂CF₃ | Me | F | 1 | CH(Me)CH₂CH₂CH₂CH₃ |
| A-0050 | CH₂CF₃ | Me | F | 1 | CH(Me)CH₂CH₂CH₂CH₃ |
| A-0051 | CH₂CF₃ | Me | F | 0 | CH₂CH₂CH₂CH₂CH(Me)CH₃ |
| A-0052 | CH₂CF₃ | Me | F | 1 | CH₂CH₂CH₂CH₂CH(Me)CH₃ |
| A-0053 | CH₂CF₃ | Cl | F | 1 | CH₂CH₂CH₂CH₂CH(Me)CH₃ |
| A-0054 | CH₂CF₃ | Me | H | 1 | CH₂CH₂CH₂CH₂CH(Me)CH₃ |
| A-0055 | CH₂CF₃ | CN | F | 0 | CH₂CH₂CH₂CH₂CH(Me)CH₃ |
| A-0056 | CH₂CF₃ | CN | F | 1 | CH₂CH₂CH₂CH₂CH(Me)CH₃ |
| A-0057 | CH₂CF₃ | Me | F | 1 | CH₂CH₂CH₂CH(Me)CH₂CH₃ |
| A-0058 | CH₂CF₃ | Me | F | 1 | CH₂CH₂CH(Me)CH₂CH₂CH₃ |
| A-0059 | CH₂CF₃ | Me | F | 1 | CH(Me)CH₂CH₂CH₂CH₂CH₃ |
| A-0060 | CH₂CF₃ | Me | F | 1 | CH(Me)CH₂CH₂CH₂CH₂CH₃ |

TABLE 2-continued

| Compound No. | R¹ | R² | R³ | n | R⁴ |
|---|---|---|---|---|---|
| A-0061 | CH₂CF₃ | Cl | F | 0 | CH₂CH₂CH₂CH₂CH₂CH(Me)CH₃ |
| A-0062 | CH₂CF₃ | Me | F | 1 | CH₂CH₂CH₂CH₂CH₂CH(Me)CH₃ |
| A-0063 | CH₂CF₃ | Me | F | 1 | CH₂tBu |
| A-0064 | CH₂CF₃ | CN | F | 0 | CH₂tBu |
| A-0065 | CH₂CF₃ | CN | F | 1 | CH₂tBu |
| A-0066 | CH₂CF₃ | Me | F | 1 | CH₂tBu |
| A-0067 | CH₂CF₃ | Me | F | 1 | CH₂CH₂tBu |
| A-0068 | CH₂CF₃ | CN | F | 0 | CH₂CH₂tBu |
| A-0069 | CH₂CF₃ | CN | F | 1 | CH₂CH₂tBu |
| A-0070 | CH₂CF₃ | Me | F | 0 | CH₂CH₂tBu |

TABLE 3

| Compound No. | R¹ | R² | R³ | n | R⁴ |
|---|---|---|---|---|---|
| A-0071 | CH₂CF₃ | Me | F | 1 | CH₂CH₂tBu |
| A-0072 | CH₂CF₃ | Me | F | 1 | CH₂CH(Me)tBu |
| A-0073 | CH₂CF₃ | Me | F | 1 | CH(Me)CH₂tBu |
| A-0074 | CH₂CF₃ | Me | F | 0 | CH₂CH₂CH₂tBu |
| A-0075 | CH₂CF₃ | Me | F | 1 | CH₂CH₂CH₂tBu |
| A-0076 | CH₂CF₃ | Cl | F | 0 | CH₂CH₂CH₂tBu |
| A-0077 | CH₂CF₃ | Cl | F | 1 | CH₂CH₂CH₂tBu |
| A-0078 | CH₂CF₃ | CN | F | 0 | CH₂CH₂CH₂tBu |
| A-0079 | CH₂CF₃ | CN | F | 1 | CH₂CH₂CH₂tBu |
| A-0080 | CH₂CF₃ | Me | H | 1 | CH₂CH₂CH₂tBu |
| A-0081 | CH₂CF₃ | Me | F | 2 | CH₂CH₂CH₂tBu |
| A-0082 | CH₂CF₃ | Me | F | 1 | CH₂CH₂CH(Me)tBu |
| A-0083 | CH₂CF₃ | Me | F | 1 | CH₂CH(Me)CH₂tBu |
| A-0084 | CH₂CF₃ | Me | F | 1 | CH(Me)CH₂CH₂tBu |
| A-0085 | CH₂CF₃ | Me | F | 0 | CH₂CH₂CH₂CH₂tBu |
| A-0086 | CH₂CF₃ | Me | F | 1 | CH₂CH₂CH₂CH₂tBu |
| A-0087 | CH₂CF₃ | Cl | F | 0 | CH₂CH₂CH₂CH₂tBu |
| A-0088 | CH₂CF₃ | Cl | F | 1 | CH₂CH₂CH₂CH₂tBu |
| A-0089 | CH₂CF₃ | CN | F | 0 | CH₂CH₂CH₂CH₂tBu |
| A-0090 | CH₂CF₃ | CN | F | 1 | CH₂CH₂CH₂CH₂tBu |
| A-0091 | CH₂CF₃ | Me | H | 0 | CH₂CH₂CH₂CH₂tBu |
| A-0092 | CH₂CF₃ | Me | H | 1 | CH₂CH₂CH₂CH₂tBu |
| A-0093 | CH₂CF₃ | Me | Cl | 0 | CH₂CH₂CH₂CH₂tBu |
| A-0094 | CH₂CF₃ | Me | Cl | 1 | CH₂CH₂CH₂CH₂tBu |
| A-0095 | CH₂CF₃ | Me | Me | 1 | CH₂CH₂CH₂CH₂tBu |
| A-0096 | CH₂CF₃ | Cl | Cl | 1 | CH₂CH₂CH₂CH₂tBu |
| A-0097 | CF₃ | Me | F | 1 | CH₂CH₂CH₂CH₂tBu |
| A-0098 | CHF₂ | Me | F | 1 | CH₂CH₂CH₂CH₂tBu |
| A-0099 | tBu | Me | F | 1 | CH₂CH₂CH₂CH₂tBu |
| A-0100 | CH₂tBu | Me | F | 1 | CH₂CH₂CH₂CH₂tBu |
| A-0101 | CH₂CH(Me)₂ | Me | F | 1 | CH₂CH₂CH₂CH₂tBu |
| A-0102 | CH₂CH=CCl₂ | Me | F | 1 | CH₂CH₂CH₂CH₂tBu |
| A-0103 | CH₂CH=CH | Me | F | 1 | CH₂CH₂CH₂CH₂tBu |
| A-0104 | CH₂CH₂CF₃ | Me | F | 1 | CH₂CH₂CH₂CH₂tBu |
| A-0105 | CH₂cPr | Me | F | 1 | CH₂CH₂CH₂CH₂tBu |
| A-0106 | CF₂CF₃ | Me | F | 1 | CH₂CH₂CH₂CH₂tBu |
| A-0107 | CH₂CHF₂ | Me | F | 1 | CH₂CH₂CH₂CH₂tBu |
| A-0108 | CH₂CF₃ | Cl | H | 1 | CH₂CH₂CH₂CH₂tBu |
| A-0109 | CH₂COOMe | Me | F | 1 | CH₂CH₂CH₂CH₂tBu |
| A-0110 | CH₂CF₃ | Me | F | 2 | CH₂CH₂CH₂CH₂tBu |

TABLE 4

| Compound No. | R¹ | R² | R³ | n | R⁴ |
|---|---|---|---|---|---|
| A-0111 | CH₂COOH | Me | F | 1 | CH₂CH₂CH₂tBu |
| A-0112 | CH₂tBu | Me | F | 0 | CH₂CH₂CH₂tBu |
| A-0113 | CH₂CHF₂ | Me | F | 1 | CH₂CH₂CH₂tBu |
| A-0114 | CH₂tBu | Me | F | 1 | CH₂CH₂CH₂tBu |
| A-0115 | CH₂cPr | Me | F | 0 | CH₂CH₂CH₂tBu |
| A-0116 | CH₂CH₂CF₃ | Me | F | 1 | CH₂CH₂CH₂tBu |
| A-0117 | CH₂cPr | Me | F | 1 | CH₂CH₂CH₂tBu |
| A-0118 | CH₂CF₃ | Me | Me | 0 | CH₂CH₂CH₂tBu |
| A-0119 | CH₂CF₃ | Me | Me | 1 | CH₂CH₂CH₂tBu |
| A-0120 | CH₂CH₂CF₃ | Me | F | 0 | CH₂CH₂CH₂tBu |

TABLE 4-continued

| Compound No. | R¹ | R² | R³ | n | R⁴ |
|---|---|---|---|---|---|
| A-0121 | CH₂CF₃ | Me | F | 1 | CH₂CH₂CH₂CH(Me)tBu |
| A-0122 | CH₂CF₃ | Me | F | 0 | CH₂CH₂CH(Me)CH₂tBu |
| A-0123 | CH₂CF₃ | Me | F | 1 | CH₂CH₂CH(Me)CH₂tBu |
| A-0124 | CH₂CF₃ | Me | H | 1 | CH₂CH₂CH(Me)CH₂tBu |
| A-0125 | CH₂CF₃ | CN | F | 0 | CH₂CH₂CH(Me)CH₂tBu |
| A-0126 | CH₂CF₃ | CN | F | 1 | CH₂CH₂CH(Me)CH₂tBu |
| A-0127 | CH₂CF₃ | Me | F | 1 | CH₂CH(Me)CH₂CH₂tBu |
| A-0128 | CH₂CF₃ | Me | F | 1 | CH(Me)CH₂CH₂CH₂tBu |
| A-0129 | CH₂CF₃ | Me | F | 0 | CH₂CH₂CH₂CH₂CH₂tBu |
| A-0130 | CH₂CF₃ | Me | F | 1 | CH₂CH₂CH₂CH₂CH₂tBu |
| A-0131 | CH₂CF₃ | Me | H | 1 | CH₂CH₂CH₂CH₂CH₂tBu |
| A-0132 | CH₂CF₃ | Cl | F | 0 | CH₂CH₂CH₂CH₂CH₂tBu |
| A-0133 | CH₂CF₃ | Cl | F | 1 | CH₂CH₂CH₂CH₂CH₂tBu |
| A-0134 | CH₂CF₃ | Cl | H | 1 | CH₂CH₂CH₂CH₂CH₂tBu |
| A-0135 | CH₂CF₃ | Me | F | 1 | CH₂CH₂CH₂CH₂CH(Me)tBu |
| A-0136 | CH₂CF₃ | Me | F | 1 | CH₂CH₂CH₂CH(Me)CH₂tBu |
| A-0137 | CH₂CF₃ | Me | F | 1 | CH₂CH₂CH(Me)CH₂CH₂tBu |
| A-0138 | CH₂CF₃ | Me | F | 1 | CH₂CH(Me)CH₂CH₂CH₂tBu |
| A-0139 | CH₂CF₃ | Me | F | 1 | CH(Me)CH₂CH₂CH₂CH₂tBu |
| A-0140 | CH₂CF₃ | Me | F | 0 | CH₂CH₂CH₂CH₂CH₂CH₂tBu |
| A-0141 | CH₂CF₃ | Me | F | 1 | CH₂CH₂CH₂CH₂CH₂CH₂tBu |
| A-0142 | CH₂CF₃ | Me | H | 1 | CH₂CH₂CH₂CH₂CH₂CH₂tBu |
| A-0143 | CH₂CF₃ | Cl | F | 0 | CH₂CH₂CH₂CH₂CH₂CH₂tBu |
| A-0144 | CH₂CF₃ | Cl | F | 1 | CH₂CH₂CH₂CH₂CH₂CH₂tBu |
| A-0145 | CH₂CF₃ | CN | F | 1 | CH₂CH₂CH₂CH₂CH₂CH₂tBu |
| A-0146 | CH₂CF₃ | Me | H | 0 | CH₂CH₂CH₂CH₂CH₂CH₂tBu |
| A-0147 | CH₂CF₃ | Me | H | 1 | CH₂CH₂CH₂CH₂CH₂CH₂tBu |
| A-0148 | CH₂CF₃ | Me | Cl | 1 | CH₂CH₂CH₂CH₂CH₂CH₂tBu |
| A-0149 | CH₂CF₃ | Me | F | 1 | CH₂CH₂CH₂CH₂CH₂CH(Me)tBu |
| A-0150 | CH₂CF₃ | Me | F | 1 | CH₂CH₂CH₂CH₂CH(Me)CH₂tBu |

TABLE 5

| Compound No. | R¹ | R² | R³ | n | R⁴ |
|---|---|---|---|---|---|
| A-0151 | CH₂CF₃ | Me | F | 1 | CH₂CH₂CH₂CH(Me)CH₂CH₂tBu |
| A-0152 | CH₂CF₃ | Me | F | 1 | CH₂CH₂CH(Me)CH₂CH₂CH₂tBu |
| A-0153 | CH₂CF₃ | Me | F | 1 | CH₂CH(Me)CH₂CH₂CH₂CH₂tBu |
| A-0154 | CH₂CF₃ | Me | F | 1 | CH(Me)CH₂CH₂CH₂CH₂CH₂tBu |
| A-0155 | CH₂CF₃ | Me | F | 1 | CH₂CF₃ |
| A-0156 | CH₂CF₃ | Me | F | 1 | CH(Me)CF₃ |
| A-0157 | CH₂CF₃ | Me | F | 1 | CH₂CH₂CF₃ |
| A-0158 | CH₂CF₃ | Cl | F | 1 | CH₂CH₂CF₃ |
| A-0159 | CH₂CF₃ | Me | F | 0 | CH₂CH₂CH₂CF₃ |
| A-0160 | CH₂CF₃ | Me | F | 1 | CH₂CH₂CH₂CF₃ |
| A-0161 | CH₂CF₃ | Cl | F | 1 | CH₂CH₂CH₂CF₃ |
| A-0162 | CH₂CF₃ | Me | H | 1 | CH₂CH₂CH₂CF₃ |
| A-0163 | CH₂CF₃ | Me | F | 0 | CH₂CH₂CH₂CH₂CF₃ |
| A-0164 | CH₂CF₃ | Me | F | 1 | CH₂CH₂CH₂CH₂CF₃ |
| A-0165 | CH₂CF₃ | Cl | F | 1 | CH₂CH₂CH₂CH₂CF₃ |
| A-0166 | CH₂CF₃ | Me | H | 1 | CH₂CH₂CH₂CH₂CF₃ |
| A-0167 | CH₂CF₃ | Me | F | 0 | CH₂CH₂CH₂CH₂CH₂CF₃ |
| A-0168 | CH₂CF₃ | Me | F | 1 | CH₂CH₂CH₂CH₂CH₂CF₃ |
| A-0169 | CH₂CF₃ | Cl | F | 0 | CH₂CH₂CH₂CH₂CH₂CF₃ |
| A-0170 | CH₂CF₃ | Cl | F | 1 | CH₂CH₂CH₂CH₂CH₂CF₃ |
| A-0171 | CH₂CF₃ | Me | F | 1 | CH(CF₃)CF₃ |
| A-0172 | CH₂CF₃ | Me | F | 0 | CH₂CF₂CF₃ |
| A-0173 | CH₂CF₃ | Me | F | 1 | CH₂CF₂CF₃ |
| A-0174 | CH₂CF₃ | Cl | F | 0 | CH₂CF₂CF₃ |
| A-0175 | CH₂CF₃ | Cl | F | 1 | CH₂CF₂CF₃ |
| A-0176 | CH₂CF₃ | Me | F | 1 | CH₂CF₂CF₃ |
| A-0177 | CH₂CF₃ | Me | F | 1 | CH₂CF(CF₃)CF₃ |
| A-0178 | CH₂CF₃ | Me | F | 1 | CH₂CF₂CF₂CF₃ |
| A-0179 | CH₂CF₃ | Cl | F | 1 | CH₂CF₂CF₂CF₃ |
| A-0180 | CH₂CF₃ | CN | F | 0 | CH₂CF₂CF₂CF₃ |
| A-0181 | CH₂CF₃ | CN | F | 1 | CH₂CF₂CF₂CF₃ |
| A-0182 | CH₂CF₃ | Me | F | 1 | CH₂CF₂CF(CF₃)CF₃ |
| A-0183 | CH₂CF₃ | Me | F | 1 | CH₂CF(CF₃)CF₂CF₃ |
| A-0184 | CH₂CF₃ | Me | F | 0 | CH₂CF₂CF₂CF₂CF₃ |
| A-0185 | CH₂CF₃ | Me | F | 1 | CH₂CF₂CF₂CF₂CF₃ |
| A-0186 | CH₂CF₃ | Cl | F | 0 | CH₂CF₂CF₂CF₂CF₃ |
| A-0187 | CH₂CF₃ | Cl | F | 1 | CH₂CF₂CF₂CF₂CF₃ |
| A-0188 | CH₂CF₃ | CN | F | 0 | CH₂CF₂CF₂CF₂CF₃ |
| A-0189 | CH₂CF₃ | CN | F | 1 | CH₂CF₂CF₂CF₂CF₃ |
| A-0190 | CH₂CF₃ | Me | H | 1 | CH₂CF₂CF₂CF₂CF₃ |

TABLE 6

| Compound No. | R¹ | R² | R³ | n | R⁴ |
|---|---|---|---|---|---|
| A-0191 | CH₂CF₃ | Me | Cl | 1 | CH₂CF₂CF₂CF₃ |
| A-0192 | CH₂CF₃ | Me | F | 1 | CH₂CF₂CF₂CF(CF₃)CF₃ |
| A-0193 | CH₂CF₃ | Me | F | 1 | CH₂CF₂CF(CF₃)CF₂CF₃ |
| A-0194 | CH₂CF₃ | Me | F | 1 | CH₂CF(CF₃)CF₂CF₂CF₃ |
| A-0195 | CH₂CF₃ | Me | F | 1 | CH₂CH₂CH₂OCHF₂ |
| A-0196 | CH₂CF₃ | Me | F | 1 | CH₂CH₂CH₂CH₂OCHF₂ |
| A-0197 | CH₂CF₃ | Me | F | 1 | CH₂CH₂CH₂CH₂CH₂OCHF₂ |
| A-0198 | CH₂CF₃ | Me | F | 1 | CH₂CH₂CH₂CH₂CH₂CH₂OCHF₂ |
| A-0199 | CH₂CF₃ | Me | F | 0 | CH₂CH₂OCH₂CF₃ |
| A-0200 | CH₂CF₃ | Me | F | 1 | CH₂CH₂OCH₂CF₃ |
| A-0201 | CH₂CF₃ | Me | F | 1 | CH₂CH₂CH₂OCH₂CF₃ |
| A-0202 | CH₂CF₃ | Me | F | 1 | CH₂CH₂CH₂CH₂OCH₂CF₃ |
| A-0203 | CH₂CF₃ | Me | F | 0 | CH₂CH₂CH₂CH₂CH₂OCH₂CF₃ |
| A-0204 | CH₂CF₃ | Me | F | 1 | CH₂CH₂CH₂CH₂CH₂OCH₂CF₃ |
| A-0205 | CH₂CF₃ | Cl | F | 0 | CH₂CH₂CH₂CH₂CH₂OCH₂CF₃ |
| A-0206 | CH₂CF₃ | Cl | F | 1 | CH₂CH₂CH₂CH₂CH₂OCH₂CF₃ |
| A-0207 | CH₂CF₃ | CN | F | 0 | CH₂CH₂CH₂CH₂CH₂OCH₂CF₃ |
| A-0208 | CH₂CF₃ | CN | F | 1 | CH₂CH₂CH₂CH₂CH₂OCH₂CF₃ |
| A-0209 | CH₂CF₃ | Me | F | 1 | CH₂CH₂CH₂CH₂CH₂CH₂OCH₂CF₃ |
| A-0210 | CH₂CF₃ | Me | F | 1 | CH₂CH₂CH₂CH₂CH₂CH₂CH₂OCH₂CF₃ |
| A-0211 | CH₂CF₃ | Me | F | 0 | CH₂CH₂CH₂OC(CF₃)₃ |
| A-0212 | CH₂CF₃ | Me | F | 1 | CH₂CH₂CH₂OC(CF₃)₃ |
| A-0213 | CH₂CF₃ | Cl | F | 0 | CH₂CH₂CH₂OC(CF₃)₃ |
| A-0214 | CH₂CF₃ | Cl | F | 1 | CH₂CH₂CH₂OC(CF₃)₃ |
| A-0215 | CH₂CF₃ | Me | F | 0 | CH₂CH₂CH₂CH₂OC(CF₃)₃ |
| A-0216 | CH₂CF₃ | Me | F | 1 | CH₂CH₂CH₂CH₂OC(CF₃)₃ |
| A-0217 | CH₂CF₃ | Cl | F | 0 | CH₂CH₂CH₂CH₂OC(CF₃)₃ |
| A-0218 | CH₂CF₃ | Cl | F | 1 | CH₂CH₂CH₂CH₂OC(CF₃)₃ |
| A-0219 | CH₂CF₃ | Me | F | 0 | CH₂CH₂CH₂CH₂CH₂OC(CF₃)₃ |

TABLE 6-continued

| Compound No. | $R^1$ | $R^2$ | $R^3$ | n | $R^4$ |
|---|---|---|---|---|---|
| A-0220 | $CH_2CF_3$ | Me | F | 1 | $CH_2CH_2CH_2CH_2CH_2OC(CF_3)_3$ |
| A-0221 | $CH_2CF_3$ | Cl | F | 0 | $CH_2CH_2CH_2CH_2CH_2OC(CF_3)_3$ |
| A-0222 | $CH_2CF_3$ | Cl | F | 1 | $CH_2CH_2CH_2CH_2CH_2OC(CF_3)_3$ |
| A-0223 | $CH_2CF_3$ | OMe | F | 0 | $CH_2CH_2CH_2CH_2CH_2OC(CF_3)_3$ |
| A-0224 | $CH_2CF_3$ | OMe | F | 1 | $CH_2CH_2CH_2CH_2CH_2OC(CF_3)_3$ |
| A-0225 | $CH_2CF_3$ | Cl | F | 0 | $CF_2CHFOCF_2CF_3$ |
| A-0226 | $CH_2CF_3$ | Cl | F | 1 | $CF_2CHFOCF_2CF_3$ |
| A-0227 | $CH_2CF_3$ | Me | F | 0 | $CH_2CF_2OCF_2CF_2OCF_3$ |
| A-0228 | $CH_2CF_3$ | Me | F | 1 | $CH_2CF_2OCF_2CF_2OCF_3$ |
| A-0229 | $CH_2CF_3$ | Cl | F | 0 | $CH_2CF_2OCF_2CF_2OCF_3$ |
| A-0230 | $CH_2CF_3$ | Cl | F | 1 | $CH_2CF_2OCF_2CF_2OCF_3$ |

TABLE 7

| Compound No. | $R^1$ | $R^2$ | $R^3$ | n | $R^4$ |
|---|---|---|---|---|---|
| A-0231 | $CH_2CF_3$ | Me | F | 0 | $CF_2CHFOCF_2CF(CF_3)OCF_2CF_2CF_3$ |
| A-0232 | $CH_2CF_3$ | Me | F | 1 | $CF_2CHFOCF_2CF(CF_3)OCF_2CF_2CF_3$ |
| A-0233 | $CH_2CF_3$ | Cl | F | 0 | $CF_2CHFOCF_2CF(CF_3)OCF_2CF_2CF_3$ |
| A-0234 | $CH_2CF_3$ | Cl | F | 1 | $CF_2CHFOCF_2CF(CF_3)OCF_2CF_2CF_3$ |
| A-0235 | $CH_2CF_3$ | Me | F | 0 | $CH_2CH_2CH_2CH_2OcPr$ |
| A-0236 | $CH_2CF_3$ | Me | F | 1 | $CH_2CH_2CH_2CH_2OcPr$ |
| A-0237 | $CH_2CF_3$ | Cl | F | 0 | $CH_2CH_2CH_2CH_2OcPen$ |
| A-0238 | $CH_2CF_3$ | Cl | F | 1 | $CH_2CH_2CH_2CH_2OcPen$ |
| A-0239 | $CH_2CF_3$ | Me | F | 1 | $CH_2CH_2CH=CH_2$ |
| A-0240 | $CH_2CF_3$ | Me | F | 1 | $CH_2CH_2C\equiv CH$ |
| A-0241 | $CH_2CF_3$ | Me | F | 1 | $CH_2CH_2CH=C(Me)Me$ |
| A-0242 | $CH_2CF_3$ | Me | F | 1 | $CH_2CH_2CH_2CH=CH_2$ |
| A-0243 | $CH_2CF_3$ | Me | F | 0 | $CH_2CH_2CH_2C\equiv CH$ |
| A-0244 | $CH_2CF_3$ | Me | F | 1 | $CH_2CH_2CH_2C\equiv CH$ |
| A-0245 | $CH_2CF_3$ | Me | F | 1 | $CH_2CH_2CH_2CH=C(Me)Me$ |
| A-0246 | $CH_2CF_3$ | Me | F | 1 | $CH_2CH_2CH_2CH_2CH=CH_2$ |
| A-0247 | $CH_2CF_3$ | Me | F | 1 | $CH_2CH_2CH_2CH_2C\equiv CH$ |
| A-0248 | $CH_2CF_3$ | Me | F | 1 | $CH_2CH_2CH_2CH_2CH=C(Me)Me$ |
| A-0249 | $CH_2CF_3$ | Me | F | 0 | $CH_2CH_2CH(Me)CH_2CH_2CH=C(Me)_2$ |
| A-0250 | $CH_2CF_3$ | Me | F | 1 | $CH_2CH_2CH(Me)CH_2CH_2CH=C(Me)_2$ |
| A-0251 | $CH_2CF_3$ | Me | F | 0 | $CH_2CH_2CF=CF_2$ |
| A-0252 | $CH_2CF_3$ | Me | F | 1 | $CH_2CH_2CF=CF_2$ |
| A-0253 | $CH_2CF_3$ | Me | F | 0 | $CH_2CH=C(Cl)CF_3$ |
| A-0254 | $CH_2CF_3$ | Me | F | 1 | $CH_2CH=C(Cl)CF_3$ |
| A-0255 | $CH_2CF_3$ | Me | F | 1 | $CH_2CH_2CH_2CF=CF_2$ |
| A-0256 | $CH_2CF_3$ | Me | F | 0 | $CH_2CH_2CH_2CF=CF_2$ |
| A-0257 | $CH_2CF_3$ | Me | F | 1 | $CH_2CH_2CH_2CF=CF_2$ |
| A-0258 | $CH_2CF_3$ | Me | F | 1 | $CH_2CH_2CH_2CH_2CF=CF_2$ |
| A-0259 | $CH_2CF_3$ | Me | F | 1 | $CH_2CH=C=CF_2$ |
| A-0260 | $CH_2CF_3$ | Me | F | 0 | $CH_2CH_2CH_2Cl$ |
| A-0261 | $CH_2CF_3$ | Me | F | 0 | $CH_2CH_2CH_2Br$ |
| A-0262 | $CH_2CF_3$ | Me | F | 1 | $CH_2CH_2CH_2Br$ |
| A-0263 | $CH_2CF_3$ | Cl | F | 0 | $CH_2CH_2CH_2Br$ |
| A-0264 | $CH_2CF_3$ | Me | F | 0 | $CH_2CH_2CH_2CH_2Br$ |
| A-0265 | $CH_2CF_3$ | Me | F | 1 | $CH_2CH_2CH_2CH_2Br$ |
| A-0266 | $CH_2CF_3$ | Cl | F | 0 | $CH_2CH_2CH_2CH_2Br$ |
| A-0267 | $CH_2CF_3$ | Cl | Cl | 0 | $CH_2CH_2CH_2CH_2Br$ |
| A-0268 | $CH_2CF_3$ | Cl | F | 1 | $CH_2CH_2CH_2CH_2Br$ |
| A-0269 | $CH_2CF_3$ | Me | F | 0 | $CH_2CH_2CH_2CH_2CH_2Br$ |
| A-0270 | $CH_2CF_3$ | Me | F | 1 | $CH_2CH_2CH_2CH_2CH_2Br$ |

TABLE 8

| Compound No. | $R^1$ | $R^2$ | $R^3$ | n | $R^4$ |
|---|---|---|---|---|---|
| A-0271 | $CH_2CF_3$ | Cl | F | 0 | $CH_2CH_2CH_2CH_2CH_2Cl$ |
| A-0272 | $CH_2CF_3$ | Cl | F | 1 | $CH_2CH_2CH_2CH_2CH_2Cl$ |
| A-0273 | $CH_2CF_3$ | Cl | F | 0 | $CH_2CH_2CH_2CH_2CH_2Br$ |
| A-0274 | $CH_2CF_3$ | Cl | F | 1 | $CH_2CH_2CH_2CH_2CH_2Br$ |
| A-0275 | $CH_2CF_3$ | OMe | F | 0 | $CH_2CH_2CH_2CH_2CH_2Br$ |
| A-0276 | $CH_2CF_3$ | OMe | F | 1 | $CH_2CH_2CH_2CH_2CH_2Br$ |
| A-0277 | $CH_2CF_3$ | CN | F | 0 | $CH_2CH_2CH_2CH_2CH_2Cl$ |
| A-0278 | $CH_2CF_3$ | CN | F | 1 | $CH_2CH_2CH_2CH_2CH_2Cl$ |
| A-0279 | $CH_2CF_3$ | Me | H | 0 | $CH_2CH_2CH_2CH_2CH_2Cl$ |
| A-0280 | $CH_2CF_3$ | Me | H | 1 | $CH_2CH_2CH_2CH_2CH_2Cl$ |
| A-0281 | $CH_2CF_3$ | Me | F | 0 | $CH_2CH_2CH_2CH_2CH_2Br$ |
| A-0282 | $CH_2CF_3$ | Me | F | 1 | $CH_2CH_2CH_2CH_2CH_2Br$ |
| A-0283 | $CH_2CF_3$ | Cl | Cl | 0 | $CH_2CH_2CH_2CH_2CH_2Br$ |
| A-0284 | $CH_2CF_3$ | Me | Me | 0 | $CH_2CH_2CH_2CH_2CH_2Br$ |

TABLE 8-continued

| Compound No. | R¹ | R² | R³ | n | R⁴ |
|---|---|---|---|---|---|
| A-0285 | $CH_2CF_3$ | Me | F | 0 | $CH_2CH_2CH_2CH_2CH_2CH_2Cl$ |
| A-0286 | $CH_2CF_3$ | Me | F | 1 | $CH_2CH_2CH_2CH_2CH_2CH_2Cl$ |
| A-0287 | $CH_2CF_3$ | Me | H | 0 | $CH_2CH_2CH_2CH_2CH_2CH_2Br$ |
| A-0288 | $CH_2CF_3$ | Me | H | 1 | $CH_2CH_2CH_2CH_2CH_2CH_2Br$ |
| A-0289 | $CH_2CF_3$ | Me | F | 0 | $CH_2CH_2CH_2CH_2CH_2CH_2CH_2Cl$ |
| A-0290 | $CH_2CF_3$ | Me | F | 1 | $CH_2CH_2CH_2CH_2CH_2CH_2CH_2Cl$ |
| A-0291 | $CH_2CF_3$ | Me | F | 0 | $CH_2CH_2CH(CH_3)CH_2CH_2Br$ |
| A-0292 | $CH_2CF_3$ | Me | F | 0 | $CH_2CH_2OH$ |
| A-0293 | $CH_2CF_3$ | Me | F | 1 | $CH_2CH_2OH$ |
| A-0294 | $CH_2CF_3$ | Me | H | 0 | $CH_2CH_2OH$ |
| A-0295 | $CH_2CF_3$ | Me | F | 0 | $CH_2CH_2CH_2OH$ |
| A-0296 | $CH_2CF_3$ | Me | F | 1 | $CH_2CH_2CH_2OH$ |
| A-0297 | $CH_2CF_3$ | Me | H | 0 | $CH_2CH_2CH_2OH$ |
| A-0298 | $CH_2CF_3$ | Me | H | 1 | $CH_2CH_2CH_2OH$ |
| A-0299 | $CH_2CF_3$ | Cl | F | 0 | $CH_2CH_2CH_2CH_2OH$ |
| A-0300 | $CH_2CF_3$ | Cl | F | 1 | $CH_2CH_2CH_2CH_2OH$ |
| A-0301 | $CH_2CF_3$ | Me | F | 0 | $CH_2CH_2CH_2CH_2CH_2OH$ |
| A-0302 | $CH_2CF_3$ | Me | F | 1 | $CH_2CH_2CH_2CH_2CH_2OH$ |
| A-0303 | $CH_2CF_3$ | Cl | F | 0 | $CH_2CH_2CH_2CH_2CH_2OH$ |
| A-0304 | $CH_2CF_3$ | Cl | F | 1 | $CH_2CH_2CH_2CH_2CH_2OH$ |
| A-0305 | $CH_2CF_3$ | Me | F | 0 | $CH_2CH_2cPr$ |
| A-0306 | $CH_2CF_3$ | Me | F | 1 | $CH_2CH_2cPr$ |
| A-0307 | $CH_2CF_3$ | Me | F | 0 | $CH_2CH_2cPr(2,2-F_2)$ |
| A-0308 | $CH_2CF_3$ | Me | F | 1 | $CH_2CH_2cPr(2,2-F_2)$ |
| A-0309 | $CH_2CF_3$ | Me | F | 0 | $CH_2CH_2CH_2CH_2cPr$ |
| A-0310 | $CH_2CF_3$ | Me | F | 1 | $CH_2CH_2CH_2CH_2cPr$ |

TABLE 9

| Compound No. | R¹ | R² | R³ | n | R⁴ |
|---|---|---|---|---|---|
| A-0311 | $CH_2CF_3$ | Me | F | 0 | $CH_2CH_2CH_2CH_2cPr(2,2-F_2)$ |
| A-0312 | $CH_2CF_3$ | Me | F | 1 | $CH_2CH_2CH_2CH_2cPr(2,2-F_2)$ |
| A-0313 | $CH_2CF_3$ | Me | F | 1 | $CH_2cPr(1-Ph)$ |
| A-0314 | $CH_2CF_3$ | Cl | F | 1 | $CH_2cPr(1-Ph)$ |
| A-0315 | $CH_2CF_3$ | Me | F | 0 | $CH_2cHex(4-tBu)$ |
| A-0316 | $CH_2CF_3$ | Me | F | 1 | $CH_2cHex(4-tBu)$ |
| A-0317 | $CH_2CF_3$ | Me | F | 0 | $CH_2cHex(4-CF_3)$ |
| A-0318 | $CH_2CF_3$ | Me | F | 1 | $CH_2cHex(4-CF_3)$ |
| A-0319 | $CH_2CF_3$ | Me | F | 0 | $CH_2cHex(4,4-F_2)$ |
| A-0320 | $CH_2CF_3$ | Me | F | 1 | $CH_2cHex(4,4-F_2)$ |
| A-0321 | $CH_2CF_3$ | Cl | F | 0 | $CH_2cHex(4,4-F_2)$ |
| A-0322 | $CH_2CF_3$ | Cl | F | 1 | $CH_2cHex(4,4-F_2)$ |
| A-0323 | $CH_2CF_3$ | Me | F | 1 | $CH_2CH_2cHex$ |
| A-0324 | $CH_2CF_3$ | Me | F | 0 | $CH_2CH_2cHex(4-CF_3)$ |
| A-0325 | $CH_2CF_3$ | Cl | F | 0 | $CH_2CH_2cHex(4-CF_3)$ |
| A-0326 | $CH_2CF_3$ | Me | F | 1 | $CH_2CH_2cHex(4-CF_3)$ |
| A-0327 | $CH_2CF_3$ | Cl | F | 1 | $CH_2CH_2cHex(4-CF_3)$ |
| A-0328 | $CH_2CF_3$ | Me | F | 0 | $CH_2CH_2cHex(4,4-F_2)$ |
| A-0329 | $CH_2CF_3$ | Cl | F | 0 | $CH_2CH_2cHex(4,4-F_2)$ |
| A-0330 | $CH_2CF_3$ | Me | F | 1 | $CH_2CH_2cHex(4,4-F_2)$ |
| A-0331 | $CH_2CF_3$ | Cl | F | 1 | $CH_2CH_2cHex(4,4-F_2)$ |
| A-0332 | $CH_2CF_3$ | Me | F | 1 | $CH_2CH_2cHex(4-SCF_3)$ |
| A-0333 | $CH_2CF_3$ | Cl | F | 1 | $CH_2CH_2cHex(4-SCF_3)$ |
| A-0334 | $CH_2CF_3$ | Me | F | 1 | $CH_2CH_2cHex(4-SCHF_2)$ |
| A-0335 | $CH_2CF_3$ | Me | F | 1 | $CH_2CH_2cHex(4-OCHF_2)$ |
| A-0336 | $CH_2CF_3$ | Me | F | 1 | $CH_2CH_2cHex(4-OCF_3)$ |
| A-0337 | $CH_2CF_3$ | Me | F | 1 | $CH_2CH_2CH_2cHex$ |
| A-0338 | $CH_2CF_3$ | Me | F | 0 | $CH_2CH_2CH_2cHex(4-CF_3)$ |
| A-0339 | $CH_2CF_3$ | Me | F | 1 | $CH_2CH_2CH_2cHex(4-CF_3)$ |
| A-0340 | $CH_2CF_3$ | Cl | F | 0 | $CH_2CH_2CH_2cHex(4-CF_3)$ |
| A-0341 | $CH_2CF_3$ | Cl | F | 1 | $CH_2CH_2CH_2cHex(4-CF_3)$ |
| A-0342 | $CH_2CF_3$ | Me | F | 0 | $CH_2CH_2CH_2cHex(4-tBu)$ |
| A-0343 | $CH_2CF_3$ | Me | F | 1 | $CH_2CH_2CH_2cHex(4-tBu)$ |
| A-0344 | $CH_2CF_3$ | Me | F | 1 | $CH_2CH_2CH_2cHex(4-SCF_3)$ |
| A-0345 | $CH_2CF_3$ | Me | F | 1 | $CH_2CH_2CH_2CH_2cHex$ |
| A-0346 | $CH_2CF_3$ | Me | F | 0 | $CH_2CH_2CH_2CH_2cHex$ |
| A-0347 | $CH_2CF_3$ | Me | F | 1 | $CH_2CH_2CH_2CH_2cHex$ |
| A-0348 | $CH_2CF_3$ | Me | F | 1 | $CH_2CH_2CH_2CH_2cHex(4-CF_3)$ |
| A-0349 | $CH_2CF_3$ | Me | F | 0 | $CH_2CH_2(adamant-1-yl)$ |
| A-0350 | $CH_2CF_3$ | Me | F | 1 | $CH_2CH_2(adamant-1-yl)$ |

TABLE 10

| Compound No. | R¹ | R² | R³ | n | R⁴ |
|---|---|---|---|---|---|
| A-0351 | $CH_2CF_3$ | Me | F | 1 | $CH_2CH_2StBu$ |
| A-0352 | $CH_2CF_3$ | Me | F |   | $CH_2CH_2CH_2StBu$ |
| A-0353 | $CH_2CF_3$ | Me | F |   | $CH_2CH_2CH_2SCH_2tBu$ |
| A-0354 | $CH_2CF_3$ | Me | Cl |   | $CH_2CH_2CH_2SCH_2tBu$ |
| A-0355 | $CH_2CF_3$ | Me | F |   | $CH_2CH(CH_3)StBu$ |
| A-0356 | $CH_2CF_3$ | Me | F |   | $CH_2CH_2CH_2CH_2StBu$ |
| A-0357 | $CH_2CF_3$ | Me | F |   | $CH_2CH_2CH(CH_3)StBu$ |
| A-0358 | $CH_2CF_3$ | Me | F |   | $CH_2CH(CH_3)CH_2StBu$ |
| A-0359 | $CH_2CF_3$ | Me | F |   | $CH_2CH_2CH_2CH_2CH_2SCH_3$ |
| A-0360 | $CH_2CF_3$ | Me | F | 0 | $CH_2CH_2CH_2CH_2CH_2SCH_3$ |
| A-0361 | $CH_2CF_3$ | Me | F | 1 | $CH_2CH_2CH_2CH_2CH_2SCH(CH_3)_2$ |
| A-0362 | $CH_2CF_3$ | Me | F | 0 | $CH_2CH_2CH_2CH_2CH_2SCH(CH_3)_2$ |
| A-0363 | $CH_2CF_3$ | Me | F | 0 | $CH_2CH_2CH_2CH_2CH_2StBu$ |
| A-0364 | $CH_2CF_3$ | Me | F | 1 | $CH_2CH_2CH_2CH_2CH_2StBu$ |
| A-0365 | $CH_2CF_3$ | Cl | F | 0 | $CH_2CH_2CH_2CH_2CH_2StBu$ |
| A-0366 | $CH_2CF_3$ | Cl | F | 1 | $CH_2CH_2CH_2CH_2CH_2StBu$ |
| A-0367 | $CH_2CF_3$ | Me | H | 1 | $CH_2CH_2CH_2CH_2CH_2StBu$ |
| A-0368 | $CH_2CF_3$ | Me | F | 1 | $CH_2CH_2CH_2CH_2CH_2CH_2SCH_3$ |
| A-0369 | $CH_2CF_3$ | Me | F | 0 | $CH_2CH_2CH_2CH_2CH_2CH_2SCH_3$ |
| A-0370 | $CH_2CF_3$ | Me | F | 1 | $CH_2CH_2CH_2CH_2CH_2CH_2SCH(CH_3)_2$ |
| A-0371 | $CH_2CF_3$ | Me | F | 1 | $CH_2CH_2CH_2CH(CH_3)StBu$ |
| A-0372 | $CH_2CF_3$ | Me | F | 1 | $CH_2CH_2CH(CH_3)CH_2StBu$ |
| A-0373 | $CH_2CF_3$ | Me | F | 1 | $CH_2CH(CH_3)CH_2CH_2StBu$ |
| A-0374 | $CH_2CF_3$ | Me | F | 0 | $CH_2CH_2CH_2CH_2CH_2CH_2StBu$ |
| A-0375 | $CH_2CF_3$ | Me | F | 1 | $CH_2CH_2CH_2CH_2CH_2CH_2StBu$ |
| A-0376 | $CH_2CF_3$ | Me | F | 1 | $CH_2CH_2CH_2CH_2CH_2CH_2CH_2StBu$ |
| A-0377 | $CH_2CF_3$ | Me | F | 0 | $CH_2CH_2CH_2CH_2ScPen$ |
| A-0378 | $CH_2CF_3$ | Me | F | 0 | $CH_2CH_2CH_2CH_2ScHex$ |
| A-0379 | $CH_2CF_3$ | Cl | F | 0 | $CH_2CH_2CH_2CH_2CH_2ScPr$ |
| A-0380 | $CH_2CF_3$ | Cl | F | 1 | $CH_2CH_2CH_2CH_2CH_2ScPr$ |
| A-0381 | $CH_2CF_3$ | Me | F | 1 | $CH_2CH_2CH_2S(=O)Me$ |

TABLE 10-continued

| Compound No. | R¹ | R² | R³ | n | R⁴ |
| --- | --- | --- | --- | --- | --- |
| A-0382 | $CH_2CF_3$ | Me | F | 1 | $CH_2CH_2CH_2CH_2S(=O)tBu$ |
| A-0383 | $CH_2CF_3$ | Me | F | 1 | $CH_2CH_2CH_2CH_2CH_2S(=O)Me$ |
| A-0384 | $CH_2CF_3$ | Me | F | 1 | $CH_2CH_2CH_2CH_2CH_2CH_2S(=O)tBu$ |
| A-0385 | $CH_2CF_3$ | Me | F | 0 | $CH_2CH_2CH_2CH_2S(=O)cPen$ |
| A-0386 | $CH_2CF_3$ | Me | F | 1 | $CH_2CH_2CH_2CH_2S(=O)cHex$ |
| A-0387 | $CH_2CF_3$ | Cl | F | 0 | $CH_2CH_2CH_2CH_2S(=O)cPr$ |
| A-0388 | $CH_2CF_3$ | Cl | F | 1 | $CH_2CH_2CH_2CH_2S(=O)cPr$ |
| A-0389 | $CH_2CF_3$ | Me | F | 1 | $CH_2CH_2S(=O)_2Me$ |
| A-0390 | $CH_2CF_3$ | Me | F | 1 | $CH_2CH_2CH_2S(=O)_2Me$ |

TABLE 11

| Compound No. | R¹ | R² | R³ | n | R⁴ |
| --- | --- | --- | --- | --- | --- |
| A-0391 | $CH_2CF_3$ | Me | F | 0 | $CH_2CH_2CH_2CH_2S(=O)_2Me$ |
| A-0392 | $CH_2CF_3$ | Me | F | 1 | $CH_2CH_2CH_2CH_2S(=O)_2Me$ |
| A-0393 | $CH_2CF_3$ | Me | F | 0 | $CH_2CH_2CH_2CH_2CH_2S(=O)_2Me$ |
| A-0394 | $CH_2CF_3$ | Me | F | 1 | $CH_2CH_2CH_2CH_2CH_2S(=O)_2Me$ |
| A-0395 | $CH_2CF_3$ | Me | F | 0 | $CH_2CH_2CH_2CH_2CH_2S(=O)_2tBu$ |
| A-0396 | $CH_2CF_3$ | Me | F | 1 | $CH_2CH_2CH_2CH_2CH_2S(=O)_2tBu$ |
| A-0397 | $CH_2CF_3$ | Me | F | 1 | $CH_2CH_2CH_2CH_2CH_2CH_2S(=O)_2Me$ |
| A-0398 | $CH_2CF_3$ | Me | F | 1 | $CH_2CH_2CH_2CH_2CH_2CH_2CH_2S(=O)_2Me$ |
| A-0399 | $CH_2CF_3$ | Me | F | 0 | $CH_2CH_2CH_2CH_2CH_2S(=O)_2cPr$ |
| A-0400 | $CH_2CF_3$ | Me | F | 1 | $CH_2CH_2CH_2CH_2CH_2S(=O)_2cPr$ |
| A-0401 | $CH_2CF_3$ | Me | F | 0 | $CH_2SCF_3$ |
| A-0402 | $CH_2CF_3$ | Me | F | 1 | $CH_2SCF_3$ |
| A-0403 | $CH_2CF_3$ | Me | F | 1 | $CH_2CH_2SCF_3$ |
| A-0404 | $CH_2CF_3$ | Me | H | 1 | $CH_2CH_2SCF_3$ |
| A-0405 | $CH_2CF_3$ | Me | F | 0 | $CH_2CH_2CH_2SCF_3$ |
| A-0406 | $CH_2CF_3$ | Me | F | 1 | $CH_2CH_2CH_2SCF_3$ |
| A-0407 | $CH_2CF_3$ | Cl | F | 1 | $CH_2CH_2CH_2SCF_3$ |
| A-0408 | $CH_2CF_3$ | Me | H | 1 | $CH_2CH_2CH_2SCF_3$ |
| A-0409 | $CH_2CF_3$ | Me | Cl | 1 | $CH_2CH_2CH_2SCF_3$ |
| A-0410 | $CH_2CF_3$ | Me | Me | 0 | $CH_2CH_2CH_2SCF_3$ |
| A-0411 | $CH_2CF_3$ | Me | Me | 1 | $CH_2CH_2CH_2SCF_3$ |
| A-0412 | $CH_2CF_3$ | Cl | Cl | 0 | $CH_2CH_2CH_2SCF_3$ |
| A-0413 | $CH_2CF_3$ | Cl | Cl | 1 | $CH_2CH_2CH_2SCF_3$ |
| A-0414 | $CH_2CF_3$ | Me | F | 1 | $CH_2CH(CH_3)SCF_3$ |
| A-0415 | $CH_2CF_3$ | Me | F | 0 | $CH_2CH_2CH_2CH_2SCF_3$ |
| A-0416 | $CH_2CF_3$ | Me | F | 1 | $CH_2CH_2CH_2CH_2SCF_3$ |
| A-0417 | $CH_2CF_3$ | Cl | F | 0 | $CH_2CH_2CH_2CH_2SCF_3$ |
| A-0418 | $CH_2CF_3$ | Cl | F | 1 | $CH_2CH_2CH_2CH_2SCF_3$ |
| A-0419 | $CH_2CF_3$ | Me | H | 1 | $CH_2CH_2CH_2CH_2SCF_3$ |
| A-0420 | $CH_2CF_3$ | Me | Cl | 0 | $CH_2CH_2CH_2CH_2SCF_3$ |
| A-0421 | $CH_2CF_3$ | Me | Cl | 1 | $CH_2CH_2CH_2CH_2SCF_3$ |
| A-0422 | $CH_2CF_3$ | Me | Me | 0 | $CH_2CH_2CH_2CH_2SCF_3$ |
| A-0423 | $CH_2CF_3$ | Me | Me | 1 | $CH_2CH_2CH_2CH_2SCF_3$ |
| A-0424 | $CH_2CF_3$ | Cl | Cl | 0 | $CH_2CH_2CH_2CH_2SCF_3$ |
| A-0425 | $CH_2CF_3$ | Cl | Cl | 1 | $CH_2CH_2CH_2CH_2SCF_3$ |
| A-0426 | $CH_2CF_3$ | Me | F | 1 | $CH_2CH_2CH(CH_3)SCF_3$ |
| A-0427 | $CH_2CF_3$ | Me | F | 1 | $CH_2CH(CH_3)CH_2SCF_3$ |
| A-0428 | $CH_2CF_3$ | Me | F | 1 | $CH_2CH_2CH_2CH_2SCF_2CF_3$ |
| A-0429 | $CH_2CF_3$ | Me | F | 0 | $CH_2CH_2CH_2CH_2SCF(CF_3)_2$ |
| A-0430 | $CH_2CF_3$ | Me | F | 1 | $CH_2CH_2CH_2CH_2SCF(CF_3)_2$ |

TABLE 12

| Compound No. | R¹ | R² | R³ | n | R⁴ |
| --- | --- | --- | --- | --- | --- |
| A-0431 | $CH_2CF_3$ | Me | F | 0 | $CH_2CH_2CH_2CH_2CH_2SCF_3$ |
| A-0432 | $CH_2CF_3$ | Me | F | 1 | $CH_2CH_2CH_2CH_2CH_2SCF_3$ |
| A-0433 | $CH_2CF_3$ | Cl | F | 0 | $CH_2CH_2CH_2CH_2CH_2SCF_3$ |
| A-0434 | $CH_2CF_3$ | Cl | F | 1 | $CH_2CH_2CH_2CH_2CH_2SCF_3$ |
| A-0435 | $CH_2CF_3$ | Cl | F | 2 | $CH_2CH_2CH_2CH_2CH_2SCF_3$ |
| A-0436 | $CH_2CF_3$ | CN | F | 0 | $CH_2CH_2CH_2CH_2CH_2SCF_3$ |
| A-0437 | $CH_2CF_3$ | CN | F | 1 | $CH_2CH_2CH_2CH_2CH_2SCF_3$ |

TABLE 12-continued

| Compound No. | R¹ | R² | R³ | n | R⁴ |
|---|---|---|---|---|---|
| A-0438 | CH₂CF₃ | Me | H | 0 | CH₂CH₂CH₂CH₂CH₂SCF₃ |
| A-0439 | CH₂CF₃ | Me | H | 1 | CH₂CH₂CH₂CH₂CH₂SCF₃ |
| A-0440 | CH₂CF₃ | Me | Cl | 0 | CH₂CH₂CH₂CH₂CH₂SCF₃ |
| A-0441 | CH₂CF₃ | Me | Cl | 1 | CH₂CH₂CH₂CH₂CH₂SCF₃ |
| A-0442 | CH₂CF₃ | Me | Me | 0 | CH₂CH₂CH₂CH₂CH₂SCF₃ |
| A-0443 | CH₂CF₃ | Me | Me | 1 | CH₂CH₂CH₂CH₂CH₂SCF₃ |
| A-0444 | CH₂CF₃ | Cl | Cl | 0 | CH₂CH₂CH₂CH₂CH₂SCF₃ |
| A-0445 | CH₂CF₃ | Cl | Cl | 1 | CH₂CH₂CH₂CH₂CH₂SCF₃ |
| A-0446 | CH₂CF₃ | Cl | H | 0 | CH₂CH₂CH₂CH₂CH₂SCF₃ |
| A-0447 | CH₂CF₃ | Cl | H | 1 | CH₂CH₂CH₂CH₂CH₂SCF₃ |
| A-0448 | CH₂CF₃ | OMe | F | 0 | CH₂CH₂CH₂CH₂CH₂SCF₃ |
| A-0449 | CH₂CF₃ | OMe | F | 1 | CH₂CH₂CH₂CH₂CH₂SCF₃ |
| A-0450 | CF₃ | Me | F | 1 | CH₂CH₂CH₂CH₂CH₂SCF₃ |
| A-0451 | CHF₂ | Me | F | 1 | CH₂CH₂CH₂CH₂CH₂SCF₃ |
| A-0452 | tBu | Me | F | 1 | CH₂CH₂CH₂CH₂CH₂SCF₃ |
| A-0453 | CH₂tBu | Me | F | 1 | CH₂CH₂CH₂CH₂CH₂SCF₃ |
| A-0454 | CH₂CH(Me)₂ | Me | F | 1 | CH₂CH₂CH₂CH₂CH₂SCF₃ |
| A-0455 | CH₂CH=CCl₂ | Me | F | 1 | CH₂CH₂CH₂CH₂CH₂SCF₃ |
| A-0456 | CH₂CH≡CH | Me | F | 1 | CH₂CH₂CH₂CH₂CH₂SCF₃ |
| A-0457 | CH₂CH₂CF₃ | Me | F | 1 | CH₂CH₂CH₂CH₂CH₂SCF₃ |
| A-0458 | CH₂cPr | Me | F | 1 | CH₂CH₂CH₂CH₂CH₂SCF₃ |
| A-0459 | CF₂CF₃ | Me | F | 1 | CH₂CH₂CH₂CH₂CH₂SCF₃ |
| A-0460 | CH₂CHF₂ | Me | F | 1 | CH₂CH₂CH₂CH₂CH₂SCF₃ |
| A-0461 | CH₂CF₃ | Me | F | 1 | CH₂CH₂CH₂CH₂CH₂SCF₂CF₃ |
| A-0462 | CH₂CF₃ | Me | F | 0 | CH₂CH₂CH₂CH₂CH₂SCF(CF₃)₂ |
| A-0463 | CH₂CF₃ | Me | F | 1 | CH₂CH₂CH₂CH₂CH₂SCF(CF₃)₂ |
| A-0464 | CH₂CF₃ | Me | F | 1 | CH₂CH₂CH₂CH(CH₃)SCF₃ |
| A-0465 | CH₂CF₃ | Me | F | 1 | CH₂CH₂CH(CH₃)CH₂SCF₃ |
| A-0466 | CH₂CF₃ | Me | F | 1 | CH₂CH(CH₃)CH₂CH₂SCF₃ |
| A-0467 | CH₂CF₃ | Me | F | 1 | CH₂CH₂CH₂CH₂SCF₂CF₃ |
| A-0468 | CH₂CF₃ | Me | F | 1 | CH₂CH₂CH(SCF₃)CH₂CH₂ |
| A-0469 | CH₂CF₃ | Me | F | 1 | CH₂CH(SCF₃)CH₂CH₂CH₂ |
| A-0470 | CH₂CF₃ | Me | F | 0 | CH₂CH₂CH₂CH₂CH₂CH₂SCF₃ |

TABLE 13

| Compound No. | R¹ | R² | R³ | n | R⁴ |
|---|---|---|---|---|---|
| A-0471 | CH₂CF₃ | Me | F | 1 | CH₂CH₂CH₂CH₂CH₂CH₂SCF₃ |
| A-0472 | CH₂CF₃ | Cl | F | 0 | CH₂CH₂CH₂CH₂CH₂CH₂SCF₃ |
| A-0473 | CH₂CF₃ | Cl | F | 1 | CH₂CH₂CH₂CH₂CH₂CH₂SCF₃ |
| A-0474 | CH₂CF₃ | Me | H | 0 | CH₂CH₂CH₂CH₂CH₂CH₂SCF₃ |
| A-0475 | CH₂CF₃ | Me | H | 1 | CH₂CH₂CH₂CH₂CH₂CH₂SCF₃ |
| A-0476 | CH₂CF₃ | Me | Cl | 0 | CH₂CH₂CH₂CH₂CH₂CH₂SCF₃ |
| A-0477 | CH₂CF₃ | Me | Cl | 1 | CH₂CH₂CH₂CH₂CH₂CH₂SCF₃ |
| A-0478 | CH₂CF₃ | Cl | Cl | 0 | CH₂CH₂CH₂CH₂CH₂CH₂SCF₃ |
| A-0479 | CH₂CF₃ | Cl | Cl | 1 | CH₂CH₂CH₂CH₂CH₂CH₂SCF₃ |
| A-0480 | CH₂CF₃ | Me | Me | 0 | CH₂CH₂CH₂CH₂CH₂CH₂SCF₃ |
| A-0481 | CH₂CF₃ | Me | Me | 1 | CH₂CH₂CH₂CH₂CH₂CH₂SCF₃ |
| A-0482 | CH₂CHF₂ | Me | F | 0 | CH₂CH₂CH₂CH₂CH₂CH₂SCF₃ |
| A-0483 | CH₂CHF₂ | Me | F | 1 | CH₂CH₂CH₂CH₂CH₂CH₂SCF₃ |
| A-0484 | CH₂CH₂CF₃ | Me | F | 0 | CH₂CH₂CH₂CH₂CH₂CH₂SCF₃ |
| A-0485 | CH₂CH₂CF₃ | Me | F | 1 | CH₂CH₂CH₂CH₂CH₂CH₂SCF₃ |
| A-0486 | CH₂cPr | Me | F | 0 | CH₂CH₂CH₂CH₂CH₂CH₂SCF₃ |
| A-0487 | CH₂cPr | Me | F | 1 | CH₂CH₂CH₂CH₂CH₂CH₂SCF₃ |
| A-0488 | CH₂tBu | Me | F | 0 | CH₂CH₂CH₂CH₂CH₂CH₂SCF₃ |
| A-0489 | CH₂tBu | Me | F | 1 | CH₂CH₂CH₂CH₂CH₂CH₂SCF₃ |
| A-0490 | CH₂C≡CH | Me | F | 1 | CH₂CH₂CH₂CH₂CH₂CH₂SCF₃ |
| A-0491 | CH₂CF₃ | Me | F | 0 | CH₂CH₂CH₂CH₂CH₂CH₂SCF(CF₃)₂ |
| A-0492 | CH₂CF₃ | Me | F | 1 | CH₂CH₂CH₂CH₂CH₂CH₂SCF(CF₃)₂ |
| A-0493 | CH₂CF₃ | Me | F | 1 | CH₂CH₂CH₂CH₂CH(CH₃)SCF₃ |
| A-0494 | CH₂CF₃ | Me | F | 1 | CH₂CH₂CH₂CH(CH₃)CH₂SCF₃ |
| A-0495 | CH₂CF₃ | Me | F | 0 | CH₂CH₂CH(CH₃)CH₂CH₂SCF₃ |
| A-0496 | CH₂CF₃ | Me | F | 1 | CH₂CH(CH₃)CH₂CH₂CH₂SCF₃ |
| A-0497 | CH₂CF₃ | Me | F | 1 | CH₂CH(CH₃)CH₂CH₂SCF₃ |
| A-0498 | CH₂CF₃ | Me | F | 1 | CH₂CH₂CH₂CH₂CH₂SCF₂CF₃ |
| A-0499 | CH₂CF₃ | Me | F | 1 | CH₂CH₂CH₂CH(SCF₃)CH₂CH₃ |
| A-0500 | CH₂CF₃ | Me | F | 1 | CH₂CH₂CH(SCF₃)CH₂CH₂ |
| A-0501 | CH₂CF₃ | Me | F | 1 | CH₂CH(SCF₃)CH₂CH₂CH₂ |
| A-0502 | CH₂CF₃ | Me | F | 0 | CH₂CH₂CH₂CH₂CH₂CH₂CH₂SCF₃ |
| A-0503 | CH₂CF₃ | Me | F | 1 | CH₂CH₂CH₂CH₂CH₂CH₂CH₂SCF₃ |
| A-0504 | CH₂CF₃ | Cl | F | 0 | CH₂CH₂CH₂CH₂CH₂CH₂CH₂SCF₃ |

TABLE 13-continued

| Compound No. | R¹ | R² | R³ | n | R⁴ |
|---|---|---|---|---|---|
| A-0505 | $CH_2CF_3$ | Cl | F | 1 | $CH_2CH_2CH_2CH_2CH_2CH_2CH_2SCF_3$ |
| A-0506 | $CH_2CF_3$ | Me | H | 1 | $CH_2CH_2CH_2CH_2CH_2CH_2CH_2SCF_3$ |
| A-0507 | $CH_2CF_3$ | Me | Cl | 0 | $CH_2CH_2CH_2CH_2CH_2CH_2CH_2SCF_3$ |
| A-0508 | $CH_2CF_3$ | Me | Cl | 1 | $CH_2CH_2CH_2CH_2CH_2CH_2CH_2SCF_3$ |
| A-0509 | $CH_2CF_3$ | Cl | Cl | 0 | $CH_2CH_2CH_2CH_2CH_2CH_2CH_2SCF_3$ |
| A-0510 | $CH_2CF_3$ | Cl | Cl | 1 | $CH_2CH_2CH_2CH_2CH_2CH_2CH_2SCF_3$ |

TABLE 14

| Compound No. | R¹ | R² | R³ | n | R⁴ |
|---|---|---|---|---|---|
| A-0511 | $CH_2CF_3$ | Me | Me | 0 | $CH_2CH_2CH_2CH_2CH_2CH_2CH_2SCF_3$ |
| A-0512 | $CH_2CF_3$ | Me | Me | 1 | $CH_2CH_2CH_2CH_2CH_2CH_2CH_2SCF_3$ |
| A-0513 | $CH_2CF_3$ | Me | F | 1 | $CH_2CH_2CH_2CH_2CH_2CH(CH_3)SCF_3$ |
| A-0514 | $CH_2CF_3$ | Me | F | 1 | $CH_2CH_2CH_2CH(CH_3)CH_2SCF_3$ |
| A-0515 | $CH_2CF_3$ | Me | F | 1 | $CH_2CH_2CH_2CH(CH_3)CH_2SCF_3$ |
| A-0516 | $CH_2CF_3$ | Me | F | 1 | $CH_2CH_2CH(CH_3)CH_2CH_2SCF_3$ |
| A-0517 | $CH_2CF_3$ | Me | F | 1 | $CH_2CH(CH_3)CH_2CH_2CH_2SCF_3$ |
| A-0518 | $CH_2CF_3$ | Me | F | 1 | $CH_2CH_2CH_2CH_2CH_2CH_2SCF_2CF_3$ |
| A-0519 | $CH_2CF_3$ | Me | F | 1 | $CH_2CH_2CH_2CH_2CH_2CH_2SCF(CF_3)_2$ |
| A-0520 | $CH_2CF_3$ | Me | F | 1 | $CH_2CH_2CH_2S(=O)CF_3$ |
| A-0521 | $CH_2CF_3$ | Me | F | 1 | $CH_2CH_2CH_2S(=O)CF_3$ |
| A-0522 | $CH_2CF_3$ | Me | F | 1 | $CH_2CH_2CH_2CH_2CH_2S(=O)CF_3$ |
| A-0523 | $CH_2CF_3$ | Cl | F | 0 | $CH_2CH_2CH_2CH_2CH_2S(=O)CF_3$ |
| A-0524 | $CH_2CF_3$ | Cl | F | 1 | $CH_2CH_2CH_2CH_2CH_2S(=O)CF_3$ |
| A-0525 | $CH_2CF_3$ | Cl | F | 2 | $CH_2CH_2CH_2CH_2CH_2S(=O)CF_3$ |
| A-0526 | $CH_2CF_3$ | Me | F | 1 | $CH_2CH_2CH_2CH_2CH_2CH_2S(=O)CF_3$ |
| A-0527 | $CH_2CF_3$ | Cl | F | 1 | $CH_2CH_2CH_2CH_2CH_2CH_2S(=O)CF_3$ |
| A-0528 | $CH_2CF_3$ | Me | F | 1 | $CH_2CH_2CH_2CH_2CH_2CH_2CH_2S(=O)CF_3$ |
| A-0529 | $CH_2CF_3$ | Me | F | 1 | $CH_2CH_2CH_2S(=O)_2CF_3$ |
| A-0530 | $CH_2CF_3$ | Me | F | 1 | $CH_2CH_2CH_2CH_2S(=O)_2CF_3$ |
| A-0531 | $CH_2CF_3$ | Me | F | 1 | $CH_2CH_2CH_2CH_2S(=O)_2CF_3$ |
| A-0532 | $CH_2CF_3$ | Cl | F | 0 | $CH_2CH_2CH_2CH_2CH_2S(=O)_2CF_3$ |
| A-0533 | $CH_2CF_3$ | Cl | F | 1 | $CH_2CH_2CH_2CH_2CH_2S(=O)_2CF_3$ |
| A-0534 | $CH_2CF_3$ | Cl | F | 2 | $CH_2CH_2CH_2CH_2CH_2S(=O)_2CF_3$ |
| A-0535 | $CH_2CF_3$ | Me | F | 0 | $CH_2CH_2CH_2CH_2CH_2CH_2S(=O)_2CF_3$ |
| A-0536 | $CH_2CF_3$ | Me | F | 1 | $CH_2CH_2CH_2CH_2CH_2CH_2S(=O)_2CF_3$ |
| A-0537 | $CH_2CF_3$ | Me | F | 1 | $CH_2CH_2CH_2CH_2CH_2CH_2CH_2S(=O)_2CF_3$ |
| A-0538 | $CH_2CF_3$ | Me | F | 1 | $CH_2CH_2SCHF_2$ |
| A-0539 | $CH_2CF_3$ | Me | F | 1 | $CH_2CH_2CH_2SCHF_2$ |
| A-0540 | $CH_2CF_3$ | Cl | F | 1 | $CH_2CH_2CH_2SCHF_2$ |
| A-0541 | $CH_2CF_3$ | Me | H | 1 | $CH_2CH_2CH_2SCHF_2$ |
| A-0542 | $CH_2CF_3$ | Me | F | 1 | $CH_2CH(CH_3)SCHF_2$ |
| A-0543 | $CH_2CF_3$ | Me | F | 0 | $CH_2CH_2CH_2CH_2SCHF_2$ |
| A-0544 | $CH_2CF_3$ | Me | F | 1 | $CH_2CH_2CH_2CH_2SCHF_2$ |
| A-0545 | $CH_2CF_3$ | Cl | F | 1 | $CH_2CH_2CH_2CH_2SCHF_2$ |
| A-0546 | $CH_2CF_3$ | Me | H | 1 | $CH_2CH_2CH_2CH_2SCHF_2$ |
| A-0547 | $CH_2CF_3$ | Me | Cl | 1 | $CH_2CH_2CH_2CH_2SCHF_2$ |
| A-0548 | $CH_2CF_3$ | Cl | Cl | 1 | $CH_2CH_2CH_2CH_2SCHF_2$ |
| A-0549 | $CH_2CF_3$ | Me | Me | 1 | $CH_2CH_2CH_2CH_2SCHF_2$ |
| A-0550 | $CH_2CF_3$ | Me | F | 1 | $CH_2CH_2CH(CH_3)SCHF_2$ |

TABLE 15

| Compound No. | R¹ | R² | R³ | n | R⁴ |
|---|---|---|---|---|---|
| A-0551 | $CH_2CF_3$ | Me | F | 1 | $CH_2CH(CH_3)CH_2SCHF_2$ |
| A-0552 | $CH_2CF_3$ | Me | F | 1 | $CH_2CH_2CH_2CH_2SCH_2CHF_2$ |
| A-0553 | $CH_2CF_3$ | Me | F | 0 | $CH_2CH_2CH_2CH_2CH_2SCHF_2$ |
| A-0554 | $CH_2CF_3$ | Me | F | 1 | $CH_2CH_2CH_2CH_2CH_2SCHF_2$ |
| A-0555 | $CH_2CF_3$ | Cl | F | 0 | $CH_2CH_2CH_2CH_2CH_2SCHF_2$ |
| A-0556 | $CH_2CF_3$ | Cl | F | 1 | $CH_2CH_2CH_2CH_2CH_2SCHF_2$ |
| A-0557 | $CH_2CF_3$ | Me | H | 0 | $CH_2CH_2CH_2CH_2CH_2SCHF_2$ |
| A-0558 | $CH_2CF_3$ | Me | H | 1 | $CH_2CH_2CH_2CH_2CH_2SCHF_2$ |
| A-0559 | $CH_2CF_3$ | Cl | H | 1 | $CH_2CH_2CH_2CH_2CH_2SCHF_2$ |
| A-0560 | $CH_2CF_3$ | Cl | Cl | 1 | $CH_2CH_2CH_2CH_2CH_2SCHF_2$ |

TABLE 15-continued

| Compound No. | R¹ | R² | R³ | n | R⁴ |
|---|---|---|---|---|---|
| A-0561 | $CH_2CF_3$ | Cl | Cl | 0 | $CH_2CH_2CH_2CH_2CH_2SCHF_2$ |
| A-0562 | $CH_2CF_3$ | Me | Cl | 1 | $CH_2CH_2CH_2CH_2CH_2SCHF_2$ |
| A-0563 | $CH_2CF_3$ | Me | Me | 1 | $CH_2CH_2CH_2CH_2CH_2SCHF_2$ |
| A-0564 | $CH_2CF_3$ | Me | F | 1 | $CH_2CH_2CH_2CH(CH_3)SCHF_2$ |
| A-0565 | $CH_2CF_3$ | Me | F | 1 | $CH_2CH_2CH(CH_3)CH_2SCHF_2$ |
| A-0566 | $CH_2CF_3$ | Me | F | 1 | $CH_2CH(CH_3)CH_2CH_2SCHF_2$ |
| A-0567 | $CH_2CF_3$ | Me | F | 1 | $CH_2CH_2CH_2CH_2CH_2SCH_2CHF_2$ |
| A-0568 | $CH_2CF_3$ | Me | F | 1 | $CH_2CH_2CH(SCHF_2)CH_2CH_2$ |
| A-0569 | $CH_2CF_3$ | Me | F | 1 | $CH_2CH(SCHF_2)CH_2CH_2CH_2$ |
| A-0570 | $CH_2CF_3$ | Me | F | 0 | $CH_2CH_2CH_2CH_2CH_2CH_2SCHF_2$ |
| A-0571 | $CH_2CF_3$ | Me | F | 1 | $CH_2CH_2CH_2CH_2CH_2CH_2SCHF_2$ |
| A-0572 | $CH_2CF_3$ | Cl | F | 0 | $CH_2CH_2CH_2CH_2CH_2CH_2SCHF_2$ |
| A-0573 | $CH_2CF_3$ | Cl | F | 1 | $CH_2CH_2CH_2CH_2CH_2CH_2SCHF_2$ |
| A-0574 | $CH_2CF_3$ | Me | H | 1 | $CH_2CH_2CH_2CH_2CH_2CH_2SCHF_2$ |
| A-0575 | $CH_2CF_3$ | Cl | H | 1 | $CH_2CH_2CH_2CH_2CH_2CH_2SCHF_2$ |
| A-0576 | $CH_2CF_3$ | Me | Cl | 1 | $CH_2CH_2CH_2CH_2CH_2CH_2SCHF_2$ |
| A-0577 | $CH_2CF_3$ | Cl | Cl | 1 | $CH_2CH_2CH_2CH_2CH_2CH_2SCHF_2$ |
| A-0578 | $CH_2CF_3$ | Me | Me | 1 | $CH_2CH_2CH_2CH_2CH_2CH_2SCHF_2$ |
| A-0579 | $CH_2CF_3$ | Me | F | 1 | $CH_2CH_2CH_2CH_2CH(CH_3)SCHF_2$ |
| A-0580 | $CH_2CF_3$ | Me | F | 1 | $CH_2CH_2CH_2CH(CH_3)CH_2SCHF_2$ |
| A-0581 | $CH_2CF_3$ | Me | F | 1 | $CH_2CH_2CH(CH_3)CH_2CH_2SCHF_2$ |
| A-0582 | $CH_2CF_3$ | Me | F | 1 | $CH_2CH(CH_3)CH_2CH_2CH_2SCHF_2$ |
| A-0583 | $CH_2CF_3$ | Me | F | 1 | $CH_2CH_2CH_2CH(SCHF_2)CH_2CH_2$ |
| A-0584 | $CH_2CF_3$ | Me | F | 1 | $CH_2CH_2CH(SCHF_2)CH_2CH_2CH_2$ |
| A-0585 | $CH_2CF_3$ | Me | F | 1 | $CH_2CH(SCHF_2)CH_2CH_2CH_2CH_2$ |
| A-0586 | $CH_2CF_3$ | Me | F | 1 | $CH_2CH_2CH_2CH_2CH_2CH_2SCH_2CHF_2$ |
| A-0587 | $CH_2CF_3$ | Me | F | 1 | $CH_2CH_2CH_2CH_2CH_2CH_2CH_2SCHF_2$ |
| A-0588 | $CH_2CF_3$ | Cl | F | 0 | $CH_2CH_2CH_2CH_2CH_2CH_2CH_2SCHF_2$ |
| A-0589 | $CH_2CF_3$ | Cl | F | 1 | $CH_2CH_2CH_2CH_2CH_2CH_2CH_2SCHF_2$ |
| A-0590 | $CH_2CF_3$ | Cl | Cl | 1 | $CH_2CH_2CH_2CH_2CH_2CH_2CH_2SCHF_2$ |

TABLE 16

| Compound No. | R¹ | R² | R³ | n | R⁴ |
|---|---|---|---|---|---|
| A-0591 | $CH_2CF_3$ | Me | Cl | 1 | $CH_2CH_2CH_2CH_2CH_2CH_2CH_2SCHF_2$ |
| A-0592 | $CH_2CF_3$ | Me | H | 1 | $CH_2CH_2CH_2CH_2CH_2CH_2CH_2SCHF_2$ |
| A-0593 | $CH_2CF_3$ | Me | Me | 1 | $CH_2CH_2CH_2CH_2CH_2CH_2CH_2SCHF_2$ |
| A-0594 | $CH_2CF_3$ | Me | F | 1 | $CH_2CH_2CH_2S(=O)CHF_2$ |
| A-0595 | $CH_2CF_3$ | Me | F | 1 | $CH(CH_3)CH_2S(=O)CHF_2$ |
| A-0596 | $CH_2CF_3$ | Me | F | 1 | $CH_2CH_2CH_2CH_2S(=O)CHF_2$ |
| A-0597 | $CH_2CF_3$ | Me | F | 1 | $CH_2CH_2CH(CH_3)S(=O)CHF_2$ |
| A-0598 | $CH_2CF_3$ | Me | F | 1 | $CH_2CH(CH_3)CH_2S(=O)CHF_2$ |
| A-0599 | $CH_2CF_3$ | Cl | F | 1 | $CH_2CH_2CH_2CH_2CH_2S(=O)CHF_2$ |
| A-0600 | $CH_2CF_3$ | Me | H | 1 | $CH_2CH_2CH_2CH_2CH_2S(=O)CHF_2$ |
| A-0601 | $CH_2CF_3$ | Me | F | 1 | $CH_2CH_2CH_2CH(CH_3)S(=O)CHF_2$ |
| A-0602 | $CH_2CF_3$ | Me | F | 1 | $CH_2CH_2CH(CH_3)CH_2S(=O)CHF_2$ |
| A-0603 | $CH_2CF_3$ | Me | F | 1 | $CH_2CH(CH_3)CH_2CH_2S(=O)CHF_2$ |
| A-0604 | $CH_2CF_3$ | Me | F | 1 | $CH_2CH_2CH_2CH_2CH_2CH_2S(=O)CHF_2$ |
| A-0605 | $CH_2CF_3$ | Cl | F | 1 | $CH_2CH_2CH_2CH_2CH_2CH_2S(=O)CHF_2$ |
| A-0606 | $CH_2CF_3$ | Me | Cl | 1 | $CH_2CH_2CH_2CH_2CH_2CH_2S(=O)CHF_2$ |
| A-0607 | $CH_2CF_3$ | Me | F | 1 | $CH_2CH_2CH_2CH_2CH_2CH_2CH_2S(=O)CHF_2$ |
| A-0608 | $CH_2CF_3$ | Me | F | 1 | $CH_2CH_2CH_2S(=O)_2CHF_2$ |
| A-0609 | $CH_2CF_3$ | Me | F | 1 | $CH(CH_3)CH_2S(=O)_2CHF_2$ |
| A-0610 | $CH_2CF_3$ | Me | F | 0 | $CH_2CH_2CH_2CH_2S(=O)_2CHF_2$ |
| A-0611 | $CH_2CF_3$ | Me | F | 1 | $CH_2CH_2CH_2CH_2S(=O)_2CHF_2$ |
| A-0612 | $CH_2CF_3$ | Cl | F | 1 | $CH_2CH_2CH_2CH_2S(=O)_2CHF_2$ |
| A-0613 | $CH_2CF_3$ | Me | F | 1 | $CH_2CH_2CH(CH_3)S(=O)_2CHF_2$ |
| A-0614 | $CH_2CF_3$ | Me | F | 1 | $CH_2CH(CH_3)CH_2S(=O)_2CHF_2$ |
| A-0615 | $CH_2CF_3$ | Me | F | 0 | $CH_2CH_2CH_2CH_2CH_2S(=O)_2CHF_2$ |
| A-0616 | $CH_2CF_3$ | Me | F | 1 | $CH_2CH_2CH_2CH_2CH_2S(=O)_2CHF_2$ |
| A-0617 | $CH_2CF_3$ | Cl | F | 0 | $CH_2CH_2CH_2CH_2CH_2S(=O)_2CHF_2$ |
| A-0618 | $CH_2CF_3$ | Cl | F | 1 | $CH_2CH_2CH_2CH_2CH_2S(=O)_2CHF_2$ |
| A-0619 | $CH_2CF_3$ | Me | F | 1 | $CH_2CH_2CH_2CH(CH_3)S(=O)_2CHF_2$ |
| A-0620 | $CH_2CF_3$ | Me | F | 1 | $CH_2CH_2CH(CH_3)CH_2S(=O)_2CHF_2$ |
| A-0621 | $CH_2CF_3$ | Me | F | 1 | $CH_2CH(CH_3)CH_2CH_2S(=O)_2CHF_2$ |
| A-0622 | $CH_2CF_3$ | Me | F | 0 | $CH_2CH_2CH_2CH_2CH_2CH_2S(=O)_2CHF_2$ |
| A-0623 | $CH_2CF_3$ | Me | F | 1 | $CH_2CH_2CH_2CH_2CH_2CH_2S(=O)_2CHF_2$ |
| A-0624 | $CH_2CF_3$ | Me | F | 1 | $CH_2CH_2SCH_2CF_3$ |
| A-0625 | $CH_2CF_3$ | Me | F | 1 | $CH_2CH_2CH_2SCH_2CF_3$ |
| A-0626 | $CH_2CF_3$ | Me | H | 1 | $CH_2CH_2CH_2SCH_2CF_3$ |
| A-0627 | $CH_2CF_3$ | Me | F | 1 | $CH_2CH(CH_3)SCH_2CF_3$ |

TABLE 16-continued

| Compound No. | $R^1$ | $R^2$ | $R^3$ | n | $R^4$ |
|---|---|---|---|---|---|
| A-0628 | $CH_2CF_3$ | Me | F | 1 | $CH_2CH_2CH_2CH_2SCH_2CF_3$ |
| A-0629 | $CH_2CF_3$ | Cl | F | 1 | $CH_2CH_2CH_2CH_2SCH_2CF_3$ |
| A-0630 | $CH_2CF_3$ | Me | H | 1 | $CH_2CH_2CH_2CH_2SCH_2CF_3$ |

TABLE 17

| Compound No. | $R^1$ | $R^2$ | $R^3$ | n | $R^4$ |
|---|---|---|---|---|---|
| A-0631 | $CH_2CF_3$ | Me | F | 1 | $CH_2CH_2CH_2CH_2SCH_2CF_3$ |
| A-0632 | $CH_2CF_3$ | Cl | F | 1 | $CH_2CH_2CH_2CH_2SCH_2CF_3$ |
| A-0633 | $CH_2CF_3$ | Me | Cl | 1 | $CH_2CH_2CH_2CH_2SCH_2CF_3$ |
| A-0634 | $CH_2CF_3$ | Cl | Cl | 1 | $CH_2CH_2CH_2CH_2SCH_2CF_3$ |
| A-0635 | $CH_2CF_3$ | Me | Me | 1 | $CH_2CH_2CH_2CH_2SCH_2CF_3$ |
| A-0636 | $CH_2CF_3$ | Me | F | 1 | $CH_2CH_2CH(CH_3)SCH_2CF_3$ |
| A-0637 | $CH_2CF_3$ | Me | F | 1 | $CH_2CH(CH_3)CH_2SCH_2CF_3$ |
| A-0638 | $CH_2CF_3$ | Me | F | 1 | $CH_2CH_2CH_2CH_2CH_2SCH_2CF_3$ |
| A-0639 | $CH_2CF_3$ | Cl | F | 1 | $CH_2CH_2CH_2CH_2CH_2SCH_2CF_3$ |
| A-0640 | $CH_2CF_3$ | Me | H | 1 | $CH_2CH_2CH_2CH_2CH_2SCH_2CF_3$ |
| A-0641 | $CH_2CF_3$ | Me | Cl | 1 | $CH_2CH_2CH_2CH_2CH_2SCH_2CF_3$ |
| A-0642 | $CH_2CF_3$ | Cl | Cl | 1 | $CH_2CH_2CH_2CH_2CH_2SCH_2CF_3$ |
| A-0643 | $CH_2CF_3$ | Me | Me | 1 | $CH_2CH_2CH_2CH_2CH_2SCH_2CF_3$ |
| A-0644 | $CH_2CF_3$ | Cl | H | 1 | $CH_2CH_2CH_2CH_2CH_2SCH_2CF_3$ |
| A-0645 | $CH_2CF_3$ | Me | F | 1 | $CH_2CH_2CH_2CH(CH_3)SCH_2CF_3$ |
| A-0646 | $CH_2CF_3$ | Me | F | 1 | $CH_2CH_2CH(CH_3)CH_2SCH_2CF_3$ |
| A-0647 | $CH_2CF_3$ | Me | F | 1 | $CH_2CH(CH_3)CH_2CH_2SCH_2CF_3$ |
| A-0648 | $CH_2CF_3$ | Me | F | 1 | $CH_2CH_2CH_2CH_2CH_2CH_2SCH_2CF_3$ |
| A-0649 | $CH_2CF_3$ | Cl | F | 1 | $CH_2CH_2CH_2CH_2CH_2CH_2SCH_2CF_3$ |
| A-0650 | $CH_2CF_3$ | Me | Cl | 1 | $CH_2CH_2CH_2CH_2CH_2CH_2SCH_2CF_3$ |
| A-0651 | $CH_2CF_3$ | Cl | Cl | 1 | $CH_2CH_2CH_2CH_2CH_2CH_2SCH_2CF_3$ |
| A-0652 | $CH_2CF_3$ | Me | Me | 1 | $CH_2CH_2CH_2CH_2CH_2CH_2SCH_2CF_3$ |
| A-0653 | $CH_2CF_3$ | Me | F | 1 | $CH_2CH_2CH_2CH_2CH(CH_3)SCH_2CF_3$ |
| A-0654 | $CH_2CF_3$ | Me | F | 1 | $CH_2CH_2CH_2CH(CH_3)CH_2SCH_2CF_3$ |
| A-0655 | $CH_2CF_3$ | Me | F | 1 | $CH_2CH(CH_3)CH_2CH_2CH_2SCH_2CF_3$ |
| A-0656 | $CH_2CF_3$ | Me | F | 1 | $CH_2CH_2CH_2CH_2CH_2CH_2CH_2SCH_2CF_3$ |
| A-0657 | $CH_2CF_3$ | Me | F | 1 | $CH_2CH_2CH_2SCH(CF_3)_2$ |
| A-0658 | $CH_2CF_3$ | Me | F | 1 | $CH_2CH_2CH_2CH_2SCH(CF_3)_2$ |
| A-0659 | $CH_2CF_3$ | Me | F | 1 | $CH_2CH_2CH_2CH_2CH_2SCH(CF_3)_2$ |
| A-0660 | $CH_2CF_3$ | Me | F | 1 | $CH_2CH_2CH_2CH_2CH_2CH_2SCH(CF_3)_2$ |
| A-0661 | $CH_2CF_3$ | Cl | F | 0 | $CH_2CH_2CH_2CH_2SCCl_3$ |
| A-0662 | $CH_2CF_3$ | Cl | F | 1 | $CH_2CH_2CH_2CH_2SCCl_3$ |
| A-0663 | $CH_2CF_3$ | Me | F | 0 | $CH_2CH_2CH_2SCN$ |
| A-0664 | $CH_2CF_3$ | Me | Me | 0 | $CH_2CH_2CH_2SCN$ |
| A-0665 | $CH_2CF_3$ | Cl | F | 0 | $CH_2CH_2CH_2CH_2SCN$ |
| A-0666 | $CH_2CF_3$ | Me | Me | 0 | $CH_2CH_2CH_2CH_2SCN$ |
| A-0667 | $CH_2CF_3$ | Cl | Cl | 0 | $CH_2CH_2CH_2CH_2SCN$ |
| A-0668 | $CH_2CF_3$ | Me | F | 0 | $CH_2CH_2CH_2CH_2CH_2SCN$ |
| A-0669 | $CH_2CF_3$ | Me | F | 1 | $CH_2CH_2CH_2CH_2CH_2SCN$ |
| A-0670 | $CH_2CF_3$ | Cl | F | 0 | $CH_2CH_2CH_2CH_2CH_2SCN$ |

TABLE 18

| Compound No. | $R^1$ | $R^2$ | $R^3$ | n | $R^4$ |
|---|---|---|---|---|---|
| A-0671 | $CH_2CF_3$ | CN | F | 0 | $CH_2CH_2CH_2CH_2CH_2SCN$ |
| A-0672 | $CH_2CF_3$ | Me | H | 0 | $CH_2CH_2CH_2CH_2CH_2SCN$ |
| A-0673 | $CH_2CF_3$ | OMe | F | 0 | $CH_2CH_2CH_2CH_2CH_2SCN$ |
| A-0674 | $CH_2CF_3$ | Me | F | 0 | $CH_2CH_2CH(Me)CH_2CH_2SCN$ |
| A-0675 | $CH_2CF_3$ | Me | F | 0 | $CH_2CH_2CH_2CH_2CH_2CH_2SCN$ |
| A-0676 | $CH_2CF_3$ | Cl | F | 0 | $CH_2CH_2CH_2CH_2CH_2CH_2SCN$ |
| A-0677 | $CH_2CF_3$ | Me | H | 0 | $CH_2CH_2CH_2CH_2CH_2CH_2SCN$ |
| A-0678 | $CH_2CF_3$ | Cl | Cl | 0 | $CH_2CH_2CH_2CH_2CH_2CH_2SCN$ |
| A-0679 | $CH_2CF_3$ | Me | Me | 0 | $CH_2CH_2CH_2CH_2CH_2CH_2SCN$ |
| A-0680 | $CH_2CF_3$ | Me | F | 0 | $CH_2CH_2CH_2CH_2CH_2CH_2CH_2SCN$ |
| A-0681 | $CH_2CF_3$ | Me | Me | 0 | $CH_2CH_2CH_2CH_2CH_2CH_2CH_2SCN$ |
| A-0682 | $CH_2CF_3$ | Me | F | 1 | $CH_2CH_2CH_2CH_2CH_2SCH_2SMe_3$ |
| A-0683 | $CH_2CF_3$ | Me | F | 1 | $CH_2CH_2CH_2SCF=CFCF_3$ |

TABLE 18-continued

| Compound No. | R¹ | R² | R³ | n | R⁴ |
|---|---|---|---|---|---|
| A-0684 | $CH_2CF_3$ | Me | F | 0 | $CH_2Ph$ |
| A-0685 | $CH_2CF_3$ | Me | F | 0 | $CH(Me)Ph$ |
| A-0686 | $CH_2CF_3$ | Me | F | 1 | $CH_2Ph$ |
| A-0687 | $CH_2CF_3$ | Me | F | 0 | $CH_2Ph(2-CF_3)$ |
| A-0688 | $CH_2CF_3$ | Me | F | 1 | $CH_2Ph(2-CF_3)$ |
| A-0689 | $CH_2CF_3$ | Me | F | 0 | $CH_2Ph(3-CF_3)$ |
| A-0690 | $CH_2CF_3$ | Me | F | 0 | $CH_2Ph(4-CF_3)$ |
| A-0691 | $CH_2CF_3$ | Me | F | 0 | $CH(Me)Ph(4-CF_3)$ |
| A-0692 | $CH_2CF_3$ | Me | F | 1 | $CH_2Ph(4-CF_3)$ |
| A-0693 | $CH_2CF_3$ | Cl | F | 0 | $CH_2Ph(4-CF_3)$ |
| A-0694 | $CH_2CF_3$ | Cl | F | 1 | $CH_2Ph(4-CF_3)$ |
| A-0695 | $CH_2CF_3$ | Me | Cl | 0 | $CH_2Ph(4-CF_3)$ |
| A-0696 | $CH_2CF_3$ | Me | Cl | 1 | $CH_2Ph(4-CF_3)$ |
| A-0697 | $CH_2CF_3$ | CN | H | 0 | $CH_2Ph(4-CF_3)$ |
| A-0698 | $CH_2CF_3$ | CN | H | 1 | $CH_2Ph(4-CF_3)$ |
| A-0699 | $CH_2CF_3$ | Me | F | 0 | $CH_2Ph(2,5-(CF_3)_2)$ |
| A-0700 | $CH_2CF_3$ | Me | F | 1 | $CH_2Ph(2,5-(CF_3)_2)$ |
| A-0701 | $CH_2CF_3$ | Me | F | 1 | $CH_2Ph(4-OCHF_2)$ |
| A-0702 | $CH_2CF_3$ | Me | F | 1 | $CH_2Ph(2-OCF_3)$ |
| A-0703 | $CH_2CF_3$ | Me | F | 1 | $CH_2Ph(3-OCF_3)$ |
| A-0704 | $CH_2CF_3$ | Me | F | 1 | $CH_2Ph(4-OCF_3)$ |
| A-0705 | $CH_2CF_3$ | Me | F | 1 | $CH_2Ph(4-SCHF_2)$ |
| A-0706 | $CH_2CF_3$ | Me | F | 1 | $CH_2Ph(2-SCF_3)$ |
| A-0707 | $CH_2CF_3$ | Me | F | 0 | $CH_2Ph(3-SCF_3)$ |
| A-0708 | $CH_2CF_3$ | Me | F | 1 | $CH_2Ph(3-SCF_3)$ |
| A-0709 | $CH_2CF_3$ | Cl | F | 0 | $CH_2Ph(4-SCF_3)$ |
| A-0710 | $CH_2CF_3$ | Cl | F | 1 | $CH_2Ph(4-SCF_3)$ |

TABLE 19

| Compound No. | R¹ | R² | R³ | n | R⁴ |
|---|---|---|---|---|---|
| A-0711 | $CH_2CF_3$ | Me | F | 0 | $CH_2Ph(4-SCF_3)$ |
| A-0712 | $CH_2CF_3$ | Me | F | 1 | $CH_2Ph(4-SCF_3)$ |
| A-0713 | $CH_2CF_3$ | Me | F | 1 | $CH_2Ph(3-CH_2SCF_3)$ |
| A-0714 | $CH_2CF_3$ | Me | F | 1 | $CH_2Ph(4-CH_2SCF_3)$ |
| A-0715 | $CH_2CF_3$ | Me | F | 0 | $CH_2Ph(4-F)$ |
| A-0716 | $CH_2CF_3$ | Me | F | 0 | $CH_2Ph(4-Cl)$ |
| A-0717 | $CH_2CF_3$ | Me | F | 1 | $CH_2Ph(4-Cl)$ |
| A-0718 | $CH_2CF_3$ | Me | F | 0 | $CH_2Ph(4-Br)$ |
| A-0719 | $CH_2CF_3$ | Me | F | 1 | $CH_2Ph(4-Br)$ |
| A-0720 | $CH_2CF_3$ | Me | F | 0 | $CH_2Ph(4-Me)$ |
| A-0721 | $CH_2CF_3$ | Me | F | 1 | $CH_2Ph(4-Me)$ |
| A-0722 | $CH_2CF_3$ | Me | F | 0 | $CH_2Ph(4-tBu)$ |
| A-0723 | $CH_2CF_3$ | Me | F | 1 | $CH_2Ph(4-tBu)$ |
| A-0724 | $CH_2CF_3$ | Me | F | 0 | $CH_2Ph(4-CN)$ |
| A-0725 | $CH_2CF_3$ | Me | F | 1 | $CH_2Ph(4-CN)$ |
| A-0726 | $CH_2CF_3$ | Me | F | 0 | $CH_2Ph(4-NO_2)$ |
| A-0727 | $CH_2CF_3$ | Me | F | 1 | $CH_2Ph(4-NO_2)$ |
| A-0728 | $CH_2CF_3$ | Me | F | 0 | $CH_2Ph(2,4-Cl_2)$ |
| A-0729 | $CH_2CF_3$ | Me | F | 1 | $CH_2Ph(2,4-Cl_2)$ |
| A-0730 | $CH_2CF_3$ | Me | F | 0 | $CH_2Ph(3,4-Cl_2)$ |
| A-0731 | $CH_2CF_3$ | Me | F | 1 | $CH_2Ph(3,4-Cl_2)$ |
| A-0732 | $CH_2CF_3$ | Me | F | 0 | $CH_2Ph(2,4,6-F_3)$ |
| A-0733 | $CH_2CF_3$ | Me | F | 1 | $CH_2Ph(2,4,6-F_3)$ |
| A-0734 | $CH_2CF_3$ | Me | F | 0 | $CH_2Ph(3,4,5-F_3)$ |
| A-0735 | $CH_2CF_3$ | Me | F | 1 | $CH_2Ph(3,4,5-F_3)$ |
| A-0736 | $CH_2CF_3$ | Me | F | 1 | $CH_2Ph(2,3,4-F_3)$ |
| A-0737 | $CH_2CF_3$ | Me | F | 0 | $CH_2Ph(2,3,4-Cl_3)$ |
| A-0738 | $CH_2CF_3$ | Me | F | 0 | $CH_2Ph(3,4,5-Cl_3)$ |
| A-0739 | $CH_2CF_3$ | Me | F | 0 | $CH_2Ph(3,4,5-Cl_3)$ |
| A-0740 | $CH_2CF_3$ | Me | F | 1 | $CH_2Ph(3,4,5-Cl_3)$ |
| A-0741 | $CH_2CF_3$ | Me | F | 0 | $CH_2Ph(3-CF_3, 4-Cl)$ |
| A-0742 | $CH_2CF_3$ | Me | F | 1 | $CH_2Ph(3-CF_3, 4-Cl)$ |
| A-0743 | $CH_2CF_3$ | Me | F | 0 | $CH_2Ph(3-CF_3, 4-F)$ |
| A-0744 | $CH_2CF_3$ | Me | F | 1 | $CH_2Ph(3-CF_3, 4-F)$ |
| A-0745 | $CH_2CF_3$ | Me | F | 0 | $CH_2Ph(3-F, 4-CF_3)$ |
| A-0746 | $CH_2CF_3$ | Me | F | 1 | $CH_2Ph(3-F, 4-CF_3)$ |
| A-0747 | $CH_2CF_3$ | Me | F | 0 | $CH_2Ph(4-CF(CF_3)_2)$ |
| A-0748 | $CH_2CF_3$ | Me | F | 1 | $CH_2Ph(4-CF(CF_3)_2)$ |
| A-0749 | $CH_2CF_3$ | Me | F | 1 | $CH_2Ph(4-CH_2SCF_3)$ |
| A-0750 | $CH_2CF_3$ | Me | F | 0 | $CH_2Ph(4-Ph(4-CF_3))$ |

TABLE 20

| Compound No. | R¹ | R² | R³ | n | R⁴ |
|---|---|---|---|---|---|
| A-0751 | $CH_2CF_3$ | Me | F | 0 | $CH_2CH_2Ph$ |
| A-0752 | $CH_2CF_3$ | Me | F | 1 | $CH_2CH_2Ph$ |
| A-0753 | $CH_2CF_3$ | Me | F | 0 | $CH_2CH_2Ph(4-F)$ |
| A-0754 | $CH_2CF_3$ | Me | F | 1 | $CH_2CH_2Ph(4-F)$ |
| A-0755 | $CH_2CF_3$ | Me | F | 0 | $CH_2CH_2Ph(4-Cl)$ |
| A-0756 | $CH_2CF_3$ | Me | F | 1 | $CH_2CH_2Ph(4-Cl)$ |
| A-0757 | $CH_2CF_3$ | Me | F | 0 | $CH_2CH_2Ph(4-Br)$ |
| A-0758 | $CH_2CF_3$ | Me | F | 1 | $CH_2CH_2Ph(4-Br)$ |
| A-0759 | $CH_2CF_3$ | Me | F | 0 | $CH_2CH_2Ph(2-CF_3)$ |
| A-0760 | $CH_2CF_3$ | Me | F | 1 | $CH_2CH_2Ph(2-CF_3)$ |
| A-0761 | $CH_2CF_3$ | Me | F | 0 | $CH_2CH_2Ph(3-CF_3)$ |
| A-0762 | $CH_2CF_3$ | Me | F | 1 | $CH_2CH_2Ph(3-CF_3)$ |
| A-0763 | $CH_2CF_3$ | Me | F | 0 | $CH_2CH_2Ph(4-CF_3)$ |
| A-0764 | $CH_2CF_3$ | Me | F | 1 | $CH_2CH_2Ph(4-CF_3)$ |
| A-0765 | $CH_2CF_3$ | Cl | F | 0 | $CH_2CH_2Ph(4-CF_3)$ |
| A-0766 | $CH_2CF_3$ | Cl | F | 1 | $CH_2CH_2Ph(4-CF_3)$ |
| A-0767 | $CH_2CF_3$ | Cl | Cl | 1 | $CH_2CH_2Ph(4-CF_3)$ |
| A-0768 | $CH_2CF_3$ | Me | Me | 1 | $CH_2CH_2Ph(4-CF_3)$ |
| A-0769 | $CH_2CF_3$ | Me | Cl | 1 | $CH_2CH_2Ph(4-CF_3)$ |
| A-0770 | tBu | CN | F | 0 | $CH_2CH_2Ph(4-CF_3)$ |
| A-0771 | tBu | CN | F | 1 | $CH_2CH_2Ph(4-CF_3)$ |
| A-0772 | $CH_2CF_3$ | Cl | F | 0 | $CH_2CH_2Ph(4-OCHF_2)$ |
| A-0773 | $CH_2CF_3$ | Cl | F | 1 | $CH_2CH_2Ph(4-OCHF_2)$ |
| A-0774 | $CH_2CF_3$ | Me | F | 1 | $CH_2CH_2Ph(4-OCHF_2)$ |
| A-0775 | $CH_2CF_3$ | Me | Me | 1 | $CH_2CH_2Ph(4-OCHF_2)$ |
| A-0776 | $CH_2CF_3$ | Cl | Cl | 1 | $CH_2CH_2Ph(4-OCHF_2)$ |
| A-0777 | $CH_2CF_3$ | Me | F | 0 | $CH_2Ph(3-OCF_3)$ |
| A-0778 | $CH_2CF_3$ | Me | F | 0 | $CH_2CH_2Ph(4-OCF_3)$ |
| A-0779 | $CH_2CF_3$ | Me | F | 1 | $CH_2CH_2Ph(4-OCF_3)$ |
| A-0780 | $CH_2CF_3$ | Cl | F | 0 | $CH_2CH_2Ph(4-OCF_3)$ |
| A-0781 | $CH_2CF_3$ | Cl | F | 1 | $CH_2CH_2Ph(4-OCF_3)$ |
| A-0782 | $CH_2CF_3$ | Cl | Cl | 1 | $CH_2CH_2Ph(4-OCF_3)$ |
| A-0783 | $CH_2CF_3$ | Me | Me | 1 | $CH_2CH_2Ph(4-OCF_3)$ |
| A-0784 | $CH_2CF_3$ | Me | Cl | 1 | $CH_2CH_2Ph(4-OCF_3)$ |
| A-0785 | $CH_2CF_3$ | Me | F | 0 | $CH_2CH_2Ph(4-SCHF_2)$ |
| A-0786 | $CH_2CF_3$ | Me | F | 0 | $CH_2CH_2Ph(4-SCF_3)$ |
| A-0787 | $CH_2CF_3$ | Cl | F | 0 | $CH_2CH_2Ph(4-SCF_3)$ |
| A-0788 | $CH_2CF_3$ | Me | F | 1 | $CH_2CH_2Ph(4-SCF_3)$ |
| A-0789 | $CH_2CF_3$ | Cl | F | 1 | $CH_2CH_2Ph(4-SCF_3)$ |
| A-0790 | $CH_2CF_3$ | Cl | Cl | 0 | $CH_2CH_2Ph(4-SCF_3)$ |

TABLE 21

| Compound No. | R¹ | R² | R³ | n | R⁴ |
|---|---|---|---|---|---|
| A-0791 | CH₂CF₃ | Cl | Cl | 1 | CH₂CH₂Ph(4-SCF₃) |
| A-0792 | CH₂CF₃ | Me | Me | 1 | CH₂CH₂Ph(4-SCF₃) |
| A-0793 | CH₂CF₃ | Me | Cl | 1 | CH₂CH₂Ph(4-SCF₃) |
| A-0794 | CH₂CF₃ | Me | F | 1 | CH₂CH₂Ph(4-CF(CF₃)₂) |
| A-0795 | CH₂CF₃ | Me | F | 0 | CH₂CH₂Ph(4-NO₂) |
| A-0796 | CH₂CF₃ | Me | F | 1 | CH₂CH₂Ph(4-NO₂) |
| A-0797 | CH₂CF₃ | Cl | F | 0 | CH₂CH₂Ph(4-OS(=O)₂CF₃) |
| A-0798 | CH₂CF₃ | Me | F | 0 | CH₂CH₂Ph(4-OS(=O)₂CF₃) |
| A-0799 | CH₂CF₃ | Me | F | 1 | CH₂CH₂Ph(4-OS(=O)₂CF₃) |
| A-0800 | CH₂CF₃ | Cl | F | 1 | CH₂CH₂Ph(4-OS(=O)₂CF₃) |
| A-0801 | CH₂CF₃ | Me | F | 1 | CH₂CH₂Ph(2,4-Cl₂) |
| A-0802 | CH₂CF₃ | Me | F | 0 | CH₂CH₂Ph(3,4-Cl₂) |
| A-0803 | CH₂CF₃ | Me | F | 1 | CH₂CH₂Ph(3,4-Cl₂) |
| A-0804 | CH₂CF₃ | Me | F | 1 | CH₂CH₂Ph(3,4,5-Cl₃) |
| A-0805 | CH₂CF₃ | Me | F | 1 | CH₂CH₂Ph(2,3,4-F₃) |
| A-0806 | CH₂CF₃ | Cl | F | 1 | CH₂CH₂Ph(2,3,4-F₃) |
| A-0807 | CH₂CF₃ | Me | F | 1 | CH₂CH₂Ph(2,4,5-F₃) |
| A-0808 | CH₂CF₃ | Cl | F | 1 | CH₂CH₂Ph(2,4,5-F₃) |
| A-0809 | CH₂CF₃ | Me | F | 0 | CH₂CH₂Ph(3,4,5-F₃) |
| A-0810 | CH₂CF₃ | Me | F | 1 | CH₂CH₂Ph(3,4,5-F₃) |
| A-0811 | CH₂CF₃ | Me | F | 0 | CH₂CH₂Ph(2,4,6-F₃) |
| A-0812 | CH₂CF₃ | Me | F | 1 | CH₂CH₂Ph(2,4,6-F₃) |
| A-0813 | CH₂CF₃ | Me | F | 0 | CH₂CH₂Ph(3-CF₃,4-F) |
| A-0814 | CH₂CF₃ | Me | F | 1 | CH₂CH₂Ph(3-CF₃,4-F) |
| A-0815 | CH₂CF₃ | Cl | F | 0 | CH₂CH₂Ph(3-CF₃,4-F) |
| A-0816 | CH₂CF₃ | Cl | F | 1 | CH₂CH₂Ph(3-CF₃,4-F) |
| A-0817 | CH₂CF₃ | Cl | F | 1 | CH₂CH₂Ph(2-F,4-CF₃) |
| A-0818 | CH₂CF₃ | Me | Cl | 1 | CH₂CH₂Ph(2-F,4-CF₃) |
| A-0819 | CH₂CF₃ | Cl | Cl | 0 | CH₂CH₂Ph(2-F,4-CF₃) |
| A-0820 | CH₂CF₃ | Cl | Cl | 1 | CH₂CH₂Ph(2-F,4-CF₃) |
| A-0821 | CH₂CF₃ | Me | F | 1 | CH₂CH₂Ph(3-F,4-CF₃) |
| A-0822 | CH₂CF₃ | Me | F | 0 | CH₂CH₂Ph(3-F,4-CF₃) |
| A-0823 | CH₂CF₃ | Cl | F | 1 | CH₂CH₂Ph(3-F,4-CF₃) |
| A-0824 | CH₂CF₃ | Cl | F | 0 | CH₂CH₂Ph(3-F,4-CF₃) |
| A-0825 | CH₂CF₃ | Me | F | 1 | CH₂CH₂Ph(2-F,4-CF₃) |
| A-0826 | CH₂CF₃ | Cl | F | 0 | CH₂CH₂Ph(3-Cl,4-OCHF₂) |
| A-0827 | CH₂CF₃ | Cl | F | 1 | CH₂CH₂Ph(3-Cl,4-OCHF₂) |
| A-0828 | CH₂CF₃ | Me | F | 0 | CH₂CH₂Ph(4-Ph(4-CF₃)) |
| A-0829 | CH₂CF₃ | Me | F | 1 | CH₂CH₂Ph(4-Ph(4-CF₃)) |
| A-0830 | CH₂CF₃ | Me | F | 0 | CH₂CH₂Ph(4-OCH₂Ph) |

TABLE 22

| Compound No. | R¹ | R² | R³ | n | R⁴ |
|---|---|---|---|---|---|
| A-0831 | CH₂CF₃ | Me | F | 1 | CH₂CH₂Ph(4-OCH₂Ph) |
| A-0832 | CH₂CF₃ | Cl | F | 0 | CH₂C(Me)₂Ph(4-Cl) |
| A-0833 | CH₂CF₃ | Cl | F | 1 | CH₂C(Me)₂Ph(4-Cl) |
| A-0834 | CH₂CF₃ | Me | F | 0 | CH₂CH₂CH₂Ph |
| A-0835 | CH₂CF₃ | Me | F | 0 | CH₂CH(CH₃)Ph |
| A-0836 | CH₂CF₃ | Me | F | 0 | CH(CH₃)CH₂Ph |
| A-0837 | CH₂CF₃ | Me | F | 1 | CH₂CH₂CH₂Ph |
| A-0838 | CH₂CF₃ | Me | F | 0 | CH₂CH₂CH₂Ph(4-CF₃) |
| A-0839 | CH₂CF₃ | Me | F | 1 | CH₂CH₂CH₂Ph(4-CF₃) |
| A-0840 | CH₂CF₃ | Cl | F | 1 | CH₂CH₂CH₂Ph(4-CF₃) |
| A-0841 | CH₂CF₃ | Me | Cl | 1 | CH₂CH₂CH₂Ph(4-CF₃) |
| A-0842 | CH₂CF₃ | Cl | Cl | 1 | CH₂CH₂CH₂Ph(4-CF₃) |
| A-0843 | CH₂CF₃ | Me | Me | 1 | CH₂CH₂CH₂Ph(4-CF₃) |
| A-0844 | CH₂CF₃ | Me | F | 0 | CH₂CH₂CH₂Ph(3-CF₃) |
| A-0845 | CH₂CF₃ | Me | F | 1 | CH₂CH₂CH₂Ph(3-CF₃) |
| A-0846 | CH₂CF₃ | Me | F | 0 | CH₂CH₂CH₂Ph(4-tBu) |
| A-0847 | CH₂CF₃ | Me | F | 1 | CH₂CH₂CH₂Ph(4-tBu) |
| A-0848 | CH₂CF₃ | Me | F | 0 | CH₂CH₂CH₂Ph(4-CN) |
| A-0849 | CH₂CF₃ | Me | F | 1 | CH₂CH₂CH₂Ph(4-CN) |
| A-0850 | CH₂CF₃ | Me | F | 1 | CH₂CH₂CH₂Ph(4-OCHF₂) |
| A-0851 | CH₂CF₃ | Me | F | 1 | CH₂CH₂CH₂Ph(4-OCF₃) |
| A-0852 | CH₂CF₃ | Me | F | 1 | CH₂CH₂CH₂Ph(4-SCHF₂) |

TABLE 22-continued

| Compound No. | R¹ | R² | R³ | n | R⁴ |
|---|---|---|---|---|---|
| A-0853 | CH₂CF₃ | Me | F | 0 | CH₂CH₂CH₂Ph(4-SCF₃) |
| A-0854 | CH₂CF₃ | Me | F | 1 | CH₂CH₂CH₂Ph(4-SCF₃) |
| A-0855 | CH₂CF₃ | Me | F | 0 | CH₂CH₂CH₂Ph(3,4,5-F₃) |
| A-0856 | CH₂CF₃ | Me | F | 1 | CH₂CH₂CH₂Ph(3,4,5-F₃) |
| A-0857 | CH₂CF₃ | Me | F | 0 | CH₂CH₂CH₂Ph(2,4,6-F₃) |
| A-0858 | CH₂CF₃ | Me | F | 1 | CH₂CH₂CH₂Ph(2,4,6-F₃) |
| A-0859 | CH₂CF₃ | Me | F | 1 | CH₂CH₂CH₂Ph(4-CF(CF₃)₂) |
| A-0860 | CH₂CF₃ | Me | F | 0 | CH₂CH₂CH₂CH₂Ph |
| A-0861 | CH₂CF₃ | Me | F | 0 | CH₂CH₂CH(CH₃)Ph |
| A-0862 | CH₂CF₃ | Me | F | 0 | CH₂CH(CH₃)CH₂Ph |
| A-0863 | CH₂CF₃ | Me | F | 0 | CH(CH₃)CH₂CH₂Ph |
| A-0864 | CH₂CF₃ | Me | F | 1 | CH₂CH₂CH₂CH₂Ph |
| A-0865 | CH₂CF₃ | Me | F | 1 | CH₂CH₂CH₂CH₂Ph(4-F) |
| A-0866 | CH₂CF₃ | Me | F | 1 | CH₂CH₂CH₂CH₂Ph(4-CF₃) |
| A-0867 | CH₂CF₃ | Me | F | 1 | CH₂CH₂CH₂CH₂Ph(4-OCF₃) |
| A-0868 | CH₂CF₃ | Me | F | 1 | CH₂CH₂CH₂CH₂Ph(4-SCF₃) |
| A-0869 | CH₂CF₃ | Me | F | 0 | CH₂CH₂CH₂CH₂CH₂Ph |
| A-0870 | CH₂CF₃ | Me | F | 0 | CH₂CH₂CH₂CH₂CH₂CH₂Ph |

TABLE 23

| Compound No. | R¹ | R² | R³ | n | R⁴ |
|---|---|---|---|---|---|
| A-0871 | CH₂CF₃ | Me | F | 0 | CH₂CH₂SPh |
| A-0872 | CH₂CF₃ | Me | F | 0 | CH₂CH₂CH₂SPh |
| A-0873 | CH₂CF₃ | Me | F | 1 | CH₂CH₂CH₂SPh |
| A-0874 | CH₂CF₃ | Me | F | 0 | CH₂CH(CH₃)SPh |
| A-0875 | CH₂CF₃ | Me | F | 0 | CH(CH₃)CH₂SPh |
| A-0876 | CH₂CF₃ | Me | F | 1 | CH₂CH₂CH₂SPh(4-Cl) |
| A-0877 | CH₂CF₃ | Me | F | 1 | CH₂CH₂CH₂SPh(4-tBu) |
| A-0878 | CH₂CF₃ | Me | F | 1 | CH₂CH₂CH₂SPh(4-F) |
| A-0879 | CH₂CF₃ | Me | F | 0 | CH₂CH₂CH₂SPh(4-Br) |
| A-0880 | CH₂CF₃ | Me | F | 0 | CH₂CH₂CH₂SPh(4-CF₃) |
| A-0881 | CH₂CF₃ | Me | F | 1 | CH₂CH₂CH₂SPh(4-CF₃) |
| A-0882 | CH₂CF₃ | Cl | F | 0 | CH₂CH₂CH₂SPh(4-CF₃) |
| A-0883 | CH₂CF₃ | Me | H | 0 | CH₂CH₂CH₂SPh(4-CF₃) |
| A-0884 | CH₂CF₃ | Me | F | 0 | CH₂CH₂CH₂SPh(3-CF₃) |
| A-0885 | CH₂CF₃ | Me | F | 1 | CH₂CH₂CH₂SPh(3-CF₃) |
| A-0886 | CH₂CF₃ | Me | F | 1 | CH₂CH₂CH₂SPh(3-SCF₃) |
| A-0887 | CH₂CF₃ | Me | F | 1 | CH₂CH₂CH₂SPh(4-SCF₃) |
| A-0888 | CH₂CF₃ | Me | F | 0 | CH₂CH₂CH₂CH₂SPh |
| A-0889 | CH₂CF₃ | Me | F | 0 | CH₂CH₂CH₂CH₂SPh(4-Cl) |
| A-0890 | CH₂CF₃ | Me | F | 0 | CH₂CH₂CH₂CH₂SPh(4-F) |
| A-0891 | CH₂CF₃ | Me | F | 0 | CH₂CH₂CH₂CH₂SPh(4-tBu) |
| A-0892 | CH₂CF₃ | Me | F | 0 | CH₂CH₂CH₂CH₂SPh(3-CF₃) |
| A-0893 | CH₂CF₃ | Me | F | 0 | CH₂CH₂CH₂CH₂CH₂SPh |
| A-0894 | CH₂CF₃ | Me | F | 0 | CH₂CH₂CH₂CH₂CH₂SPh(4-CF₃) |
| A-0895 | CH₂CF₃ | Me | F | 0 | CH₂CH₂CH₂CH₂CH₂SPh(4-Cl) |
| A-0896 | CH₂CF₃ | Me | F | 0 | CH₂CH₂CH₂CH₂CH₂SPh(4-F) |
| A-0897 | CH₂CF₃ | Me | F | 0 | CH₂CH₂S(=O)Ph |
| A-0898 | CH₂CF₃ | Me | F | 0 | CH₂CH₂CH₂S(=O)Ph |
| A-0899 | CH₂CF₃ | Me | F | 1 | CH₂CH₂CH₂S(=O)Ph |
| A-0900 | CH₂CF₃ | Me | F | 0 | CH₂CH₂CH₂S(=O)Ph(4-CF₃) |
| A-0901 | CH₂CF₃ | Me | F | 1 | CH₂CH₂CH₂S(=O)Ph(4-CF₃) |
| A-0902 | CH₂CF₃ | Me | F | 1 | CH₂CH₂CH₂S(=O)Ph(4-F) |
| A-0903 | CH₂CF₃ | Me | F | 1 | CH₂CH₂CH₂S(=O)Ph(4-tBu) |
| A-0904 | CH₂CF₃ | Me | F | 1 | CH₂CH₂CH₂S(=O)₂Ph(4-CF₃) |
| A-0905 | CH₂CF₃ | Me | F | 1 | CH₂CH₂CH₂S(=O)₂Ph(4-Cl) |
| A-0906 | CH₂CF₃ | Me | F | 1 | CH₂CH₂CH₂S(=O)₂Ph(4-F) |
| A-0907 | CH₂CF₃ | Me | F | 0 | CH₂CH₂CH₂CH₂S(=O)₂Ph |
| A-0908 | CH₂CF₃ | Cl | F | 0 | CH₂CH₂CH₂CH₂S(=O)₂Ph |
| A-0909 | CH₂CF₃ | Cl | F | 1 | CH₂CH₂CH₂CH₂S(=O)₂Ph |
| A-0910 | CH₂CF₃ | Me | F | 0 | CH₂CH₂CH₂CH₂S(=O)₂Ph(4-CF₃) |

TABLE 24

| Compound No. | R¹ | R² | R³ | n | R⁴ |
|---|---|---|---|---|---|
| A-0911 | CH₂CF₃ | Me | F | 0 | CH₂CH₂CH₂CH₂S(=O)₂Ph(4-Cl) |
| A-0912 | CH₂CF₃ | Me | F | 0 | CH₂CH₂SCH₂Ph |

TABLE 24-continued

| Compound No. | R$^1$ | R$^2$ | R$^3$ | n | R$^4$ |
|---|---|---|---|---|---|
| A-0913 | CH$_2$CF$_3$ | Me | F | 0 | CH$_2$CH$_2$CH$_2$SCH$_2$Ph |
| A-0914 | CH$_2$CF$_3$ | Cl | F | 0 | CH$_2$CH$_2$CH$_2$SCH$_2$Ph |
| A-0915 | CH$_2$CF$_3$ | Me | Cl | 0 | CH$_2$CH$_2$CH$_2$SCH$_2$Ph |
| A-0916 | CH$_2$CF$_3$ | CN | F | 0 | CH$_2$CH$_2$CH$_2$SCH$_2$Ph |
| A-0917 | CH$_2$CF$_3$ | Me | H | 0 | CH$_2$CH$_2$CH$_2$SCH$_2$Ph |
| A-0918 | CH$_2$CF$_3$ | Me | F | 1 | CH$_2$CH$_2$CH$_2$SCH$_2$Ph |
| A-0919 | CH$_2$CF$_3$ | Me | F | 0 | CH$_2$CH$_2$CH$_2$SCH$_2$Ph(2-Cl) |
| A-0920 | CH$_2$CF$_3$ | Me | F | 0 | CH$_2$CH$_2$CH$_2$SCH$_2$Ph(3-Cl) |
| A-0921 | CH$_2$CF$_3$ | Me | F | 0 | CH$_2$CH$_2$CH$_2$SCH$_2$Ph(4-Cl) |
| A-0922 | CH$_2$CF$_3$ | Me | F | 1 | CH$_2$CH$_2$CH$_2$SCH$_2$Ph(4-Cl) |
| A-0923 | CH$_2$CF$_3$ | Me | F | 0 | CH$_2$CH$_2$CH$_2$SCH$_2$Ph(4-CF$_3$) |
| A-0924 | CH$_2$CF$_3$ | Me | F | 1 | CH$_2$CH$_2$CH$_2$SCH$_2$Ph(4-CF$_3$) |
| A-0925 | CH$_2$CF$_3$ | Me | F | 1 | CH$_2$CH$_2$CH$_2$SCH$_2$Ph(3-CF$_3$) |
| A-0926 | CH$_2$CF$_3$ | Me | F | 0 | CH$_2$CH$_2$CH$_2$SCH$_2$Ph(4-NO$_2$) |
| A-0927 | CH$_2$CF$_3$ | Me | F | 1 | CH$_2$CH$_2$CH$_2$SCH$_2$Ph(2-SCF$_3$) |
| A-0928 | CH$_2$CF$_3$ | Me | F | 0 | CH$_2$CH$_2$CH$_2$CH$_2$SCH$_2$Ph |
| A-0929 | CH$_2$CF$_3$ | Me | F | 0 | CH$_2$CH$_2$CH$_2$CH$_2$SCH$_2$Ph(4-CF$_3$) |
| A-0930 | CH$_2$CF$_3$ | Me | F | 0 | CH$_2$CH$_2$CH$_2$CH$_2$SCH$_2$Ph(4-Cl) |
| A-0931 | CH$_2$CF$_3$ | Me | F | 0 | CH$_2$CH$_2$CH$_2$CH$_2$SCH$_2$Ph(4-CN) |
| A-0932 | CH$_2$CF$_3$ | Me | F | 0 | CH$_2$CH$_2$CH$_2$CH$_2$CH$_2$SCH$_2$Ph |
| A-0933 | CH$_2$CF$_3$ | Me | F | 0 | CH$_2$CH$_2$SCH$_2$CH$_2$Ph |
| A-0934 | CH$_2$CF$_3$ | Me | F | 0 | CH$_2$CH$_2$SCH(Me)Ph |
| A-0935 | CH$_2$CF$_3$ | Me | F | 0 | CH$_2$CH$_2$CH$_2$SCH$_2$CH$_2$Ph |
| A-0936 | CH$_2$CF$_3$ | Me | F | 0 | CH$_2$CH$_2$CH$_2$SCH(Me)Ph |
| A-0937 | CH$_2$CF$_3$ | Me | F | 0 | CH$_2$CH$_2$CH$_2$CH$_2$SCH$_2$CH$_2$Ph |
| A-0938 | CH$_2$CF$_3$ | Me | F | 0 | CH$_2$CH$_2$CH$_2$CH$_2$SCH(Me)Ph |
| A-0939 | CH$_2$CF$_3$ | Me | F | 0 | CH$_2$CH$_2$S(=O)CH$_2$Ph(4-CF$_3$) |
| A-0940 | CH$_2$CF$_3$ | Me | F | 0 | CH$_2$CH$_2$CH$_2$S(=O)CH$_2$Ph |
| A-0941 | CH$_2$CF$_3$ | Me | F | 0 | CH$_2$CH$_2$CH$_2$S(=O)CH$_2$Ph(4-CF$_3$) |
| A-0942 | CH$_2$CF$_3$ | Me | F | 1 | CH$_2$CH$_2$CH$_2$S(=O)CH$_2$Ph(4-Cl) |
| A-0943 | CH$_2$CF$_3$ | Me | F | 1 | CH$_2$CH$_2$CH$_2$S(=O)CH$_2$Ph(2-SCF$_3$) |
| A-0944 | CH$_2$CF$_3$ | Me | F | 0 | CH$_2$CH$_2$CH$_2$S(=O)CH$_2$Ph(4-SCF$_3$) |
| A-0945 | CH$_2$CF$_3$ | Me | F | 0 | CH$_2$CH$_2$CH$_2$CH$_2$S(=O)CH$_2$Ph(4-CF$_3$) |
| A-0946 | CH$_2$CF$_3$ | Me | F | 0 | CH$_2$CH$_2$CH$_2$CH$_2$CH$_2$S(=O)CH$_2$Ph(4-CF$_3$) |
| A-0947 | CH$_2$CF$_3$ | Me | F | 0 | CH$_2$CH$_2$S(=O)$_2$CH$_2$Ph(4-CF$_3$) |
| A-0948 | CH$_2$CF$_3$ | Me | F | 0 | CH$_2$CH$_2$CH$_2$S(=O)$_2$CH$_2$Ph |
| A-0949 | CH$_2$CF$_3$ | Me | F | 0 | CH$_2$CH$_2$CH$_2$S(=O)$_2$CH$_2$Ph(4-CF$_3$) |
| A-0950 | CH$_2$CF$_3$ | Me | F | 1 | CH$_2$CH$_2$CH$_2$S(=O)$_2$CH$_2$Ph(4-Cl) |

TABLE 25

| Compound No. | R$^1$ | R$^2$ | R$^3$ | n | R$^4$ |
|---|---|---|---|---|---|
| A-0951 | CH$_2$CF$_3$ | Me | F | 0 | CH$_2$CH$_2$CH$_2$CH$_2$S(=O)$_2$CH$_2$Ph(4-CF$_3$) |
| A-0952 | CH$_2$CF$_3$ | Me | F | 0 | CH$_2$CH$_2$CH$_2$CH$_2$CH$_2$S(=O)$_2$CH$_2$Ph(4-CF$_3$) |
| A-0953 | CH$_2$CF$_3$ | Me | F | 0 | CH$_2$CH$_2$OPh(4-CF$_3$) |
| A-0954 | CH$_2$CF$_3$ | Me | F | 0 | CH$_2$CH$_2$CH$_2$OPh |
| A-0955 | CH$_2$CF$_3$ | Me | F | 0 | CH$_2$CH$_2$CH$_2$OPh(4-Cl) |
| A-0956 | CH$_2$CF$_3$ | Cl | F | 0 | CH$_2$CH$_2$CH$_2$OPh(4-CF$_3$) |
| A-0957 | CH$_2$CF$_3$ | Cl | F | 1 | CH$_2$CH$_2$CH$_2$OPh(4-CF$_3$) |
| A-0958 | CH$_2$CF$_3$ | Me | F | 0 | CH$_2$CH$_2$CH$_2$OPh(4-CF$_3$) |
| A-0959 | CH$_2$CF$_3$ | Me | F | 0 | CH$_2$CH$_2$CH$_2$OPh(4-OCF$_3$) |
| A-0960 | CH$_2$CF$_3$ | Me | F | 1 | CH$_2$CH$_2$CH$_2$OPh(4-OCF$_3$) |
| A-0961 | CH$_2$CF$_3$ | Me | F | 0 | CH$_2$CH$_2$CH$_2$CH$_2$OPh(4-CF$_3$) |
| A-0962 | CH$_2$CF$_3$ | Me | H | 0 | CH$_2$CH$_2$OCH$_2$Ph |
| A-0963 | CH$_2$CF$_3$ | Me | H | 0 | CH$_2$CH$_2$CH$_2$OCH$_2$Ph |
| A-0964 | CH$_2$CF$_3$ | Me | H | 1 | CH$_2$CH$_2$CH$_2$OCH$_2$Ph |
| A-0965 | CH$_2$CF$_3$ | Me | F | 0 | CH$_2$CH$_2$CH$_2$OCH$_2$Ph |
| A-0966 | CH$_2$CF$_3$ | Me | F | 1 | CH$_2$CH$_2$CH$_2$OCH$_2$Ph |
| A-0967 | CH$_2$CF$_3$ | Me | F | 0 | CH$_2$CH$_2$CH$_2$CH$_2$OCH$_2$Ph |
| A-0968 | CH$_2$CF$_3$ | Me | F | 0 | CH$_2$CH$_2$ON=C(Me)CF$_3$ |
| A-0969 | CH$_2$CF$_3$ | Me | F | 1 | CH$_2$CH$_2$ON=C(Me)CF$_3$ |
| A-0970 | CH$_2$CF$_3$ | Me | F | 0 | CH$_2$CH$_2$CH$_2$ON=CHtBu |
| A-0971 | CH$_2$CF$_3$ | Me | F | 1 | CH$_2$CH$_2$CH$_2$ON=CHtBu |
| A-0972 | CH$_2$CF$_3$ | Me | F | 0 | CH$_2$CH$_2$CH$_2$ON=C(Me)CF$_3$ |
| A-0973 | CH$_2$CF$_3$ | Me | F | 1 | CH$_2$CH$_2$CH$_2$ON=C(Me)CF$_3$ |
| A-0974 | CH$_2$CF$_3$ | Me | F | 1 | CH$_2$CH(CH$_3$)ON=C(Me)CF$_3$ |
| A-0975 | CH$_2$CF$_3$ | Me | F | 0 | CH$_2$CH$_2$CH$_2$ON=CHCF$_3$ |
| A-0976 | CH$_2$CF$_3$ | Me | F | 1 | CH$_2$CH$_2$CH$_2$ON=CHCF$_3$ |
| A-0977 | CH$_2$CF$_3$ | Cl | F | 0 | CH$_2$CH$_2$CH$_2$ON=C(Me)CF$_3$ |
| A-0978 | CH$_2$CF$_3$ | Cl | F | 1 | CH$_2$CH$_2$CH$_2$ON=C(Me)CF$_3$ |
| A-0979 | CH$_2$CF$_3$ | Me | F | 0 | CH$_2$CH$_2$CH$_2$ON=C(Me)CCl$_3$ |
| A-0980 | CH$_2$CF$_3$ | Me | F | 1 | CH$_2$CH$_2$CH$_2$ON=C(Me)CCl$_3$ |
| A-0981 | CH$_2$CF$_3$ | Me | F | 0 | CH$_2$CH$_2$CH$_2$CH$_2$ON=CHCF$_3$ |

TABLE 25-continued

| Compound No. | $R^1$ | $R^2$ | $R^3$ | n | $R^4$ |
|---|---|---|---|---|---|
| A-0982 | $CH_2CF_3$ | Me | F | 1 | $CH_2CH_2CH_2CH_2ON=CHCF_3$ |
| A-0983 | $CH_2CF_3$ | Me | F | 0 | $CH_2CH_2CH_2CH_2ON=C(Me)CF_3$ |
| A-0984 | $CH_2CF_3$ | Cl | F | 0 | $CH_2CH_2CH_2CH_2ON=C(Me)CF_3$ |
| A-0985 | $CH_2CF_3$ | Me | F | 1 | $CH_2CH_2CH_2CH_2ON=C(Me)CF_3$ |
| A-0986 | $CH_2CF_3$ | Me | F | 1 | $CH_2CH_2CH(CH_3)ON=C(Me)CF_3$ |
| A-0987 | $CH_2CF_3$ | Me | F | 1 | $CH_2CH(CH_3)CH_2ON=C(Me)CF_3$ |
| A-0988 | $CH_2CF_3$ | Cl | F | 1 | $CH_2CH_2CH_2CH_2ON=C(Me)CF_3$ |
| A-0989 | $CH_2CF_3$ | Me | F | 0 | $CH_2CH_2CH_2CH_2ON=C(Me)cPr$ |
| A-0990 | $CH_2CF_3$ | Me | F | 1 | $CH_2CH_2CH_2CH_2ON=C(Me)cPr$ |

TABLE 26

| Compound No. | $R^1$ | $R^2$ | $R^3$ | n | $R^4$ |
|---|---|---|---|---|---|
| A-0991 | $CH_2CF_3$ | Me | F | 0 | $CH_2CH_2CH_2CH_2CH_2ON=C(Me)CF_3$ |
| A-0992 | $CH_2CF_3$ | Me | F | 1 | $CH_2CH_2CH_2CH_2CH_2ON=C(Me)CF_3$ |
| A-0993 | $CH_2CF_3$ | Me | F | 1 | $CH_2CH_2CH_2CH(CH_3)ON=C(Me)CF_3$ |
| A-0994 | $CH_2CF_3$ | Me | F | 1 | $CH_2CH_2CH(CH_3)CH_2ON=C(Me)CF_3$ |
| A-0995 | $CH_2CF_3$ | Me | F | 1 | $CH_2CH(CH_3)CH_2CH_2ON=C(Me)CF_3$ |
| A-0996 | $CH_2CF_3$ | Me | F | 0 | 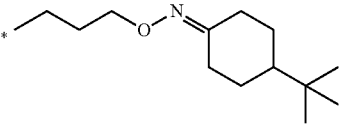 |
| A-0997 | $CH_2CF_3$ | Me | F | 1 | 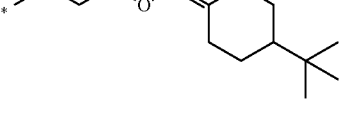 |
| A-0998 | $CH_2CF_3$ | Me | F | 0 | $CH_2CH_2ON=CHPh$ |
| A-0999 | $CH_2CF_3$ | Me | F | 0 | $CH_2CH_2ON=CHPh(4-CF_3)$ |
| A-1000 | $CH_2CF_3$ | Me | F | 1 | $CH_2CH_2ON=CHPh(4-CF_3)$ |
| A-1001 | $CH_2CF_3$ | Me | F | 0 | $CH_2CH_2ON=CHPh(4-SCF_3)$ |
| A-1002 | $CH_2CF_3$ | Me | F | 1 | $CH_2CH_2ON=CHPh(4-SCF_3)$ |
| A-1003 | $CH_2CF_3$ | Me | F | 0 | $CH_2CH_2CH_2ON=CHPh(4-CF_3)$ |
| A-1004 | $CH_2CF_3$ | Me | F | 0 | $CH_2CH_2CH_2ON=CHPh(3-CF_3)$ |
| A-1005 | $CH_2CF_3$ | Me | F | 1 | $CH_2CH_2CH_2ON=CHPh(4-CF_3)$ |
| A-1006 | $CH_2CF_3$ | Me | F | 1 | $CH_2CH_2CH_2ON=CHPh(3-CF_3)$ |
| A-1007 | $CH_2CF_3$ | Me | F | 0 | $CH_2CH_2CH_2ON=CHPh(4-SCF_3)$ |
| A-1008 | $CH_2CF_3$ | Me | F | 1 | $CH_2CH_2CH_2ON=CHPh(4-SCF_3)$ |
| A-1009 | $CH_2CF_3$ | Me | F | 0 | $CH_2CH_2CH_2ON=C(Me)Ph(4-CF_3)$ |
| A-1010 | $CH_2CF_3$ | Me | F | 1 | $CH_2CH_2CH_2ON=C(Me)Ph(4-CF_3)$ |
| A-1011 | $CH_2CF_3$ | Me | F | 0 | $CH_2CH_2CH_2CH_2ON=CHPh(4-SCF_3)$ |
| A-1012 | $CH_2CF_3$ | Me | F | 1 | $CH_2CH_2CH_2CH_2ON=CHPh(4-SCF_3)$ |
| A-1013 | $CH_2CF_3$ | Me | F | 1 | $CH_2CH_2SC(=O)NMe_2$ |
| A-1014 | $CH_2CF_3$ | Me | F | 1 | $CH_2CH_2SC(=O)NHCH_2CF_3$ |
| A-1015 | $CH_2CF_3$ | Me | F | 0 | $CH_2CH_2CH_2SC(=O)NMe_2$ |
| A-1016 | $CH_2CF_3$ | Me | F | 1 | $CH_2CH_2CH_2SC(=O)NMe_2$ |
| A-1017 | $CH_2CF_3$ | Me | F | 1 | $CH_2CH_2CH_2SC(=O)NHtBu$ |
| A-1018 | $CH_2CF_3$ | Me | F | 1 | $CH_2CH_2CH_2CH_2SC(=O)NHCH_2CF_3$ |
| A-1019 | $CH_2CF_3$ | Me | F | 1 | $CH_2CH_2CH_2CH_2CH_2SC(=O)NHtBu$ |
| A-1020 | $CH_2CF_3$ | Cl | F | 0 | $CH_2CH_2CH_2NHC(=O)OtBu$ |
| A-1021 | $CH_2CF_3$ | Cl | F | 1 | $CH_2CH_2CH_2NHC(=O)OtBu$ |
| A-1022 | $CH_2CF_3$ | Me | F | 1 | $CH_2CH_2CH_2NHC(=O)OCH_2CF_3$ |
| A-1023 | $CH_2CF_3$ | Me | F | 1 | $CH_2CH_2CH_2NHC(=O)OCH_2CH_2CF_3$ |
| A-1024 | $CH_2CF_3$ | Cl | F | 0 | $CH_2CH_2CH_2CH_2CH_2OC(=O)Me$ |
| A-1025 | $CH_2CF_3$ | Me | F | 0 | $CH_2CH_2CH_2CH_2CH_2OC(=O)Me$ |
| A-1026 | $CH_2CF_3$ | Me | H | 0 | $CH_2CH_2OC(=O)Ph$ |
| A-1027 | $CH_2CF_3$ | Me | H | 1 | $CH_2CH_2OC(=O)Ph$ |
| A-1028 | $CH_2CF_3$ | Me | F | 0 | $CH_2CH_2OC(=O)Ph(4-CF_3)$ |

TABLE 27

| Compound No. | $R^1$ | $R^2$ | $R^3$ | n | $R^4$ |
|---|---|---|---|---|---|
| A-1029 | $CH_2CF_3$ | Me | F | 0 | $CH_2CH_2CH_2OC(=O)Ph(4-CF_3)$ |
| A-1030 | $CH_2CF_3$ | Me | F | 0 | $CH_2CH_2CH_2CH_2OC(=O)Ph(4-CF_3)$ |
| A-1031 | $CH_2CF_3$ | Me | F | 0 | $CH_2CH_2CH_2CH_2CH_2OC(=O)Ph(4-CF_3)$ |
| A-1032 | $CH_2CF_3$ | Me | F | 0 | $CH_2CH_2OS(=O)_2Me$ |
| A-1033 | $CH_2CF_3$ | Me | F | 0 | $CH_2CH_2CH_2OS(=O)_2Me$ |
| A-1034 | $CH_2CF_3$ | Me | F | 1 | $CH_2CH_2CH_2OS(=O)_2CF_3$ |
| A-1035 | $CH_2CF_3$ | Me | F | 1 | $CH_2CH_2CH_2CH_2OS(=O)_2CF_3$ |
| A-1036 | $CH_2CF_3$ | Me | F | 1 | $CH_2CH_2CH_2CH_2CH_2OS(=O)_2CF_3$ |
| A-1037 | $CH_2CF_3$ | Me | F | 0 | $CH_2CH_2CH_2CH_2CH_2OS(=O)_2CF_2CF_2CF_2CF_3$ |
| A-1038 | $CH_2CF_3$ | Me | F | 1 | $CH_2CH_2OS(=O)CF_3$ |
| A-1039 | $CH_2CF_3$ | Me | F | 1 | $CH_2CH_2CH_2OS(=O)CF_3$ |
| A-1040 | $CH_2CF_3$ | Me | F | 1 | $CH_2CH_2CH_2CH_2OS(=O)CF_3$ |
| A-1041 | $CH_2CF_3$ | Me | F | 1 | $CH_2CH_2CH_2CH_2CH_2OS(=O)CF_3$ |
| A-1042 | $CH_2CF_3$ | Me | F | 0 | $CH_2CH_2CH_2CH_2CH_2CH_2OS(=O)CF_3$ |
| A-1043 | $CH_2CF_3$ | Me | F | 0 | $CH_2CH_2ONH_2$ |
| A-1044 | $CH_2CF_3$ | Me | F | 0 | $CH_2CH_2CH_2ONH_2$ |
| A-1045 | $CH_2CF_3$ | Me | F | 0 | $CH_2CH_2CH_2CH_2ONH_2$ |
| A-1046 | $CH_2CF_3$ | Me | F | 0 | $CH_2CH_2CH_2CH_2CH_2ONH_2$ |
| A-1047 | $CH_2CF_3$ | Me | F | 0 | $CH_2CH_2CH_2CH_2CH_2CH_2ONH_2$ |
| A-1048 | $CH_2CF_3$ | Me | F | 0 | $CH_2C(=O)OEt$ |
| A-1049 | $CH_2CF_3$ | Me | F | 1 | $CH_2CH_2C(=O)OtBu$ |
| A-1050 | $CH_2CF_3$ | Me | F | 0 | $CH_2CH_2CH_2C(=O)OEt$ |
| A-1051 | $CH_2CF_3$ | Me | F | 0 | $CH_2CH_2CH_2C(=O)OtBu$ |
| A-1052 | $CH_2CF_3$ | Me | F | 1 | $CH_2CH_2CH_2C(=O)OtBu$ |
| A-1053 | $CH_2CF_3$ | Me | F | 1 | $CH_2CH_2CH_2C(=O)OtBu$ |
| A-1054 | $CH_2CF_3$ | Me | F | 1 | $CH_2CH_2CH_2CH_2C(=O)OtBu$ |
| A-1055 | $CH_2CF_3$ | Me | F | 1 | $CH_2CH_2CH_2CH_2CH_2C(=O)OtBu$ |

TABLE 27-continued

| Compound No. | $R^1$ | $R^2$ | $R^3$ | n | $R^4$ |
|---|---|---|---|---|---|
| A-1056 | $CH_2CF_3$ | Me | F | 1 | $CH_2CH_2CH_2CH_2CH_2CH_2C(=O)OtBu$ |
| A-1057 | $CH_2CF_3$ | Me | F | 0 | $CH_2CH_2CH_2CH_2CH_2CH_2CH_2C(=O)OEt$ |
| A-1058 | $CH_2CF_3$ | Cl | F | 0 | $CH_2CH_2CH_2CH_2CH_2CH_2CH_2C(=O)OEt$ |
| A-1059 | $CH_2CF_3$ | Cl | F | 0 | $CH_2CH_2CH_2CH_2C(=O)OH$ |
| A-1060 | $CH_2CF_3$ | Cl | Cl | 0 | $CH_2CH_2CH_2CH_2C(=O)OH$ |
| A-1061 | $CH_2CF_3$ | Me | F | 0 | $CH_2CH_2CH_2CH_2CH_2CH_2C(=O)OH$ |
| A-1062 | $CH_2CF_3$ | Me | F | 0 | $CH_2CH_2CH_2C(=O)NH(tert-pentyl)$ |
| A-1063 | $CH_2CF_3$ | Me | F | 0 | $CH_2CH_2C(=O)NHtBu$ |
| A-1064 | $CH_2CF_3$ | Me | F | 0 | $CH_2CH_2C(=O)NHCH_2CF_3$ |
| A-1065 | $CH_2CF_3$ | Me | F | 0 | $CH_2CH_2CH_2C(=O)NHtBu$ |
| A-1066 | $CH_2CF_3$ | Me | F | 0 | $CH_2CH_2CH_2C(=O)NHCH_2CF_3$ |
| A-1067 | $CH_2CF_3$ | Me | F | 0 | $CH_2CH_2CH_2CH_2C(=O)NHtBu$ |
| A-1068 | $CH_2CF_3$ | Me | F | 0 | $CH_2CH_2CH_2CH_2C(=O)NHCH_2CF_3$ |

TABLE 28

| Compound No. | $R^1$ | $R^2$ | $R^3$ | n | $R^4$ |
|---|---|---|---|---|---|
| A-1069 | $CH_2CF_3$ | Me | F | 1 | $CH_2CH_2CH_2C(=O)CF_3$ |
| A-1070 | $CH_2CF_3$ | Cl | F | 1 | $CH_2CH_2CH_2C(=O)CF_3$ |
| A-1071 | $CH_2CF_3$ | Me | F | 1 | $CH_2CH_2CH_2CH_2C(=O)CF_3$ |
| A-1072 | $CH_2CF_3$ | Cl | F | 0 | $CH_2CH_2CH_2CH_2C(=O)CF_3$ |
| A-1073 | $CH_2CF_3$ | Cl | F | 1 | $CH_2CH_2CH_2CH_2C(=O)CF_3$ |
| A-1074 | $CH_2CF_3$ | Cl | Cl | 0 | $CH_2CH_2CH_2CH_2C(=O)CF_3$ |
| A-1075 | $CH_2CF_3$ | Cl | Cl | 1 | $CH_2CH_2CH_2CH_2C(=O)CF_3$ |
| A-1076 | $CH_2CF_3$ | Me | Me | 1 | $CH_2CH_2CH_2CH_2C(=O)CF_3$ |
| A-1077 | $CH_2CF_3$ | Me | F | 1 | $CH_2CH_2CH_2CH_2CH_2C(=O)CF_3$ |
| A-1078 | $CH_2CF_3$ | Cl | F | 1 | $CH_2CH_2CH_2CH_2CH_2C(=O)CF_3$ |
| A-1079 | $CH_2CF_3$ | Me | F | 0 | $CH_2C(=O)Ph(4-Cl)$ |
| A-1080 | $CH_2CF_3$ | Me | F | 1 | $CH_2C(=O)Ph(4-Cl)$ |
| A-1081 | $CH_2CF_3$ | Me | F | 0 | $CH_2C(=O)Ph(4-CF_3)$ |
| A-1082 | $CH_2CF_3$ | Me | F | 1 | $CH_2C(=O)Ph(4-CF_3)$ |
| A-1083 | $CH_2CF_3$ | Me | F | 0 | $CH_2CH_2C(=O)Ph(4-CF_3)$ |
| A-1084 | $CH_2CF_3$ | Me | F | 0 | $CH_2CH_2CH_2C(=O)Ph(4-CF_3)$ |
| A-1085 | $CH_2CF_3$ | Me | F | 0 | $CH_2CH_2CH_2CH_2C(=O)Ph(4-CF_3)$ |
| A-1086 | $CH_2CF_3$ | Me | F | 0 | $CH_2CH_2CH_2CH_2CH_2C(=O)Ph(4-CF_3)$ |
| A-1087 | $CH_2CF_3$ | Me | F | 0 | $CH_2CH_2CN$ |
| A-1088 | $CH_2CF_3$ | Me | F | 1 | $CH_2CH_2CN$ |
| A-1089 | $CH_2CF_3$ | Me | F | 1 | $CH_2CH_2CH_2CN$ |
| A-1090 | $CH_2CF_3$ | Me | F | 1 | $CH_2CH_2CH_2CH_2CN$ |
| A-1091 | $CH_2CF_3$ | Me | F | 1 | $CH_2CH_2CH_2CH_2CH_2CN$ |
| A-1092 | $CH_2CF_3$ | Me | F | 1 | cPr |
| A-1093 | $CH_2CF_3$ | Me | F | 0 | cPen |
| A-1094 | $CH_2CF_3$ | Me | F | 1 | cPen |
| A-1095 | $CH_2CF_3$ | Me | F | 0 | cHex |
| A-1096 | $CH_2CF_3$ | Me | F | 1 | cHex |
| A-1097 | $CH_2CF_3$ | CN | F | 0 | cHex |
| A-1098 | $CH_2CF_3$ | CN | F | 1 | cHex |
| A-1099 | $CH_2CF_3$ | Me | F | 0 | $CH_2CH_2NH_2$ |
| A-1100 | $CH_2CF_3$ | Cl | F | 0 | $CH_2CH_2CH_2NH_2$ |
| A-1101 | $CH_2CF_3$ | Me | F | 0 | $CH_2CH_2CH_2CH_2NH_2$ |
| A-1102 | $CH_2CF_3$ | Cl | F | 1 | $CH_2CH_2CH_2CH_2NH_2$ |
| A-1103 | $CH_2CF_3$ | Me | F | 1 | $CH_2CH_2CH_2N(Me)tBu$ |
| A-1104 | $CH_2CF_3$ | Me | F | 1 | $CH_2CH_2CH_2NHCH_2CF_3$ |
| A-1105 | $CH_2CF_3$ | Me | F | 1 | $CH_2CH_2CH_2CH_2N(Me)tBu$ |
| A-1106 | $CH_2CF_3$ | Me | F | 1 | $CH_2CH_2CH_2CH_2NHCH_2CF_3$ |
| A-1107 | $CH_2CF_3$ | Cl | F | 0 | $CH_2CH_2NHC(=O)C(Me)(CF_3)_2$ |
| A-1108 | $CH_2CF_3$ | Cl | F | 1 | $CH_2CH_2NHC(=O)C(Me)(CF_3)_2$ |

TABLE 29

| Compound No. | $R^1$ | $R^2$ | $R^3$ | n | $R^4$ |
|---|---|---|---|---|---|
| A-1109 | $CH_2CF_3$ | Me | F | 1 | $CH_2CH_2CH_2N(Me)C(=O)tBu$ |
| A-1110 | $CH_2CF_3$ | Me | F | 1 | $CH_2CH_2CH_2NHC(=O)CH_2CF_3$ |
| A-1111 | $CH_2CF_3$ | Me | F | 0 | $CH_2CH_2CH_2CH_2NHC(=O)CH(CH_3)_2$ |
| A-1112 | $CH_2CF_3$ | Me | F | 0 | $CH_2CH_2CH_2CH_2NHC(=O)tBu$ |
| A-1113 | $CH_2CF_3$ | Me | F | 1 | $CH_2CH_2CH_2CH_2NHC(=O)tBu$ |
| A-1114 | $CH_2CF_3$ | Me | F | 1 | $CH_2CH_2CH_2CH_2NHC(=O)CH_2tBu$ |

TABLE 29-continued

| Compound No. | R¹ | R² | R³ | n | R⁴ |
|---|---|---|---|---|---|
| A-1115 | CH₂CF₃ | Me | F | 1 | CH₂CH₂CH₂CH₂N(Me)C(=O)tBu |
| A-1116 | CH₂CF₃ | Me | F | 0 | CH₂CH₂CH₂CH₂NHC(=O)CF₃ |
| A-1117 | CH₂CF₃ | Me | F | 1 | CH₂CH₂CH₂CH₂NHC(=O)CF₃ |
| A-1118 | CH₂CF₃ | Me | F | 1 | CH₂CH₂CH₂CH₂NHC(=O)CH₂CF₃ |
| A-1119 | CH₂CF₃ | Cl | F | 1 | CH₂CH₂CH₂CH₂NHC(=O)CH₂CF₃ |
| A-1120 | CH₂CF₃ | Me | F | 1 | CH₂CH₂CH₂CH₂NHC(=O)CCl₃ |
| A-1121 | CH₂CF₃ | Me | F | 1 | CH₂CH₂CH₂CH₂NHC(=O)CF(CF₃)₂ |
| A-1122 | CH₂CF₃ | Me | F | 0 | CH₂CH₂CH₂CH₂NHC(=O)Ph |
| A-1123 | CH₂CF₃ | Me | F | 1 | CH₂CH₂CH₂CH₂NHC(=O)Ph |
| A-1124 | CH₂CF₃ | Me | F | 1 | CH₂CH₂CH₂CH₂NHC(=O)OCH(CH₃)₂ |
| A-1125 | CH₂CF₃ | Me | F | 0 | CH₂CH₂CH₂CH₂NHC(=O)OtBu |
| A-1126 | CH₂CF₃ | Me | F | 1 | CH₂CH₂CH₂CH₂NHC(=O)OtBu |
| A-1127 | CH₂CF₃ | Me | F | 0 | CH₂CH₂CH₂CH₂NHC(=O)OCH₂CCl₃ |
| A-1128 | CH₂CF₃ | Me | F | 1 | CH₂CH₂CH₂CH₂NHC(=O)OCH₂CCl₃ |
| A-1129 | CH₂CF₃ | Me | F | 1 | CH₂CH₂CH₂CH₂NHC(=O)OCH₂CF₃ |
| A-1130 | CH₂CF₃ | Me | F | 0 | CH₂CH₂CH₂CH₂NHC(=O)NHEt |
| A-1131 | CH₂CF₃ | Me | F | 0 | CH₂CH₂CH₂CH₂NHC(=O)NHtBu |
| A-1132 | CH₂CF₃ | Me | F | 1 | CH₂CH₂CH₂CH₂NHC(=O)NHtBu |
| A-1133 | CH₂CF₃ | Me | F | 1 | CH₂CH₂CH₂CH₂NHC(=O)NHCH₂CCl₃ |
| A-1134 | CH₂CF₃ | Me | F | 1 | CH₂CH₂CH₂CH₂NHC(=O)NHCH₂CH₂F |
| A-1135 | CH₂CF₃ | Me | F | 1 | CH₂CH₂CH₂CH₂NHC(=O)NHCH₂CF₃ |
| A-1136 | CH₂CF₃ | Me | F | 0 | CH₂CH₂NHS(=O)₂CF₃ |
| A-1137 | CH₂CF₃ | Me | F | 1 | CH₂CH₂NHS(=O)₂CF₃ |
| A-1138 | CH₂CF₃ | Cl | F | 0 | CH₂CH₂NHS(=O)₂CF₃ |
| A-1139 | CH₂CF₃ | Cl | F | 1 | CH₂CH₂NHS(=O)₂CF₃ |
| A-1140 | CH₂CF₃ | Me | F | 0 | CH₂CH₂CH₂NHS(=O)₂CF₃ |
| A-1141 | CH₂CF₃ | Me | F | 1 | CH₂CH₂CH₂NHS(=O)₂CF₃ |
| A-1142 | CH₂CF₃ | Cl | F | 0 | CH₂CH₂CH₂NHS(=O)₂CF₃ |
| A-1143 | CH₂CF₃ | Cl | F | 1 | CH₂CH₂CH₂NHS(=O)₂CF₃ |
| A-1144 | CH₂CF₃ | Me | Cl | 1 | CH₂CH₂CH₂NHS(=O)₂CF₃ |
| A-1145 | CH₂CF₃ | CN | F | 1 | CH₂CH₂CH₂NHS(=O)₂CF₃ |
| A-1146 | CH₂CF₃ | CN | F | 1 | CH₂CH₂CH₂NHS(=O)₂CHF₂ |
| A-1147 | CH₂CF₃ | Me | F | 1 | CH₂CH₂CH₂NHS(=O)₂CF(CF₃)₂ |
| A-1148 | CH₂CF₃ | Cl | F | 1 | CH₂CH₂CH₂NHS(=O)₂CF(CF₃)₂ |

TABLE 30

| Compound No. | R¹ | R² | R³ | n | R⁴ |
|---|---|---|---|---|---|
| A-1149 | CH₂CF₃ | Me | F | 0 | CH₂CH₂CH₂CH₂NHS(=O)₂CH₃ |
| A-1150 | CH₂CF₃ | Me | F | 1 | CH₂CH₂CH₂CH₂NHS(=O)₂CH₃ |
| A-1151 | CH₂CF₃ | Cl | F | 0 | CH₂CH₂CH₂CH₂NHS(=O)₂CH₃ |
| A-1152 | CH₂CF₃ | Cl | F | 1 | CH₂CH₂CH₂CH₂NHS(=O)₂CH₃ |
| A-1153 | CH₂CF₃ | Cl | F | 1 | CH₂CH₂CH₂CH₂NHS(=O)₂CH(CH₃)₂ |
| A-1154 | CH₂CF₃ | Cl | F | 1 | CH₂CH₂CH₂CH₂NHS(=O)₂CHF₂ |
| A-1155 | CH₂CF₃ | Me | F | 1 | CH₂CH₂CH₂CH₂NHS(=O)₂CHF₂ |
| A-1156 | CH₂CF₃ | Cl | F | 0 | CH₂CH₂CH₂CH₂NHS(=O)₂CF₃ |
| A-1157 | CH₂CF₃ | Cl | F | 1 | CH₂CH₂CH₂CH₂NHS(=O)₂CF₃ |
| A-1158 | CH₂CF₃ | Me | F | 0 | CH₂CH₂CH₂CH₂NHS(=O)₂CF₃ |
| A-1159 | CH₂CF₃ | Me | F | 1 | CH₂CH₂CH₂CH₂NHS(=O)₂CF₃ |
| A-1160 | CH₂CF₃ | Me | Cl | 1 | CH₂CH₂CH₂CH₂NHS(=O)₂CF₃ |
| A-1161 | CH₂CF₃ | Me | H | 1 | CH₂CH₂CH₂CH₂NHS(=O)₂CF₃ |
| A-1162 | CH₂CF₃ | Cl | Cl | 1 | CH₂CH₂CH₂CH₂NHS(=O)₂CF₃ |
| A-1163 | CH₂CF₃ | Me | Me | 1 | CH₂CH₂CH₂CH₂NHS(=O)₂CF₃ |
| A-1164 | CH₂CF₃ | Me | F | 0 | CH₂CH₂CH₂CH₂CH₂NHS(=O)₂CH₃ |
| A-1165 | CH₂CF₃ | Me | F | 1 | CH₂CH₂CH₂CH₂CH₂NHS(=O)₂CH₃ |
| A-1166 | CH₂CF₃ | Me | F | 1 | CH₂CH₂CH₂CH₂CH₂NHS(=O)₂CHF₂ |
| A-1167 | CH₂CF₃ | Me | F | 1 | CH₂CH₂CH₂CH₂CH₂NHS(=O)₂CF₃ |
| A-1168 | CH₂CF₃ | Cl | F | 1 | CH₂CH₂CH₂CH₂CH₂NHS(=O)₂CF₃ |
| A-1169 | CH₂CF₃ | Me | Cl | 1 | CH₂CH₂CH₂CH₂CH₂NHS(=O)₂CF₃ |
| A-1170 | CH₂CF₃ | Cl | Cl | 1 | CH₂CH₂CH₂CH₂CH₂NHS(=O)₂CF₃ |
| A-1171 | CH₂CF₃ | Me | F | 0 | CH₂CH₂CH₂CH₂CH₂NHS(=O)₂Ph |
| A-1172 | CH₂CF₃ | Me | F | 1 | CH₂CH₂CH₂CH₂CH₂NHS(=O)₂Ph |
| A-1173 | CH₂CF₃ | Me | F | 0 | CH₂CH₂CH₂CH₂CH₂NHS(=O)₂Ph(4-CF₃) |
| A-1174 | CH₂CF₃ | Me | F | 1 | CH₂CH₂CH₂CH₂CH₂NHS(=O)₂Ph(4-CF₃) |
| A-1175 | CH₂CF₃ | Me | F | 0 | CH₂CH₂CH₂CH₂CH₂NHS(=O)₂CF₃ |
| A-1176 | CH₂CF₃ | Me | F | 1 | CH₂CH₂N(Me)S(=O)₂CF₃ |
| A-1177 | CH₂CF₃ | Me | F | 0 | CH₂CH₂N(Ac)S(=O)₂CF₃ |
| A-1178 | CH₂CF₃ | Me | F | 1 | CH₂CH₂N(Ac)S(=O)₂CF₃ |
| A-1179 | CH₂CF₃ | Me | F | 1 | CH₂CH₂N(COt)S(=O)₂CF₃ |
| A-1180 | CH₂CF₃ | Me | F | 0 | CH₂CH₂N(CO₂CH₃)S(=O)₂CF₃ |
| A-1181 | CH₂CF₃ | Me | F | 1 | CH₂CH₂N(CO₂CH₃)S(=O)₂CF₃ |
| A-1182 | CH₂CF₃ | Cl | F | 0 | CH₂CH₂N(CO₂CH₃)S(=O)₂CF₃ |
| A-1183 | CH₂CF₃ | Cl | F | 1 | CH₂CH₂N(CO₂CH₃)S(=O)₂CF₃ |

TABLE 30-continued

| Compound No. | R$^1$ | R$^2$ | R$^3$ | n | R$^4$ |
|---|---|---|---|---|---|
| A-1184 | CH$_2$CF$_3$ | Me | F | 1 | CH$_2$CH$_2$CH$_2$N(Me)S(=O)$_2$CF$_3$ |
| A-1185 | CH$_2$CF$_3$ | Me | F | 0 | CH$_2$CH$_2$CH$_2$N(Ac)S(=O)$_2$CF$_3$ |
| A-1186 | CH$_2$CF$_3$ | Me | F | 1 | CH$_2$CH$_2$CH$_2$N(Ac)S(=O)$_2$CF$_3$ |
| A-1187 | CH$_2$CF$_3$ | Cl | F | 1 | CH$_2$CH$_2$CH$_2$N(CO$_2$CH$_3$)S(=O)$_2$CF$_3$ |
| A-1188 | CH$_2$CF$_3$ | Me | F | 1 | CH$_2$CH$_2$CH$_2$N(CO$_2$CH$_3$)S(=O)$_2$CF$_3$ |

TABLE 31

| Compound No. | R1 | R2 | R3 | n | R4 |
|---|---|---|---|---|---|
| A-1189 | CH$_2$CF$_3$ | Me | F | 1 | CH$_2$CH$_2$CH$_2$N(CO$_2$tBu)S(=O)$_2$CF$_3$ |
| A-1190 | CH$_2$CF$_3$ | Me | F | 1 | CH$_2$CH$_2$CH$_2$CH$_2$N(Me)S(=O)$_2$CF$_3$ |
| A-1191 | CH$_2$CF$_3$ | Me | F | 1 | CH$_2$CH$_2$CH$_2$CH$_2$N(Ac)S(=O)$_2$CF$_3$ |
| A-1192 | CH$_2$CF$_3$ | Cl | F | 1 | CH$_2$CH$_2$CH$_2$CH$_2$N(Ac)S(=O)$_2$CF$_3$ |
| A-1193 | CH$_2$CF$_3$ | Cl | F | 1 | CH$_2$CH$_2$CH$_2$CH$_2$N(propionyl)S(=O)$_2$CF$_3$ |
| A-1194 | CH$_2$CF$_3$ | Cl | F | 1 | CH$_2$CH$_2$CH$_2$CH$_2$N(pivaloyl)S(=O)$_2$CF$_3$ |
| A-1195 | CH$_2$CF$_3$ | Me | F | 0 | CH$_2$CH$_2$CH$_2$CH$_2$N(CO$_2$CH$_3$)S(=O)$_2$CF$_3$ |
| A-1196 | CH$_2$CF$_3$ | Me | F | 1 | CH$_2$CH$_2$CH$_2$CH$_2$N(CO$_2$CH$_3$)S(=O)$_2$CF$_3$ |
| A-1197 | CH$_2$CF$_3$ | Cl | F | 1 | CH$_2$CH$_2$CH$_2$CH$_2$N(CO$_2$CH$_3$)S(=O)$_2$CF$_3$ |
| A-1198 | CH$_2$CF$_3$ | Me | F | 1 | CH$_2$CH$_2$CH$_2$CH$_2$N(CO$_2$tBu)S(=O)$_2$CF$_3$ |
| A-1199 | CH$_2$CF$_3$ | Cl | F | 1 | CH$_2$CH$_2$CH$_2$CH$_2$N(CO$_2$tBu)S(=O)$_2$CF$_3$ |
| A-1200 | CH$_2$CF$_3$ | Me | F | 1 | CH$_2$CH$_2$CH$_2$CH$_2$CH$_2$N(Ac)S(=O)$_2$CF$_3$ |
| A-1201 | CH$_2$CF$_3$ | Me | F | 0 | CH$_2$CH$_2$CH$_2$CH$_2$CH$_2$N(CO$_2$CH$_3$)S(=O)$_2$CF$_3$ |
| A-1202 | CH$_2$CF$_3$ | Me | F | 1 | CH$_2$CH$_2$CH$_2$CH$_2$CH$_2$N(CO$_2$CH$_3$)S(=O)$_2$CF$_3$ |
| A-1203 | CH$_2$CF$_3$ | Me | F | 1 | CH$_2$CH$_2$SMe$_3$ |
| A-1204 | CH$_2$CF$_3$ | Cl | F | 1 | CH$_2$CH$_2$SMe$_3$ |
| A-1205 | CH$_2$CF$_3$ | Me | F | 0 | CH$_2$CH$_2$CH$_2$SMe$_3$ |
| A-1206 | CH$_2$CF$_3$ | Me | H | 0 | CH$_2$CH$_2$CH$_2$SMe$_3$ |
| A-1207 | CH$_2$CF$_3$ | Me | F | 1 | CH$_2$CH$_2$CH$_2$SMe$_3$ |
| A-1208 | CH$_2$CF$_3$ | Cl | F | 1 | CH$_2$CH$_2$CH$_2$SMe$_3$ |
| A-1209 | CH$_2$CF$_3$ | Me | H | 1 | CH$_2$CH$_2$CH$_2$SMe$_3$ |
| A-1210 | CH$_2$CF$_3$ | Me | F | 0 | CH$_2$CH$_2$CH$_2$CH$_2$SMe$_3$ |
| A-1211 | CH$_2$CF$_3$ | Me | F | 1 | CH$_2$CH$_2$CH$_2$CH$_2$SMe$_3$ |
| A-1212 | CH$_2$CF$_3$ | Cl | F | 0 | CH$_2$CH$_2$CH$_2$CH$_2$SMe$_3$ |
| A-1213 | CH$_2$CF$_3$ | Cl | F | 1 | CH$_2$CH$_2$CH$_2$CH$_2$SMe$_3$ |
| A-1214 | CH$_2$CF$_3$ | Cl | F | 1 | SO$_2$CH$_2$Ph |
| A-1215 | CH$_2$CF$_3$ | Me | F | 1 | C(=O)Ph |
| A-1216 | CH$_2$CF$_3$ | Me | F | 0 | C(=O)Ph |
| A-1217 | CH$_2$CF$_3$ | Cl | F | 0 | C(=O)Ph |
| A-1218 | CH$_2$CF$_3$ | Cl | F | 1 | C(=O)Ph |

TABLE 32

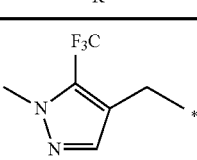

[I]

| Compound No. | R$^1$ | R$^2$ | R$^3$ | n | R$^4$ |
|---|---|---|---|---|---|
| B-0001 | CH$_2$CF$_3$ | Me | F | 0 | 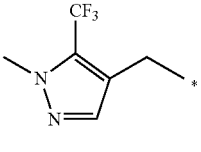 |
| B-0002 | CH$_2$CF$_3$ | Me | F | 1 | 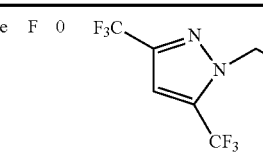 |
| B-0003 | CH$_2$CF$_3$ | Me | F | 0 | 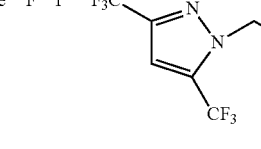 |
| B-0004 | CH$_2$CF$_3$ | Me | F | 1 | (same as B-0003) |

TABLE 32-continued

[I]

| Compound No. | R¹ | R² | R³ | n | R⁴ |
|---|---|---|---|---|---|
| B-0005 | CH₂CF₃ | Me | F | 0 | 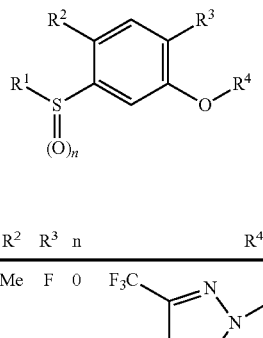 |
| B-0006 | CH₂CF₃ | Me | F | 1 | 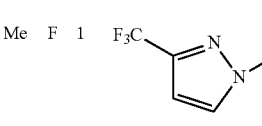 |
| B-0007 | CH₂CF₃ | Me | F | 0 | 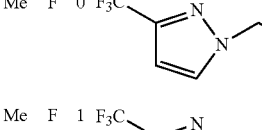 |
| B-0008 | CH₂CF₃ | Me | F | 1 | 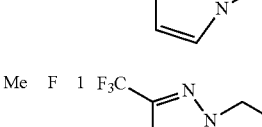 |
| B-0009 | CH₂CF₃ | Me | F | 1 | 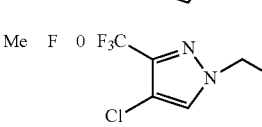 |
| B-0010 | CH₂CF₃ | Me | F | 0 |  |

TABLE 33

| Compound No. | R¹ | R² | R³ | n | R⁴ |
|---|---|---|---|---|---|
| B-0011 | CH₂CF₃ | Me | F | 1 | 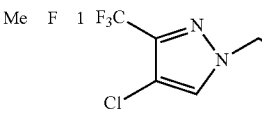 |
| B-0012 | CH₂CF₃ | Me | F | 0 | 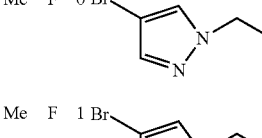 |
| B-0013 | CH₂CF₃ | Me | F | 1 | 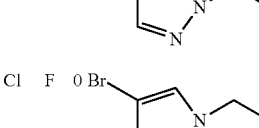 |
| B-0014 | CH₂CF₃ | Cl | F | 0 | 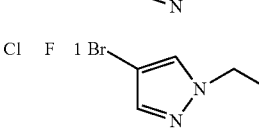 |
| B-0015 | CH₂CF₃ | Cl | F | 1 |  |

TABLE 33-continued

| Compound No. | R¹ | R² | R³ | n | R⁴ |
|---|---|---|---|---|---|
| B-0016 | CH₂CF₃ | Cl | F | 0 | 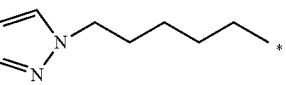 |
| B-0017 | CH₂CF₃ | Me | F | 0 | 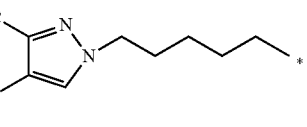 |
| B-0018 | CH₂CF₃ | Me | F | 1 | 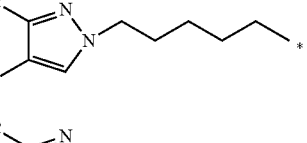 |
| B-0019 | CH₂CF₃ | Me | F | 1 | 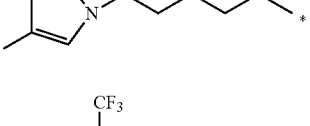 |
| B-0020 | CH₂CF₃ | Me | F | 0 | 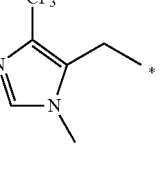 |
| B-0021 | CH₂CF₃ | Me | F | 1 | 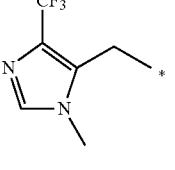 |
| B-0022 | CH₂CF₃ | Me | F | 0 | 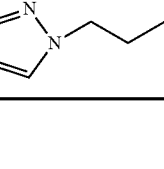 |

TABLE 34

| Compound No. | R¹ | R² | R³ | n | R⁴ |
|---|---|---|---|---|---|
| B-0023 | CH₂CF₃ | Me | F | 1 | 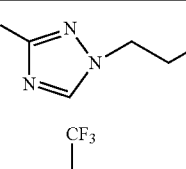 |
| B-0024 | CH₂CF₃ | Me | F | 0 | 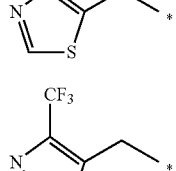 |
| B-0025 | CH₂CF₃ | Me | F | 1 |  |

TABLE 34-continued
| Compound No. | R¹ | R² | R³ | n | R⁴ |
|---|---|---|---|---|---|
| B-0026 | CH₂CF₃ | Me | F | 1 | 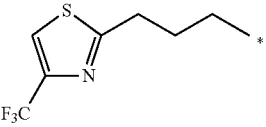 |
| B-0027 | CH₂CF₃ | Me | F | 1 | 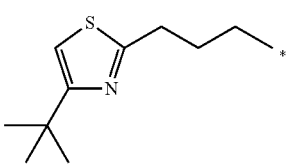 |
| B-0028 | CH₂CF₃ | Me | F | 0 | 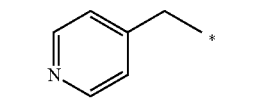 |
| B-0029 | CH₂CF₃ | Me | F | 0 | 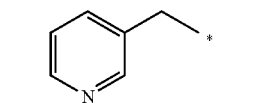 |
| B-0030 | CH₂CF₃ | Me | F | 1 | 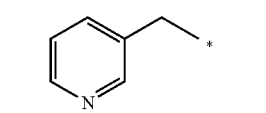 |
| B-0031 | CH₂CF₃ | Me | F | 0 | 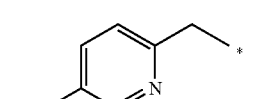 |
| B-0032 | CH₂CF₃ | Me | F | 1 | 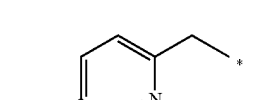 |
| B-0033 | CH₂CF₃ | Me | F | 0 | 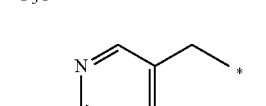 |
TABLE 35
| Compound No. | R¹ | R² | R³ | n | R⁴ |
|---|---|---|---|---|---|
| B-0034 | CH₂CF₃ | Me | F | 1 | 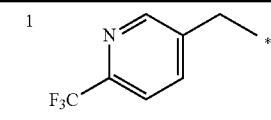 |
| B-0035 | CH₂CF₃ | Me | F | 0 | 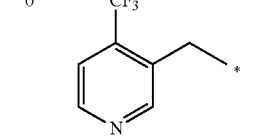 |
| B-0036 | CH₂CF₃ | Me | H | 0 | 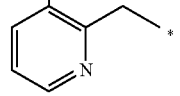 |
| B-0037 | CH₂CF₃ | Me | H | 1 | 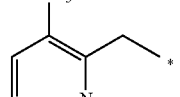 |
| B-0038 | CH₂CF₃ | CHF2 | H | 0 | 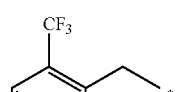 |
| B-0039 | CH₂CF₃ | CHF2 | H | 1 | 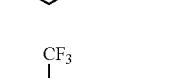 |
| B-0040 | CH₂CF₃ | Me | F | 2 | 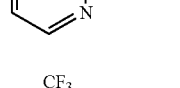 |
| B-0041 | CH₂CF₃ | Me | F | 1 | 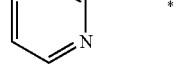 |
| B-0042 | CH₂CF₃ | Me | F | 0 | 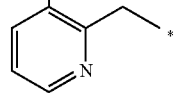 |
| B-0043 | CH₂CF₃ | Cl | F | 0 | 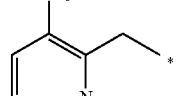 |
| B-0044 | CH₂CF₃ | Cl | F | 1 | 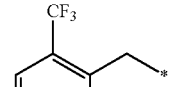 |

TABLE 35-continued

| Compound No. | R¹ | R² | R³ | n | R⁴ |
|---|---|---|---|---|---|
| B-0045 | CH₂CF₃ | CN | F | 0 | 3-CF₃-pyridin-2-ylmethyl |

TABLE 36

| Compound No. | R¹ | R² | R³ | n | R⁴ |
|---|---|---|---|---|---|
| B-0046 | CH₂CF₃ | CN | F | 1 | 3-CF₃-pyridin-2-ylmethyl |
| B-0047 | CH₂CF₃ | Me | F | 1 | 3-NO₂-pyridin-2-ylmethyl |
| B-0048 | CH₂CF₃ | Me | F | 0 | 4-NO₂-pyridin-2-ylmethyl |
| B-0049 | CH₂CF₃ | Me | F | 1 | 4-NO₂-pyridin-2-ylmethyl |
| B-0050 | CH₂CF₃ | Me | F | 1 | 3-CN-pyridin-2-ylmethyl |
| B-0051 | CH₂CF₃ | Me | F | 0 | 6-CF₃-pyridin-2-ylmethyl |
| B-0052 | CH₂CF₃ | Me | F | 1 | 6-CF₃-pyridin-2-ylmethyl |
| B-0053 | CH₂CF₃ | Me | F | 0 | 6-Cl-pyridin-3-ylmethyl |
| B-0054 | CH₂CF₃ | Me | F | 1 | 6-Cl-pyridin-3-ylmethyl |

TABLE 36-continued

| Compound No. | R¹ | R² | R³ | n | R⁴ |
|---|---|---|---|---|---|
| B-0055 | CH₂CF₃ | Me | F | 0 | 3-Cl-5-CF₃-pyridin-2-ylmethyl |
| B-0056 | CH₂CF₃ | Me | F | 1 | 3-Cl-5-CF₃-pyridin-2-ylmethyl |
| B-0057 | CH₂CF₃ | Me | F | 0 | 6-CF₃-pyridin-3-ylbutyl |

TABLE 37

| Compound No. | R1 | R2 | R3 | n | R4 |
|---|---|---|---|---|---|
| B-0058 | CH₂CF₃ | Me | F | 1 | 6-CF₃-pyridin-3-ylbutyl |
| B-0059 | CH₂CF₃ | Me | F | 1 | 3-Cl-5-CF₃-pyridin-2-ylbutyl |
| B-0060 | CH₂CF₃ | Me | F | 0 | 3-Cl-5-CF₃-pyridin-2-ylbutyl |
| B-0061 | CH₂CF₃ | Me | F | 1 | 4-CF₃-pyrimidin-2-ylmethyl |
| B-0062 | CH₂CF₃ | Me | F | 1 | 3-OCHF₂-pyridin-2-ylmethyl |
| B-0063 | CH₂CF₃ | Me | F | 0 | 4-CF₃-pyrimidin-5-ylmethyl |
| B-0064 | CH₂CF₃ | Me | F | 0 | 3-OCHF₂-pyridin-2-ylmethyl |

TABLE 37-continued

| Compound No. | R1 | R2 | R3 | n | R4 |
|---|---|---|---|---|---|
| B-0065 | CH₂CF₃ | Me | F | 1 | 3-CF₃-pyridin-2-yl N-oxide-CH₂-* |
| B-0066 | CH₂CF₃ | Me | F | 0 | (tetrahydrofuran-3-yl)-CH₂-* |
| B-0067 | CH₂CF₃ | Me | F | 1 | (tetrahydrofuran-3-yl)-CH₂-* |
| B-0068 | CH₂CF₃ | Cl | F | 0 | 5-CF₃-pyridin-2-yl-O-CH₂CH₂-* |
| B-0069 | CH₂CF₃ | Cl | F | 1 | 5-CF₃-pyridin-2-yl-O-CH₂CH₂-* |

TABLE 38

| Compound No. | R¹ | R² | R³ | n | R⁴ |
|---|---|---|---|---|---|
| B-0070 | CH₂CF₃ | Me | F | 0 | 5-CF₃-pyridin-2-yl-O-CH₂CH₂-* |
| B-0071 | CH₂CF₃ | Me | F | 1 | 5-CF₃-pyridin-2-yl-O-CH₂CH₂-* |
| B-0072 | CH₂CF₃ | Cl | F | 0 | 5-CF₃-pyridin-2-yl-O-(CH₂)₃-* |
| B-0073 | CH₂CF₃ | Cl | F | 1 | 5-CF₃-pyridin-2-yl-O-(CH₂)₃-* |
| B-0074 | CH₂CF₃ | Me | F | 0 | 5-CF₃-pyridin-2-yl-O-(CH₂)₃-* |
| B-0075 | CH₂CF₃ | Me | F | 1 | 5-CF₃-pyridin-2-yl-O-(CH₂)₃-* |
| B-0076 | CH₂CF₃ | Me | F | 0 | 5-CF₃-pyridin-2-yl-O-(CH₂)₄-* |
| B-0077 | CH₂CF₃ | Me | F | 1 | 5-CF₃-pyridin-2-yl-O-(CH₂)₄-* |

TABLE 38-continued
| Compound No. | R¹ | R² | R³ | n | R⁴ |
|---|---|---|---|---|---|
| B-0078 | $CH_2CF_3$ | Cl | F | 0 | 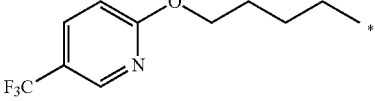 |
| B-0079 | $CH_2CF_3$ | Cl | F | 1 | 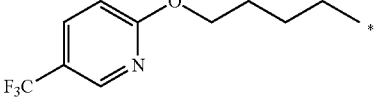 |
| B-0080 | $CH_2CF_3$ | Cl | F | 0 | 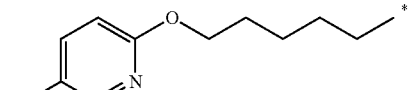 |
| B-0081 | $CH_2CF_3$ | Cl | F | 1 | 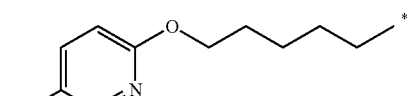 |
TABLE 39
| Compound No. | R¹ | R² | R³ | n | R⁴ |
|---|---|---|---|---|---|
| B-0082 | $CH_2CF_3$ | Me | F | 0 | 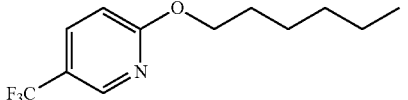 |
| B-0083 | $CH_2CF_3$ | Me | F | 1 | 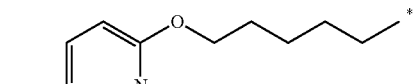 |
| B-0084 | $CH_2CF_3$ | Cl | F | 0 | 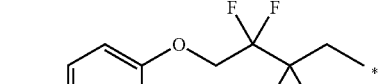 |
| B-0085 | $CH_2CF_3$ | Cl | F | 1 | 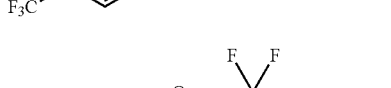 |
| B-0086 | $CH_2CF_3$ | Me | F | 0 |  |
| B-0087 | $CH_2CF_3$ | Me | F | 1 |  |

TABLE 39-continued
| Compound No. | R¹ | R² | R³ | n | R⁴ |
|---|---|---|---|---|---|
| B-0088 | $CH_2CF_3$ | Me | F | 0 | 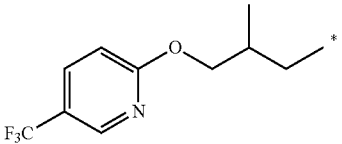 |
| B-0089 | $CH_2CF_3$ | Me | F | 1 | 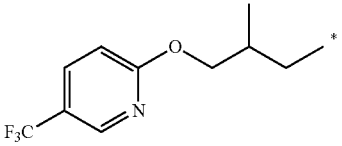 |
| B-0090 | $CH_2CF_3$ | Cl | F | 0 | 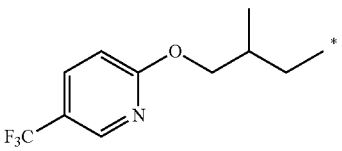 |
| B-0091 | $CH_2CF_3$ | Cl | F | 1 | 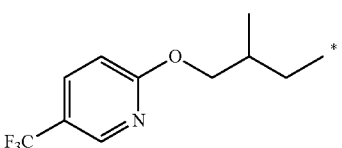 |
| B-0092 | $CH_2CF_3$ | Cl | F | 1 | 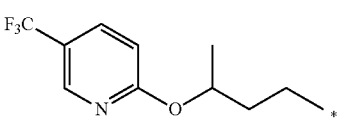 |
| B-0093 | $CH_2CF_3$ | Me | F | 0 | 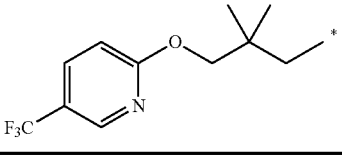 |
TABLE 40
| Compound No. | R¹ | R² | R³ | n | R⁴ |
|---|---|---|---|---|---|
| B-0094 | $CH_2CF_3$ | Cl | F | 0 | 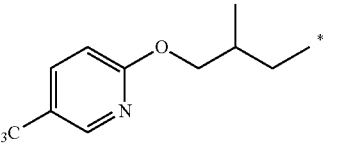 |
| B-0095 | $CH_2CF_3$ | Cl | F | 1 | 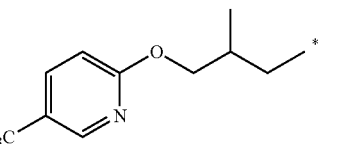 |
| B-0096 | $CH_2CF_3$ | Me | F | 0 | 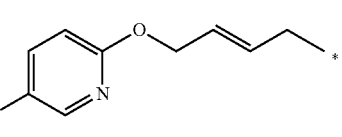 |

TABLE 40-continued

| Compound No. | R¹ | R² | R³ | n | R⁴ |
|---|---|---|---|---|---|
| B-0097 | $CH_2CF_3$ | Me | F | 0 | 5-trifluoromethyl-pyridin-2-yloxy-but-2-ynyl |
| B-0098 | $CH_2CF_3$ | Me | F | 1 | 5-trifluoromethyl-pyridin-2-yloxy-but-2-ynyl |
| B-0099 | $CH_2CF_3$ | Me | F | 0 | 3-chloro-5-trifluoromethyl-pyridin-2-yloxy-propyl |
| B-0100 | $CH_2CF_3$ | Me | F | 1 | 3-chloro-5-trifluoromethyl-pyridin-2-yloxy-propyl |
| B-0101 | $CH_2CF_3$ | Me | F | 0 | 3-chloro-5-trifluoromethyl-pyridin-2-yloxy-butyl |
| B-0102 | $CH_2CF_3$ | Cl | F | 0 | 3-chloro-5-trifluoromethyl-pyridin-2-yloxy-butyl |
| B-0103 | $CH_2CF_3$ | Cl | F | 1 | 3-chloro-5-trifluoromethyl-pyridin-2-yloxy-butyl |
| B-0104 | $CH_2CF_3$ | Me | F | 0 | 3-chloro-5-trifluoromethyl-pyridin-2-yloxy-pentyl |
| B-0105 | $CH_2CF_3$ | Me | F | 1 | 3-chloro-5-trifluoromethyl-pyridin-2-yloxy-pentyl |

TABLE 41
| Compound No. | R¹ | R² | R³ | n | R⁴ |
|---|---|---|---|---|---|
| B-0106 | CH₂CF₃ | Cl | F | 0 | 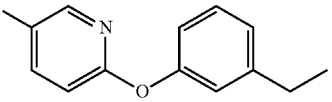 |
| B-0107 | CH₂CF₃ | Cl | F | 1 | 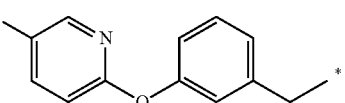 |
| B-0108 | CH₂CF₃ | Me | F | 0 | 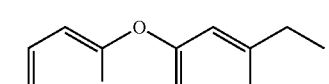 |
| B-0109 | CH₂CF₃ | Me | F | 0 | 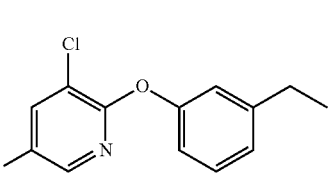 |
| B-0110 | CH₂CF₃ | Me | F | 1 | 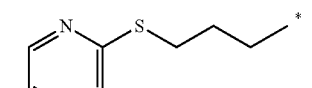 |
| B-0111 | CH₂CF₃ | Me | F | 1 | 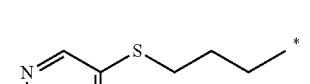 |
| B-0112 | CH₂CF₃ | Me | F | 1 | 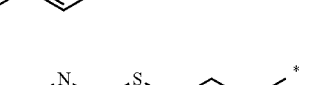 |
| B-0113 | CH₂CF₃ | Me | F | 0 | 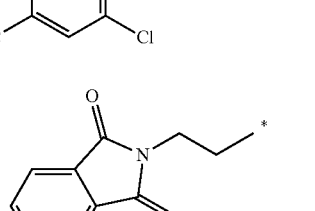 |
| B-0114 | CH₂CF₃ | Cl | F | 0 | 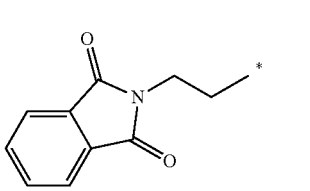 |
| B-0115 | CH₂CF₃ | Me | F | 0 | 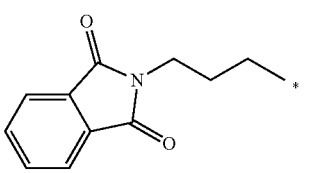 |

TABLE 41-continued

| Compound No. | R¹ | R² | R³ | n | R⁴ |
|---|---|---|---|---|---|
| B-0116 | CH₂CF₃ | Cl | F | 0 | 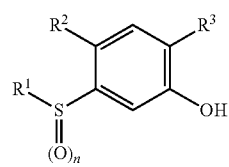 |
| B-0117 | CH₂CF₃ | Cl | F | 0 | 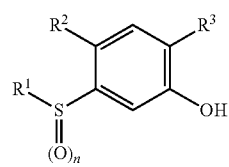 |

TABLE 42

[I']

$$\text{R}^2\text{-}\text{C}_6\text{H}_2(\text{R}^3)(\text{OH})\text{-}\text{S}(\text{O})_n\text{-}\text{R}^1$$

| Compound No. | R1 | R2 | R3 | n |
|---|---|---|---|---|
| C-0001 | CH₂CF₃ | Me | F | 0 |
| C-0002 | CH₂CF₃ | Me | F | 1 |
| C-0003 | CH₂CF₃ | Cl | F | 0 |
| C-0004 | CH₂CF₃ | Cl | F | 1 |
| C-0005 | CH₂CF₃ | Me | H | 0 |
| C-0006 | CH₂CF₃ | Me | H | 1 |
| C-0007 | CH₂CF₃ | Me | Cl | 0 |
| C-0008 | CH₂CF₃ | Me | Cl | 1 |
| C-0009 | CH₂CF₃ | Cl | H | 0 |
| C-0010 | CH₂CF₃ | Cl | H | 1 |
| C-0011 | CH₂CF₃ | CN | F | 0 |
| C-0012 | CH₂CF₃ | CN | F | 1 |
| C-0013 | CH₂CF₃ | OMe | F | 0 |
| C-0014 | CH₂CF₃ | Cl | Cl | 0 |
| C-0015 | CH₂CF₃ | Cl | Cl | 1 |
| C-0016 | CH₂CF₃ | Cl | F | 2 |
| C-0017 | CH₂CF₃ | Me | Me | 0 |
| C-0018 | CH₂CF₃ | Me | Me | 1 |

The present compound represented by the general formula [I] and general formula [I'] can be produced by the methods shown below, but the production methods of the present compound are not restricted thereto. Incidentally, for example, "the compound represented by the general formula [I-1]", "the compound represented by formula [I-1]" and "the compound [I-1]", mentioned below have the same meaning.

<Production Method 1>

Of the present compounds, a compound represented by the general formula [I-1] can be produced, for example, by the following method.

[Formula 3]

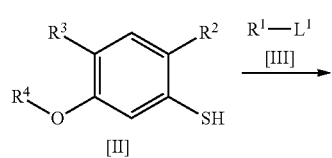

(In the above formula, $L^1$ is halogen atom, $C_1$~$C_6$ alkylsulfonyloxy group, trifluoromethanesulfonyloxy group, nonafluorobutylsulfonyloxy group, phenylsulfonyloxy group, 4-toluenesulfonyloxy group or $SO_2M$; M is alkali metal or alkaline earth metal, and the alkali metal is preferably sodium or potassium; and $R^1$, $R^2$, $R^3$ and $R^4$ each have the same meaning as given above.)

Thus, the compound represented by the general formula [I-1] can be produced by reacting a compound represented by the general formula [II] with a compound represented by the general formula [III] in an appropriate solvent in the presence or absence of an appropriate base in the presence or absence of an appropriate radical initiator.

The amount of the compound [III] used in the present reaction is selected appropriately, and ordinarily in a range of 1.0 to 5.0 mols and is preferably 1.0 to 2.0 mols relative to 1 mol of the compound [II].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; a halogenated hydrocarbon such as dichloromethane, chloroform, 1,2-dichloroethane or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a nitrile such as acetonitrile, propionitrile or the like; an ester such as ethyl acetate, ethyl propionate or the like; an aliphatic hydrocarbon such as pentane, hexane, cyclohexane, heptane or the like; a pyridine such as pyridine, picoline or the like; water; and a mixture thereof. Incidentally, the use amount of the solvent is 0.1 to 100 liters, preferably 0.3 to 5 liters relative to 1 mol of the compound [II].

As the base usable in the present reaction, there can be mentioned, for example, an inorganic base such as alkali metal hydroxide (e.g. sodium hydroxide or potassium hydroxide), alkaline earth metal hydroxide (e.g. calcium hydroxide or magnesium hydroxide), alkali metal carbonate (e.g. sodium carbonate or potassium carbonate), alkali metal bicarbonate (e.g. sodium hydrogencarbonate or potassium hydrogencarbonate) or the like; a metal hydride (e.g. sodium hydride or potassium hydride); a metal alcoholate (e.g. sodium methoxide, sodium ethoxide or potassium tert-butoxide); and an organic base (e.g. triethylamine, N,N-dimethylaniline, pyridine, 4-N,N-dimethylaminopyridine or 1,8-diazabicyclo[5.4.0]-7-undecene). Incidentally, the use amount of the base is appropriately selected in a range of 0 to 5.0 mols and is preferably 0 to 1.2 mols relative to 1 mol of the compound [II].

As the radical initiator usable in the present reaction, there can be mentioned, for example, sulfurous acid, sodium sulfite, potassium sulfite, sodium hydrogensulfite, potassium hydrogensulfite, and a sulfurous acid adduct such as Rongalit (trade name, sodium formaldehyde sulfoxylate). A base and a radical initiator may be used in combination. The use amount of the radical initiator is appropriately selected in a range of 0 to 5.0 mols and is preferably 0 to 1.2 mols relative to 1 mol of the compound [II].

The temperature of the present reaction is selected freely, and ordinarily in a temperature range from −30° C. to the reflux temperature of the reaction system and is preferably 0° C. to 150° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water, extraction with organic solvent, concentration and the like, whereby a compound [I-1] can be isolated. The isolated compound [I-1] may be as necessary purified by column chromatography, recrystallization, etc.

[Production Method 2>

Of the present compounds, the compound represented by the general formula [I-1] can also be produced, for example, by the following method using a compound represented by the general formula [IV].

like; an aprotic polar solvent such as N,N-dimethylformamide, N,N-dimethylacetamide, N-methyl-2-pyrrolidone, dimethyl sulfoxide, sulfolane or the like; a nitrile such as acetonitrile, propionitrile or the like; an ester such as ethyl acetate, ethyl propionate or the like; an aliphatic hydrocarbon such as pentane, hexane, cyclohexane, heptane or the like; a pyridine such as pyridine, picoline or the like; water; and a mixture thereof. Incidentally, the use amount of the solvent is 0.1 to 100 liters, preferably 0.3 to 5 liters relative to 1 mol of the compound [IV].

As the radical initiator usable in the present reaction, there can be mentioned, for example, sulfurous acid, sodium sulfite, potassium sulfite, sodium hydrogensulfite, potassium hydrogensulfite, and a sulfurous acid adduct such as Rongalit (trade name, sodium formaldehyde sulfoxylate). The use amount of the radical initiator is appropriately selected in a range of 0.01 to 5.0 mols and is preferably 0.05 to 1.2 mols relative to 1 mol of the compound [IV].

The temperature of the present reaction is selected freely, and ordinarily in a temperature range from −30° C. to the reflux temperature of the reaction system and is preferably 0° C. to 150° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water, extraction with organic solvent, concentration and the like, whereby a compound [I-1] can be isolated. The isolated compound [I-1] may be as necessary purified by column chromatography, recrystallization, etc.

[Production Method 3>

Of the present compounds, the compound represented by the general formula [I-1'] can also be produced, for example, by the following method using a compound represented by the general formula [VI].

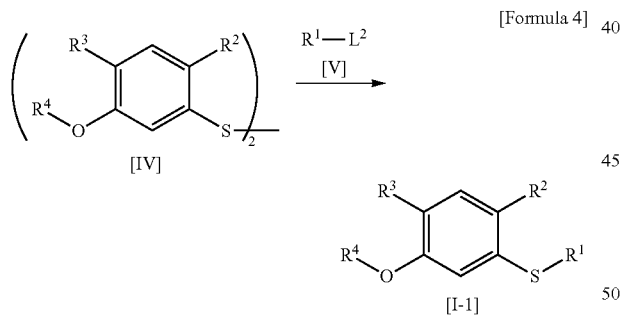

[Formula 4]

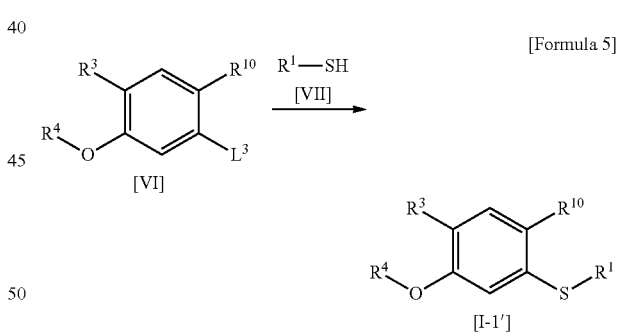

[Formula 5]

(In the above formula, $L^2$ is halogen atom or $SO_2M$; and $R^1$, $R^2$, $R^3$, $R^4$ and M each have the same meaning as given above.)

The compound represented by the general formula [I-1] can be produced by reacting a compound [IV] with a compound [V] in an appropriate solvent in the presence of an appropriate radical initiator.

The amount of the compound [V] used in the present reaction is selected appropriately in a range of 1.0 to 5.0 mols and is preferably 2.0 to 3.0 mols relative to 1 mol of the compound [IV].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the (In the above formula, $R^{10}$ is electron withdrawing group such as trifluoromethyl group, nitro group, cyano group or the like; $R^1$, $R^3$ and $R^4$ each have the same meaning as given above; $L^3$ is halogen atom, $C_1$~$C_6$ alkylsulfonyloxy group, trifluoromethanesulfonyloxy group, nonafluorobutylsulfonyloxy group, phenylsulfonyloxy group, 4-toluenesulfonyloxy group, $C_1$~$C_6$ alkylsulfonyl group or phenylsulfonyl group.)

The compound represented by the general formula [I-1'] can be produced by reacting a compound [VI] with a compound [VII] in an appropriate solvent in the presence of any of an appropriate base, copper and copper oxide (I), or in the presence of an appropriate base and copper, or in the presence of an appropriate base and copper oxide (I).

The amount of the compound [VII] used in the present reaction is selected appropriately in a range of 1.0 to 5.0 mols and is preferably 1.0 to 1.2 mols relative to 1 mol of the compound [VI].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol, methyl cellosolve or the like; an aliphatic hydrocarbon such as pentane, hexane, cyclohexane, heptane or the like; a pyridine such as pyridine, picoline or the like; water; and a mixture thereof. Incidentally, the use amount of the solvent is 0.1 to 100 liters, preferably 0.3 to 10 liters relative to 1 mol of the compound [VI].

As the base usable in the present reaction, there can be mentioned, for example, an inorganic base such as alkali metal hydroxide (e.g. sodium hydroxide or potassium hydroxide), alkaline earth metal hydroxide (e.g. calcium hydroxide or magnesium hydroxide), alkali metal carbonate (e.g. sodium carbonate or potassium carbonate), alkali metal bicarbonate (e.g. sodium hydrogencarbonate or potassium hydrogencarbonate) or the like; a metal hydride (e.g. sodium hydride or potassium hydride); a metal alcoholate (e.g. sodium methoxide, sodium ethoxide or potassium tert-butoxide); and an organic base (e.g. triethylamine, N,N-dimethylaniline, pyridine, 4-N,N-dimethylaminopyridine or 1,8-diazabicyclo[5.4.0]-7-undecene).

The amounts of the base, copper and copper oxide (I) used in the present reaction are each selected appropriately in a range of 1.0 to 5.0 mols and are preferably 1.0 to 1.2 mols relative to 1 mol of the compound [VI].

The temperature of the present reaction is selected freely, and ordinarily in a temperature range from −70° C. to the reflux temperature of the reaction system and is preferably 0° C. to 150° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water, extraction with organic solvent, concentration and the like, whereby a compound [I-1] can be isolated. The isolated compound [I-1'] may be as necessary purified by column chromatography, recrystallization, etc.

[Production Method 4]

Of the present compounds, a compound represented by the general formula [I-1] can also be produced, for example, by a method represented by the following reaction formula using a compound represented by the general formula [VIII].

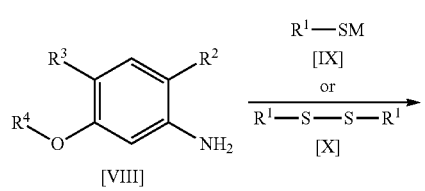

[Formula 6]

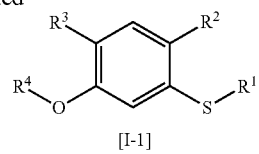

(In the above formula, $R^1$, $R^2$, $R^3$, $R^4$ and M each have the same meaning as given above.)

The compound represented by the general formula [I-1] can be produced by converting a compound [VIII] to a diazonium salt in an appropriate solvent based on the method described in Organic Syntheses Coll., Vol. 3, p. 185 (1955) (for example, a method of using a mineral acid (e.g. hydrochloric acid or sulfuric acid) and a nitrous acid salt or an alkyl nitrite) and then reacting the diazonium salt with a mercaptan salt represented by a compound [IX] or a disulfide represented by a compound [X].

The amount of the compound [IX] or the compound [X] used in the present reaction is appropriately selected in a range of 0.3 to 5.0 mols and is preferably 0.5 to 2.0 mols relative to 1 mol of the compound [VIII].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; a halogenated hydrocarbon such as dichloromethane, chloroform, 1,2-dichloroethane or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a nitrile such as acetonitrile, propionitrile or the like; an ester such as ethyl acetate, ethyl propionate or the like; an aliphatic hydrocarbon such as pentane, hexane, cyclohexane, heptane or the like; a pyridine such as pyridine, picoline or the like; water; and a mixture thereof. Incidentally, the use amount of the solvent is 0.1 to 100 liters, preferably 0.3 to 10 liters relative to 1 mol of the compound [VIII].

The temperature of the present reaction is selected freely, and ordinarily in a temperature range from −30° C. to the reflux temperature of the reaction system and is preferably −10° C. to 100° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water, extraction with organic solvent, concentration and the like, whereby a compound [I-1] can be isolated. The isolated compound [I-1] may be as necessary purified by column chromatography, recrystallization, etc.

<Production Method 5>

Of the present compounds, a compound represented by the general formula [I-1] can also be produced, for example, by a method represented by the following reaction formula using a compound represented by the general formula [XI].

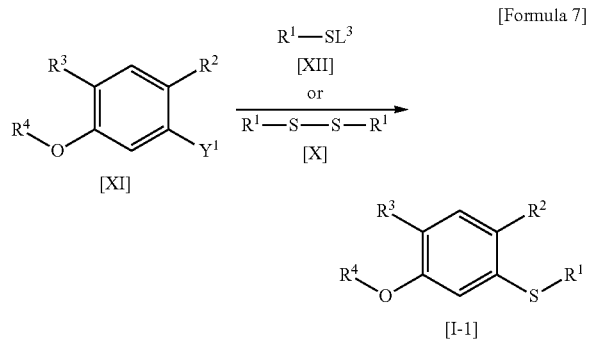

[Formula 7]

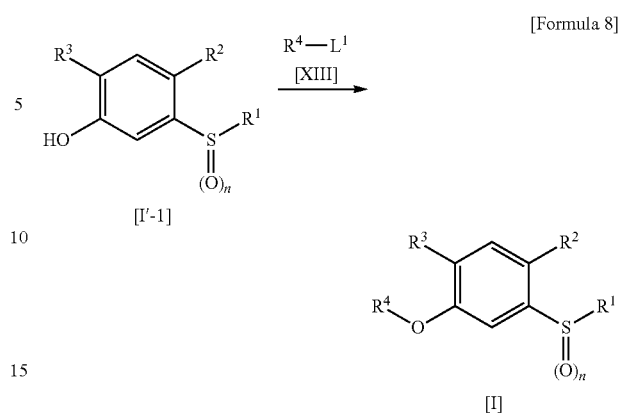

[Formula 8]

(In the above formula, $Y^1$ is hydrogen atom or a halogen atom; and $L^3$, $R^1$, $R^2$, $R^3$ and $R^4$ each have the same meaning as given above.)

The compound represented by the general formula [I-1] can be produced by reacting a compound [XI] with a metal or an organometallic compound in an appropriate solvent and then reacting the reaction product with a compound [XII] or a compound [X].

As the metal usable in the present reaction, there can be mentioned an alkali metal such as lithium, sodium, potassium or the like; an alkaline earth metal such as magnesium or the like; and so forth.

As the organometallic compound usable in the present reaction, there can be mentioned an alkyl lithium such as n-butyl lithium or the like; and so forth.

The amount of the metal or organometallic compound used in the present reaction is appropriately selected in a range of 1.0 to 3.0 mols and is preferably 1.0 to 1.1 mols relative to 1 mol of the compound [XI].

The amount of the compound [XII] or compound [X] used in the present reaction is appropriately selected in a range of 0.3 to 5.0 mols and is preferably 0.5 to 2.0 mols relative to 1 mol of the compound [XI].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aliphatic hydrocarbon such as pentane, hexane, cyclohexane, heptane or the like; a pyridine such as pyridine, picoline or the like; and a mixed solvent thereof. Incidentally, the use amount of the solvent is 0.1 to 100 liters, preferably 0.3 to 10 liters relative to 1 mol of the compound [XI].

The temperature of the present reaction is selected freely, and ordinarily in a temperature range from −100° C. to the reflux temperature of the reaction system and is preferably −78° C. to 100° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [I-1] can be isolated. The isolated compound [I-1] may be as necessary purified by column chromatography, recrystallization, etc.

<Production Method 6>

A present compound represented by the general formula [I] can be produced by a method of the following reaction formula.

(In the above formula, $L^1$, $R^1$, $R^2$, $R^3$, $R^4$ and n each have the same meaning as given above.)

The present compound can be produced by reacting a compound [I'-1] with a compound [XIII] in an appropriate solvent in the presence of an appropriate base.

The amount of the compound [XIII] used in the present reaction is appropriately selected in a range of 1.0 to 5.0 mols and is preferably 1.0 to 2.0 mols relative to 1 mol of the compound [I'-1].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; a halogenated hydrocarbon such as dichloromethane, chloroform, 1,2-dichloroethane or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a nitrile such as acetonitrile, propionitrile or the like; an ester such as ethyl acetate, ethyl propionate or the like; an aliphatic hydrocarbon such as pentane, hexane, cyclohexane, heptane or the like; a pyridine such as pyridine, picoline or the like; water; and a mixture thereof. Incidentally, the use amount of the solvent is 0.1 to 100 liters, preferably 0.1 to 15 liters relative to 1 mol of the compound [I'-1].

As the base usable in the present reaction, there can be mentioned, for example, an inorganic base such as alkali metal hydroxide (e.g. sodium hydroxide or potassium hydroxide), alkaline earth metal hydroxide (e.g. calcium hydroxide or magnesium hydroxide), alkali metal carbonate (e.g. sodium carbonate or potassium carbonate), alkali metal bicarbonate (e.g. sodium hydrogencarbonate or potassium hydrogencarbonate) or the like; a metal hydride (e.g. sodium hydride or potassium hydride); a metal alcoholate (e.g. sodium methoxide, sodium ethoxide or potassium tert-butoxide); and an organic base (e.g. triethylamine, N,N-dimethylaniline, pyridine, 4-N,N-dimethylaminopyridine or 1,8-diazabicyclo[5.4.0]-7-undecene). Incidentally, the use amount of the base is appropriately selected in a range of 1.0 to 5.0 mols and is preferably 1.0 to 1.5 mols relative to 1 mol of the compound [I'-1].

The temperature of the present reaction is selected freely, and ordinarily in a temperature range from −30° C. to the reflux temperature of the reaction system and is preferably 0° C. to 150° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [I] can be isolated. The isolated compound [I] may be as necessary purified by column chromatography, recrystallization, etc.

<Production Method 7>

A present compound represented by the general formula [I] can also be produced by a method of the following reaction formula.

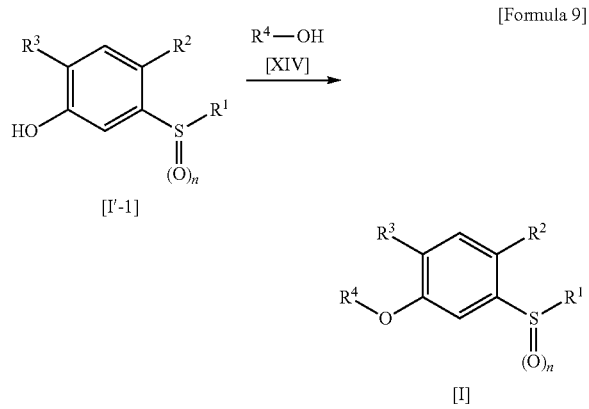

[Formula 9]

(In the above formula, $R^1$, $R^2$, $R^3$, $R^4$ and n each have the same meaning as given above.)

The present compound can be produced by reacting a compound [I'-1] with a compound [XIV] in an appropriate solvent in the presence of a tri-substituted phosphine and an azodicarboxylic acid derivative or in the presence of phosphorane.

The amount of the compound [XIV] used in the present reaction is appropriately selected in a range of 1.0 to 5.0 mols and is preferably 1.0 to 2.0 mols relative to 1 mol of the compound [I'-1].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a halogenated hydrocarbon such as dichloromethane, chloroform, 1,2-dichloroethane or the like; an aliphatic hydrocarbon such as pentane, hexane, cyclohexane, heptane or the like; a ketone such as acetone, methyl ethyl ketone, cyclohexanone or the like; acetic acid; water; and a mixed solvent thereof. Incidentally, the use amount of the solvent is 0.1 to 100 liters, preferably 0.3 to 30 liters relative to 1 mol of the compound [I'-1].

As the tri-substituted phosphine usable in the present reaction, there can be mentioned, for example, triphenylphosphine, tributylphosphine, and trimethylphosphine. Incidentally, the use amount of the tri-substituted phosphine is appropriately selected in a range of 1.0 to 5.0 mols and is preferably 1.0 to 3.0 mols relative to 1 mol of the compound [I'-1].

As the azodicarboxylic acid derivative usable in the present reaction, there can be mentioned, for example, diethyl azodicarboxylate, diisopropyl azodicarboxylate, dimethoxyethyl azodicarboxylate, and N,N,N',N'-tetramethylazodicarboxylic acid amide. Incidentally, the use amount of the azodicarboxylic acid derivative is appropriately selected in a range of 1.0 to 5.0 mols and is preferably 1.0 to 2.0 mols relative to 1 mol of the compound [I'-1].

As the phosphorane usable in the present reaction, there can be mentioned, for example, cyanomethylenetrimethylphosphorane and cyanomethylenetributylphosphorane. Incidentally, the use amount of the phosphorane is appropriately selected in a range of 1.0 to 5.0 mols and is preferably 1.0 to 2.0 mols relative to 1 mol of the compound [I'-1].

The temperature of the present reaction is selected freely, and ordinarily in a temperature range from −30° C. to the reflux temperature of the reaction system and is preferably 0° C. to 150° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [I] can be isolated. The isolated compound [I] may be as necessary purified by column chromatography, recrystallization, etc.

<Production Method 8>

Of the present compounds represented by the general formula [I], a compound represented by the general formula [I-2] can be produced, for example, by a method represented by the following reaction formula using a compound represented by the general formula [I-1].

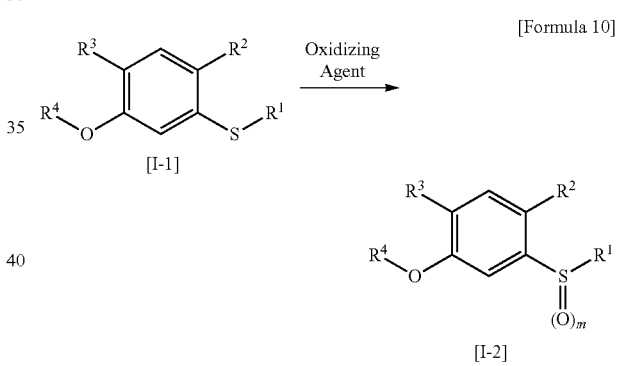

[Formula 10]

(In the above formula, $R^1$, $R^2$, $R^3$ and $R^4$ each have the same meaning as given above; and m is an integer of 1 or 2.)

The compound represented by the general formula [I-2] can be produced by reacting a compound [I-1] with an oxidizing agent in an appropriate solvent in the presence or absence of an appropriate catalyst.

As the oxidizing agent usable in the present reaction, there can be mentioned, for example, hydrogen peroxide, m-chloroperbenzoic acid, sodium periodate, OXONE (trade name of E.I. DuPont, a substance containing potassium hydrogenperoxosulfate), N-chlorosuccinimide, N-bromosuccinimide, tert-butyl hypochlorite, and sodium hypochlorite. Incidentally, the use amount of the oxidizing agent depends upon the oxidation number m of the sulfur atom of the compound represented by the general formula [I-2], but is appropriately selected in a range of 1.0 to 5.0 mols and is preferably 0.5 to 2.5 mols relative to 1 mol of the compound [I-1].

As the catalyst usable in the present reaction, there can be mentioned, for example, sodium tungstate. Incidentally, the use amount of the catalyst is appropriately selected in a range of 0 to 1.0 mol and is preferably 0 to 0.1 mol relative to 1 mol of the compound [I-1].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a halogenated hydrocarbon such as dichloromethane, chloroform, 1,2-dichloroethane or the like; an aliphatic hydrocarbon such as pentane, hexane, cyclohexane, heptane or the like; a ketone such as acetone, methyl ethyl ketone, cyclohexanone or the like; acetic acid; water; and a mixed solvent thereof. Incidentally, the use amount of the solvent is 0.1 to 100 liters, preferably 0.3 to 45 liters relative to 1 mol of the compound [I-1].

The temperature of the present reaction is selected freely, and ordinarily in a temperature range from −30° C. to the reflux temperature of the reaction system and is preferably −10° C. to 100° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [I-2] can be isolated. The isolated compound [I-2] may be as necessary purified by column chromatography, recrystallization, etc.

<Production Method 9>

A present compound represented by the general formula [I'] can be produced, for example, by the method shown by the following reaction formula using a compound represented by the general formula [XV-2].

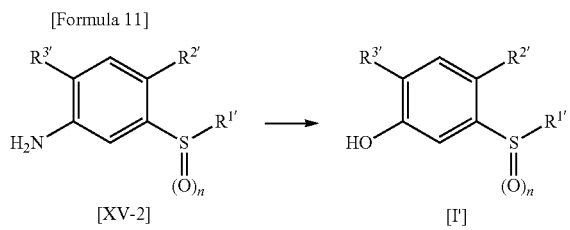

[Formula 11]

[XV-2] → [I']

(In the above formula, $R^{1'}$, $R^{2'}$, $R^{3'}$ and n each have the same meaning as give above.)

The compound represented by the general formula [I'] can be produced by reacting the compound [XV-2] with an acid and a nitrous acid derivative in a solvent and then, as necessary, reacting the reaction product with a metal salt.

As the acid usable in the present reaction, there can be mentioned a mineral acid such as sulfuric acid, nitric acid or the like, or an organic acid such as trifluoroacetic acid, trifluoromethanesulfonic acid or the like. Incidentally, the use amount of the acid is appropriately selected in a range of 1 to 20 mols and is preferably 1.0 to 5.0 mols relative to 1 mol of the compound [XV-2].

As the nitrous acid derivative usable in the present reaction, there can be mentioned a nitrous acid salt such as sodium nitrite, potassium nitrite or the like, or an alkyl nitrite such as n-butyl nitrite, isopentyl nitrite, tert-butyl nitrite or the like. Incidentally, the use amount of the nitrous acid derivative is appropriately selected in a range of 1.0 to 3.0 mols and is preferably 1.0 to 1.5 mols relative to 1 mol of the compound [XV-2].

As the metal salt as necessary usable in the present reaction, there can be mentioned copper sulfate, copper nitrate, copper oxide, etc. Incidentally, the use amount of the metal salt is appropriately selected in a range of 0 to 2.0 mols and is preferably 0 to 1.1 mols relative to 1 mol of the compound [XV-2].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; a halogenated hydrocarbon such as dichloromethane, chloroform, dichloroethane or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a nitrile such as acetonitrile, propionitrile or the like; an ester such as ethyl acetate, ethyl propionate or the like; an aliphatic hydrocarbon such as pentane, hexane, cyclohexane, heptane or the like; a pyridine such as pyridine, picoline or the like; water; and a mixed solvent thereof. Incidentally, the use amount of the solvent is 0.1 to 100 liters, preferably 0.3 to 10 liters relative to 1 mol of the compound [XV-2].

The temperature of the present reaction is selected freely in a temperature range from −30° C. to the reflux temperature of the reaction system and is preferably 0° C. to 150° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [I'] can be isolated. The isolated compound [I'] may be as necessary purified by column chromatography, recrystallization, etc.

<Production Method 10>

The present compound represented by the general formula [I'] can also be produced by the method shown by the following reaction formula.

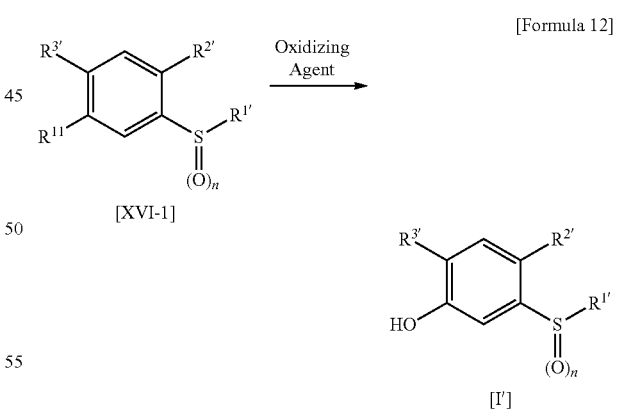

[Formula 12]

[XVI-1] → [I']

(In the above formula, $R^{11}$ is boronic acid (—B(OH)$_2$ group) or pinacolateboran-2-yl group; $R^{1'}$, $R^{2'}$, $R^{3'}$ and n each have the same meaning as given above.)

The compound represented by the general formula [I'] can be produced by reacting a compound [XVI-1] with an oxidizing agent in a solvent.

As the oxidizing agent usable in the present reaction, there can be mentioned, for example, hydrogen peroxide and 4-methylmorpholine-N-oxide. Incidentally, the use amount of the oxidizing agent is appropriately selected in a range of 1.0 to 6.0 mols and is preferably 1.0 to 1.4 mols relative to 1 mol of the compound [XVI-1].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a halogenated hydrocarbon such as dichloromethane, chloroform, 1,2-dichloroethane or the like; an aliphatic hydrocarbon such as pentane, hexane, cyclohexane, heptane or the like; a ketone such as acetone, methyl ethyl ketone, cyclohexanone or the like; acetic acid; water; and a mixed solvent thereof. Incidentally, the use amount of the solvent is 0.1 to 100 liters, preferably 0.3 to 15 liters relative to 1 mol of the compound [XVI-1].

The temperature of the present reaction is selected freely in a temperature range from −30° C. to the reflux temperature of the reaction system and is preferably −10° C. to 150° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [I'] can be isolated. The isolated compound [I'] may be as necessary purified by column chromatography, recrystallization, etc.

<Production Method 11>

Of the present compounds represented by the general formula [I], the compound represented by the general formula [I-4] can be produced, for example, by the method shown by the following reaction formula, using a compound represented by the general formula [I-3].

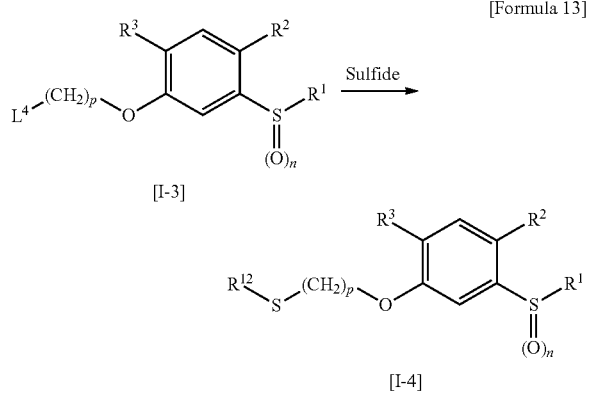

[Formula 13]

(In the above formula, $L^4$ is a halogen atom, methanesulfonyloxy group, trifluoromethanesulfonyloxy group, 1,1,2,2,3,3,4,4,4-nonafluorobutylsulfonyloxy group, 4-toluenesulfonyloxy group or benzenesulfonyloxy group; $R^{12}$ is hydrogen atom, cyano group, $C_1$~$C_6$ alkyl group, $C_1$~$C_6$ haloalkyl group, $C_3$~$C_8$ cycloalkyl $C_1$~$C_6$ alkyl group, $C_3$~$C_8$ halocycloalkyl $C_1$~$C_6$ alkyl group, $C_3$~$C_8$ cycloalkyl group or $C_3$~$C_8$ halocycloalkyl group; p is an integer of 1~12; $R^1$, $R^2$, $R^3$ and n each have the same meaning as given above.)

The compound represented by the general formula [I-4] can be produced by reacting a compound [I-3] and sulfide in an appropriate solvent in the presence or absence of base.

As the sulfide usable in the present reaction, there can be mentioned, for example, hydrosulfide of alkali metal such as sodium hydrosulfide or potassium hydrosulfide; thiocyanate of alkali metal such as sodium thiocyanate or potassium thiocyanate; alkylmercaptane such as methyl mercaptane, ethyl mercaptane or tert-butyl mercaptane; haloalkylmercaptane such as 2,2,2-trifluoroethyl mercaptane; and cycloalkylalkylmercaptane such as cyclopropylmethyl mercaptane. Incidentally, the use amount of the sulfide is appropriately selected in a range of 1.0 to 20 mols and is preferably 1.0 to 10 mols relative to 1 mol of the compound [I-3].

As the base usable in the present reaction, there can be mentioned, for example, an inorganic base such as alkali metal hydroxide (e.g. sodium hydroxide or potassium hydroxide), alkaline earth metal hydroxide (e.g. calcium hydroxide or magnesium hydroxide), alkali metal carbonate (e.g. sodium carbonate or potassium carbonate), alkali metal bicarbonate (e.g. sodium hydrogencarbonate or potassium hydrogencarbonate) or the like; a metal hydride (e.g. sodium hydride or potassium hydride); a metal alcoholate (e.g. sodium methoxide, sodium ethoxide or potassium tert-butoxide); and an organic base (e.g. triethylamine, N,N-dimethylaniline, pyridine, 4-N,N-dimethylaminopyridine or 1,8-diazabicyclo[5.4.0]-7-undecene). Incidentally, the use amount of the base is appropriately selected in a range of 1.0 to 5.0 mols and is preferably 1.0 to 2.0 mols relative to 1 mol of the compound [I-3].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a nitrile such as acetonitrile, propionitrile or the like; an aliphatic hydrocarbon such as pentane, hexane, cyclohexane, heptane or the like; a pyridine such as pyridine, picoline or the like; and a mixture thereof. Incidentally, the use amount of the solvent is 0.1 to 100 liters, preferably 0.3 to 10 liters relative to 1 mol of the compound [I-3].

The temperature of the present reaction is selected freely in a temperature range from 0° C. to the reflux temperature of the reaction system and is preferably room temperature to 150° C.

The time of the present reaction differs depending upon the temperature of reaction, the substrate of reaction, the amount of reactant, etc., but is ordinarily 10 minutes to 24 hours.

In conducting the present reaction, potassium iodide may be added, and the use amount of potassium iodide is 0 to 5.0 mol, preferably 0 to 1.0 mol relative to 1 mol of the compound [I-3].

After the completion of the reaction, the reaction mixture is subjected to operations such as pouring into water or the like, extraction with organic solvent, concentration and the like, whereby a compound [I-4] can be isolated. The isolated compound [I-4] may be as necessary purified by column chromatography, recrystallization, etc.

<Production Method 12>

Of the present compounds represented by the general formula [I], the compound represented by the general formula [I-6] can be produced by, for example, the method shown by the following reaction formula, using a compound represented by the general formula [I-5].

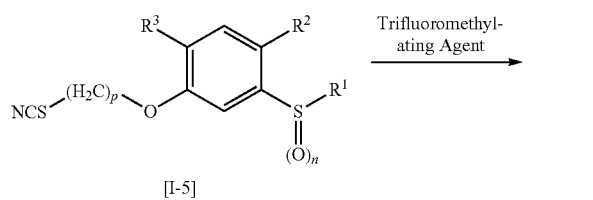

[Formula 14]

[I-5]

Trifluoromethylating Agent

[I-6]

(In the above formula, $R^1$, $R^2$, $R^3$, n and p each have the same meaning as given above.)

The compound represented by the general formula [I-6] can be produced by reacting a compound [I-5] and trifluoromethylating agent in an appropriate solvent in the presence of an appropriate catalyst.

As the trifluoromethylating agent usable in the present reaction, there can be mentioned, for example, trifluoromethyltrimethylsilane or triethyltrifluoromethylsilane. Incidentally, the use amount of the trifluoromethlating agent is appropriately selected in a range of 1.0 to 5.0 mols and is preferably 1.0 to 3.0 mols relative to 1 mol of the compound [I-5].

As the catalyst usable in the present reaction, there can be mentioned, for example, tetra-n-butylammoniumfluoride, cesium fluoride or potassium fluoride. Incidentally, the use amount of the catalyst is appropriately selected in a range of 0.01 to 10 mols and is preferably 0.1 to 6.0 mols relative to 1 mol of the compound [I-5].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; a halogenated hydrocarbon such as dichloromethane, chloroform, 1,2-dichloroethane or the like; a nitrile such as acetonitrile, propionitrile or the like; an aliphatic hydrocarbon such as pentane, hexane, cyclohexane, heptane or the like; and a mixture thereof. Incidentally, the use amount of the solvent is 0.1 to 100 liters, preferably 0.3 to 15 liters relative to 1 mol of the compound [I-5].

The temperature of the present reaction is selected freely in a temperature range from −30° C. to the reflux temperature of the reaction system and is preferably 0° C. to room temperature.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [I-6] can be isolated. The isolated compound [I-6] may be as necessary purified by column chromatography, recrystallization, etc.

<Production Method 13>

From the compound represented by the general formula [I-7], having asymmetrical sulfur atom, of the present compounds represented by the general formula [I], respective optical isomer (enantiomer) can be separated by optical resolution.

[Formula 15]

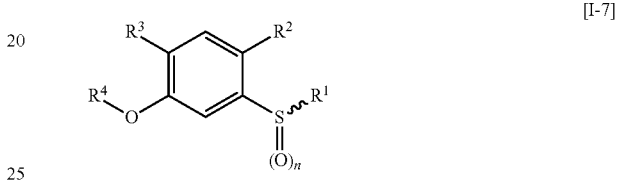

[I-7]

(In the above formula, $R^1$, $R^2$, $R^3$ and $R^4$ each have the same meaning as given above.)

From the recemic mixture of compound represented by the general formula [I-7], respective (+)-enantiomer and (−)-enantiomer can be obtained by using a column for high performance liquid chromatography for optical isomer separation.

As the column for high performance liquid chromatography for optical isomer separation usable, there can be mentioned the column already marketed, for example, CHIRAL PAK AD (trade name) manufactured and sold by Daicel Corporation.

As the solvent usable in the optical resolution, there can be mentioned, for example, an aliphatic hydrocarbon such as hexane, heptane or the like; an alcohol such as methanol, ethanol, propanol, 2-propanol, butanol or the like; a halogenated hydrocarbon such as dichloromethane, chloroform, or the like; an ether such as diethyl ether, 1,2-dimethoxyethane, diisopropyl ether, tetrahydrofuran, 1,4-dioxane or the like; an ester such as ethyl acetate or the like; a nitrile such as acetonitrile or the like; an organic acid such as acetic acid, formic acid and the like; water; and a mixture thereof.

The temperature and time of the optical resolution may be changed freely in a wide range. Ordinally temperature is from −20° C. to 60° C., preferably 5° C. to 50° C., and time is 0.01 hour to 50 hours, preferably 0.1 hour to 2 hours.

<Production Method 1 of Intermediate>

A compound represented by the general formula [II] can be produced by each of the reaction formulas shown by the following step 1 to step 4. A compound represented by the general formula [IV] can be produced by the reaction formula shown by the following step 5. Incidentally, the compound [II] and the compound [IV] are interchangeable to each other by an oxidation reaction or a reduction reaction. Further, the compound [II] is also oxidized easily by the oxygen in the air, generating the compound [IV].

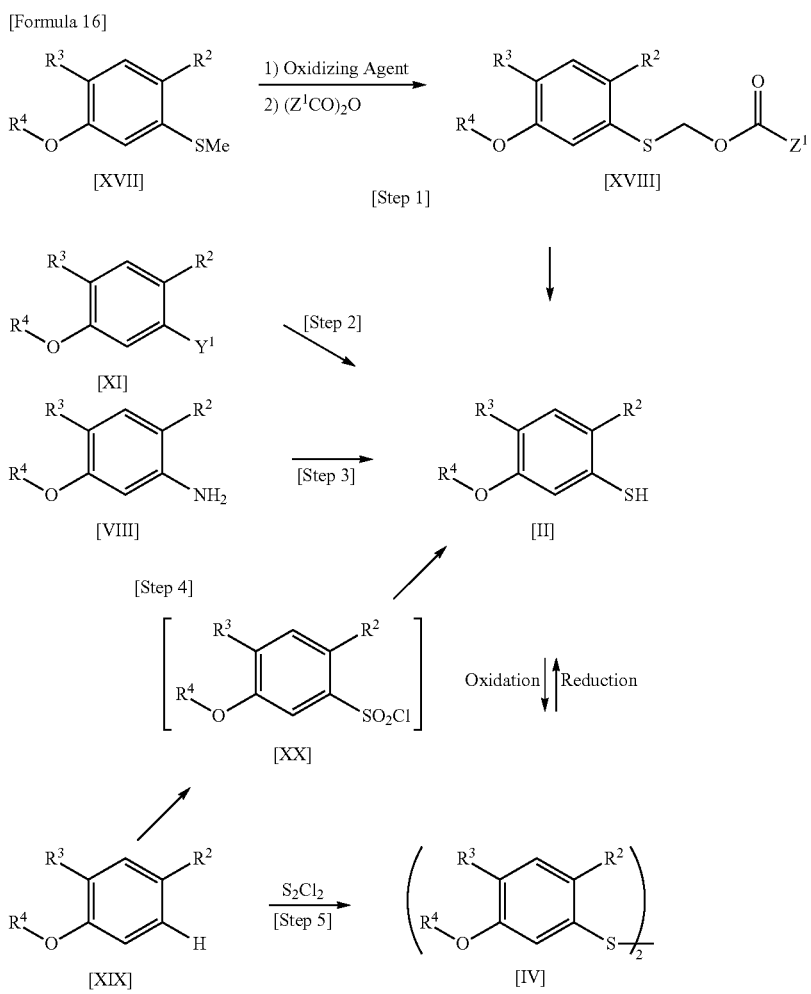

(In the above reaction formulas, $Z^1$ is a methyl group or a trifluoromethyl group; and $R^2$, $R^3$, $R^4$ and $Y^1$ each have the same meaning as given above.)

[Step 1]

A compound represented by the general formula [II] can be produced by oxidizing a compound [XVII] with an appropriate oxidizing agent to convert to a corresponding sulfoxide form, then reacting the sulfoxide form with acetic anhydride or trifluoroacetic anhydride to produce a compound [XVIII], thereafter hydrolyzing the compound [XVIII] based on the method described in Chem. Ber., Vol. 43, p. 1407 (1910). The compound [XVIII] may be used in the next reaction without being isolated and purified.

As the oxidizing agent usable in the present step, there can be mentioned, for example, hydrogen peroxide, m-chloroperbenzoic acid, sodium periodate, OXONE (trade name of E.I. DuPont, a substance containing potassium hydrogenperoxosulfate), N-chlorosuccinimide, N-bromosuccinimide, tert-butyl hypochlorite, and sodium hypochlorite. Incidentally, the use amount of the oxidizing agent is appropriately selected in a range of 1.0 to 3.0 mols and is preferably 1.0 to 1.2 mols relative to 1 mol of the compound [XVII].

The amount of the acetic anhydride or trifluoroacetic anhydride used in the present step is selected in a range from 1 mol to an amount sufficient to act as a solvent and is preferably 1.0 to 3.0 mols relative to 1 mol of the compound [XVII]

The reaction temperature of the present step is freely selected, in any reaction, in a range from $-10°$ C. to the reflux temperature of the reaction system and is preferably 0° C. to 50° C.

The reaction time of the present step differs depending upon the temperature of reaction, the substrate of reaction, the amount of reactant, etc., in any reaction, but is ordinarily 5 minutes to 12 hours.

After the completion of the reaction, the reaction mixture is subjected to operations such as pouring into water or the like, extraction with organic solvent, concentration and the like, whereby a compound [II] can be isolated. The isolated compound [II] may be as necessary purified by column chromatography, recrystallization, etc.

[Step 2]

The compound represented by the general formula [II] can also be produced by reacting a compound [XI] with a metal or an organometallic compound in a solvent and then reacting the reaction product with sulfur.

As the solvent usable in the present step, there can be mentioned, for example, an ether such as diethyl ether, tetrahydrofuran, 1,4-dioxane or the like; an aromatic hydrocarbon such as benzene, toluene, xylene, chlorobenzene or the like; an aliphatic hydrocarbon such as pentane, hexane, cyclohexane, heptane or the like; a pyridine such as pyridine, picoline or the like; and a mixture thereof. Incidentally, the use amount of the solvent is 0.1 to 100 liters, preferably 0.1 to 10 liters relative to 1 mol of the compound [XI].

As the metal usable in the present step, there can be mentioned lithium, magnesium, etc. Incidentally, the use amount of the metal is appropriately selected in a range of 1.0 to 3.0 mols and is preferably 1.0 to 1.2 mols relative to 1 mol of the compound [XI].

As the organometallic compound usable in the present step, there can be mentioned an alkyllithium such as n-butyllithium or the like. Incidentally, the use amount of the organometallic compound is appropriately selected in a range of 1.0 to 3.0 mols and is preferably 1.0 to 1.2 mols relative to 1 mol of the compound [XI].

The amount of the sulfur used in the present step is appropriately selected in a range of 1.0 to 5.0 mols and is preferably 1.0 to 2.0 mols relative to 1 mol of the compound [XI].

The reaction temperature of the present step is freely selected in a range from −60° C. to the reflux temperature of the reaction system and is preferably −60° C. to room temperature.

The reaction time of the present step differs depending upon the temperature of reaction, the substrate of reaction, the amount of reactant, etc., but is ordinarily 30 minutes to 12 hours.

After the completion of the reaction, the reaction mixture is subjected to operations such as pouring into water or the like, extraction with organic solvent, concentration and the like, whereby a compound [II] can be isolated. The isolated compound [II] may be as necessary purified by column chromatography, recrystallization, etc.

[Step 3]

The compound represented by the general formula [II] can also be produced by converting a compound [VIII] to a diazonium salt in the same manner as in the above-mentioned Production method 4, then reacting the diazonium salt with a xanthogenic acid salt or a thiocyanic acid salt, thereafter hydrolyzing the reaction product.

As the xanthogenic acid salt usable in the present step, there can be mentioned, for example, sodium ethylxanthogenate, potassium ethylxanthogenate, potassium isopropylxanthogenate, and potassium butylxanthogenate. As the thiocyanic acid salt, there can be mentioned, for example, sodium thiocyanate, potassium thiocyanate, and ammonium thiocyanate. Incidentally, the use amount of the xanthogenic acid salt or thiocyanic acid salt is appropriately selected in a range of 1.0 to 3.0 mols and is preferably 1.0 to 1.5 mols relative to 1 mol of the compound [VIII].

As the solvent usable in the present step, there can be mentioned, for example, an ether such as diethyl ether, tetrahydrofuran, 1,4-dioxane or the like; an aromatic hydrocarbon such as benzene, toluene, xylene, chlorobenzene or the like; a halogenated hydrocarbon such as dichloromethane, chloroform, 1,2-dichloroethane or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a nitrile such as acetonitrile, propionitrile or the like; an ester such as ethyl acetate, ethyl propionate or the like; an aliphatic hydrocarbon such as pentane, hexane, cyclohexane, heptane or the like; a pyridine such as pyridine, picoline or the like; water; and a mixed solvent thereof. Incidentally, the use amount of the solvent is 0.1 to 100 liters, preferably 0.3 to 10 liters relative to 1 mol of the compound [VIII].

The reaction temperature of the present step is freely selected in a range from −70° C. to the reflux temperature of the reaction system and is preferably −20° C. to 100° C.

The reaction time of the present step differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [II] can be isolated. The isolated compound [II] may be as necessary purified by column chromatography, recrystallization, etc.

[Step 4]

The compound represented by the general formula [II] can also be produced by reacting a compound [XIX] with chlorosulfonic acid to obtain a compound [XX] and then reacting the compound [XX] with a reducing agent.

The amount of the chlorosulfonic acid used in the present step is appropriately selected in a range of 2.0 to 10 mols and is preferably 2.2 to 3.5 mols relative to 1 mol of the compound [XIX].

As the reducing agent usable in the present step, there can be mentioned lithium aluminum hydride, a combination of zinc and an acid, a combination of tin and an acid, and a combination of red phosphorus and iodine. Incidentally, the use amount of the reducing agent is appropriately selected in a range of 1.0 to 5.0 mols and is preferably 1.5 to 2.0 mols relative to 1 mol of the compound [XIX].

As the acid usable as a component of the reducing agent in the present step, there can be mentioned a mineral acid such as hydrochloric acid, sulfuric acid or the like.

The reaction temperature of the present step is freely selected, in any reaction, in a range from 0° C. to the reflux temperature of the reaction system and is preferably 0° C. to 100° C.

The reaction time of the present step differs depending upon the temperature of reaction, the substrate of reaction, the amount of reactant, etc., in any reaction, but is ordinarily 10 minutes to 24 hours.

After the completion of the reaction, the reaction mixture is subjected to operations such as pouring into water or the like, extraction with organic solvent, concentration and the like, whereby a compound [II] can be isolated. The isolated compound [II] may be as necessary purified by column chromatography, recrystallization, etc.

[Step 5]

The compound represented by the general formula [IV] can be produced by reacting a compound [XIX] with disulfur dichloride in a solvent in the presence or absence of a catalyst.

The amount of the disulfur dichloride used in the present step is appropriately selected in a range of 1.0 to 5.0 mols and is preferably 1.0 to 1.5 mols relative to 1 mol of the compound [XIX].

As the catalyst usable in the present step, there can be mentioned, for example, a metal halide such as aluminum chloride, tin (II) chloride, tin (IV) chloride or the like. Incidentally, the use amount of the catalyst is appropriately selected in a range of 0 to 5.0 mols and is preferably 1.0 to 2.0 mols relative to 1 mol of the compound [XIX].

As the solvent usable in the present step, there can be mentioned, for example, a halogenated hydrocarbon such as dichloromethane, chloroform, 1,2-dichloroethane or the like; and an aromatic hydrocarbon such as chlorobenzene, dichlorobenzene or the like. Incidentally, the use amount of the solvent is 0.1 to 100 liters, preferably 0.3 to 10 liters relative to 1 mol of the compound [XIX].

The reaction temperature of the present step is freely selected in a range from −30° C. to the reflux temperature of the reaction system and is preferably −10° C. to 100° C.

The reaction time of the present step differs depending upon the temperature of reaction, the substrate of reaction, the amount of reactant, etc., but is ordinarily 1 to 24 hours.

Further, the compound [II] can be produced by reducing the compound [IV] based on the methods described in Organic Syntheses, Coll. Vol. 2, p. 580 (1943), J. Am. Chem. Soc., 60, 428 (1928), J. Am. Chem. Soc., 79, 2553 (1957), J. Org. Chem., 26, 3436 (1961), and J. Am. Chem. Soc., 96, 6081 (1974).

<Production Method 2 of Intermediate>

Of the compounds represented by the general formula [II], a compound represented by the general formula [II-1] can be produced by the method shown by the following reaction formula.

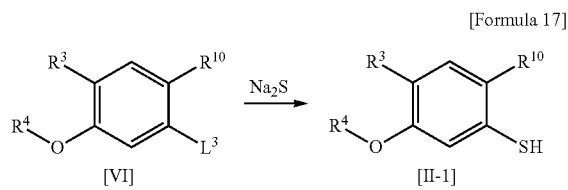

[Formula 17]

(In the above reaction formula, $R^3$, $R^4$, $R^{10}$ and $L^3$ each have the same meaning as given above.)

The compound represented by the general formula [II-1] can be produced by reacting a compound [VI] with sodium sulfide in a solvent in the presence of a base and then neutralizing the reaction product with a mineral acid or the like.

The amount of the sodium sulfide used in the present reaction is appropriately selected in a range of 1.0 to 3.0 mols and is preferably 1.0 to 1.5 mols relative to 1 mol of the compound [VI].

As the solvent usable in the present reaction, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a halogenated hydrocarbon such as dichloromethane, chloroform, 1,2-dichloroethane or the like; an aliphatic hydrocarbon such as pentane, hexane, cyclohexane, heptane or the like; a ketone such as acetone, methyl ethyl ketone, cyclohexanone or the like; water; and a mixed solvent thereof. Incidentally, the use amount of the solvent is 0.1 to 100 liters, preferably 0.3 to 10 liters relative to 1 mol of the compound [VI].

As the base usable in the present reaction, there can be mentioned, for example, an inorganic base such as alkali metal hydroxide (e.g. sodium hydroxide or potassium hydroxide), alkaline earth metal hydroxide (e.g. calcium hydroxide or magnesium hydroxide), alkali metal carbonate (e.g. sodium carbonate or potassium carbonate), alkali metal bicarbonate (e.g. sodium hydrogencarbonate or potassium hydrogencarbonate) or the like; a metal hydride (e.g. sodium hydride or potassium hydride); a metal alcoholate (e.g. sodium methoxide, sodium ethoxide or potassium tert-butoxide); and an organic base (e.g. triethylamine, N,N-dimethylaniline, pyridine, 4-N,N-dimethylaminopyridine or 1,8-diazabicyclo[5.4.0]-7-undecene). Incidentally, the use amount of the base is appropriately selected in a range of 1.0 to 5.0 mols and is preferably 1.0 to 1.2 mols relative to 1 mol of the compound [VI].

As the mineral acid usable in the present reaction, there can be mentioned hydrochloric acid, sulfuric acid, etc. The use amount of the mineral acid is appropriately selected in a range of 1.0 to 5.0 mols and is preferably 1.0 to 2.0 mols relative to 1 mol of the compound [VI].

The temperature of the present reaction is selected freely in a temperature range from −30° C. to the reflux temperature of the reaction system, and is preferably −20° C. to 100° C.

The time of the present reaction differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [II-1] can be isolated. The isolated compound [II-1] may be as necessary purified by column chromatography, recrystallization, etc.

<Production Method 3 of Intermediate>

A compound represented by the general formula [XV] can be produced by the method of the reaction formulas shown by the following [step 6] and [step 7].

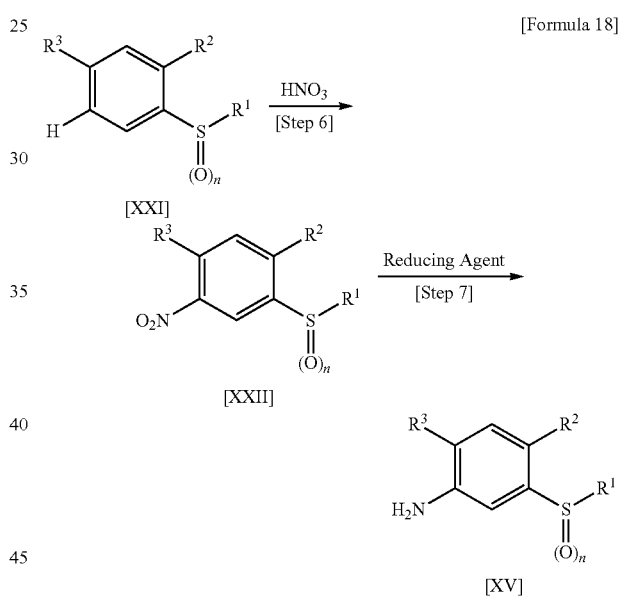

[Formula 18]

(In the above reaction formulas, $R^1$, $R^2$, $R^3$ and n each have the same meaning as given above.)

[Step 6]

A compound represented by the general formula [XXII] can be produced by reacting a compound [XXI] with nitric acid in a solvent in the presence or absence of sulfuric acid.

As the solvent usable in the present step, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a halogenated hydrocarbon such as dichloromethane, chloroform, 1,2-dichloroethane or the like; an aliphatic hydrocarbon such as pentane, hexane, cyclohexane, heptane or the like; a ketone such as acetone, methyl ethyl ketone, cyclohexanone or the like; water; and a mixed solvent thereof. Incidentally, the use amount of the solvent is 0.1 to 100 liters, preferably 0.3 to 10 liters relative to 1 mol of the compound [XXI].

The amount of the nitric acid used in the present step is appropriately selected in a range of 1.0 to 40 mols and is preferably 1.0 to 10 mols relative to 1 mol of the compound [XXI]. The amount of sulfuric acid when used is appropriately selected in a range of 1 to 40 mols and is preferably 1.0 to 10 mols relative to 1.0 mol of the compound [XXI].

The reaction temperature of the present step is freely selected in a range from 0° C. to the reflux temperature of the reaction system and is preferably 0° C. to 150° C.

The reaction time of the present step differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [XXII] can be isolated. The isolated compound [XXII] may be as necessary purified by column chromatography, recrystallization, etc.

[Step 7]

The compound represented by the general formula [XV] can be produced by reacting the compound [XXII] with iron/acid, zinc/acid, tin/acid, tin dichloride/acid, nickel chloride/sodium tetrahydroborate, lithium aluminum hydride, palladium-activated carbon/hydrogen, or the like, for reduction.

As the acid usable in the present step, there can be mentioned a mineral acid such as hydrochloric acid, sulfuric acid or the like. The amount of the iron/acid, zinc/acid, tin/acid, tin dichloride/acid, nickel(II) chloride/sodium tetrahydroborate, lithium aluminum hydride, palladium-activated carbon/hydrogen, or the like, used in the present step is appropriately selected in a range of 1.0 to 5.0 mols and is preferably 1.0 to 2.0 mols relative to 1 mol of the compound [XXII].

The reaction temperature of the present step is freely selected in a range from 0° C. to the reflux temperature of the reaction system and is preferably 0° C. to 100° C.

The reaction time of the present step differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [XV] can be isolated. The isolated compound [XV] may be as necessary purified by column chromatography, recrystallization, etc.

<Production Method 4 of Intermediate>

A compound represented by the general formula [XXV] can be produced by the method of the reaction formulas shown in the following [step 8] and [step 9].

[Formula 19]

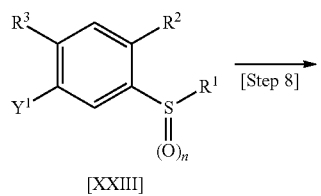

[XXIII]

-continued (In the above reaction formulas, $Z^2$ is a same or different $C_1$~$C_6$ alkyl group; and $R^1$, $R^2$, $R^3$, $Y^1$ and n each have the same meaning as given above.)

[Step 8]

A compound represented by the general formula [XXIV] can be produced by reacting a compound [XXIII] with a metal or an organometallic compound in an appropriate solvent and then reacting the reaction product with a boric acid ester.

As the solvent usable in the present step, there can be mentioned, for example, an ether such as diethyl ether, tetrahydrofuran, 1,4-dioxane or the like; an aromatic hydrocarbon such as benzene, toluene, xylene, chlorobenzene or the like; an aliphatic hydrocarbon such as pentane, hexane, cyclohexane, heptane or the like; a pyridine such as pyridine, picoline or the like; and a mixed solvent thereof. Incidentally, the use amount of the solvent is 0.1 to 100 liters, preferably 0.1 to 5.0 liters relative to 1 mol of the compound [XXIII].

As the metal usable in the present step, there can be mentioned lithium, magnesium, etc. The use amount of the metal is appropriately selected in a range of 1.0 to 3.0 mols and is preferably 1.0 to 1.2 mols relative to 1 mol of the compound [XXIII].

As the organometallic compound usable in the present step, there can be mentioned an alkyllithium such as n-butyllithium or the like. The use amount of the organometallic compound is appropriately selected in a range of 1.0 to 3.0 mols and is preferably 1.0 to 1.2 mols relative to 1 mol of the compound [XXIII].

The reaction temperature of the present step is freely selected in a range from −100° C. to the reflux temperature of the reaction system, and is preferably −60° C. to room temperature.

The reaction time of the present step differs depending upon the temperature of reaction, the substrate of reaction, the amount of reactant, etc., but is ordinarily 5 minutes to 12 hours.

After the completion of the reaction, the reaction mixture is subjected to operations such as pouring into water or the like, extraction with organic solvent, concentration and the like, whereby a compound [XXIV] can be isolated. The isolated compound [XXIV] may be as necessary purified by column chromatography, recrystallization, etc.

[Step 9]

The compound [XXV] can be produced by reacting the compound [XXIV] with an acid in an appropriate solvent.

As the solvent usable in the present step, there can be mentioned, for example, an ether such as diethyl ether, tetrahydrofuran, 1,4-dioxane or the like; an aromatic hydrocarbon such as benzene, toluene, xylene, chlorobenzene or the like; an aprotic polar solvent such as N,N-dimethylformamide, N,N-dimethylacetamide, N-methyl-2-pyrrolidone, dimethyl sulfoxide, sulfolane or the like; an alcohol such as methanol, ethanol, 2-propanol or the like; a halogenated hydrocarbon such as dichloromethane, chloroform, dichloroethane or the like; an aliphatic hydrocarbon such as pentane, hexane, cyclohexane, heptane or the like; a ketone such as acetone, methyl ethyl ketone, cyclohexanone or the like; water; and a mixed solvent thereof. Incidentally, the use amount of the solvent is 0.1 to 100 liters, preferably 0.1 to 5.0 liters relative to 1 mol of the compound [XXIV].

As the acid usable in the present step, there can be mentioned a mineral acid such as sulfuric acid, hydrochloric acid or the like. The use amount of the acid is appropriately selected in a range of 1.0 to 5.0 mols and is preferably 0.5 to 2.0 mols relative to 1 mol of the compound [XXIV].

The reaction temperature of the present step is freely selected in a range from 0° C. to the reflux temperature of the reaction system and is preferably 0° C. to 100° C.

The reaction time of the present step differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [XXV] can be isolated. The isolated compound [XXV] may be as necessary purified by column chromatography, recrystallization, etc.

<Production Method 5 of Intermediate>

Of the compounds represented by the general formula [XV], a compound represented by [XV-1] can be produced by the method shown by the reaction formulas of the following [step 10] and [step 11].

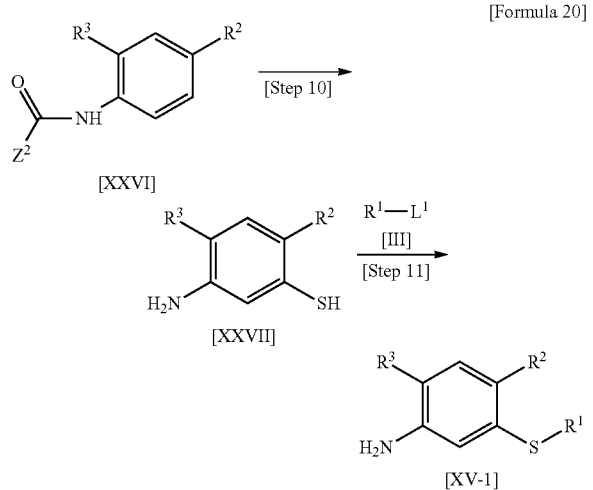

[Formula 20]

(In the above reaction formulas, $R^1$, $R^2$, $R^3$, $Z^2$ and $L^1$ each have the same meaning as given above.)

[Step 10]

A compound represented by the general formula [XXVII] can be produced by reacting a compound [XXVI] with chlorosulfonic acid, then reducing the reaction product with lithium aluminum hydride, zinc/acid, tin/acid, or red phosphorus/iodine, thereafter hydrolyzing the reaction product with a base.

As the acid usable in the present step, there can be mentioned a mineral acid such as hydrochloric acid, sulfuric acid or the like. The use amount of chlorosulfonic acid in the present step is appropriately selected in a range of 2.0 to 10 mols and is preferably 2.2 to 3.5 mols relative to 1 mol of the compound [XXVI].

The use amount of the lithium aluminum hydride, zinc/acid, tin/acid, or red phosphorus/iodine, in the present step is appropriately selected in a range of 1.0 to 5.0 mols and is preferably 1.5 to 2.0 mols relative to 1 mol of the compound [XXVI].

As the base usable in the present step, there can be mentioned sodium hydroxide, potassium hydroxide or the like. The use amount of the base is appropriately selected in a range of 1 to 5 mols and is preferably 1.0 to 3.0 mols relative to 1 mol of the compound [XXVI].

The reaction temperature of the present step is freely selected in a range from 0° C. to the reflux temperature of the reaction system and is preferably 0° C. to 100° C.

The reaction time of the present step differs depending upon the temperature of reaction, the substrate of reaction, the amount of reactant, etc., but is ordinarily 10 minutes to 24 hours.

After the completion of the reaction, the reaction mixture is subjected to operations such as pouring into water or the like, extraction with organic solvent, concentration and the like, whereby a compound [XXVII] can be isolated. The isolated compound [XXVII] may be as necessary purified by column chromatography, recrystallization, etc.

[Step 11]

The compound represented by the general formula [XV-1] can be produced by reacting the compound [XXVII] with a compound [III] in a solvent in the presence or absence of a base in the presence or absence of a radical initiator, in the same manner as in the Production method 1.

Each amount of the solvent and the base, usable in the present step is the same as in the Production method 1, and the reaction time and the reaction temperature in the present step are each the same as in the Production method 1.

After the completion of the reaction, the reaction mixture is subjected to operations such as pouring into water or the like, extraction with organic solvent, concentration and the like, whereby a compound [XV-1] can be isolated. The isolated compound [XV-1] may be as necessary purified by column chromatography, recrystallization, etc.

The pest control agent of the present invention is characterized by containing, as an active ingredient, an alkyl phenyl sulfide derivative represented by the general formulas [I] or [I'], or an agriculturally acceptable salt thereof. The present pest control agent is representatively an insecticide and miticide.

The present pest control agent may as necessary contain an additive component (carrier) ordinarily used in agricultural chemical formulations.

As the additive component, there can be mentioned a carrier (e.g. solid carrier or liquid carrier), a surfactant, a binder or a tackifier, a thickening agent, a coloring agent, a spreader, a sticker, an anti-freeze, a solidification inhibitor, a disintegrator, a decomposition inhibitor, etc. As necessary, there may be used other additive components such as antiseptic, vegetable chip and the like. These additive components may be used in one kind or in combination of two or more kinds.

The above additive components are explained.

As the solid carrier, there can be mentioned, for example, mineral carriers such as pyrophyllite clay, kaolin clay, silicastone clay, talc, diatomaceous earth, zeolite, bentonite, acid clay, active clay, Attapulgus clay, vermiculite, perlite, pumice, white carbon (e.g. synthetic silicic acid or synthetic silicate), titanium dioxide and the like; vegetable carriers such as wood flour, corn culm, walnut shell, fruit stone, rice hull, sawdust, wheat bran, soybean flour, powder cellulose, starch, dextrin, saccharide and the like; inorganic salt carriers such as calcium carbonate, ammonium sulfate, sodium sulfate, potassium chloride and the like; and polymer carriers such as polyethylene, polypropylene, polyvinyl chloride, polyvinyl acetate, ethylene-vinyl acetate copolymer, urea-aldehyde resin and the like.

As the liquid carrier, there can be mentioned, for example, monohydric alcohols such as methanol, ethanol, propanol, isopropanol, butanol, cyclohexanol and the like; polyhydric alcohols such as ethylene glycol, diethylene glycol, propylene glycol, hexylene glycol, polyethylene glycol, polypropylene glycol, glycerine and the like; polyhydric alcohol derivatives such as propylene type glycol ether and the like; ketones such as acetone, methyl ethyl ketone, methyl isobutyl ketone, diisobutyl ketone, cyclohexanone, isophorone and the like; ethers such as diethyl ether, 1,4-dioxane, cellosolve, dipropyl ether, tetrahydrofuran and the like; aliphatic hydrocarbons such as normal paraffin, naphthene, isoparaffin, kerosene, mineral oil and the like; aromatic hydrocarbons such as toluene, $C_9$~$C_{10}$ alkylbenzene, xylene, solvent naphtha, alkylnaphthalene, high-boiling aromatic hydrocarbon and the like; halogenated hydrocarbons such as 1,2-dichloroethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, coconut oil, castor oil and the like; and water.

As to the surfactant, there is no particular restriction. However, the surfactant preferably gels or swells in water. There can be mentioned, for example, non-ionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl etherformalin condensate, polyoxyethylene polyoxypropylene block polymer, alkyl polyoxyethylene polypropylene block polymer ether, polyoxyethylene alkyl amine, polyoxyethylene fatty acid amide, polyoxyethylene fatty acid bisphenyl ether, polyalkylene benzyl phenyl ether, polyoxyalkylene styryl phenyl ether, acetylene diol, polyoxyalkylene-added acetylene diol, polyoxyethylene ether type silicone, ester type silicone, fluorine-containing surfactant, polyoxyethylene castor oil, polyoxyethylene hardened castor oil and the like; anionic surfactants such as alkyl sulfate, polyoxyethylene alkyl ether sulfate, polyoxyethylene alkyl phenyl ether sulfate, polyoxyethylene styryl phenyl ether sulfate, alkylbenzenesulfonic acid salt, ligninsulfonic acid salt, alkylsulfosuccinic acid salt, naphthalenesulfonic acid salt, alkylnaphthalenesulfonic acid salt, naphthalenesulfonic acid-formalin condensate salt, alkylnaphthalenesulfonic acid-formalin condensate salt, fatty acid salt, polycarboxylic acid salt, N-methyl-fatty acid sarcosinate, resin acid salt, polyoxyethylene alkyl ether phosphate, polyoxyethylene alkylphenyl ether phosphate and the like; cationic surfactants including alkyl amine salts such as laurylamine hydrochloride, stearylamine hydrochloride, oleylamine hydrochloride, stearylamine acetate, stearylaminopropylamine acetate, alkyl trimethyl ammonium chloride, alkyl dimethyl benzalkonium chloride and the like; and ampholytic surfactants such as betaine type (e.g. dialkyldiaminoethylbetaine or alkyldimethylbenzylbetaine), amino acid type (e.g. dialkylaminoethylglycine or alkyldimethylbenzylglycine) and the like.

As the binder and tackifier, there can be mentioned, for example, carboxymethyl cellulose or a salt thereof, dextrin, water-soluble starch, xanthane gum, guar gum, sucrose, polyvinylpyrrolidone, gum arabi, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, and natural phospholipid (e.g. cephalinic acid or lecithin).

As the thickening agent, there can be mentioned, for example, water-soluble polymers such as xanthan gum, guar gum, carboxymethyl cellulose, polyvinylpyrrolidone, carboxyvinyl polymer, acrylic polymer, starch derivative, polysaccharide and the like; and inorganic fine powders such as high-purity bentonite, white carbon and the like.

As the coloring agent, there can be mentioned, for example, inorganic pigments such as iron oxide, titanium oxide, Prussian Blue and the like; and organic dyes such as Alizarine dye, azo dye, metal phthalocyanine dye and the like.

As the spreader, there can be mentioned, for example, silicone-based surfactant, cellulose powder, dextrin, processed starch, polyaminocarboxylic acid chelate compound, crosslinked polyvinylpyrrolidone, maleic acid and styrene, methacrylic acid copolymer, half ester between polyhydric alcohol polymer and dicarboxylic acid anhydride, and water-soluble salt of polystyrenesulfonic acid.

As the sticker, there can be mentioned, for example, surfactant (e.g. sodium dialkylsulfosuccinate, polyoxyethylene alkyl ether, polyoxyethylene alkylphenyl ether, or polyoxyethylene fatty acid ester), paraffin, terpene, polyamide resin, polyacrylic acid salt, polyoxyethylene, wax, polyvinyl alkyl ether, alkylphenol-formalin condensate, and synthetic resin emulsion.

As the anti-freeze, there can be mentioned, for example, polyhydric alcohol (e.g. ethylene glycol, diethylene glycol, propylene glycol, or glycerine).

As the solidification inhibitor, there can be mentioned, for example, polysaccharide (e.g. starch, alginic acid, mannonse or galactose), polyvinylpyrrolidone, white carbon, ester gum and petroleum resin.

As the disintegrator, there can be mentioned, for example, sodium tripolyphosphate, sodium hexametaphosphate, stearic acid metal salt, cellulose powder, dextrin, methacrylic acid ester copolymer, polyvinylpyrrolidone, polyaminocarboxylic acid chelate compound, sulfonated styreneisobutylene-maleic anhydride copolymer, and starchpolyacrylonitrile graft copolymer.

As the decomposition inhibitor, there can be mentioned, for example, desiccants such as zeolite, quick lime, magnesium oxide and the like; antioxidants such as phenol type, amine type, sulfur type, phosphoric acid type and the like; and ultraviolet absorbents such as salicylic acid type, benzophenone type and the like.

When the present pest control agent contains the above-mentioned additive components, their contents based on mass are selected in a range of ordinarily 5 to 95%, preferably 20 to 90% in the case of carrier (e.g. solid carrier or liquid carrier), ordinarily 0.1 to 30%, preferably 0.5 to 10% in the case of surfactant, and ordinarily 0.1 to 30%, preferably 0.5 to 10% in the case of other additives.

The present pest control agent is used in any formulation selected from dust formulation, dust-granule mixture, granule, wettable powder, water-soluble concentrate, water-dispersible granule, tablet, Jumbo, emulsifiable concentrate, oil formulation, solution, flowable concentrate, emulsion, microemulsion, suspoemulsion, ultra-low volume formulation, microcapsule, smoking agent, aerosol, baiting agent, paste, etc.

In actual use of the formulation, the formulation can be used per se or after dilution with a diluent (e.g. water) in a given concentration. The application of the formulation containing the present compound or of its dilution product can be conducted by a method ordinarily used, such as dispersion (e.g. spraying, misting, atomizing, powder dispersion, granule dispersion, on-water-surface dispersion, or inbox dispersion), in-soil application (e.g. mixing or drenching), on-surface application (e.g. coating, dust coating or covering), immersion, poison bait, smoking and the like. It is also possible to mix the above-mentioned active ingredient with a livestock feed in order to prevent the infestation and growth of injurious pest, particularly injurious insect in the excreta of livestock.

The proportion (mass %) of the active ingredient in the present pest control agent is appropriately selected so as to meet the necessity. The active ingredient is appropriately selected, for example, in the following range.

In dust formulation, dust-granule mixture, etc.
0.01 to 20%, preferably 0.05 to 10%
In granule, etc.
0.1 to 30%, preferably 0.5 to 20%
In wettable powder, water-dispersible granule, etc.
1 to 70%, preferably 5 to 50%
In water-soluble concentrate, solution, etc
1-95%, preferably 10 to 80%
In emulsifiable concentrate, etc.
5 to 90%, preferably 10 to 80%
In oil formulation, etc.
1 to 50%, preferably 5 to 30%
In flowable concentrate, etc.
5 to 60%, preferably 10 to 50%
In emulsion, microemulsion, suspoemulsion, etc.
5 to 70%, preferably 10 to 60%
In tablet, bait, paste, etc.
1 to 80%, preferably 5 to 50%
In smoking agent, etc.
0.1 to 50%, preferably 1 to 30%
In aerosol, etc.
0.05 to 20%, preferably 0.1 to 10%

The formulation is sprayed after dilution in an appropriate concentration, or applied directly.

When the present pest control agent is used after dilution with a diluent, the concentration of active ingredient is generally 0.1 to 5,000 ppm. When the formulation is used per se, the application amount thereof per unit area is 0.1 to 5,000 g per 1 ha in terms of active ingredient compound; however, the application amount is not restricted thereto.

Incidentally, the present pest control agent is sufficiently effective when using the present compound alone as an active ingredient. However, in the present pest control agent, there may be mixed or used in combination, as necessary, fertilizers and agricultural chemicals such as insecticide, miticide, nematicide, synergist, fungicide, anti-viral agent, attractant, herbicide, plant growth-controlling agent and the like. In this case, a higher effect is exhibited.

Below are shown examples of the known insecticides, miticides, nematicides and synergist compounds, which may be mixed or used in combination.

1. Acetylcholineesterase Inhibitiors
(1A) carbamates: alanycarb, aldicarb, aldoxycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb;

(1B) Organophosphates: acephate, azamethiphos, azinphosethyl, azinphos-methyl, cadusafos, chlorethoxyfos, chlorfenvinphos, chlormephos, chlorpyrifos, chlorpyrifos-methyl, coumaphos, cyanophos, demoton-S-methyl, diamidafos, diazinon, dichlorvos, dicrotophos, dimethoate, dimethylvinphos, dioxabenzofos, disulfoton, DSP, EPN, ethion, ethoprophos, etrimfos, famphur, fenamiphos, fenitrothion, fenthion, fonofos, fosthiazate, fosthietan, heptenophos, isamidofos, isazophos, isofenphos-methyl, isopropyl O-(methoxyaminothiophosphoryl)salicylate, isoxathion, malathion, mecarbam, methamidophos, methidathion, mevinphos, monocrotophos, naled, omethoate, oxydemeton-methyl, oxydeprofos, parathion, parathion-methyl, phenthoate, phorate, phosalone, phosmet, phosphamidon, phoxim, pirimiphos-methyl, profenofos, propaphos, propetamphos, prothiofos, pyraclofos, pyridaphenthion, quinalphos, sulfotep, tebupirimfos, temephos, terbufos, tetrachlorvinphos, thiometon, thionazin, triazophos, trichlorfon, vamidothion, dichlofenthion, imicyafos, isocarbophos, mesulfenfos, flupyrazofos 2. GABA-Gated Chloride Channel Antagonists
(2A) Cyclodiene organochlorines: chlordane, endosulfan, gamma-BCH;
(2B) Phenylpyrazoles: acetoprol, ethiprole, fipronil, pyrafluprole, pyriprole, RZI-02-003 (code number)

3. Sodium Channel Modulators
(3A) Pyrethroids/Pyrethrins: acrinathrin, allethrin (includes d-cis-trans and d-trans), bifenthrin, bioallethrin, bioallethrin S-cyclopentenyl, bioresmethrin, cycloprothrin, cyfluthrin (includes beta-), cyhalothrin (includes gamma- and lambda-), cypermethrin (includes alpha-, beta-, theta- and zeta-), cyphenothrin [includes (IR)-trans-isomers], deltamethrin, empenthrin, esfenvalerate, etofenprox, fenpropathrin, fenvalerate, flucythrinate, flumethrin, halfenprox, imiprothrin, metofluthrin, permethrin, phenothrin [includes (IR) trans-isomer], prallethrin, profluthrin, pyrethrine, resmethrin, RU15525 (code number), silafluofen, tefluthrin, tetramethrin, tralomethrin, transfluthrin, ZX18901 (code number), fluvalinate (includes tau-), tetramethylfluthrin, meperfluthrin;
(3B) DDT/Methoxychlor: DDT, methoxychlor 4. Nicotinic Acetylcholine Receptor Agonist/Antagonist
(4A) Neonicotinoids: acetamiprid, clothianidin, dinotefuran, imidacloprid, nitenpyram, thiacloprid, thiamethoxam;
(4B) Nicotine: nicotine-sulfate 5. Nicotinic Acetylcholine Receptor Allosteric Activators
Spinosines: spinetoram, spinosad 6. Chloride Channel Activators
Abamectins, Milbemycins: abamectin, emamectin benzoate, lepimectin, milbemectin, ivermectin, polynactins 7. Juvenile Hormone Mimics
diofenolan, hydroprene, kinoprene, methothrin, fenoxycarb, pyriproxyfen 8. Miscellaneous Non-Specific (Multi-Site) Inhibitors
1,3-dichloropropene, DCIP, ethylene dibromide, methyl bromide, chloropicrin, sulfuryl fluoride 9. Antifeedant
pymetrozine, flonicamid, pyrifluquinazon 10. Mite Growth Inhibitor
clofentezine, diflovidazin, hexythiazox, etoxazole 11. Microbial Disruptors of Insect Midgut Membranes
BT agent: *Bacillus sphaericus, Bacillus thuringiensis* subsp. *aizawai, Bacillus thuringiensis* subsp. *israelensis, Bacillus thuringiensis* subsp. *kurstaki, Bacillus thuringiensis* subsp. *tenebrionis*, Bt crop proteins (Cry1Ab, Cry1Ac, Cry1Fa, Cry2Ab, mCry3A, Cry3Ab, Cry3Bb, Cry34/35Ab1), *Bacillus popilliae, Bacillus subtillis*

12. Inhibitors of Mitochondrial ATP Synthase
    diafenthiuron;
    Organotin miticides: azocyclotin, cyhexatin, fenbutatin oxide;
    propargite, tetradifon
13. Uncouplers of Oxidative Phosphorylation Via Disruption of the Proton Gradient
    chlorfenapyr, DNOC
14. Nicotinic Acetylcholine Receptor Channel Blockers
    Nereistoxin analogues: bensultap, cartap, thiocyclam, thiosultap
15. Inhibitors of Chitin Biosynthesis, Type O
    Benzoylureas: bistrifluron, chlorfluazoron, diflubenzuron, flucycloxuron, flufenoxuron, hexaflumuron, lufenuron, novaluron, noviflumuron, teflubenzuron, triflumuron, fluazuron
16. Inhibitors of Chitin Biosynthesis, Type 1
    buprofezin
17. Molting Disruptor, Dipteran
    cyromazine
18. Ecdysone Receptor Agonist (Ecdysis Acceleration)
    Diacylhydrazines: chromafenozide, halofenozide, methoxyfenozide, tebufenozide
19. Octopamine receptor agonist
    amitraz
20. Mitochondrial Complex III Electron Transport Inhibitors
    hydramethylnon, acequinocyl, fluacrypyrim, cyenopyrafen
21. Mitochondrial Complex II Electron Transport Inhibitors
    cyflumetofen, cyenopyrafen, NNI-0711 (code number)
22. Mitochondrial Complex I Electron Transport Inhibitors
    METI miticides and insecticides: fenazaquin, fenpyroximate, pyridaben, pyrimidifen, tebufenpyrad, tolfenpyrad
    Other: rotenone
23. Sodium Channel Blockers
    indoxacarb, metaflumizon
24. Inhibitors of Lipid Synthesis
    Tetronic and Tetramic acid derivatives: spirodiclofen, spiromesifen, spirotetramat
25. Mitochondrial Complex IV Electron Transport Inhibitors
    aluminum phosphide, phosphine, zinc phosphide, calcium cyanide
26. Neuronal inhibitors (unknown mode of action)
    bifenazate
27. Aconitase inhibitors
    sodium fluoroacetate
28. Synergists
    piperonyl butoxide, DEF
29. Ryanodine Receptor Modulators
    chlorantraniliprole, flubendiamide, cyantraniliprole
30. Compounds with unknown mode of action
    azadirachtin, amidoflumet, benclothiaz, benzoximate, bromopropylate, chinomethionat, CL900167 (code number), cryolite, dicofol, dicyclanil, dienochlor, dinobuton, fenbutatin oxide, fenothiocarb, fluensulfone, flufenerim, flsulfamide, karanjin, metham, methoprene, methoxyfenozide, methyl isothiocyanate, pyridalyl, pyrifluquinazon, sulcofuron-sodium, sulfluramid, sulfoxaflor, flupyradifurone, flometoquin, IKI-3106 (code number)
31. Entomopathogenic Fungi, Nematode-Pathogenic Microorganisms
    *Beauveria bassiana, Beauveria tenella, Verticillium lecanii, Pacilimyces tenuipes, Paecilomyces fumosoroceus, Beauveria brongniartii, Monacrosporium phymatophagum, Pasteuriapenetrans*
32. Sex Pheromone
    (Z)-11-hexadecenal, (Z)-11-hexadecenyl acetate, litlure-A, litlure-B, Z-13-eicosene-10-one, (Z,E)-9,12-tetradecadienyl acetate, (Z)-9-tetradecen-1-ol, (Z)-11-tetradecenyl acetate, (Z)-9,12-tetradecadienyl acetate, (Z,E)-9,11-detradecadienyl acetate Next, there are shown examples of the known fungicide or disease damage control agent compounds which may be mixed or used in combination.

1. Nucleic Acid Biosynthesis Inhibitor
    Acylalanines: benalaxyl, benalaxyl-M, furalaxyl, metalaxyl, metalaxyl-M;
    Oxazolidinones: oxadixyl;
    Butyrolactones: clozylacon, ofurace;
    Hydroxy-(2-amino)pyrimidines: bupirimate, dimethirimol,
    ethirimol;
    Isoxazole: hymexazol;
    Isothiazolones: octhilinone;
    Carboxylic acids: oxolinic acid
2. Mitosis and Cell Division Inhibitors
    Benzoimidazoles: benomyl, carbendazim, fuberidazole, thiabendazole;
    Thiophanates: thiophanate, thiophanate-methyl;
    N-phenylcarbamates: diethofencarb;
    Toluamides: zoxamide;
    Phenylureas: pencycuron;
    Pyridinylmethylbenzamides: fluopicolide
3. Respiratory Inhibitors
    Pyrimidineamines: diflumetorim;
    Carboxamides: benodanil, flutolanil, mepronil, fluopyram, fenfuram, carboxin, oxycarboxin, thifluzamide, bixafen, furametpyr, isopyrazam, penflufen, penthiopyrad, sedaxane, boscalid, fluxapyroxad, isofetamid, benzovindiflupyr;
    Methoxy-acrylates: azoxystrobin, enestroburin, picoxystrobin, pyraoxystrobin, coumoxystrobin, enoxastrobin, flufenoxystrobin;
    Methoxy-carbamates: pyraclostrobin, pyrametostrobin, triclopyricarb;
    Oxyimino acetates: kresoxim-methyl, trifloxystrobin;
    Oxyimino-acetamides: dimoxystrobin, metominostrobin, orysastrobin, fenaminstrobin;
    Oxazolidine-diones: famoxadone;
    Dihydro-dioxazines: fluoxastrobin;
    Imidazolinones: fenamidone;
    Benzyl-carbamates: pyribencarb;
    Cyano-imidazoles: cyazofamid;
    Sulfamoyl-triazoles: amisulbrom;
    Dinitrophenyl crotonates: binapacryl, methyldinocap, dinocap;
    2,6-Dinitro-anilines: fluazinam;
    Pyrimidinone hydrazones: ferimzone;
    Triphenyl tin: TPTA, TPTC, TPTH;
    Thiophene-carboxamides: silthiofam
    Triazolo-pyrimidylamines: ametoctradin
4. Amino Acid and Protein Synthesis Inhibitors
    Anilino-pyrimidines: cyprodinil, mepanipyrim, pyrimethanil;
    Enopyranuronic acid: blasticidin-S, mildiomycin;
    Hexopyranosyl antibiotic: kasugamycin;
    Glucopyranosyl antibiotic: streptomycin;
    Tetracycline antibiotic: oxytetracycline 5. Signal transduction inhibitors
  Quinoline: quinoxyfen;
  Quinazolines: proquinazid;
  Phenylpyrroles: fenpiclonil, fludioxonil;
  Dicarboxylmides: chlozolinate, iprodione, procymidone, vinclozolin
6. Lipid synthesis and membrane integrity inhibitors
  Phosphoro-thiolates: edifenphos, iprobenfos, pyrazophos;
  Dithiolanes: isoprothiolane;
  Aromatic hydrocarbons: biphenyl, chloroneb, dicloran, quintozene, tecnazene, tolclofos-methyl;
  1,2,4-Thiadiazoles: etridiazole;
  Carbamates: iodocarb, propamocarb-hydrochloride, prothiocarb;
  Cinnamic acid amides: dimethomorph, flumorph;
  Valineamide carbamates: benthiavalicarb-isopropyl, iprovalicarb, valifenalate;
  Mandelic acid amides: mandipropamid;
  *Bacillus subtilis* and the fungicidal lipopeptides produced: *Bacillus subtilis* (strain: QST 713)
7. Inhibitors of sterol biosynthesis in membranes
  Piperazines: triforine;
  Pyridines: pyrifenox;
  Pyrimidines: fenarimol, nuarimol;
  Imidazoles: imazalil, oxpoconazole-fumarate, pefurazoate, prochloraz, triflumizole;
  Triazoles: azaconazole, bitertanol, bromuconazole, cyproconazole, difenoconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, furconazole, furconazole-cis, quinconazole;
  Morpholines: aldimorph, dodemorph, fenpropimorph, tridemorph;
  Piperidines: fenpropidin, piperalin;
  Spiroketal amines: spiroxamine;
  Hydroxyanilides: fenhexamid;
  Thiocarbamates: pyributicarb;
  Allylamines: naftifine, terbinafine
8. Glucan Synthesis Inhibitors
  Glucopyranosyl type antibiotic: validamycin;
  Peptidylpyridine nucleotide compound: polyoxin
9. Melanine Synthesis Inhibitors
  Isobenzo-furanones: phthalide;
  Pyrrolo-quinolines: pyroquilon;
  Triazolobenzo-thiazoles: tricyclazole;
  Carboxamides: carpropamid, diclocymet;
  Propionamides: fenoxanil
10. Host Plant Defence Inducers
  Benzothiadiazoles: acibenzolar-5-methyl;
  Benzoisothiazoles: probenazole;
  Thiadiazole-carboxamides: tiadinil, isotianil
  Natural product: laminarin
11. Compounds with Unknown Mode of Action
  Copper compound: copper hydroxide, copper dioctanoate, copper oxychloride, copper sulfate, cuprous oxide, oxine-copper, Bordeaux mixture, copper nonyl phenol sulphonate;
  Sulfur compound: sulfur;
  Dithiocarbamates: ferbam, mancozeb, maneb, metiram, propineb, thiram, zineb, ziram, cufraneb;
  Phthalimides: captan, folpet, captafol;
  Chloronitriles: chlorothalonil;
  Sulfamides: dichlofluanid, tolylfluanid;
  Guanidines: guazatine, iminoctadine-albesilate, iminoctadine-triacetate, dodine;
  Other compound: anilazine, dithianon, cymoxanil, fosetyl (aluminum, calcium, sodium), phosphorus acid and salts, tecloftalam, triazoxide, flusulfamide, diclomezine, methasulfocarb, ethaboxam, cyflufenamid, metrafenone, potassium bicarbonate, sodium bicarbonate, BAF-045 (code number), BAG-010 (code number), benthiazole, bronopol, carvone, chinomethionat, dazomet, DBEDC, debacarb, dichlorophen, difenzoquat-methyl sulfate, dimethyl disulfide, diphenylamine, ethoxyquin, flumetover, fluoroimide, flutianil, furan-carboxylic acid, metam, nabam, natamycin, nitrapyrin, nitrothal-isopropyl, ophenylphenol, oxazinylazole, oxyquinoline sulfate, phenazine oxide, polycarbamate, pyriofenone, fenpyrazamine, silver, pyrisoxazole, tebufloquin, tolnifanide, trichlamide, mineral oils, organic oils, tolprocarb, oxathiapiprolin Below are shown examples of the known herbicidal compounds and plant growth regulators which may be mixed or used in combination.

A1. Acetyl CoA Carboxylase (ACCase) Inhibitors
(A1-1) Aryloxyphenoxy propionates: clodinafop-propargyl, cyhalofop-butyl, diclofop-methyl, diclofop-P-methyl, fenoxaprop-P-ethyl, fluazifop-butyl, fluazifop-P-butyl, haloxyfop, haloxyfop-etotyl, haloxyfop-P, metamifop, propaquizafop, quizalofop-ethyl, quizalofop-P-ethyl, quizalofop-P-tefuryl, fenthiaprop-ethyl;
(A1-2) Cyclohexandiones: alloxydim, butroxydim, clethodim, cycloxydim, profoxydim, sethoxydim, tepraloxydim, tralkoxydim;
(A1-3) Phenylpyrazolines: aminopyralid, pinoxaden;
B. Acetolactate Synthase (ALS) Inhibitors
(B-1) Imidazolinones: imazamethabenz-methyl, imazamox, imazapic (includes salts with amine, etc.), imazapyr (includes salts with isopropylamine, etc.), imazaquin, imazathapyr;
(B-2) Pyrimidinyloxy benzoate: bispyribac-sodium, pyribenzoxim, pyriftalid, pyriminobac-methyl, pyrithiobac-sodium, pyrimisulfan, triafamone;
(B-3) Sulfonylaminocarbonyl-triazolinones: flucarbazone-sodium, thiencarbazone (includes sodium salt, methyl ester, etc.), propoxycarbazone-sodium, procarbazone-sodium, iofensulfuron-sodium;
(B-4) Sulfonylureas: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfulon-methylsodium, mesosulfuron-methyl, thifensulfuron-methyl, triasulfuron, tribenuron-methyl, trifloxysulfuron-sodium, triflusulfuron-methyl, tritosulfuron, orthosulfamuron, propgirisulfuron, metazosulfuron, flucetosulfuron;
(B-5) Triazolopyrimidines: cloransulam-methyl, diclosulam, florasulam, flumetsulam, metosulam, penoxsulam, pyroxsulam;
C1. Photosynthesis at Photosystem II Inhibitors (1)
(C1-1) Phenylcarbamates: desmedipham, phenmedipham;
(C1-2) Pyridazinones: chloridazon, brompyrazon;
(C1-3) Triazines: ametryn, atrazine, cyanazine, desmetryne, dimethametryn, eglinazine-ethyl, prometon, prometryn, propazine, simazine, simetryn, terbumeton, terbuthylazine, terbutryn, trietazine;
(C1-4) Triazinones: metamitron, metribuzin;
(C1-5) Triazolinones: amicarbazone;
(C1-6) Uracils: bromacil, lenacil, terbacil;
C2. Photosynthesis at Photosystem II Inhibitors (2)
(C2-1) Amides: pentanochlor, propanil;
(C2-2) Ureas: chlorbromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron, metobenzuron;

C3. Photosynthesis at Photosystem II Inhibitors (3)
(C3-1) Benzothiadiazones: bentazone;
(C3-2) Nitriles: bromofenoxim, bromoxynil (includes esters of butyric acid, octanoic acid, heptanoic acid, etc.), ioxynil;
(C3-3) Phenylpyrazines: pyridafol, pyridate;
D. Photosystem-I-Electron Acceptors
(D-1) Bipyridyliums: diquat, paraquat dichloride;
E. Protoporphyrinogen Oxydaze (PPO) Inhibitors
(E-1) Diphenylethers: acifluorfen-sodium, bifenox, chlomethoxyfen, ethoxyfen-ethyl, fluoroglycofen-ethyl, fomesafen, lactofen, oxyfluorfen;
(E-2) N-phenylphthalimides: cinidon-ethyl, flumiclorac-pentyl, flumioxazin, chlorphthalim;
(E-3) Oxydiazoles: oxadiargyl, oxadiazon;
(E-4) Oxazolidinediones: pentoxazone;
(E-5) Phenylpyrazoles: fluazolate, pyraflufen-ethyl;
(E-6) Pyrimidinediones: benzfendizone, butafenacil, saflufenacil, tiafenacil;
(E-7) Thiadiazoles: fluthiacet-methyl, thidiazimin;
(E-8) Triazolinones: azafenidin, carfentrazone-ethyl, sulfentrazone, bencarbazone;
(E-9) Other compound: flufenpyr-ethyl, profluazol, pyraclonil, SYP-298 (code number), SYP-300 (code number);
F1. Inhibitors of Carotenoid Biosynthesis at the Phytoene Desaturase Step (PDS)
(F1-1) Pyridazinones: norflurazon;
(F1-2) Pyrimidinecarboxamides: diflufenican, picolinafen;
(F1-3) Other compound: beflubutamid, fluridone, fluorochloridone, flurtamone;
F2. 4-Hydroxyphenyl-pyruvate-dioxygenase (HPPD) inhibitors
(F2-1) Callistemones: mesotrione;
(F2-2) Isoxazoles: pyrasulfotole, isoxaflutole, isoxachlortole;
(F2-3) Pyrazoles: benzofenap, pyrazolynate, pyrazoxyfen, topramezone;
(F2-4) Triketones: sulcotrione, tefuryltrione, tembotrione, pyrasulfotole, topramezone, bicyclopyrone;
F3. Carotinoid Biosynthesis Inhibitors (Unknown Target)
(F3-1) Diphenyl ethers: aclonifen;
(F3-2) Isoxazolidinones: clomazone;
(F3-3) Triazoles: amitrole;
G. EPSP Synthase Inhibitors (Aromatic Amino Acid Biosynthesis Inhibitors)
(G-1) Glycines: glyphosate (includes salts of sodium, amine, propylamine, ispropylamine, dimethylamine, trimesium, etc.);
H. Glutamine Synthetase Inhibitors
(H-1) Phosphinic acids: bilanafos, glufosinate (includes salts of amine, sodium, etc.);
I. Dihydropteroate (DHP) Synthetase Inhibitors
(I-1) Carbamates: asulam;
K1. Microtubule Assembly Inhibitors
(K1-1) Benzamides: propyzamide, tebutam;
(K1-2) Benzoic acids: chlorthal-dimethyl;
(K1-3) Dinitroanilines: benfluralin, butralin, dinitramine, ethalfluralin, fluchloralin, oryzalin, pendimethalin, prodiamine, trifluralin;
(K1-4) Phosphoroamidates: amiprofos-methyl, butamifos;
(K1-5) Pyridines: dithiopyr, thiazopyr;
K2. Inhibitors of Mitosis/Microtubule Organization
(K2-1) Carbamates: carbetamide, chlorpropham, propham, swep, karbutilate;

K3. Very-long-chain fatty acids (VLCFAs) inhibitors (cell division inhibitors)
(K3-1) Acetamides: diphenamid, napropamide, naproanilide;
(K3-2) Chloroacetamides: acetochlor, alachlor, butachlor, butenachlor, diethatyl-ethyl, dimethachlor, dimethenamid, dimethenamid-P, metazachlor, metolachlor, pethoxamid, pretilachlor, propachlor, propisochlor, S-metolachlor, thenylchlor;
(K3-3) Oxyacetamides: flufenacet, mefenacet;
(K3-4) Tetrazolinones: fentrazamide;
(K3-5) Other compound: anilofos, bromobutide, cafenstrole, indanofan, piperophos, fenoxasulfone, pyroxasulfone, ipfencarbazone;
L. Cellulose Synthesis Inhibitors
(L-1) Benzamides: isoxaben;
(L-2) Nitriles: dichlobenil, chlorthiamid;
(L-3) Triazolocarboxamides: flupoxame;
M. Uncouplers (Membrane Disruptors)
(M-1) Dinitrophenols: dinoterb, DNOC (includes salts of amine, sodium, etc.);
N. Lipid Biosynthesis Inhibitors (Excluding ACCase Inhibitors)
(N-1) Benzofurans: benfuresate, ethofumesate;
(N-2) Halogenated carboxylic acids: dalapon, flupropanate, TCA (includes salts of sodium, calcium, ammonia, etc.);
(N-3) Phosphorodithioates: bensulide;
(N-4) Thiocarbamates: butylate, cycloate, dimepiperate, EPTC, esprocarb, molinate, orbencarb, pebulate, prosulfocarb, thiobencarb, iocarbazil, tri-allate, vernolate;
O. Synthetic Auxins
(O-1) Benzoic acids: chloramben, 2,3,6-TBA, dicamba (includes salts of amine, diethylamine, isopropylamine, diglycolamine, sodium, lithium, etc.);
(O-2) Phenoxycarboxylic acids: 2,4,5-T, 2,4-D (includes salts of amine, diethylamine, triethanolamine, isopropylamine, sodium, lithium, etc.), 2,4-DB, clomeprop, dichlorprop, dichlorprop-P, MCPA, MCPA-thioethyl, MCPB (includes sodium salt, ethylester, etc.), mecoprop (includes salts of sodium, potassium, isopropylamine, triethanolamine, dimethylamine, etc.), mecoprop-P;
(O-3) Pyridine carboxylic acids: clopyralid, fluoroxypyr, picloram, triclopyr, triclopyr-butotyl, halauxifen-methyl;
(O-4) Quinoline carboxylic acids: quinclorac, quinmerac;
(O-5) Other compound: benazolin;
P. Auxin Transport Inhibitors
(P-1) Phthalamates: naptalam (includes salts with sodium, etc.);
(P-2) Semicarbazones: diflufenzopyr;
Z. Compounds with Unknown Mode of Action
flamprop-M (includes methyl, ethyl and isopropyl esters), flamprop (includes methyl, ethyl and isopropyl esters), chlorflurenol-methyl, cinmethylin, cumyluron, daimuron, methyldymuron, difenzoquat, etobenzanid, fosamine, pyributicarb, oxaziclomefone, acrolein, AE-F-150954 (code number), aminocyclopyrachlor, cyanamide, heptamaloxyloglucan, indaziflam, triaziflam, quinoclamine, endothal-disodium, phenisopham, SL-573 (code number), cyclopyrimonate Plant growth-controlling agent: 1-methylcyclopropene, 1-naphthylacetamide, 2,6-diisopropylnaphthalene, 4-CPA, benzylaminopurine, ancymidol, aviglycine, carvone, chlormequat, cloprop, cloxyfonac, cloxyfonac-potassium, cyclanilide, cytokinins, daminozide, dikegulac, dimethipin, ethephon, ethychlozate, flumetralin, flurenol, flurprimidol, forchlorfenuron, gibberellin acid, inabenfide, indole acetic acid, indole butyric acid, maleic hydrazide, mefluidide, mepiquat chloride, n-decanol, paclobutrazol, prohexadionecalcium, prohydrojasmon, sintofen, thidiazuron, triacontanol, trinexapac-ethyl, uniconazole, uniconazole-P, 4-oxo-4-(2-phenylethyl)aminobutyric acid (chemical name, CAS registration No.: 1083-55-2)

Next, there are shown examples of the known safners which may be mixed or used in combination.
benoxacor, furilazole, dichlormid, dicyclonone, DKA-24 (N1,N2-diallyl-N2-dichloroacetylglycineamide), AD-67 (4-dichloroacetyl-1-oxa-4-azaspiro[4.5]decane), PPG-1292 (2,2-dichloro-N-(1,3-dioxolan-2-ylmethyl)-N-(2)acetamide), R-29148 (3-dichloroacetyl-2,2,5-trimethyl-1,3-oxazolidine), cloquintcet-methyl, 1,8-Naphthalic Anhydride, mefenpyr-diethyl, mefenpyr, mefenpyr-ethyl, fenchlorazole O ethyl, fenclorim, MG-191 (2-dichloromethyl-2-methyl-1,3-dioxane), cyometrinil, flurazole, fluxofenim, isoxadifen, isoxadifen-ethyl, mecoprop, MCPA, daimuron, 2,4-D, MON 4660 (code number), oxabetrinil, cyprosulfamide, lower alkyl-substituted benzoic acid, TI-35 (code number) and N-(2-methoxybenzoyl)-4-[(methylaminocarbonyl)amino] benzenesulfonamide(chemical name, CAS registration No.: 129531-12-0)

The pest control agent of the present invention constituted as above exhibits an excellent control effect to pest of Orthoptera, Thysanoptera, Hemiptera, Coleoptera, Diptera, Lepidoptera, Hymenoptera, Collembola, Thysanura, Blattodea, Isoptera, Psocoptera, *Mallophaga, Anoplura*, plant-feeding mites, plant parasitic nematodes, plant parasitic mollusc pests, other crop pests, nuisance pests, sanitary insects, parasites, etc. As examples of such pests, the following organism species can be mentioned.

As the Orthopteran pest, there can be mentioned, for example,
   Tettigoniidae: Ruspolia lineosa, etc.,
   Gryllidae: Teleogryllus emma, etc.,
   Gryllotalpidae: *Gryllotalpa orientalis,*
   Acrididae: Oxya *hyla* intricate, *Locusta migratoria, Melanoplus sanguinipes*, etc.,
   Pyrgomorphidae: Atractomorpha lata,
   Eneopteridae: Euscrytus *japonicus,*
   Tridactylidae: Xya *japonica*, etc.

As the Thysanopteran pests, there can be mentioned, for example,
   Thripidae: *Frankliniella intonsa, Frankliniella occidentalis, Scirtothrips dorsalis, Thrips palmi, Thrips tabaci*, etc.,
   Phlaeothripidaes: *Ponticulothrips diospyrosi, Haplothrips aculeatus*, etc.

As the Hemipteran pests, there can be mentioned, for example,
   Cicadidae: Mogannia minuta, etc.,
   Aphrophoridae: Aphorphora *intermedia*, etc.,
   Membracidae: Machaerotypus *sibiricus*, etc.,
   Cicadellidae: Arboridia *apicalis, Empoasca* onukii, *Nephotettix cincticeps*, Recilia *dorsalis*, etc.,
   Cixiidae: Pentastiridius *apicalis*, etc.,
   Delphacidae: Laodelphax striatella, *Nilaparvata lugens, Sogatella furcifera*, etc.,
   Meenoplidae: Nisia nervosa, etc.,
   Derbidae: Kamendaka saccharivora, etc.,
   Cixidia okunii: Achilus flammeus, etc.,
   Ricaniidae: Orosanga *japonicus*, etc.,
   Flatidae: Mimophantia *maritima*, etc.,
   Psyllidae: Cacopsylla pyrisuga, etc.,
   Calophyidae: Calophya *mangiferae*, etc.,
   Phylloxeridae: Daktulosphaira vitifoliae, etc.,
   Adelgidae: *Adelges laricis, Adelges tsugae*, etc.,
   Aphydidae: *Acyrthosiphon pisum, Aphis gossypii, Aphis spiraecola, Lipaphis erysimi, Myzus persicae, Schizaphis graminum, Rhopalosiphum padi*, etc.,
   Aleyrodidae: Aleurocanthus spiniferus, *Bemisia tabaci, Bemisia argentifolii, Trialeurodes vaporariorum*, etc.,
   Margarodidae: Drosicha corpulenta, *Icerya purchasi*, etc.,
   Pseudococcidae: Dysmicoccus *brevipes, Planococcus citri*, Pseudococcus *comstocki*, etc.,
   Coccidae: Ceroplastes ceriferus, etc.,
   Aclerdidae: Aclerda takahasii, etc.,
   Diaspididae Aonidella *aurantii*, Diaspidiotus *perniciosus*, Unaspis yanonensis, etc.,
   Miridae: *Lygus hesperus*, Trigonotylus caelestialium, etc.,
   Tingidae: Stephanitis pyrioides, Stephanitis nashi, etc.,
   Pentatomidae: *Eysarcoris aeneus, Lagynotomus elongatus, Nezara viridula, Plautia crossota*, etc.,
   Plataspidae: *Megacopta* cribaria, etc.,
   Lygaeidae: Cavelerius saccharivorus, etc.,
   Malcidae: Malcus *japonicus*, etc.,
   Pyrrhocoridae: *Dysdercus cingulatus*, etc.,
   Alydidae: Leptocorisa *acuta*, Leptocorisa *chinensis*, etc.,
   Coreidae: Anacanthocoris striicornis, etc.,
   Rhopalidae: Rhopalus *maculatus*, etc.,
   Cimicidae: *Cimex lectularius*, etc.

As the Coleoptera pests, there can be mentioned, for example,
   Scarabaeidae: *Anomala cuprea, Anomala* rufocuprea, *Popillia japonica*, Oryctes rhinoceros, etc.,
   Elateridae: *Agriotes* ogurae fuscicollis, Melanotus okinawensis, Melanotos fortnumi fortnumi, etc.,
   Dermestidae: Anthrenus *verbasci*, etc.,
   Bostrychidae: Heterobostrychus hamatipennis, etc.,
   Anobiidae: Stegobium paniceum, etc.,
   Ptinidae: Pitinus clavipes, etc.,
   Trogossitidae: Tenebroides *mauritanicus*, etc.,
   Cleridae: Necrobia *rufipes,*
   Nitidulidae: Carpophilus *hemipterus*, etc.,
   Silvanidae: Ahasverus advena, etc.,
   Laemophloeidae: Cryptolestes *ferrugineus*, etc.,
   Coccinellidae: *Epilachna varivestis*, Henosepilachna vigintioctopunctata, etc.,
   Tenebrionidae: *Tenebrio molitor*, Tribolium castaneum, etc.,
   Meloidae: Epicauta gorhami, etc.,
   Cerambycidae: *Anoplophora glabripennis*, Xylotrechus pyrrhoderus, Monochamus alternatus endai, etc.,
   Bruchidae: Callosobruchus *chinensis*, etc.,
   Chrysomelidae: *Leptinotarsa decemlineata, Diabrotica virgifera, Phaedon brassicae, Phyllotreta striolata*, etc.,
   Brentidae: Cylas formicarius, etc.,
   Curculionidae: *Hypera postica*, Listroderes costirostris, Euscepes postfasciatus, etc.,
   Erirhinidae: Echinocnemus bipunctatus, *Lissorhoptrus oryzophilus*, etc.,
   Dryophthoridae: *Sitophilus* zeamais, Sphenophrus *vestitus*, etc.,
   Scolytidae: Tomicus piniperda, etc.,
   Platypodidae: Crossotarsus niponicus, etc.,
   Lyctidae: Lyctus *brunneus*, etc.

As the Diptera pests, there can be mentioned, for example,
   Tipulidae: *Tipila aino*, etc.,
   Bibionidae: *Plecia nearctica*, etc.,
   Mycetophidae: *Exechia shiitakevora*, etc.,
   Sciaridae: *Pnyxia scabiei*, etc.,
   Cecidomyiidae: *Asphondylia yushimai, Mayetiola destructor*, etc.,
   Culicidae: *Aedes aegypti, Culex pipiens pallens*, etc.,
   Simuliidae: *Simulim takahasii*, etc., Chironomidae: *Chironomus oryzae*, etc.,
Tabanidae: *Chrysops suavis, Tabanus trigonus*, etc.,
Syrphidae: *Eumerus strigatus*, etc.,
Tephritidae: *Bactrocera dorsalis, Euphranta japonia, Ceratitis capitata*, etc.,
Agromyzidae: *Liriomyza trifolii, Chromatomyia horticola*, etc.,
Chloropidae: *Meromyza nigriventris*, etc.,
Drosophilidae: *Drosophila suzukii, Drosophila melanogaster*, etc.,
Ephydridae: *Hydrellia griseola*, etc.,
Hippoboscidae: *Hippobosca equina*, etc.,
Scatophagidae: *Parallelpmma sasakawae*, etc.,
Anthomyiidae: *Delia antiqua, Delia platura*, etc.,
Fanniidae: *Fannia canicularis*, etc.,
Muscidae: *Musca domestica, Stomoxys calcitrans*, etc.,
Sarcophagidae: *Sarcophaga peregrina*, etc.,
Gasterophilidae: *Gasterophilus intestinalis*, etc.,
Hypodermatidae: *Hypoderma lineatum*, etc.,
Oestridae: *Oestrus ovis*, etc.

As the Lepidoptera pests, there can be mentioned, for example,
Hepialidae: Endoclita excrescens, etc.,
Heliozelidae: Antispila ampelopsia, etc.,
Cossidae: Zeuzera multistrigata leuconota, etc.,
Tortricidae: *Archips* fuscocupreanus, Adoxophyes orana *fasciata, Grapholita molesta*, Homona magnanima, Leguminivora glycinivorella, *Cydia pomonella*, etc.,
Cochylidae: *Eupoecilia ambiguella*, etc.,
Psychidae: Bambalina sp., Eumeta minuscula, etc.,
Tineidae: Nemapogon granella, Tinea *translucens*, etc.,
Bucculatricidae: *Bucculatrix* pyrivorella, etc.,
Lyonetiidae: *Lyonetia clerkella*, etc.,
Gracilariidae: Caloptilia theivora, Phyllonorycter ringoniella, etc.,
Phyllocnistidae: *Phyllocnistis citrella*, etc.,
Acrolepiidae: Acrolepiopsis sapporensis, etc.,
Yponomeutidae: *Plutella xylostella*, Yponomeuta *orientalis*, etc.,
Argyresthiidae: *Argyresthia conjugella*, etc.,
Sesidae: Nokona *regalis*, etc.,
Gelechiidae: *Phthorimaea operculella, Sitotroga cerealella, Pectinophora gossypiella*, etc.,
Carposinidae: Carposina sasakii, etc.,
Zygaenidae: Illiberis *pruni*, etc.,
Limacodidae: Monema *flavescens*, etc.,
Crambidae: Ancylolomia *japonica, Chilo suppressalis, Cnaphalocrosis medinalis, Ostrinia furnacalis, Ostrinia nubilalis*, etc.,
Pyralidae: Cadra cautella, *Galleria mellonella*, etc.,
Pterophoridae: Nippoptilia *vitis*, etc.,
Papilionidae: Papilio xuthus, etc.,
Pieridae: *Pieris rapae* crucivora, etc.,
Hesperiidae: Parnara guttata guttata, etc.,
Geometridae: Ascotis selenaria, etc.,
Lasiocampidae Dendrolimus spectabilis,
Malacosomaneustrium testaceum, etc.,
Sphingidae: Agrius convolvuli, etc.,
Lymantriidae: Arna pseudoconspersa, *Lymantria dispar*, etc.,
Arctiidae: *Hyphantria cunea*, etc.,
Noctuidae: *Agrotis ipsilon, Autographa* nigrisigna, *Helicoverpa armigera, Helicoverpa zea, Heliothis virescens, Spodoptera exigua, Spodoptera litura*, etc.

As the Oder Collembola pests, there can be mentioned, for example,
Sminthuridae: *Bourletiella hortensis*, etc.

As the order Thysanura pests, there can be mentioned, for example,
Lepismatidae: *Lepisma saccharina, Ctenolepisma villosa*, etc.

As the Blattodea pests, there can be mentioned, for example,
Blattidae: *Periplaneta americana*,
Blattellidae: *Blattella germanica*, etc.

As the Order Isoptera pests, there can be mentioned, for example,
Kalotermitidae: *Incisitermes minor*, etc.,
Rhinotermitidae: *Coptotermes formosanus*, etc.,
Termitidae: *Odontotermes formosanus*, etc.

As the order Psocoptera pests, there can be mentioned, for example,
Trogiidae: *Trogium pulsatorium*, etc.,
Liposcelididae: *Liposcelis corrodens*, etc.

As the order Mallohaga pests, there can be mentioned, for example,
Menoponidae: *Lipeurus caponis*, etc.,
Trichodectidae: *Damalinia bovis*, etc.

As the order Anoplura pests, there can be mentioned, for example,
Haematopimidae: *Haematopinus suis*, etc.,
Pediculine: *Pediculus humanus*, etc.,
Linognathidae: *Linognathus setosus*, etc.,
Pthiridae: *Phthrius pubis*, etc.

As the plant-feeding mites, there can be mentioned, for example,
Eupodidae: *Penthaleus major*, etc.,
Tarsonemidae: *Phytonemus pallidus, Polyphagotarsonemus latus*, etc.,
Pyemotidae: *Siteroptes* sp., etc.,
Tenuipalpidae: *Brevipalpus lewisi*, etc.,
Tuckerellidae: *Tuckerella pavoniformis*, etc.,
Tetranychidae: *Eotetranychus boreus, Panonychus citri, Panonychus ulmi, Tetranychus urticae, Tetranychus kanzawai*, etc.,
Nalepellidae: *Trisetacus pini*, etc.,
Eriophyidae: *Aculops pelekassi, Epitrimerus pyri, Phyllocoptruta oleivola*, etc.,
Diptilomiopidae: *Diptacus crenatae*, etc.,
Acaridae: *Aleuroglyphus ovatus, Tyrophagus putrescentiae, Rhizoglyphus robini*, etc.

As the plant-parasitic nematodes, there can be mentioned, for example,
Longidoridae: *Xiphinema index*, etc.,
Trichodoridae: Paratrichodorus minor, etc.,
Rhabditidae: Rhabditella sp., etc.,
Tylenchidae: Aglenchussp., etc.,
Tylodoridae: Cephalenchus sp., etc.,
Anguinidae: Nothotylenchus *acris*, Ditylenchus destructor, etc.,
Hoplolaimidae: *Rotylenchulus reniformis, Helicotylenchus dihystera*, etc.,
Paratylenchidae: Paratylenchus *curvitatus*, etc.,
Meloidogynidae: *Meloidogyne incognita, Meloidogyne hapla*, etc.,
Heteroderidae: *Globodera rostochiensis, Heterodera glycines*, etc.,
Telotylenchidae: Tylenchorhynchus claytoni etc.,
Psilenchidae: Psilenchus sp., etc.,
Criconematidae: Criconemoides sp., etc., Tylenchulidae: Tylenchulus semipenetrans, etc.,
Sphaeronematidae: Sphaeronema camelliae, etc.,
Pratylenchidae: *Radopholus citrophilus, Radopholus similis*, Nacobbus *aberrans, Pratylenchus penetrans, Pratylenchus* coffeae, etc.,
Iotonchiidae: Iotonchium ungulatum, etc.,
Aphelenchidae: Aphelenchus *avenae*, etc.,
Aphelenchoididae: *Aphelenchoides besseyi, Aphelenchoides fragariae*, etc.,
Palasitaphelenchidae: *Bursaphelenchus xylophilus*, etc.

As the plant-parasitic mollusc pests, there can be mentioned, for example,
Pilidae: *Pomacea canaliculata*, etc.,
Veronicellidae: Leavicaulis alte, etc.,
Achatinidae: *Achatina fulica*, etc.,
Philomycidae: Meghimatium bilineatum, etc.,
Succineidae: *Succinea* lauta, etc.,
Didcidae: Discus pauper, etc.,
Zonitidae: Zonitoides yessoensis, etc.,
Limacidae: Limacus *flavus, Deroceras reticulatum*, etc.,
Helicarionidae: Parakaliella harimensis, etc.,
Bradybaenidae: Acusta despecta *sieboldiana, Bradybaena similaris*, etc.

As other pests such as injurious animals, uncomfortable animals, sanitary insects, livestock insects, parasites and the like, there can be mentioned, for example,
Acari Macronysshidae: *Ornithonyssus sylvialum*, etc.,
Varroidae: *Varroa jacobsoni*, etc.,
Dermanyssidae: *Dermanyssus gallinae*, etc.,
Macronyssidae: *Ornithonyssus sylvialum*, etc.,
Ixodidae: *Boophilus microplus, Rhipicephalus sanguineus, Haemaphysalis longicornis*, etc.,
Sacroptidae: *Sarcoptes scabiei*, etc.,
Isopoda Armadillididae: *Armadillidium vulgare*, etc.,
Decapoda Astacidae: *Procambarus clarkii*, etc.,
Porcellionidae: *Armadillidium vulgare*, etc.,
Chilopoda pests: *Scutigeromorpha Sutigeridae, Thereuonema tuberculata, Scolopendromorpha Scolopendra subpinipes*, etc.
Diplopoda pests: *Polydesmida Paradoxosomatidae Oxidus gracillis*, etc.
Araneae Latrodectus hasseltii: *Theridiiadae hasseltii*, etc.,
Clubionidae: *Chiracanthium japonicum*, etc.,
Order Scorpionida: *Androctonus crassicauda*, etc.,
Parasitic roundworm: *Ascaris lumbricoides, Syphacia* sp., *Wucherebia bancrofti*, etc.,
Parasitic flatworm: *Distomum* sp., *Paragonimus westermanii, Metagonimus yokokawai, Schistosoma japonicum, Taenia solium, Taeniarhynchus saginatus, Echinococcus* sp., *Diphyllobothrium latum*, etc.

The present pest control agent exhibits control effect also to the above-mentioned pests, etc., which already have resistances to existing pest control agents. Furthermore, the present control agent can be applied to plants which already have resistances to insects, diseases, herbicides, etc., owing to genetic modification, artificial mating, etc.

Next, there are described the production methods, formulation methods and applications of the present compound, in detail by way of Examples. However, the present invention is in no way restricted by these Examples.

There are also described the production methods of the intermediates for production of the present compound.

EXAMPLES

Example 1

Production of 2-fluoro-4-methyl-5-(2,2,2-trifluoroethylthio)phenol (present compound No. C-0001)

To 300 ml of toluene were added 32.0 g (119 mmol) of 2-fluoro-4-methyl-5-(2,2,2-trifluoroethylthio)phenyl boronic acid produced by the method described in PCT International Publication No. WO 2007/034755 and 15.4 g (131 mmol) of N-methylmorpholine-N-oxide, followed by refluxing for 1 hour under heating. The reaction mixture was allowed to cool to room temperature. The solvent was distilled off under reduced pressure. The residue was subjected to extraction with ethyl acetate. The organic phase obtained was washed with water and then dried over anhydrous magnesium sulfate. The solvent was distilled off under reduced pressure. The residue was purified by silica gel column chromatography (developing solvent: a mixed solvent of n-hexane:ethyl acetate=4:1), to obtain 25.5 g (yield: 89%) of an intended product.

$^1$H-NMR (300 MHz, CDCl$_3$/TMS δ (ppm))
2.38 (3H, s), 3.32 (2H, q), 5.28 (1H, brs), 6.95 (1H, d), 7.22 (1H, d)

Example 2

Production of 4-methyl-3-(2,2,2-trifluoroethylthio)phenol (present compound No. C-0005)

49.7 g (225 mmol) of 4-methyl-3-(2,2,2-trifluoroethylthio) aniline was suspended in 500 ml of a 15% aqueous sulfuric acid solution. Thereinto was dropwise added an aqueous solution obtained by dissolving 18.6 g (270 mmol) of sodium nitrite in 100 ml of water, at 0 to 5° C. with ice-cooling. After the completion of the dropwise addition, the mixture was stirred for 1 hour with the temperature being kept. The reaction mixture was gradually dropped at 120° C. into a solution obtained by dissolving 71.8 g (450 mmol) of anhydrous copper sulfate in 400 ml of 60% sulfuric acid. The mixture was allowed to cool to room temperature and subjected to extraction with ethyl acetate. The organic phase obtained was dried over anhydrous magnesium sulfate and concentrated under reduced pressure. The crude product obtained was purified by column chromatography (developing solvent: a mixed solvent of n-hexane:ethyl acetate=10:1), to obtain 19 g (yield: 38%) of an intended product.

$^1$H-NMR (400 MHz, CDCl$_3$/TMS δ (ppm))
2.36 (3H, s), 3.38 (2H, q), 5.61 (1H, brs), 6.69 (1H, dd), 6.93 (1H, s), 7.03 (1H, d)

Example 3

Production of 5,5-dimethylhexyl-[2-fluoro-4-methyl-5-(2,2,2-trifluoroethylthio)phenyl]ether (present compound No. A-0085)

To 70 ml of tetrahydrofuran were added 1.6 g (6.7 mmol) of 2-fluoro-4-methyl-3-(2,2,2-trifluoroethylthio)phenol, 1.7 g (13 mmol) of 5,5-dimethylhexanol, 2.0 g (9.9 mmol) of diisopropyl azodicarboxylate and 2.6 g (9.9 mmol) of triphenylphosphine. A reaction was carried out at room temperature for 16 hours. After confirmation of the completion of the reaction, the solvent was distilled off under reduced pressure. The residue was purified by silica gel column chromatography (developing solvent: a mixed solvent of n-hexane:ethyl acetate=4:1), to obtain 2.3 g (yield: 97%) of an intended product.

Incidentally, the production method of 5,5-dimethylhexanol is described in, for example, J. Am. Chem. Soc., 119 (29), 6909 (1997).

$^1$H-NMR (300 MHz, CDCl$_3$/TMS δ (ppm))

0.88 (9H, s), 1.19-1.27 (2H, m), 1.36-1.48 (2H, m), 1.77 (2H, quint), 2.41 (3H, s), 3.29 (2H, q), 4.01 (2H, t), 6.95 (1H, d), 7.15 (1H, d)

Example 4

Production of 5,5-dimethylhexyl-[2-fluoro-4-methyl-5-(2,2,2-trifluoroethylsulfinyl)phenyl]ether (present compound No. A-0086)

In 70 ml of chloroform was dissolved 2.3 g (6.5 mmol) of 5,5-dimethylhexyl-{2-fluoro-4-methyl-5-(2,2,2-trifluoroethylthio)phenyl}ether. Thereto was added, in portions in about 10 minutes, 1.5 g (6.5 mmol) of 3-chloroperbenzoic acid (purity: about 75%) at room temperature. A reaction was carried out for 1 hour. After confirmation of the completion of the reaction, the solvent was distilled off under reduced pressure. The residue was purified by silica gel column chromatography (developing solvent: a mixed solvent of n-hexane:ethyl acetate:triethylamine=5:1:0.01), to obtain 2.2 g (yield: 92%) of an intended product.

$^1$H-NMR (300 MHz, CDCl$_3$/TMS δ (ppm))

0.89 (9H, s), 1.19-1.27 (2H, m), 1.37-1.49 (2H, m), 1.81 (2H, quint), 2.31 (3H, s), 3.30-3.48 (2H, m), 4.10 (2H, t), 6.98 (1H, d), 7.55 (1H, d)

Example 5

Production of 5-trifluoromethylthiopentyl-[4-methyl-3-(2,2,2-trifluoroethylthio)phenyl]ether (present compound No. A-0438)

To 100 ml of tetrahydrofuran were added 1.5 g (4.3 mmol) of 5-thiocyanatopentyl-{4-methyl-3-(2,2,2-trifluoroethylthio)phenyl}ether and 1.8 g (13 mmol) of trifluoromethyl-trimethylsilane. Thereto was added, at 0° C., 5 ml (5.0 mmol) of a tetra-n-butylammonium fluoride-tetrahydrofuran (1 mol/liter) solution. A reaction was carried out for 1 hour. After confirmation of the completion of the reaction, the solvent was distilled off under reduced pressure. The residue was purified by silica gel column chromatography (developing solvent: a mixed solvent of n-hexane:ethyl acetate=10:1), to obtain 1.3 g (yield: 77%) of an intended product.

$^1$H-NMR (300 MHz, CDCl$_3$/TMS δ (ppm))

1.56-1.64 (2H, m), 1.73-1.85 (4H, m), 2.38 (3H, s), 2.91 (2H, t), 3.40 (2H, q), 3.94 (2H, t), 6.75 (1H, dd), 7.00 (1H, d), 7.11 (1H, d)

Example 6

Production of 5-chloropentyl-[4-methyl-3-(2,2,2-trifluoroethylthio)phenyl]ether (present compound No. A-0279)

To 100 ml of acetonitrile were added 2.5 g (11 mmol) of 4-methyl-3-(2,2,2-trifluoroethylthio)phenol, 2.5 g (13 mmol) of 1-bromo-5-chloropentane, 1.9 g (14 mmol) of potassium carbonate and 0.35 g (1.1 mmol) of tetra-n-butylammonium bromide. The mixture was refluxed for 5 hours under heating and then allowed to cool to room temperature. The solvent was distilled off under reduced pressure. The residue was purified by silica gel column chromatography (developing solvent: a mixed solvent of n-hexane:ethyl acetate=10:1), to obtain 2.9 g (yield: 79%) of an intended product.

$^1$H-NMR (300 MHz, CDCl$_3$/TMS δ (ppm))

1.56-1.66 (2H, m), 1.74-1.93 (4H, m), 2.38 (3H, s), 3.36 (2H, q), 3.56 (2H, t), 3.94 (2H, t), 6.74 (1H, d), 7.00 (1H, s), 7.09 (1H, d)

Example 7

Production of 5-thiocyanatopentyl-[4-methyl-3-(2,2,2-trifluoroethylthio)phenyl]ether (present compound No. A-0672)

To 100 ml of ethanol were added 2.0 g (6.1 mmol) of 5-chloropentyl-{4-methyl-3-(2,2,2-trifluoroethylthio)phenyl}ether, 4.0 g (41 mmol) of potassium thiocyanate and 0.10 g (0.61 mmol) of potassium iodide. The mixture was refluxed for 10 hours under heating and then allowed to cool to room temperature. The solvent was distilled off under reduced pressure. To the residue was added ethyl acetate to conduct extraction. The organic phase obtained was washed with water and dried over anhydrous magnesium sulfate. The solvent was distilled off under reduced pressure. The residue was purified by silica gel column chromatography (developing solvent: a mixed solvent of n-hexane:ethyl acetate=10:1), to obtain 1.8 g (yield: 84%) of an intended product.

$^1$H-NMR (300 MHz, CDCl$_3$/TMS δ (ppm))

1.53-1.68 (2H, m), 1.76-1.87 (4H, m), 2.38 (3H, s), 3.00 (2H, t), 3.39 (2H, q), 3.97 (2H, t), 6.74 (1H, d), 7.00 (1H, s), 7.13 (1H, d)

Example 8

Production of 5-trifluoromethylthiopentyl-[4-methyl-3-(2,2,2-trifluoroethylsulfinyl)phenyl]ether (present compound No. A-0439)

In 100 ml of chloroform was dissolved 0.98 g (2.5 mmol) of 5-trifluoromethylthiopentyl-{4-methyl-5-(2,2,2-trifluoroethylthio)phenyl}ether. Thereto was added, in portions in about 10 minutes, 0.58 g (2.5 mmol) of 3-chloroperbenzoic acid (purity: about 75%) at room temperature. A reaction was carried out for 1 hour. After confirmation of the completion of the reaction, the solvent was distilled off under reduced pressure. The residue was purified by silica gel column chromatography (developing solvent: a mixed solvent of n-hexane:ethyl acetate:triethylamine=5:1:0.01), to obtain 0.78 g (yield: 77%) of an intended product.

$^1$H-NMR (300 MHz, CDCl$_3$/TMS δ (ppm))

1.57-1.64 (2H, m), 1.73-1.88 (4H, m), 2.31 (3H, s), 2.92 (2H, t), 2.32-3.45 (2H, m), 4.05 (2H, t), 6.97 (1H, dd), 7.15 (1H, d), 7.48 (1H, d)

Example 9

Production of 4-chloro-2-fluoro-5-(2,2,2-trifluoroethylthio)phenol (present compound No. C-0003)

To 200 ml of toluene were added 33 g (114 mmol) of 4-chloro-2-fluoro-5-(2,2,2-trifluoroethylthio)phenyl boronic acid and 16 g (137 mmol) of N-methylmorpholine-N-oxide. The mixture was refluxed for 1 hour under heating. After confirmation of the completion of the reaction, the mixture was allowed to cool to room temperature. Then the solvent was distilled off under reduced pressure, and the residue was subjected to extraction with ethyl acetate. The organic phase obtained was washed with water and dried over anhydrous magnesium sulfate and the solvent was distilled off under reduced pressure. The residue was purified by silica gel column chromatography to obtain 24.5 g (yield: 82%) of an intended product.
$^1$H-NMR (300 MHz, CDCl$_3$/TMS δ (ppm))
3.43 (2H, q), 5.31 (1H, d), 7.16 (1H, d), 7.31 (1H, d)

Example 10

Production of 5-bromopentyl-[4-chloro-2-fluoro-5-(2,2,2-trifluoroethylthio)phenyl]ether (present compound No. A-0273)

To 60 ml of acetonitrile were added 3.0 g (11.5 mmol) of 4-chloro-2-fluoro-5-(2,2,2-trifluoroethylthio)phenol, 13.2 g (57.4 mmol) of 1,5-dibromopentane, 2.1 g (15.0 mmol) of potassium carbonate and 0.37 g (1.15 mmol) of tetra-n-butylammonium bromide. The mixture was refluxed for 1.5 hour under heating. The mixture was allowed to cool to room temperature, and insoluble matters were removed by filtration. Then the filtrate was concentrated under reduced pressure, and the residue was purified by silica gel column chromatography (developing solvent: a mixed solvent of n-hexane ethyl acetate=20:1), to obtain 4.2 g (yield: 89%) of an intended product.
$^1$H-NMR (400 MHz, CDCl$_3$/TMS δ (ppm))
1.59-1.69 (2H, m), 1.82-1.99 (4H, m), 3.36-3.47 (4H, m), 4.03 (2H, t), 7.20 (1H, d), 7.23 (1H, d)

Example 11

Production of 5-thiocyanatopentyl-[4-chloro-2-fluoro-5-(2,2,2-trifluoroethylthio)phenyl]ether (present compound No. A-0670)

To 60 ml of ethanol were added 4.2 g (10.3 mmol) of 5-bromopentyl-[4-chloro-2-fluoro-5-(2,2,2-trifluoroethylthio)phenyl]ether and 5.0 g (51.5 mmol) of potassium thiocyanate. The mixture was refluxed for 4 hours under heating. The mixture was allowed to cool to room temperature, and the solvent was distilled off under reduced pressure. Then extraction was conducted by adding water and ethyl acetate. The organic phase obtained was dried over anhydrous magnesium sulfate and the solvent was distilled off under reduced pressure. The residue was purified by silica gel column chromatography (developing solvent: a mixed solvent of n-hexane: ethyl acetate=10:1), to obtain 3.9 g (yield: 98%) of an intended product.
$^1$H-NMR (400 MHz, CDCl$_3$/TMS δ (ppm))
1.59-1.69 (2H, m), 1.82-1.99 (4H, m), 2.99 (2H, t) 3.42 (2H, q), 4.04 (2H, t), 7.20 (1H, d), 7.23 (1H, d)

Example 12

Production of 5-trifluoromethylthiopentyl-[4-chloro-2-fluoro-5-(2,2,2-trifluoroethylthio)phenyl]ether (present compound No. A-0433)

To 60 ml of tetrahydrofuran were added 3.9 g (10.1 mmol) of 5-thiocyanatopentyl-[4-chloro-2-fluoro-5-(2,2,2-trifluoroethylthio)phenyl]ether and 4.5 g (31.6 mmol) of trifluoromethyltrimethylsilane. Thereto was added 1.0 ml (1.04 mmol) of tetrahydrofuran solution (1 mol/liter) of tetra-n-butylammonium fluoride at 0° C., and reaction was carried out. The mixture was stirred overnight at room temperature. Then, the solvent was distilled off under reduced pressure, and the residue was purified by silica gel column chromatography (developing solvent: a mixed solvent of n-hexane:ethyl acetate=20:1), to obtain 2.60 g (yield: 60%) of an intended product.
$^1$H-NMR (400 MHz, CDCl$_3$/TMS δ (ppm))
1.58-1.66 (2H, m), 1.73-1.89 (4H, m), 2.92 (2H, t), 3.41 (2H, q), 4.03 (2H, t), 7.21 (1H, d), 7.23 (1H, d)

Example 13

Production of 5-trifluoromethylthiopentyl-[4-chloro-2-fluoro-5-5-(2,2,2-trifluoroethylsulfinyl)phenyl] ether (present compound No. A-0434)

In 50 ml of chloroform was dissolved 2.60 g (6.03 mmol) of 5-trifluoromethylthiopentyl-[4-chloro-2-fluoro-5-(2,2,2-trifluoroethylthio)phenyl]ether. Thereto was added 1.39 g (6.04 mmol) of 3-chloroperbenzoic acid (purity: about 75%) at 0° C., and the mixture was stirred overnight at room temperature. Then, the solvent was distilled off under reduced pressure, 1 ml of triethylamine was added to the residue, and the residue was purified by silica gel column chromatography (developing solvent: a mixed solvent of n-hexane:ethyl acetate=5:1), to obtain 2.06 g (yield: 76%) of an intended product.
$^1$H-NMR (400 MHz, CDCl$_3$/TMS δ (ppm))
1.57-1.66 (2H, m), 1.74-1.93 (4H, m), 2.92 (2H, t), 3.30-3.43 (1H, m), 3.66-3.78 (1H, m), 4.13 (2H, t), 7.21 (1H, d), 7.54 (1H, d)

Example 14

Production of 2,4-dichloro-5-(2,2,2-trifluoroethylthio)phenol (present compound No. C-0014)

To 150 ml of toluene was added 29.0 g (50% aqueous solution, 124 mmol) of N-methylmorpholine-N-oxide, and dehydration was conducted by heating under reflux for 1 hour. To the reaction mixture was dropwise added 31.5 g (103 mmol) of 2,4-dichloro-5-(2,2,2-trifluoroethylthio)phenylboronic acid dissolved in ethyl acetate, and the mixture was refluxed for 3 hours under heating. Then, the mixture was allowed to cool to room temperature, and 10% aqueous hydrochloric acid was added, followed by extraction with ethyl acetate. The organic phase obtained was washed with saturated sodium chloride solution, dried over anhydrous magnesium sulfate and the solvent was distilled off under reduced pressure. The residue was purified by silica gel column chromatography (developing solvent: a mixed solvent of n-hexane:ethyl acetate=10:1), to obtain 27.2 g (yield: 95%) of an intended product.
$^1$H-NMR (300 MHz, CDCl$_3$/TMS δ (ppm))
3.48 (2H, q), 5.70 (1H, s), 7.20 (1H, s), 7.41 (1H, s)

Example 15

Production of 6-bromohexyl-[2,4-dichloro-5-(2,2,2-trifluoroethylthio)phenyl]ether (present compound No. A-0283)

To 30 ml of acetonitrile were added 1.0 g (3.61 mmol) of 2,4-dichloro-5-(2,2,2-trifluoroethylthio)phenol, 3.5 g (14.4 mmol) of 1,6-dibromohexane, 0.65 g (15.0 mmol) of potassium carbonate and 0.12 g (0.37 mmol) of tetra-n-butylammonium bromide. The mixture was refluxed for 3 hours under heating. The mixture was allowed to stand at room temperature, and insoluble matters were removed by filtration. Then the filtrate was concentrated under reduced pressure, and the residue was purified by silica gel column chromatography (developing solvent: a mixed solvent of n-hexane ethyl acetate=20:1), to obtain 1.51 g (yield: 95%) of an intended product.

$^1$H-NMR (400 MHz, CDCl$_3$/TMS δ (ppm))
1.50-1.60 (4H, m), 1.81-1.93 (4H, m), 3.39-3.49 (4H, m), 4.02 (2H, t), 7.13 (1H, s), 7.45 (1H, s)

Example 16

Production of 6-thiocyanatohexyl-[2,4-dichloro-5-(2,2,2-trifluoroethylthio)phenyl]ether (present compound No. A-0678)

In 30 ml of ethanol were added 1.51 g (3.43 mmol) of 6-bromohexyl-[2,4-dichloro-5-(2,2,2-trifluoroethylthio)phenyl]ether and 1.67 g (17.2 mmol) of potassium thiocyanate. The mixture was refluxed for 3 hours under heating. The mixture was allowed to cool to room temperature, and the solvent was distilled off under reduced pressure. Then extraction was conducted by adding ethyl acetate and water. The organic phase obtained was dried over anhydrous magnesium sulfate and the solvent was distilled off under reduced pressure. The residue was purified by silica gel column chromatography (developing solvent: a mixed solvent of n-hexane:ethyl acetate=10:1), to obtain 1.04 g (yield: 73%) of an intended product.

$^1$H-NMR (400 MHz, CDCl$_3$/TMS δ (ppm))
1.50-1.62 (4H, m), 1.83-1.92 (4H, m), 2.96 (2H, t), 3.45 (2H, q), 4.03 (2H, t), 7.13 (1H, s), 7.46 (1H, s)

Example 17

Production of 6-trifluoromethylthiohexyl-[2,4-dichloro-5-(2,2,2-trifluoroethylthio)phenyl]ether (present compound No. A-0478)

To 30 ml of tetrahydrofuran were added 1.04 g (2.49 mmol) of 6-thiocyanatohexyl-[2,4-dichloro-5-(2,2,2-trifluoroethylthio)phenyl]ether and 1.06 g (7.45 mmol) of trifluoromethyltrimethylsilane. Thereto was added 0.25 ml (concentration: 1 mol/liter, 0.25 mmol) of tetrahydrofuran solution of tetra-n-butylammonium fluoride at 0° C., and reaction mixture was stirred for 2 hours at room temperature. Then, the solvent was distilled off under reduced pressure, and the residue was purified by silica gel column chromatography (developing solvent: a mixed solvent of n-hexane ethyl acetate=20:1), to obtain 0.73 g (yield: 64%) of an intended product.

$^1$H-NMR (300 MHz, CDCl$_3$/TMS δ (ppm))
1.44-1.62 (4H, m), 1.67-1.90 (4H, m), 2.90 (2H, t), 3.44 (2H, q), 4.02 (2H, t), 7.13 (1H, s), 7.46 (1H, s)

Example 18

Production of 6-trifluoromethylthiohexyl-[2,4-dichloro-5-(2,2,2-trifluoroethylsulfinyl)phenyl]ether (present compound No. A-0479)

In 30 ml of chloroform was dissolved 0.53 g (1.15 mmol) of 6-trifluoromethylthiohexyl-[2,4-dichloro-5-(2,2,2-trifluoroethylthio)phenyl]ether. Thereto was added 0.26 g (1.13 mmol) of 3-chloroperbenzoic acid (purity: about 75%) at 0° C., and the mixture was stirred for 3 hours at room temperature. Then, the solvent was distilled off under reduced pressure, 0.5 ml of triethylamine was added to the residue, and the residue was purified by silica gel column chromatography (developing solvent: a mixed solvent of n-hexane ethyl acetate=5:1), to obtain 0.41 g (yield: 75%) of an intended product.

$^1$H-NMR (300 MHz, CDCl$_3$/TMS δ (ppm))
1.48-1.64 (4H, m), 1.63-1.94 (4H, m), 2.90 (2H, t), 3.28-3.44 (1H, m), 3.68-3.81 (1H, m), 4.13 (2H, t) 7.47 (1H, s), 7.48 (1H, s)

Example 19

Production of 2,4-dichloro-5-(2,2,2-trifluoroethylsulfinyl)phenol (present compound No. C-0015)

In 80 ml of chloroform was dissolved 10.0 g (36.08 mmol) of 2,4-dichloro-5-(2,2,2-trifluoroethylthio)phenol. Thereto was added 9.80 g (39.75 mmol) of 3-chloroperbenzoic acid (purity: about 70%) under ice cooling, and the mixture was stirred for 30 minutes at room temperature. Then, saturated aqueous solution of sodium thiosulfate was added to the reaction mixture to decompose excess peroxide. Thereafter, the solvent was distilled off under reduced pressure, and extraction was conducted by adding ethyl acetate and water. The organic phase obtained was washed by aqueous potassium carbonate solution and saturated aqueous sodium chloride solution in this order, and dried over anhydrous magnesium sulfate. The solvent was distilled off under reduced pressure, to obtain 9.30 g (yield: 88%) of an intended product.

$^1$H-NMR (300 MHz, CDCl$_3$/TMS δ (ppm))
3.30-3.44 (1H, m), 3.66-3.80 (1H, m), 7.40 (1H, s), 7.61 (1H, s)

Example 20

Production of 2-(4-trifluoromethylphenyl)ethyl-[2,4-dichloro-5-(2,2,2-trifluoroethylsulfinyl)phenyl]ether (present compound No. A-0767)

In 30 ml of tetrahydrofuran were dissolved 0.5 g (1.71 mmol) of 2,4-dichloro-5-(2,2,2-trifluoroethylsulfinyl)phenol, 0.33 g (1.74 mmol) of 2-(4-trifluoromethylphenyl)ethanol and 0.49 g (1.87 mmol) of triphenylphosphine. Thereto was added 0.38 g (1.87 mmol) of diisopropyl azodicarboxylate at room temperature, and the reaction mixture was stirred for 16 hours. Then, the solvent was distilled off under reduced pressure, and the residue was purified by silica gel column chromatography (developing solvent: a mixed solvent of n-hexane:ethyl acetate=5:1), to obtain 0.41 g (yield: 52%) of an intended product.

$^1$H-NMR (300 MHz, CDCl$_3$/TMS δ (ppm))
3.21-3.40 (3H, m), 3.64-3.79 (1H, m), 4.31-4.36 (2H, m), 7.44-7.46 (4H, m), 7.58 (2H, d)

Example 21

Production of 2,4-dimethyl-5-(2,2,2-trifluoroethylthio)phenol (present compound No. C-0017)

To 200 ml of toluene were added 20.24 g (58.5 mmol) of [2,4-dimethyl-5-(2,2,2-trifluoroethylthio)phenyl]-4,4,5,5-tetramethyl-1,3,2-dioxaborolane (a compound described in PCT International Publication No. WO 2012/176856 as Compound No. 55-47) and 8.22 g (70.16 mmol) of N-methylmorpholine-N-oxide. The mixture was refluxed for 2 hours under heating. The reaction mixture was allowed to cool to room temperature, washed and dried over anhydrous magnesium sulfate. The solvent was distilled off under reduced pressure and the residue was purified by silica gel column chromatography (developing solvent: a mixed solvent of n-hexane:ethyl acetate=20:1), to obtain 10.54 g (yield: 76%) of an intended product.

$^1$H-NMR (300 MHz, CDCl$_3$/TMS δ (ppm))

2.20 (3H, s), 2.36 (3H, s), 3.32 (2H, q), 4.78 (1H, s), 6.93 (1H, s), 6.98 (1H, s)

Example 22

Production of 2,4-dimethyl-5-(2,2,2-trifluoroethylsulfinyl)phenol (present compound No. C-0018)

In 30 ml of chloroform was dissolved 2.60 g (11.0 mmol) of 2,4-dimethyl-5-(2,2,2-trifluoroethylthio)phenol. Thereto was added 3.25 g (13.18 mmol) of 3-chloroperbenzoic acid (purity: about 70%) under ice cooling, and the mixture was stirred for 30 minutes at room temperature. Then, saturated aqueous solution of sodium thiosulfate was added to the reaction mixture to decompose excess peroxide. Thereafter, the solvent was distilled off under reduced pressure, and phase separation was conducted by adding ethyl acetate and water. The organic phase obtained was washed by aqueous potassium carbonate solution and saturated aqueous sodium chloride solution, and dried over magnesium sulfate. The solvent was distilled off under reduced pressure, to obtain 2.13 g (yield: 77%) of an intended product.

$^1$H-NMR (300 MHz, CDCl$_3$/TMS δ (ppm))

2.25 (6H, s), 3.35-3.53 (2H, m), 6.98 (1H, s), 7.63 (1H, s), 7.69 (1H, s)

Example 23

Production of 2-(4'-trifluoromethoxyphenyl)ethyl-[2,4-dimethyl-5-(2,2,2-trifluoroethylsulfinyl)phenyl]ether (present compound No. A-0783)

In 30 ml of tetrahydrofuran were dissolved 0.3 g (1.19 mmol) of 2,4-dimethyl-5-(2,2,2-trifluoroethylsulfinyl)phenol, 0.29 g (1.41 mmol) of 2-(4'-trifluoromethoxyphenyl)ethanol and 0.41 g (1.56 mmol) of triphenylphosphine. Thereto was added 0.31 g (1.53 mmol) of diisopropyl azodicarboxylate at room temperature, and stirred for 16 hours. The solvent was distilled off under reduced pressure. The residue was purified by silica gel column chromatography (developing solvent: a mixed solvent of n-hexane:ethyl acetate=5:1), and the residue was washed with n-hexane, to obtain 0.21 g (yield: 40%) of an intended product.

$^1$H-NMR (300 MHz, CDCl$_3$/TMS δ (ppm))

2.18 (3H, s), 2.26 (3H, s), 3.13 (2H, t), 3.32-3.41 (2H, m), 4.24-4.25 (2H, m), 6.70 (1H, s), 7.16 (2H, d), 7.30-7.36 (3H, m)

Example 24

Production of 6-bromohexyl-[2,4-dimethyl-5-(2,2,2-trifluoroethylthio)phenyl]ether (present compound No. A-0284)

To 60 ml of acetonitrile were added 1.14 g (4.83 mmol) of 2,4-dimethyl-5-(2,2,2-trifluoroethylthio)phenol, 4.71 g (19.31 mmol) of 1,6-dibromohexane, 0.73 g (5.28 mmol) of potassium carbonate and catalytic amount of tetra-n-butylammonium bromide. The mixture was refluxed for 3 hours under heating. The mixture was allowed to cool to room temperature, and insoluble matters were removed by filtration. Then the solvent of filtrate was distilled off under reduced pressure, and the residue was purified by silica gel column chromatography (developing solvent: a mixed solvent of n-hexane:ethyl acetate=40:1~20:1), to obtain 1.87 g (yield: 97%) of an intended product.

$^1$H-NMR (300 MHz, CDCl$_3$/TMS δ (ppm))

1.53 (4H, m), 1.70-2.03 (4H, m), 2.17 (3H, s), 2.38 (3H, s), 3.26-3.43 (4H, m), 3.94 (2H, t), 6.96 (1H, s), 6.99 (1H, s)

Example 25

Production of 6-thiocyanatohexyl-[2,4-dimethyl-5-(2,2,2-trifluoroethylthio)phenyl]ether (present compound No. A-0679)

To 60 ml of ethanol were added 1.87 g (4.68 mmol) of 6-bromohexyl-[2,4-dimethyl-5-(2,2,2-trifluoroethylthio)phenyl]ether and 2.28 g (23.46 mmol) of potassium thiocyanate. The mixture was refluxed for 8 hours under heating. The mixture was allowed to cool to room temperature, and the solvent was distilled off under reduced pressure. Then extraction was conducted by adding ethyl acetate and water. The organic phase obtained was washed with water, and dried over anhydrous magnesium sulfate. The solvent was distilled off under reduced pressure. The residue was purified by silica gel column chromatography (developing solvent: a mixed solvent of n-hexane:ethyl acetate=20:1), to obtain 1.37 g (yield: 77%) of an intended product.

$^1$H-NMR (300 MHz, CDCl$_3$/TMS δ (ppm))

1.53-1.54 (4H, m), 1.82-1.87 (4H, m), 2.17 (3H, s) 2.38 (3H, s), 2.96 (2H, t), 3.31 (2H, q), 3.94 (2H, t) 6.96 (1H, s), 6.70 (1H, s)

Example 26

Production of 6-trifluoromethylthiohexyl-[2,4-dimethyl-5-(2,2,2-trifluoroethylthio)phenyl]ether (present compound No. A-0480)

To 100 ml of tetrahydrofuran were added 1.37 g (3.63 mmol) of 6-thiocyanatohexyl-[2,4-dimethyl-5-(2,2,2-trifluoroethylthio)phenyl]ether and 1.29 g (9.07 mmol) of trifluoromethyltrimethylsilane. Thereto was added 0.4 ml (0.4 mmol) of tetrahydrofuran solution of tetra-n-butylammonium fluoride (1 mol/liter) at 0° C., and the mixture was stirred for 4 hours at 0° C. Then, the solvent was distilled off under reduced pressure, and the residue was purified by silica gel column chromatography (developing solvent: a mixed solvent of n-hexane:ethyl acetate=20:1), to obtain 1.36 g (yield: 89%) of an intended product.

$^1$H-NMR (300 MHz, CDCl$_3$/TMS δ (ppm))

1.49-1.53 (4H, m), 1.71-1.82 (4H, m), 2.17 (3H, s) 2.38 (3H, s), 2.90 (2H, t), 3.30 (2H, q), 3.94 (2H, t) 6.96 (1H, s), 6.70 (1H, s)

Example 27

Production of 6-trifluoromethylthiohexyl-[2,4-dimethyl-5-(2,2,2-trifluoroethylsulfinyl)phenyl]ether (present compound No. A-0481)

In 40 ml of chloroform was dissolved 1.36 g (3.23 mmol) of 6-trifluoromethylthiohexyl-[2,4-dimethyl-5-(2,2,2-trifluoroethylthio)phenyl]ether. Thereto was added 0.67 g (2.72 mmol) of 3-chloroperbenzoic acid (purity: about 70%) under ice cooling, and the mixture was stirred for 30 minutes at room temperature. Then, saturated aqueous solution of sodium thiosulfate was added to the reaction mixture to decompose excess peroxide. Thereafter, the solvent was distilled off under reduced pressure, and extraction was conducted by adding ethyl acetate and water. The organic phase obtained was washed by aqueous potassium carbonate solution and saturated aqueous sodium chloride solution in this order, and dried over anhydrous magnesium sulfate. The solvent was distilled off under reduced pressure, and the residue was purified by silica gel column chromatography (developing solvent: a mixed solvent of n-hexane:ethyl acetate=5:1), to obtain 0.87 g (yield: 62%) of an intended product.

$^1$H-NMR (400 MHz, CDCl$_3$/TMS δ (ppm))

1.50-1.52 (4H, m), 1.72-1.85 (4H, m), 2.23 (3H, s), 2.28 (3H, s), 2.90 (2H, t), 3.28-3.47 (2H, m), 4.04 (2H, t), 7.01 (1H, s), 7.36 (1H, s)

Example 28

Production of 5-trifluoromethylthiopentyl-[4-chloro-2-fluoro-5-(2,2,2-trifluoroethylsulfinyl)phenyl]ether optical isomer An optical active column (internal diameter: 20 mm, length: 250 mm), CHIRAL PAK AD (trade name) manufactured by Daicel Corporation, was equipped with high performance liquid chromatography equipment, and a mixed solvent (hexane: 2-propanol=97:3) was perfused as mobile phase. Then, 150 mg of 5-trifluoromethylthiopentyl-[4-chloro-2-fluoro-5-(2,2,2-trifluoroethylsulfinyl)phenyl]ether (racemic mixture) dissolved in 2-propanol was injected, and analysis was conducted in a following conditions.
flow speed: 8.0 ml/minute
temperature: room temperature
detector: ultraviolet absorption detector (254 nm)

As a result, there observed peak 1 (retention time: 17.8 minutes) and peak 2 (retention time: 30.2 minutes), and 70 mg of a compound of respective peaks (both optical purity was 100% e.e.) were isolated. Measurement of respective Reflective Index revealed that Specific Rotation of the component of peak 1 was $[\alpha]_D^{25}$=−120.28° (C=0.50/methanol) and Specific Rotation of the component of peak 2 was $[\alpha]_D^{25}$=+119.320 (C=0.50/methanol).

Accordingly, the component of the peak 1 is (−)-5-trifluoromethylthiopentyl-[4-chloro-2-fluoro-5-(2,2,2-trifluoroethylsulfinyl)phenyl]ether [(−)-enantiomer of the present compound No. A-0434], and the component of the peak 2 is (+)-5-trifluoromethylthiopentyl-[4-chloro-2-fluoro-5-(2,2,2-trifluoroethylsulfinyl)phenyl]ether [(+)-enantiomer of the present compound No. A-0434].

Reference Example 1

Production of p-Acetotoluidine 100 g (933.3 mmol) of p-toluidine and 154.8 g (1.120 mmol) of potassium carbonate were dissolved in a mixed solvent of 1,000 ml of ethyl acetate and 500 ml of water. Thereinto was dropped 87.9 g (1.120 mmol) of acetyl chloride with ice-cooling, followed by stirring for 2 hours. Extraction with ethyl acetate was carried out. The organic phase obtained was dried over anhydrous magnesium sulfate. The solvent was distilled off under reduced pressure. The crude crystal obtained was washed with hexane to obtain 130 g (yield: 93%) of p-acetotoluidine.

$^1$H-NMR (400 MHz, CDCl$_3$/TMS δ (ppm))

2.16 (3H, s), 2.31 (3H, s), 7.11-7.16 (3H, m), 7.37 (2H, d)

Reference Example 2

Production of 3-chlorosulfonyl-4-methylacetoanilide 130 g (871 mmol) of p-acetotoluidine was gradually added to 405 g (3.477 mmol) of chlorosulfonic acid at room temperature, followed by stirring at 60° C. for 1 hour. The reaction mixture was allowed to stand at room temperature and then poured into ice water. Extraction with ethyl acetate was conducted. The organic phase obtained was dried over anhydrous magnesium sulfate. The solvent was distilled off under reduced pressure to obtain 162 g (yield: 75%) of 3-chlorosulfonyl-4-methylacetoanilide.

$^1$H-NMR (300 MHz, CDCl$_3$/TMS δ (ppm))

2.22 (3H, s), 2.73 (3H, s), 7.37 (2H, d), 7.50 (1H, brs), 8.00 (1H, s), 8.02 (1H, d)

Reference Example 3

Production of 3-acetylthio-4-methylacetoanilide 162 g (654 mmol) of 3-chlorosulfonyl-4-methylacetoanilide was dissolved in 700 ml of acetic acid. Thereto were added 30 g (983 mmol) of red phosphorus and 1.7 g (6.6 mmol) of iodine, followed by stirring for 5 hours under heating and refluxing. The reaction mixture was allowed to cool to room temperature and then filtered through Celite. The filtrate was concentrated under reduced pressure. The residue was dissolved in ethyl acetate. The solution was washed with an aqueous sodium thiosulfate solution and water. The organic phase obtained was dried over anhydrous magnesium sulfate. The solvent was distilled off under reduced pressure to obtain 77.5 g (yield: 53%) of 3-acetylthio-4-methylacetoanilide.

$^1$H-NMR (300 MHz, CDCl$_3$/TMS δ (ppm))

2.12 (3H, s), 2.30 (3H, s), 2.43 (3H, s), 7.21-7.28 (2H, m), 7.46 (1H, d), 7.54 (1H, s)

Reference Example 4

Production of 4-methyl-3-mercaptoaniline 77.5 g (347 mmol) of 3-acetylthio-4-methylacetoanilide was suspended in 700 ml of water. Thereto was added 111 g (2.777 mmol) of sodium hydroxide with stirring. The mixture was stirred for 2 hours under heating and refluxing, and then was allowed to cool to room temperature. The mixture was adjusted to pH 5 using an aqueous hydrochloric acid solution (36%) with stirring under ice-cooling. Extraction with ethyl acetate was conducted. The organic phase obtained was dried over anhydrous magnesium sulfate. The solvent was distilled off under reduced pressure to obtain 47.6 g (yield: 99%) of 4-methyl-3-mercaptoaniline.

$^1$H-NMR (300 MHz, CDCl$_3$/TMS δ (ppm))

2.21 (3H, s), 3.21 (1H, s), 3.64 (2H, brs), 6.43 (1H, dd), 6.64 (1H, d), 6.92 (1H, d)

Reference Example 5

Production of 4-methyl-3-(2,2,2-trifluoroethylthio)aniline 47.6 g (342 mmol) of 4-methyl-3-mercaptoaniline was dissolved in 500 ml of N,N-dimethylformamide. Thereto was added 71 g (513 mmol) of potassium carbonate, followed by stirring for 1 hour. To the reaction mixture were added 4.8 g (31.1 mmol) of Rongalit and 122 g (582 mmol) of 2,2,2-trifluoroidoethane in this order, followed by stirring overnight at room temperature. Water was added and extraction with ethyl acetate was conducted. The organic phase obtained was washed with a saturated aqueous sodium chloride solution and dried over anhydrous magnesium sulfate. The solvent was distilled off under reduced pressure. The crude product obtained was purified by silica gel column chromatography (developing solvent: a mixed solvent of n-hexane:ethyl acetate=10:1), to obtain 63.8 g (yield: 84%) of 4-methyl-3-(2,2,2-trifluoroethylthio)aniline.

$^1$H-NMR (300 MHz, CDCl$_3$/TMS δ (ppm))
2.34 (3H, s), 3.37 (2H, q), 3.59 (2H, brs), 6.56 (1H, dd), 6.82 (1H, d), 6.99 (1H, d)

Reference Example 6

Production of 4-chloro-2-fluoro-5-(2,2,2-trifluoroethylthio)phenyl boronic acid

To 180 ml of diethyl ether was dissolved 15.9 g (49.1 mmol) of (5-bromo-4-chloro-2-fluorophenyl)-2,2,2-trifluoroethylsulfide which was produced by a method described in PCT International Publication No. WO 2012/176856, and the mixture was cooled to −70° C. under nitrogen atmosphere. Thereto was dropwise added 30 ml of n-butyllithium (n-hexane solution, 1.64 mol/liter) for 10 minutes. After 5 minutes, a mixed solution obtained by dissolving 5.1 g (49.1 mmol) of trimethyl borate in 10 ml of diethylether was dropwise added in 10 minutes. Then, the temperature of the reaction mixture was rinsed to −20° C., 48 g of 20% sulfuric acid was dropwise added, and reaction was conducted in a room temperature for 1.5 hour. To the reaction mixture, ethyl acetate was added, the organic phase obtained was washed with water and aqueous sodium chloride solution, and dried over anhydrous magnesium sulfate. The solvent was distilled off under reduced pressure and the residue was washed with n-hexane, to obtain 9.64 g (yield: 68%) of an intended product.

$^1$H-NMR (400 MHz, CDCl$_3$/TMS δ (ppm))
3.49 (2H, q), 7.30 (1H, d), 8.29 (1H, d)

Reference Example 7

Production of 2,4-dichloro-5-(2,2,2-trifluoroethylthio)phenyl boronic acid

To 700 ml of diethyl ether was dissolved 46.4 g (136 mmol) of (5-bromo-2,4-dichlorophenyl)-2,2,2-trifluoroethylsulfide which was produced by a method described in PCT International Publication No. WO 2012/176856, and the mixture was cooled to −70° C. under nitrogen atmosphere. Thereto was dropwise added 82.7 ml of n-butyllithium (n-hexane solution, 1.64 mol/liter) for 10 minutes. After 5 minutes, a mixed solution obtained by dissolving 14.1 g (136 mmol) of trimethyl borate in 100 ml of diethylether was dropwise added in 10 minutes. Then, the temperature of the reaction mixture was rinsed to −20° C., 230 ml of 12% (approximately) sulfuric acid was dropwise added, and reaction was conducted in a room temperature for 1.5 hour. The solvent was distilled of under reduced pressure, and to the residue, ethyl acetate was added. The organic phase obtained was washed with water and aqueous sodium chloride solution, and dried over anhydrous magnesium sulfate. The solvent was distilled off under reduced pressure and the residue was washed with n-hexane, to obtain 32.58 g (yield: 79%) of an intended product.

$^1$H-NMR (300 MHz, CDCl$_3$/TMS δ (ppm))
3.49 (2H, q), 5.34 (2H, s), 7.47 (1H, s), 8.11 (1H, s)

The physical properties (melting point, refractive index, $^1$H-NMR spectrum data and specific rotation of optical isomer) of the present compounds [I] and [I'] synthesized based on the Examples (including the physical properties shown in the Examples) are shown in Table 43 to Table 71. Incidentally, the compound Nos. and symbols in Tables have the same meanings as given above.

TABLE 43

| Compound No. | Physical Property | |
|---|---|---|
| A-0001 | Reflective Index ($n_D^{20}$) | 1.4922 |
| A-0004 | Reflective Index ($n_D^{20}$) | 1.5072 |
| A-0005 | Melting Point (° C.) | 140-141 |
| A-0006 | Reflective Index ($n_D^{20}$) | 1.4819 |
| A-0007 | Melting Point (° C.) | 89-92 |
| A-0012 | Reflective Index ($n_D^{20}$) | 1.5055 |
| A-0013 | Melting Point (° C.) | 87-89 |
| A-0014 | Reflective Index ($n_D^{20}$) | 1.4827 |
| A-0015 | Melting Point (° C.) | 58-60 |
| A-0017 | Reflective Index ($n_D^{20}$) | 1.5016 |
| A-0018 | Melting Point (° C.) | 87-88 |
| A-0022 | Reflective Index ($n_D^{20}$) | 1.4893 |
| A-0023 | Melting Point (° C.) | 53-54 |
| A-0024 | Reflective Index ($n_D^{20}$) | 1.5008 |
| A-0025 | Melting Point (° C.) | 97-99 |
| A-0027 | Reflective Index ($n_D^{20}$) | 1.4952 |
| A-0028 | Melting Point (° C.) | 74-76 |
| A-0030 | Reflective Index ($n_D^{20}$) | 1.4800 |
| A-0031 | Melting Point (° C.) | 64-67 |
| A-0032 | Reflective Index ($n_D^{20}$) | 1.4819 |
| A-0033 | Melting Point (° C.) | 117-118 |
| A-0035 | Reflective Index ($n_D^{20}$) | 1.5032 |
| A-0036 | Melting Point (° C.) | 125-127 |
| A-0037 | Reflective Index ($n_D^{20}$) | 1.4810 |
| A-0038 | Melting Point (° C.) | 77-80 |
| A-0039 | Reflective Index ($n_D^{20}$) | 1.5032 |
| A-0040 | Melting Point (° C.) | 105-107 |
| A-0043 | Reflective Index ($n_D^{20}$) | 1.4809 |
| A-0044 | Melting Point (° C.) | 68-70 |
| A-0046 | Reflective Index ($n_D^{20}$) | 1.5004 |
| A-0047 | Melting Point (° C.) | 97-98 |
| A-0051 | Reflective Index ($n_D^{20}$) | 1.4769 |
| A-0052 | Melting Point (° C.) | 78-79 |
| A-0055 | Reflective Index ($n_D^{20}$) | 1.4987 |
| A-0056 | Melting Point (° C.) | 77-79 |
| A-0061 | Reflective Index ($n_D^{20}$) | 1.4900 |
| A-0064 | Reflective Index ($n_D^{20}$) | 1.4989 |
| A-0065 | Melting Point (° C.) | 106-109 |
| A-0066 | Melting Point (° C.) | 113-114 |

TABLE 44

| Compound No. | Physical Property | |
|---|---|---|
| A-0068 | Reflective Index ($n_D^{20}$) | 1.5011 |
| A-0069 | Melting Point (° C.) | 138-139 |
| A-0070 | Reflective Index ($n_D^{20}$) | 1.4760 |
| A-0071 | Melting Point (° C.) | 98-100 |
| A-0074 | Reflective Index ($n_D^{20}$) | 1.4748 |
| A-0075 | Melting Point (° C.) | 74-75 |
| A-0076 | Reflective Index ($n_D^{20}$) | 1.4830 |
| A-0077 | Melting Point (° C.) | 65-66 |
| A-0078 | Reflective Index ($n_D^{20}$) | 1.4961 |
| A-0079 | Melting Point (° C.) | 81-83 |
| A-0081 | Reflective Index ($n_D^{20}$) | 1.4820 |
| A-0085 | Reflective Index ($n_D^{20}$) | 1.4780 |
| A-0086 | Melting Point (° C.) | 84-85 |
| A-0087 | Reflective Index ($n_D^{20}$) | 1.4915 |
| A-0088 | Melting Point (° C.) | 62-64 |
| A-0089 | Reflective Index ($n_D^{20}$) | 1.4933 |
| A-0090 | Melting Point (° C.) | 83-84 |

TABLE 44-continued

| Compound No. | Physical Property | |
|---|---|---|
| A-0091 | Reflactive Index ($n_D^{20}$) | 1.4865 |
| A-0092 | Melting Point (° C.) | 51-52 |
| A-0094 | Melting Point (° C.) | 108-110 |
| A-0108 | Melting Point (° C.) | 50-51 |
| A-0109 | Melting Point (° C.) | 56-57 |
| A-0110 | Melting Point (° C.) | 76-77 |
| A-0111 | Melting Point (° C.) | 105-107 |
| A-0112 | Reflactive Index ($n_D^{20}$) | 1.5032 |
| A-0113 | Melting Point (° C.) | 74-75 |
| A-0114 | Melting Point (° C.) | 76-77 |
| A-0115 | Reflactive Index ($n_D^{20}$) | 1.5160 |
| A-0116 | Reflactive Index ($n_D^{20}$) | 1.4834 |
| A-0117 | Melting Point (° C.) | 52-54 |
| A-0118 | Reflactive Index ($n_D^{20}$) | 1.4899 |
| A-0119 | Melting Point (° C.) | 104-105 |
| A-0120 | Reflactive Index ($n_D^{20}$) | 1.4790 |
| A-0122 | Reflactive Index ($n_D^{20}$) | 1.4790 |
| A-0123 | Melting Point (° C.) | 58-60 |
| A-0125 | Reflactive Index ($n_D^{20}$) | 1.4949 |
| A-0126 | Melting Point (° C.) | 46-48 |
| A-0130 | Melting Point (° C.) | 59-60 |
| A-0132 | Reflactive Index ($n_D^{20}$) | 1.4842 |

TABLE 45

| Compound No. | Physical Property | |
|---|---|---|
| A-0133 | Melting Point (° C.) | 48-50 |
| A-0141 | Melting Point (° C.) | 60-61 |
| A-0143 | Reflactive Index ($n_D^{20}$) | 1.4871 |
| A-0144 | Melting Point (° C.) | 47-48 |
| A-0145 | Melting Point (° C.) | 78-81 |
| A-0147 | Reflactive Index ($n_D^{20}$) | 1.4870 |
| A-0157 | Melting Point (° C.) | 86-88 |
| A-0159 | Reflactive Index ($n_D^{20}$) | 1.4542 |
| A-0160 | Melting Point (° C.) | 100-103 |
| A-0163 | Reflactive Index ($n_D^{20}$) | 1.4549 |
| A-0164 | Melting Point (° C.) | 79-81 |
| A-0167 | Reflactive Index ($n_D^{20}$) | 1.4562 |
| A-0168 | Melting Point (° C.) | 33-35 |
| A-0169 | Reflactive Index ($n_D^{20}$) | 1.4631 |
| A-0170 | Melting Point (° C.) | 44-47 |
| A-0172 | Reflactive Index ($n_D^{20}$) | 1.4303 |
| A-0173 | Melting Point (° C.) | 72-74 |
| A-0174 | Reflactive Index ($n_D^{20}$) | 1.4365 |
| A-0175 | Melting Point (° C.) | 57-59 |
| A-0180 | Reflactive Index ($n_D^{20}$) | 1.4429 |
| A-0181 | Melting Point (° C.) | 94-96 |
| A-0184 | Reflactive Index ($n_D^{20}$) | 1.4200 |
| A-0185 | Melting Point (° C.) | 47-48 |
| A-0186 | Reflactive Index ($n_D^{20}$) | 1.4184 |
| A-0187 | Melting Point (° C.) | 56-58 |
| A-0188 | Reflactive Index ($n_D^{20}$) | 1.4445 |
| A-0199 | Reflactive Index ($n_D^{20}$) | 1.4554 |
| A-0200 | Reflactive Index ($n_D^{20}$) | 1.4613 |
| A-0203 | Reflactive Index ($n_D^{20}$) | 1.4562 |
| A-0204 | Reflactive Index ($n_D^{20}$) | 1.4644 |
| A-0205 | Reflactive Index ($n_D^{20}$) | 1.4678 |
| A-0206 | Melting Point (° C.) | 39-42 |
| A-0207 | Reflactive Index ($n_D^{20}$) | 1.4725 |
| A-0208 | Reflactive Index ($n_D^{20}$) | 1.4802 |
| A-0211 | Reflactive Index ($n_D^{20}$) | 1.419 |
| A-0212 | Reflactive Index ($n_D^{20}$) | 1.4273 |
| A-0213 | Reflactive Index ($n_D^{20}$) | 1.4382 |
| A-0214 | Reflactive Index ($n_D^{20}$) | 1.4378 |
| A-0215 | Reflactive Index ($n_D^{20}$) | 1.4309 |

TABLE 46

| Compound No. | Physical Property | |
|---|---|---|
| A-0216 | Reflactive Index ($n_D^{20}$) | 1.4341 |
| A-0217 | Reflactive Index ($n_D^{20}$) | 1.4341 |

TABLE 46-continued

| Compound No. | Physical Property | |
|---|---|---|
| A-0218 | Reflactive Index ($n_D^{20}$) | 1.4359 |
| A-0219 | Reflactive Index ($n_D^{20}$) | 1.4200 |
| A-0220 | Reflactive Index ($n_D^{20}$) | 1.4321 |
| A-0221 | Reflactive Index ($n_D^{20}$) | 1.4368 |
| A-0222 | Reflactive Index ($n_D^{20}$) | 1.4401 |
| A-0223 | Reflactive Index ($n_D^{20}$) | 1.4328 |
| A-0224 | Melting Point (° C.) | 45-47 |
| A-0225 | Reflactive Index ($n_D^{20}$) | 1.4163 |
| A-0226 | Reflactive Index ($n_D^{20}$) | 1.4115 |
| A-0227 | Reflactive Index ($n_D^{20}$) | 1.3980 |
| A-0228 | Reflactive Index ($n_D^{20}$) | 1.4079 |
| A-0229 | Reflactive Index ($n_D^{20}$) | 1.4018 |
| A-0230 | Melting Point (° C.) | 43-44 |
| A-0232 | Reflactive Index ($n_D^{20}$) | 1.3759 |
| A-0243 | Reflactive Index ($n_D^{20}$) | 1.4961 |
| A-0244 | Melting Point (° C.) | 79-80 |
| A-0249 | Reflactive Index ($n_D^{20}$) | 1.4947 |
| A-0250 | Reflactive Index ($n_D^{20}$) | 1.4929 |
| A-0253 | Reflactive Index ($n_D^{20}$) | 1.4751 |
| A-0254 | Melting Point (° C.) | 116-118 |
| A-0260 | Reflactive Index ($n_D^{20}$) | 1.4963 |
| A-0261 | Reflactive Index ($n_D^{20}$) | 1.5132 |
| A-0262 | Melting Point (° C.) | 89-92 |
| A-0263 | Reflactive Index ($n_D^{20}$) | 1.5241 |
| A-0264 | Reflactive Index ($n_D^{20}$) | 1.5102 |
| A-0266 | Reflactive Index ($n_D^{20}$) | 1.5260 |
| A-0269 | Reflactive Index ($n_D^{20}$) | 1.5092 |
| A-0270 | Melting Point (° C.) | 53-55 |
| A-0271 | Reflactive Index ($n_D^{20}$) | 1.5078 |
| A-0273 | Reflactive Index ($n_D^{20}$) | 1.5211 |
| A-0275 | Reflactive Index ($n_D^{20}$) | 1.5133 |
| A-0277 | Reflactive Index ($n_D^{20}$) | 1.5195 |
| A-0279 | Reflactive Index ($n_D^{20}$) | 1.5160 |
| A-0281 | Reflactive Index ($n_D^{20}$) | 1.5071 |
| A-0285 | Reflactive Index ($n_D^{20}$) | 1.4981 |
| A-0287 | Reflactive Index ($n_D^{20}$) | 1.5206 |
| A-0289 | Reflactive Index ($n_D^{20}$) | 1.4943 |

TABLE 47

| Compound No. | Physical Property | |
|---|---|---|
| A-0290 | Reflactive Index ($n_D^{20}$) | 1.4940 |
| A-0291 | Reflactive Index ($n_D^{20}$) | 1.5089 |
| A-0294 | Reflactive Index ($n_D^{20}$) | 1.5199 |
| A-0299 | Reflactive Index ($n_D^{20}$) | 1.5102 |
| A-0301 | Reflactive Index ($n_D^{20}$) | 1.4960 |
| A-0303 | Reflactive Index ($n_D^{20}$) | 1.5094 |
| A-0307 | Reflactive Index ($n_D^{20}$) | 1.4761 |
| A-0308 | Melting Point (° C.) | 54-56 |
| A-0311 | Reflactive Index ($n_D^{20}$) | 1.4741 |
| A-0313 | Melting Point (° C.) | 75-78 |
| A-0314 | Melting Point (° C.) | 93-96 |
| A-0315 | Reflactive Index ($n_D^{20}$) | 1.4912 |
| A-0316 | Melting Point (° C.) | 85-88 |
| A-0318 | Melting Point (° C.) | 77-80 |
| A-0319 | Reflactive Index ($n_D^{20}$) | 1.4851 |
| A-0320 | Melting Point (° C.) | 116-117 |
| A-0321 | Reflactive Index ($n_D^{20}$) | 1.4969 |
| A-0322 | Melting Point (° C.) | 117-118 |
| A-0324 | Reflactive Index ($n_D^{20}$) | 1.4752 |
| A-0325 | Reflactive Index ($n_D^{20}$) | 1.4832 |
| A-0326 | Melting Point (° C.) | 119-122 |
| A-0327 | Melting Point (° C.) | 92-95 |
| A-0330 | Melting Point (° C.) | 115-118 |
| A-0331 | Melting Point (° C.) | 120-121 |
| A-0338 | Reflactive Index ($n_D^{20}$) | 1.4751 |
| A-0339 | Reflactive Index ($n_D^{20}$) | 1.4798 |
| A-0340 | Reflactive Index ($n_D^{20}$) | 1.4831 |
| A-0341 | Reflactive Index ($n_D^{20}$) | 1.4859 |
| A-0342 | Reflactive Index ($n_D^{20}$) | 1.4968 |
| A-0343 | Melting Point (° C.) | 66-67 |
| A-0346 | Reflactive Index ($n_D^{20}$) | 1.4950 |
| A-0347 | Melting Point (° C.) | 89-90 |
| A-0349 | Reflactive Index ($n_D^{20}$) | 1.5321 |

TABLE 47-continued

| Compound No. | Physical Property | |
|---|---|---|
| A-0350 | Melting Point (° C.) | 117-118 |
| A-0352 | Melting Point (° C.) | 83-84 |
| A-0353 | Melting Point (° C.) | 51-52 |
| A-0354 | Melting Point (° C.) | 88-90 |
| A-0356 | Melting Point (° C.) | 54-56 |
| A-0359 | Melting Point (° C.) | 74-77 |

TABLE 48

| Compound No. | Physical Property | |
|---|---|---|
| A-0360 | Reflactive Index ($n_D^{20}$) | 1.5079 |
| A-0363 | Reflactive Index ($n_D^{20}$) | 1.5012 |
| A-0364 | Melting Point (° C.) | 46-47 |
| A-0365 | Reflactive Index ($n_D^{20}$) | 1.5104 |
| A-0366 | Melting Point (° C.) | 42-43 |
| A-0368 | Melting Point (° C.) | 69-71 |
| A-0369 | Reflactive Index ($n_D^{20}$) | 1.5089 |
| A-0374 | Reflactive Index ($n_D^{20}$) | 1.4990 |
| A-0375 | Melting Point (° C.) | 48-50 |
| A-0379 | Reflactive Index ($n_D^{20}$) | 1.5217 |
| A-0387 | Melting Point (° C.) | 68-70 |
| A-0388 | Melting Point (° C.) | 111-112 |
| A-0391 | Melting Point (° C.) | 88-89 |
| A-0392 | Melting Point (° C.) | 95-98 |
| A-0393 | Melting Point (° C.) | 98-99 |
| A-0394 | Melting Point (° C.) | 109-110 |
| A-0395 | Melting Point (° C.) | 93-94 |
| A-0396 | Melting Point (° C.) | 108-109 |
| A-0405 | Reflactive Index ($n_D^{20}$) | 1.4741 |
| A-0406 | Reflactive Index ($n_D^{20}$) | 1.4800 |
| A-0415 | Reflactive Index ($n_D^{20}$) | 1.4762 |
| A-0417 | Reflactive Index ($n_D^{20}$) | 1.4882 |
| A-0418 | Melting Point (° C.) | 57-59 |
| A-0422 | Reflactive Index ($n_D^{20}$) | 1.4855 |
| A-0423 | Reflactive Index ($n_D^{20}$) | 1.4869 |
| A-0431 | Reflactive Index ($n_D^{20}$) | 1.4742 |
| A-0433 | Reflactive Index ($n_D^{20}$) | 1.4932 |
| A-0434 | Melting Point (° C.) | 49-50 |
| A-0435 | Melting Point (° C.) | 51-52 |
| A-0437 | Reflactive Index ($n_D^{20}$) | 1.5000 |
| A-0438 | Reflactive Index ($n_D^{20}$) | 1.4878 |
| A-0439 | Reflactive Index ($n_D^{20}$) | 1.4889 |
| A-0441 | Melting Point (° C.) | 68-69 |
| A-0443 | Melting Point (° C.) | 41-42 |
| A-0444 | Reflactive Index ($n_D^{20}$) | 1.5006 |
| A-0445 | Melting Point (° C.) | 63-66 |
| A-0446 | Reflactive Index ($n_D^{20}$) | 1.4947 |
| A-0447 | Reflactive Index ($n_D^{20}$) | 1.4931 |
| A-0448 | Reflactive Index ($n_D^{20}$) | 1.4781 |

TABLE 49

| Compound No. | Physical Property | |
|---|---|---|
| A-0449 | Melting Point (° C.) | 69-70 |
| A-0470 | Reflactive Index ($n_D^{20}$) | 1.4770 |
| A-0471 | Melting Point (° C.) | 42-44 |
| A-0472 | Reflactive Index ($n_D^{20}$) | 1.4905 |
| A-0473 | Melting Point (° C.) | 43-46 |
| A-0474 | Reflactive Index ($n_D^{20}$) | 1.4886 |
| A-0475 | Reflactive Index ($n_D^{20}$) | 1.4862 |
| A-0476 | Reflactive Index ($n_D^{20}$) | 1.4951 |
| A-0477 | Melting Point (° C.) | 45-48 |
| A-0478 | Reflactive Index ($n_D^{20}$) | 1.5059 |
| A-0479 | Melting Point (° C.) | 43-45 |
| A-0481 | Reflactive Index ($n_D^{20}$) | 1.4859 |
| A-0482 | Reflactive Index ($n_D^{20}$) | 1.4960 |
| A-0483 | Reflactive Index ($n_D^{20}$) | 1.491 |
| A-0484 | Reflactive Index ($n_D^{20}$) | 1.4759 |
| A-0485 | Reflactive Index ($n_D^{20}$) | 1.4800 |
| A-0486 | Reflactive Index ($n_D^{20}$) | 1.5086 |
| A-0487 | Reflactive Index ($n_D^{20}$) | 1.5102 |

TABLE 49-continued

| Compound No. | Physical Property | |
|---|---|---|
| A-0488 | Reflactive Index ($n_D^{20}$) | 1.5005 |
| A-0489 | Reflactive Index ($n_D^{20}$) | 1.4978 |
| A-0490 | Reflactive Index ($n_D^{20}$) | 1.5181 |
| A-0495 | Reflactive Index ($n_D^{20}$) | 1.4839 |
| A-0496 | Reflactive Index ($n_D^{20}$) | 1.4782 |
| A-0502 | Reflactive Index ($n_D^{20}$) | 1.4813 |
| A-0503 | Reflactive Index ($n_D^{20}$) | 1.4773 |
| A-0504 | Reflactive Index ($n_D^{20}$) | 1.4814 |
| A-0505 | Melting Point (° C.) | 48-49 |
| A-0507 | Reflactive Index ($n_D^{20}$) | 1.4932 |
| A-0508 | Melting Point (° C.) | 43-44 |
| A-0510 | Melting Point (° C.) | 44-45 |
| A-0524 | Melting Point (° C.) | 82-83 |
| A-0525 | Melting Point (° C.) | 50-51 |
| A-0526 | Reflactive Index ($n_D^{20}$) | 1.4920 |
| A-0533 | Melting Point (° C.) | 80-81 |
| A-0534 | Melting Point (° C.) | 92-93 |
| A-0535 | Reflactive Index ($n_D^{20}$) | 1.4709 |
| A-0536 | Melting Point (° C.) | 73-74 |
| A-0539 | Melting Point (° C.) | 74-77 |
| A-0543 | Reflactive Index ($n_D^{20}$) | 1.4949 |

TABLE 50

| Compound No. | Physical Property | |
|---|---|---|
| A-0553 | Reflactive Index ($n_D^{20}$) | 1.4914 |
| A-0555 | Reflactive Index ($n_D^{20}$) | 1.5025 |
| A-0556 | Melting Point (° C.) | 40-42 |
| A-0558 | Reflactive Index ($n_D^{20}$) | 1.5052 |
| A-0559 | Reflactive Index ($n_D^{20}$) | 1.5125 |
| A-0560 | Melting Point (° C.) | 49-50 |
| A-0561 | Reflactive Index ($n_D^{20}$) | 1.5201 |
| A-0562 | Melting Point (° C.) | 57-59 |
| A-0563 | Reflactive Index ($n_D^{20}$) | 1.5025 |
| A-0571 | Reflactive Index ($n_D^{20}$) | 1.4957 |
| A-0572 | Reflactive Index ($n_D^{20}$) | 1.5000 |
| A-0573 | Reflactive Index ($n_D^{20}$) | 1.5023 |
| A-0574 | Reflactive Index ($n_D^{20}$) | 1.4982 |
| A-0575 | Reflactive Index ($n_D^{20}$) | 1.5098 |
| A-0576 | Reflactive Index ($n_D^{20}$) | 1.5087 |
| A-0577 | Melting Point (° C.) | 68-69 |
| A-0578 | Melting Point (° C.) | 58-59 |
| A-0587 | Reflactive Index ($n_D^{20}$) | 1.4941 |
| A-0588 | Reflactive Index ($n_D^{20}$) | 1.4981 |
| A-0589 | Reflactive Index ($n_D^{20}$) | 1.5010 |
| A-0590 | Melting Point (° C.) | 41-42 |
| A-0591 | Melting Point (° C.) | 50-51 |
| A-0592 | Reflactive Index ($n_D^{20}$) | 1.5000 |
| A-0594 | Melting Point (° C.) | 112-113 |
| A-0599 | Melting Point (° C.) | 65-67 |
| A-0605 | Melting Point (° C.) | 87-90 |
| A-0606 | Melting Point (° C.) | 78-81 |
| A-0610 | Reflactive Index ($n_D^{20}$) | 1.4909 |
| A-0611 | Melting Point (° C.) | 96-99 |
| A-0615 | Melting Point (° C.) | 60-61 |
| A-0616 | Melting Point (° C.) | 58-60 |
| A-0617 | Melting Point (° C.) | 38-41 |
| A-0618 | Melting Point (° C.) | 82-83 |
| A-0622 | Reflactive Index ($n_D^{20}$) | 1.4864 |
| A-0623 | Melting Point (° C.) | 86-88 |
| A-0625 | Reflactive Index ($n_D^{20}$) | 1.4861 |
| A-0626 | Reflactive Index ($n_D^{20}$) | 1.4899 |
| A-0631 | Reflactive Index ($n_D^{20}$) | 1.4845 |
| A-0632 | Melting Point (° C.) | 72-74 |

TABLE 51

| Compound No. | Physical Property | |
|---|---|---|
| A-0638 | Melting Point (° C.) | 39-41 |
| A-0640 | Reflactive Index ($n_D^{20}$) | 1.4902 |
| A-0641 | Melting Point (° C.) | 68-69 |

TABLE 51-continued

| Compound No. | Physical Property | |
|---|---|---|
| A-0642 | Melting Point (° C.) | 43-44 |
| A-0643 | Melting Point (° C.) | 61-63 |
| A-0644 | Reflactive Index ($n_D^{20}$) | 1.5000 |
| A-0662 | Reflactive Index ($n_D^{20}$) | 1.5353 |
| A-0663 | Reflactive Index ($n_D^{20}$) | 1.5190 |
| A-0665 | Reflactive Index ($n_D^{20}$) | 1.5309 |
| A-0666 | Reflactive Index ($n_D^{20}$) | 1.5272 |
| A-0667 | Reflactive Index ($n_D^{20}$) | 1.5509 |
| A-0668 | Reflactive Index ($n_D^{20}$) | 1.5155 |
| A-0670 | Reflactive Index ($n_D^{20}$) | 1.5281 |
| A-0671 | Reflactive Index ($n_D^{20}$) | 1.5325 |
| A-0672 | Reflactive Index ($n_D^{20}$) | 1.5299 |
| A-0673 | Reflactive Index ($n_D^{20}$) | 1.5161 |
| A-0674 | Reflactive Index ($n_D^{20}$) | 1.5130 |
| A-0675 | Reflactive Index ($n_D^{20}$) | 1.5122 |
| A-0676 | Reflactive Index ($n_D^{20}$) | 1.5210 |
| A-0677 | Reflactive Index ($n_D^{20}$) | 1.5240 |
| A-0680 | Reflactive Index ($n_D^{20}$) | 1.5085 |
| A-0682 | Reflactive Index ($n_D^{20}$) | 1.5121 |
| A-0683 | Reflactive Index ($n_D^{20}$) | 1.4769 |
| A-0684 | Reflactive Index ($n_D^{20}$) | 1.5361 |
| A-0686 | Melting Point (° C.) | 108-110 |
| A-0688 | Melting Point (° C.) | 111-112 |
| A-0690 | Reflactive Index ($n_D^{20}$) | 1.5016 |
| A-0692 | Melting Point (° C.) | 81-83 |
| A-0693 | Reflactive Index ($n_D^{20}$) | 1.5092 |
| A-0694 | Melting Point (° C.) | 86-87 |
| A-0695 | Melting Point (° C.) | 39-41 |
| A-0696 | Melting Point (° C.) | 125-127 |
| A-0697 | Melting Point (° C.) | 102-104 |
| A-0698 | Melting Point (° C.) | 113-116 |
| A-0699 | Melting Point (° C.) | 53-55 |
| A-0700 | Melting Point (° C.) | 112-114 |
| A-0703 | Melting Point (° C.) | 63-64 |
| A-0709 | Melting Point (° C.) | 59-60 |
| A-0710 | Melting Point (° C.) | 98-100 |

TABLE 52

| Compound No. | Physical Property | |
|---|---|---|
| A-0711 | Melting Point (° C.) | 61-63 |
| A-0712 | Melting Point (° C.) | 89-90 |
| A-0713 | Reflactive Index ($n_D^{20}$) | 1.5188 |
| A-0716 | Melting Point (° C.) | 66-68 |
| A-0717 | Melting Point (° C.) | 80-81 |
| A-0718 | Melting Point (° C.) | 79-82 |
| A-0720 | Reflactive Index ($n_D^{20}$) | 1.5330 |
| A-0721 | Melting Point (° C.) | 128-129 |
| A-0722 | Melting Point (° C.) | 50-51 |
| A-0723 | Melting Point (° C.) | 90-91 |
| A-0724 | Melting Point (° C.) | 96-97 |
| A-0725 | Melting Point (° C.) | 144-145 |
| A-0726 | Melting Point (° C.) | 117-119 |
| A-0727 | Melting Point (° C.) | 93-96 |
| A-0728 | Melting Point (° C.) | 47-48.5 |
| A-0729 | Melting Point (° C.) | 117-118 |
| A-0730 | Melting Point (° C.) | 70-71 |
| A-0731 | Melting Point (° C.) | 125-126 |
| A-0732 | Reflactive Index ($n_D^{20}$) | 1.5021 |
| A-0733 | Melting Point (° C.) | 144-145 |
| A-0734 | Reflactive Index ($n_D^{20}$) | 1.5072 |
| A-0735 | Melting Point (° C.) | 132-134 |
| A-0736 | Melting Point (° C.) | 122-123 |
| A-0739 | Melting Point (° C.) | 79-80 |
| A-0740 | Melting Point (° C.) | 138-140 |
| A-0741 | Melting Point (° C.) | 52-53 |
| A-0742 | Melting Point (° C.) | 114-116 |
| A-0743 | Melting Point (° C.) | 52-53 |
| A-0744 | Melting Point (° C.) | 103-104 |
| A-0746 | Melting Point (° C.) | 101-102 |
| A-0748 | Reflactive Index ($n_D^{20}$) | 1.4766 |
| A-0749 | Melting Point (° C.) | 96-98 |
| A-0750 | Melting Point (° C.) | 85-87 |
| A-0751 | Reflactive Index ($n_D^{20}$) | 1.5319 |

TABLE 52-continued

| Compound No. | Physical Property | |
|---|---|---|
| A-0752 | Melting Point (° C.) | 78-80 |
| A-0753 | Reflactive Index ($n_D^{20}$) | 1.5224 |
| A-0754 | Melting Point (° C.) | 92-94 |
| A-0755 | Reflactive Index ($n_D^{20}$) | 1.5279 |
| A-0756 | Melting Point (° C.) | 102-103 |

TABLE 53

| Compound No. | Physical Property | |
|---|---|---|
| A-0757 | Reflactive Index ($n_D^{20}$) | 1.5500 |
| A-0758 | Melting Point (° C.) | 104-105 |
| A-0759 | Reflactive Index ($n_D^{20}$) | 1.5030 |
| A-0760 | Melting Point (° C.) | 125-128 |
| A-0761 | Reflactive Index ($n_D^{20}$) | 1.4979 |
| A-0762 | Reflactive Index ($n_D^{20}$) | 1.5050 |
| A-0763 | Reflactive Index ($n_D^{20}$) | 1.4991 |
| A-0764 | Melting Point (° C.) | 95-96 |
| A-0765 | Reflactive Index ($n_D^{20}$) | 1.5085 |
| A-0766 | Melting Point (° C.) | 91-92 |
| A-0767 | Melting Point (° C.) | 109-110 |
| A-0768 | Melting Point (° C.) | 91-92 |
| A-0769 | Melting Point (° C.) | 115-116 |
| A-0771 | Melting Point (° C.) | 115-116 |
| A-0772 | Reflactive Index ($n_D^{20}$) | 1.5190 |
| A-0773 | Melting Point (° C.) | 89-90 |
| A-0774 | Melting Point (° C.) | 75-76 |
| A-0775 | Melting Point (° C.) | 81-82 |
| A-0776 | Melting Point (° C.) | 118-120 |
| A-0777 | Melting Point (° C.) | 40-41 |
| A-0778 | Reflactive Index ($n_D^{20}$) | 1.4976 |
| A-0779 | Melting Point (° C.) | 81-84 |
| A-0780 | Reflactive Index ($n_D^{20}$) | 1.5009 |
| A-0781 | Melting Point (° C.) | 94-95 |
| A-0782 | Melting Point (° C.) | 111-112 |
| A-0783 | Melting Point (° C.) | 80-81 |
| A-0784 | Melting Point (° C.) | 120-122 |
| A-0786 | Reflactive Index ($n_D^{20}$) | 1.5158 |
| A-0787 | Reflactive Index ($n_D^{20}$) | 1.5247 |
| A-0788 | Melting Point (° C.) | 89-90 |
| A-0789 | Melting Point (° C.) | 114-115 |
| A-0790 | Melting Point (° C.) | 51-54 |
| A-0791 | Melting Point (° C.) | 131-134 |
| A-0792 | Melting Point (° C.) | 110-111 |
| A-0793 | Melting Point (° C.) | 126-127 |
| A-0795 | Melting Point (° C.) | 117-118 |
| A-0796 | Melting Point (° C.) | 133-136 |
| A-0797 | Reflactive Index ($n_D^{20}$) | 1.5062 |
| A-0798 | Reflactive Index ($n_D^{20}$) | 1.4980 |

TABLE 54

| Compound No. | Physical Property | |
|---|---|---|
| A-0799 | Melting Point (° C.) | 79-81 |
| A-0800 | Melting Point (° C.) | 83-84 |
| A-0801 | Melting Point (° C.) | 109-110 |
| A-0802 | Reflactive Index ($n_D^{20}$) | 1.5540 |
| A-0803 | Melting Point (° C.) | 135-136 |
| A-0805 | Melting Point (° C.) | 92-93 |
| A-0806 | Melting Point (° C.) | 101-102 |
| A-0807 | Melting Point (° C.) | 115-116 |
| A-0808 | Melting Point (° C.) | 106-109 |
| A-0809 | Reflactive Index ($n_D^{20}$) | 1.5051 |
| A-0810 | Melting Point (° C.) | 88-90 |
| A-0811 | Reflactive Index ($n_D^{20}$) | 1.5021 |
| A-0812 | Melting Point (° C.) | 107-109 |
| A-0813 | Reflactive Index ($n_D^{20}$) | 1.4896 |
| A-0814 | Melting Point (° C.) | 104-106 |
| A-0815 | Reflactive Index ($n_D^{20}$) | 1.4987 |
| A-0816 | Melting Point (° C.) | 111-112 |
| A-0817 | Melting Point (° C.) | 98-100 |
| A-0818 | Melting Point (° C.) | 86-88 |

TABLE 54-continued

| Compound No. | Physical Property | |
|---|---|---|
| A-0819 | Reflactive Index ($n_D^{20}$) | 1.5210 |
| A-0820 | Melting Point (° C.) | 99-100 |
| A-0821 | Melting Point (° C.) | 90-91 |
| A-0823 | Melting Point (° C.) | 93-95 |
| A-0824 | Reflactive Index ($n_D^{20}$) | 1.5005 |
| A-0825 | Melting Point (° C.) | 72-73 |
| A-0826 | Reflactive Index ($n_D^{20}$) | 1.5282 |
| A-0827 | Melting Point (° C.) | 76-78 |
| A-0828 | Reflactive Index ($n_D^{20}$) | 1.5463 |
| A-0829 | Melting Point (° C.) | 144-145 |
| A-0830 | Reflactive Index ($n_D^{20}$) | 1.5589 |
| A-0831 | Reflactive Index ($n_D^{20}$) | 1.5479 |
| A-0832 | Reflactive Index ($n_D^{20}$) | 1.5406 |
| A-0833 | Melting Point (° C.) | 49-52 |
| A-0837 | Melting Point (° C.) | 96-97 |
| A-0838 | Reflactive Index ($n_D^{20}$) | 1.4970 |
| A-0839 | Melting Point (° C.) | 101-102 |
| A-0844 | Reflactive Index ($n_D^{20}$) | 1.4962 |
| A-0845 | Reflactive Index ($n_D^{20}$) | 1.5025 |
| A-0846 | Reflactive Index ($n_D^{20}$) | 1.5270 |

TABLE 55

| Compound No. | Physical Property | |
|---|---|---|
| A-0847 | Melting Point (° C.) | 58-60 |
| A-0848 | Reflactive Index ($n_D^{20}$) | 1.5382 |
| A-0849 | Melting Point (° C.) | 92-94 |
| A-0853 | Reflactive Index ($n_D^{20}$) | 1.5140 |
| A-0854 | Melting Point (° C.) | 100-103 |
| A-0855 | Reflactive Index ($n_D^{20}$) | 1.5028 |
| A-0856 | Melting Point (° C.) | 98-100 |
| A-0857 | Reflactive Index ($n_D^{20}$) | 1.4969 |
| A-0858 | Melting Point (° C.) | 101-102 |
| A-0860 | Reflactive Index ($n_D^{20}$) | 1.5256 |
| A-0864 | Melting Point (° C.) | 87-88 |
| A-0869 | Reflactive Index ($n_D^{20}$) | 1.5241 |
| A-0870 | Reflactive Index ($n_D^{20}$) | 1.5207 |
| A-0876 | Melting Point (° C.) | 82-84 |
| A-0877 | Reflactive Index ($n_D^{20}$) | 1.5442 |
| A-0878 | Melting Point (° C.) | 44-46 |
| A-0880 | Reflactive Index ($n_D^{20}$) | 1.5235 |
| A-0881 | Melting Point (° C.) | 69-72 |
| A-0884 | Reflactive Index ($n_D^{20}$) | 1.5201 |
| A-0885 | Melting Point (° C.) | 49-50 |
| A-0888 | Reflactive Index ($n_D^{20}$) | 1.5602 |
| A-0902 | Reflactive Index ($n_D^{20}$) | 1.5450 |
| A-0903 | Melting Point (° C.) | 83-85 |
| A-0906 | Melting Point (° C.) | 140-143 |
| A-0907 | Reflactive Index ($n_D^{20}$) | 1.5382 |
| A-0908 | Reflactive Index ($n_D^{20}$) | 1.5508 |
| A-0909 | Melting Point (° C.) | 103-105 |
| A-0913 | Reflactive Index ($n_D^{20}$) | 1.5486 |
| A-0914 | Reflactive Index ($n_D^{20}$) | 1.5580 |
| A-0915 | Reflactive Index ($n_D^{20}$) | 1.5679 |
| A-0916 | Reflactive Index ($n_D^{20}$) | 1.5649 |
| A-0917 | Reflactive Index ($n_D^{20}$) | 1.5578 |
| A-0918 | Reflactive Index ($n_D^{20}$) | 1.5500 |
| A-0919 | Reflactive Index ($n_D^{20}$) | 1.5552 |
| A-0920 | Reflactive Index ($n_D^{20}$) | 1.5539 |
| A-0921 | Reflactive Index ($n_D^{20}$) | 1.5549 |
| A-0922 | Melting Point (° C.) | 75-77 |
| A-0923 | Reflactive Index ($n_D^{20}$) | 1.5171 |
| A-0924 | Melting Point (° C.) | 83-86 |

TABLE 56

| Compound No. | Physical Property | |
|---|---|---|
| A-0925 | Melting Point (° C.) | 75-76 |
| A-0926 | Reflactive Index ($n_D^{20}$) | 1.5667 |
| A-0927 | Melting Point (° C.) | 75-76 |
| A-0933 | Reflactive Index ($n_D^{20}$) | 1.5471 |

TABLE 56-continued

| Compound No. | Physical Property | |
|---|---|---|
| A-0936 | Reflactive Index ($n_D^{20}$) | 1.5411 |
| A-0940 | Melting Point (° C.) | 71-72 |
| A-0941 | Reflactive Index ($n_D^{20}$) | 1.5259 |
| A-0942 | Melting Point (° C.) | 112-114 |
| A-0943 | Melting Point (° C.) | 93-96 |
| A-0948 | Melting Point (° C.) | 57-58 |
| A-0950 | Melting Point (° C.) | 136-138 |
| A-0956 | Reflactive Index ($n_D^{20}$) | 1.5046 |
| A-0957 | Melting Point (° C.) | 94-95 |
| A-0958 | Melting Point (° C.) | 49-50 |
| A-0959 | Reflactive Index ($n_D^{20}$) | 1.4908 |
| A-0960 | Melting Point (° C.) | 91-92 |
| A-0963 | Reflactive Index ($n_D^{20}$) | 1.5309 |
| A-0964 | Reflactive Index ($n_D^{20}$) | 1.5341 |
| A-0965 | Reflactive Index ($n_D^{20}$) | 1.5219 |
| A-0966 | Reflactive Index ($n_D^{20}$) | 1.5269 |
| A-0968 | Reflactive Index ($n_D^{20}$) | 1.5635 |
| A-0969 | Melting Point (° C.) | 93-94 |
| A-0972 | Reflactive Index ($n_D^{20}$) | 1.4600 |
| A-0973 | Melting Point (° C.) | 71-74 |
| A-0975 | Reflactive Index ($n_D^{20}$) | 1.5613 |
| A-0976 | Melting Point (° C.) | 50-51 |
| A-0977 | Reflactive Index ($n_D^{20}$) | 1.4741 |
| A-0978 | Melting Point (° C.) | 85-87 |
| A-0979 | Reflactive Index ($n_D^{20}$) | 1.5143 |
| A-0980 | Melting Point (° C.) | 76-77 |
| A-0981 | Reflactive Index ($n_D^{20}$) | 1.4626 |
| A-0982 | Melting Point (° C.) | 50-53 |
| A-0983 | Reflactive Index ($n_D^{20}$) | 1.5621 |
| A-0984 | Reflactive Index ($n_D^{20}$) | 1.4711 |
| A-0985 | Melting Point (° C.) | 66-69 |
| A-0988 | Melting Point (° C.) | 76-77 |
| A-0989 | Reflactive Index ($n_D^{20}$) | 1.5024 |
| A-0990 | Melting Point (° C.) | 62-63 |
| A-0991 | Reflactive Index ($n_D^{20}$) | 1.4639 |

TABLE 57

| Compound No. | Physical Property | |
|---|---|---|
| A-0992 | Melting Point (° C.) | 35-37 |
| A-0996 | Melting Point (° C.) | 48-51 |
| A-0997 | Melting Point (° C.) | 55-58 |
| A-0999 | Melting Point (° C.) | 87-88 |
| A-1000 | Melting Point (° C.) | 104-105 |
| A-1001 | Melting Point (° C.) | 91-92 |
| A-1002 | Melting Point (° C.) | 70-73 |
| A-1003 | Reflactive Index ($n_D^{20}$) | 1.5103 |
| A-1004 | Reflactive Index ($n_D^{20}$) | 1.5094 |
| A-1005 | Melting Point (° C.) | 86-88 |
| A-1006 | Melting Point (° C.) | 72-75 |
| A-1007 | Reflactive Index ($n_D^{20}$) | 1.5254 |
| A-1008 | Melting Point (° C.) | 87-88 |
| A-1009 | Reflactive Index ($n_D^{20}$) | 1.5101 |
| A-1010 | Melting Point (° C.) | 78-80 |
| A-1011 | Reflactive Index ($n_D^{20}$) | 1.5272 |
| A-1012 | Melting Point (° C.) | 91-92 |
| A-1015 | Reflactive Index ($n_D^{20}$) | 1.5226 |
| A-1016 | Melting Point (° C.) | 92-94 |
| A-1020 | Reflactive Index ($n_D^{20}$) | 1.4900 |
| A-1021 | Melting Point (° C.) | 105-108 |
| A-1024 | Reflactive Index ($n_D^{20}$) | 1.4931 |
| A-1025 | Reflactive Index ($n_D^{20}$) | 1.4852 |
| A-1026 | Melting Point (° C.) | 71-72 |
| A-1027 | Reflactive Index ($n_D^{20}$) | 1.5430 |
| A-1033 | Reflactive Index ($n_D^{20}$) | 1.4935 |
| A-1037 | Reflactive Index ($n_D^{20}$) | 1.4792 |
| A-1042 | Reflactive Index ($n_D^{20}$) | 1.4862 |
| A-1048 | Melting Point (° C.) | 60-61 |
| A-1050 | Reflactive Index ($n_D^{20}$) | 1.4850 |
| A-1051 | Reflactive Index ($n_D^{20}$) | 1.4780 |
| A-1052 | Reflactive Index ($n_D^{20}$) | 1.4802 |
| A-1057 | Reflactive Index ($n_D^{20}$) | 1.4790 |
| A-1058 | Reflactive Index ($n_D^{20}$) | 1.4859 |
| A-1059 | Melting Point (° C.) | 63-64 |

TABLE 57-continued

| Compound No. | Physical Property | |
|---|---|---|
| A-1060 | Melting Point (° C.) | 75-76 |
| A-1061 | Reflactive Index ($n_D^{20}$) | 1.4909 |
| A-1062 | Reflactive Index ($n_D^{20}$) | 1.4942 |
| A-1073 | Melting Point (° C.) | 67-70 |

TABLE 58

| Compound No. | Physical Property | |
|---|---|---|
| A-1074 | Reflactive Index ($n_D^{20}$) | 1.4919 |
| A-1075 | Melting Point (° C.) | 82-83 |
| A-1079 | Melting Point (° C.) | 81-83 |
| A-1080 | Melting Point (° C.) | 119-122 |
| A-1081 | Melting Point (° C.) | 101-102 |
| A-1082 | Melting Point (° C.) | 144-147 |
| A-1087 | Reflactive Index ($n_D^{20}$) | 1.4991 |
| A-1088 | Melting Point (° C.) | 89-92 |
| A-1093 | Reflactive Index ($n_D^{20}$) | 1.5029 |
| A-1094 | Melting Point (° C.) | 99-102 |
| A-1097 | Reflactive Index ($n_D^{20}$) | 1.523 |
| A-1098 | Melting Point (° C.) | 115-117 |
| A-1099 | Reflactive Index ($n_D^{20}$) | 1.4985 |
| A-1100 | Reflactive Index ($n_D^{20}$) | 1.5051 |
| A-1102 | Reflactive Index ($n_D^{20}$) | 1.5152 |
| A-1107 | Melting Point (° C.) | 92-93 |
| A-1108 | Melting Point (° C.) | 142-143 |
| A-1112 | Reflactive Index ($n_D^{20}$) | 1.4958 |
| A-1113 | Melting Point (° C.) | 109-111 |
| A-1117 | Melting Point (° C.) | 94-96 |
| A-1119 | Melting Point (° C.) | 135-136 |
| A-1122 | Melting Point (° C.) | 110-113 |
| A-1123 | Melting Point (° C.) | 117-118 |
| A-1125 | Reflactive Index ($n_D^{20}$) | 1.4881 |
| A-1126 | Melting Point (° C.) | 70-72 |
| A-1127 | Reflactive Index ($n_D^{20}$) | 1.5111 |
| A-1128 | Reflactive Index ($n_D^{20}$) | 1.5049 |
| A-1131 | Melting Point (° C.) | 70-73 |
| A-1132 | Melting Point (° C.) | 70-73 |
| A-1136 | Reflactive Index ($n_D^{20}$) | 1.4550 |
| A-1137 | Melting Point (° C.) | 87-90 |
| A-1138 | Reflactive Index ($n_D^{20}$) | 1.4826 |
| A-1139 | Melting Point (° C.) | 98-101 |
| A-1140 | Reflactive Index ($n_D^{20}$) | 1.4622 |
| A-1141 | Reflactive Index ($n_D^{20}$) | 1.4682 |
| A-1142 | Reflactive Index ($n_D^{20}$) | 1.4750 |
| A-1143 | Melting Point (° C.) | 85-87 |
| A-1150 | Melting Point (° C.) | 116-117 |
| A-1151 | Melting Point (° C.) | 51-52 |

TABLE 59

| Compound No. | Physical Property | |
|---|---|---|
| A-1152 | Melting Point (° C.) | 105-106 |
| A-1153 | Melting Point (° C.) | 147-148 |
| A-1154 | Melting Point (° C.) | 89-92 |
| A-1155 | Melting Point (° C.) | 92-93 |
| A-1157 | Melting Point (° C.) | 77-80 |
| A-1158 | Reflactive Index ($n_D^{20}$) | 1.4679 |
| A-1159 | Reflactive Index ($n_D^{20}$) | 1.4715 |
| A-1164 | Melting Point (° C.) | 62-63 |
| A-1165 | Melting Point (° C.) | 65-67 |
| A-1166 | Reflactive Index ($n_D^{20}$) | 1.4919 |
| A-1167 | Melting Point (° C.) | 67-68 |
| A-1171 | Reflactive Index ($n_D^{20}$) | 1.5335 |
| A-1172 | Melting Point (° C.) | 99-100 |
| A-1174 | Melting Point (° C.) | 103-106 |
| A-1175 | Reflactive Index ($n_D^{20}$) | 1.4721 |
| A-1177 | Reflactive Index ($n_D^{20}$) | 1.4755 |
| A-1178 | Melting Point (° C.) | 84-87 |
| A-1180 | Reflactive Index ($n_D^{20}$) | 1.4729 |
| A-1181 | Reflactive Index ($n_D^{20}$) | 1.4730 |
| A-1183 | Melting Point (° C.) | 79-82 |

TABLE 59-continued

| Compound No. | Physical Property | |
|---|---|---|
| A-1185 | Reflactive Index ($n_D^{20}$) | 1.4685 |
| A-1186 | Melting Point (° C.) | 107-108 |
| A-1187 | Melting Point (° C.) | 105-107 |
| A-1188 | Melting Point (° C.) | 84-85 |
| A-1190 | Reflactive Index ($n_D^{20}$) | 1.4729 |
| A-1191 | Melting Point (° C.) | 104-106 |
| A-1192 | Melting Point (° C.) | 80-81 |
| A-1195 | Reflactive Index ($n_D^{20}$) | 1.4720 |
| A-1196 | Melting Point (° C.) | 90-91 |
| A-1197 | Reflactive Index ($n_D^{20}$) | 1.4812 |
| A-1200 | Melting Point (° C.) | 102-104 |
| A-1202 | Melting Point (° C.) | 58-61 |
| A-1203 | Melting Point (° C.) | 89-90 |
| A-1205 | Reflactive Index ($n_D^{20}$) | 1.4801 |
| A-1206 | Reflactive Index ($n_D^{20}$) | 1.4899 |
| A-1207 | Melting Point (° C.) | 67-70 |
| A-1209 | Reflactive Index ($n_D^{20}$) | 1.4925 |
| A-1210 | Reflactive Index ($n_D^{20}$) | 1.4804 |
| A-1211 | Melting Point (° C.) | 71-72 |

TABLE 60

| Compound No. | Physical Property | |
|---|---|---|
| A-1212 | Reflactive Index ($n_D^{20}$) | 1.4880 |
| A-1213 | Melting Point (° C.) | 46-48 |
| A-1214 | Melting Point (° C.) | 99-100 |
| A-1215 | Reflactive Index ($n_D^{20}$) | 1.5418 |
| A-1216 | Reflactive Index ($n_D^{20}$) | 1.5391 |
| A-1217 | Melting Point (° C.) | 69-70 |
| A-1218 | Melting Point (° C.) | 80-82 |

TABLE 61

| Compound No. | Physical Property | |
|---|---|---|
| B-0001 | Reflactive Index ($n_D^{20}$) | 1.4980 |
| B-0002 | Melting Point (° C.) | 116-117 |
| B-0003 | Reflactive Index ($n_D^{20}$) | 1.4599 |
| B-0004 | Reflactive Index ($n_D^{20}$) | 1.4638 |
| B-0005 | Reflactive Index ($n_D^{20}$) | 1.4830 |
| B-0006 | Reflactive Index ($n_D^{20}$) | 1.4896 |
| B-0007 | Reflactive Index ($n_D^{20}$) | 1.4839 |
| B-0008 | Reflactive Index ($n_D^{20}$) | 1.4885 |
| B-0009 | Reflactive Index ($n_D^{20}$) | 1.4880 |
| B-0010 | Reflactive Index ($n_D^{20}$) | 1.4928 |
| B-0011 | Melting Point (° C.) | 75-76 |
| B-0012 | Reflactive Index ($n_D^{20}$) | 1.5291 |
| B-0013 | Melting Point (° C.) | 102-103 |
| B-0014 | Reflactive Index ($n_D^{20}$) | 1.5534 |
| B-0015 | Melting Point (° C.) | 103-106 |
| B-0016 | Reflactive Index ($n_D^{20}$) | 1.5528 |
| B-0017 | Reflactive Index ($n_D^{20}$) | 1.5019 |
| B-0018 | Melting Point (° C.) | 64-65 |
| B-0019 | Melting Point (° C.) | 67-68 |
| B-0020 | Reflactive Index ($n_D^{20}$) | 1.4952 |
| B-0021 | Melting Point (° C.) | 124-126 |
| B-0022 | Reflactive Index ($n_D^{20}$) | 1.4835 |
| B-0023 | Melting Point (° C.) | 88-89 |
| B-0024 | Reflactive Index ($n_D^{20}$) | 1.5051 |
| B-0025 | Melting Point (° C.) | 85-86 |
| B-0026 | Melting Point (° C.) | 57-59 |
| B-0027 | Melting Point (° C.) | 53-54 |
| B-0029 | Reflactive Index ($n_D^{20}$) | 1.5390 |
| B-0030 | Melting Point (° C.) | 88-91 |
| B-0032 | Melting Point (° C.) | 117-118 |
| B-0033 | Melting Point (° C.) | 90-92 |
| B-0034 | Melting Point (° C.) | 104-107 |
| B-0035 | Reflactive Index ($n_D^{20}$) | 1.5013 |
| B-0036 | Reflactive Index ($n_D^{20}$) | 1.5145 |
| B-0037 | Melting Point (° C.) | 94-96 |
| B-0038 | Reflactive Index ($n_D^{20}$) | 1.5028 |
| B-0039 | Melting Point (° C.) | 73-74 |

TABLE 61-continued

| Compound No. | Physical Property | |
|---|---|---|
| B-0040 | Melting Point (° C.) | 93-95 |
| B-0041 | Melting Point (° C.) | 85-87 |

TABLE 62

| Compound No. | Physical Property | |
|---|---|---|
| B-0042 | Reflactive Index ($n_D^{20}$) | 1.5040 |
| B-0043 | Reflactive Index ($n_D^{20}$) | 1.5220 |
| B-0044 | Melting Point (° C.) | 87-89 |
| B-0045 | Reflactive Index ($n_D^{20}$) | 1.5168 |
| B-0046 | Melting Point (° C.) | 114-115 |
| B-0047 | Melting Point (° C.) | 130-133 |
| B-0048 | Melting Point (° C.) | 54-56 |
| B-0049 | Melting Point (° C.) | 124-125 |
| B-0050 | Melting Point (° C.) | 133-134 |
| B-0051 | Reflactive Index ($n_D^{20}$) | 1.4976 |
| B-0052 | Melting Point (° C.) | 147-149 |
| B-0053 | Melting Point (° C.) | 54-55 |
| B-0054 | Melting Point (° C.) | 117-118 |
| B-0055 | Reflactive Index ($n_D^{20}$) | 1.5098 |
| B-0056 | Melting Point (° C.) | 74-75 |
| B-0058 | Melting Point (° C.) | 94-96 |
| B-0059 | Melting Point (° C.) | 74-77 |
| B-0061 | Melting Point (° C.) | 108-109 |
| B-0062 | Melting Point (° C.) | 99-101 |
| B-0064 | Reflactive Index ($n_D^{20}$) | 1.5210 |
| B-0065 | Melting Point (° C.) | 142-144 |
| B-0066 | Reflactive Index ($n_D^{20}$) | 1.5059 |
| B-0067 | Melting Point (° C.) | 94-96 |
| B-0068 | Reflactive Index ($n_D^{20}$) | 1.5085 |
| B-0069 | Melting Point (° C.) | 126-127 |
| B-0070 | Reflactive Index ($n_D^{20}$) | 1.4985 |
| B-0071 | Melting Point (° C.) | 109-110 |
| B-0072 | Reflactive Index ($n_D^{20}$) | 1.5031 |
| B-0073 | Melting Point (° C.) | 78-79 |
| B-0074 | Reflactive Index ($n_D^{20}$) | 1.4950 |
| B-0075 | Melting Point (° C.) | 104-105 |
| B-0076 | Reflactive Index ($n_D^{20}$) | 1.4970 |
| B-0077 | Melting Point (° C.) | 77-78 |
| B-0078 | Reflactive Index ($n_D^{20}$) | 1.4955 |
| B-0079 | Melting Point (° C.) | 83-85 |
| B-0080 | Reflactive Index ($n_D^{20}$) | 1.5051 |
| B-0081 | Melting Point (° C.) | 68-69 |
| B-0082 | Reflactive Index ($n_D^{20}$) | 1.4904 |
| B-0083 | Melting Point (° C.) | 69-70 |

TABLE 63

| Compound No. | Physical Property | |
|---|---|---|
| B-0084 | Reflactive Index ($n_D^{20}$) | 1.4713 |
| B-0085 | Melting Point (° C.) | 92-94 |
| B-0086 | Reflactive Index ($n_D^{20}$) | 1.4638 |
| B-0087 | Melting Point (° C.) | 98-100 |
| B-0088 | Reflactive Index ($n_D^{20}$) | 1.4912 |
| B-0089 | Melting Point (° C.) | 115-117 |
| B-0090 | Reflactive Index ($n_D^{20}$) | 1.5022 |
| B-0091 | Melting Point (° C.) | 106-108 |
| B-0092 | Reflactive Index ($n_D^{20}$) | 1.5005 |
| B-0093 | Reflactive Index ($n_D^{20}$) | 1.4921 |
| B-0094 | Reflactive Index ($n_D^{20}$) | 1.5022 |
| B-0095 | Melting Point (° C.) | 106-108 |
| B-0096 | Melting Point (° C.) | 57-58 |
| B-0097 | Reflactive Index ($n_D^{20}$) | 1.5038 |
| B-0098 | Melting Point (° C.) | 63-65 |
| B-0099 | Reflactive Index ($n_D^{20}$) | 1.5042 |
| B-0100 | Melting Point (° C.) | 110-111 |
| B-0101 | Reflactive Index ($n_D^{20}$) | 1.5440 |
| B-0102 | Reflactive Index ($n_D^{20}$) | 1.5120 |
| B-0103 | Melting Point (° C.) | 117-118 |
| B-0104 | Reflactive Index ($n_D^{20}$) | 1.5057 |
| B-0105 | Melting Point (° C.) | 104-106 |
| B-0106 | Reflactive Index ($n_D^{20}$) | 1.5441 |
| B-0107 | Reflactive Index ($n_D^{20}$) | 1.5428 |
| B-0108 | Reflactive Index ($n_D^{20}$) | 1.4988 |
| B-0109 | Reflactive Index ($n_D^{20}$) | 1.5384 |
| B-0113 | Reflactive Index ($n_D^{20}$) | 1.5578 |
| B-0114 | Melting Point (° C.) | 89-100 |
| B-0115 | Melting Point (° C.) | 86-89 |
| B-0116 | Melting Point (° C.) | 114-115 |
| B-0117 | Melting Point (° C.) | 84-85 |

TABLE 64

| Compound No. | Physical Property | |
|---|---|---|
| C-0001 | Reflactive Index ($n_D^{20}$) | 1.4915 |
| C-0002 | Melting Point (° C.) | 174-177 |
| C-0003 | Reflactive Index ($n_D^{20}$) | 1.5185 |
| C-0004 | Melting Point (° C.) | 145-146 |
| C-0007 | Reflactive Index ($n_D^{20}$) | 1.529 |
| C-0008 | Melting Point (° C.) | 167-169 |
| C-0009 | Reflactive Index ($n_D^{20}$) | 1.5245 |
| C-0010 | Melting Point (° C.) | 173-174 |
| C-0011 | Melting Point (° C.) | 117-120 |
| C-0013 | Reflactive Index ($n_D^{20}$) | 1.4918 |
| C-0014 | Reflactive Index ($n_D^{20}$) | 1.5275 |
| C-0016 | Melting Point (° C.) | 149-150 |

TABLE 65

| Compound No. | Physical Property ($^1$H-NMR DATA, in CDCl$_3$/TMS δ (ppm)) |
|---|---|
| A-0231 | 400 MHz 2.48 (3H, s), 3.32 (2H, q), 6.11 (1H, d), 7.08 (1H, d), 7.43 (1H, d) |
| A-0234 | 400 MHz 3.37-3.47 (1H, m), 3.70-3.81 (1H, m), 6.16 (1H, d), 7.38 (1H, d), 7.94 (1H, d) |
| A-0256 | 300 MHz 1.70-1.91 (4H, m), 2.27-2.46 (5H, m), 3.29 (2H, q), 4.03 (2H, t), 6.96 (1H, d), 7.13 (1H, d) |
| A-0257 | 300 MHz 1.71-1.94 (4H, m), 2.30-2.46 (5H, m), 3.29-3.50 (2H, m), 4.12 (2H, t), 6.99 (1H, d), 7.54 (1H, d) |
| A-0259 | 300 MHz 2.37 (3H, s), 3.30-3.51 (2H, m), 5.30 (1H, dd), 5.59 (1H, dd), 6.19-6.51 (1H, m), 7.11 (1H, d), 7.77 (1H, d) |
| A-0267 | 400 MHz 1.96-2.15 (4H, m), 3.45 (2H, q), 3.52 (2H, t), 4.06 (2H, t), 7.14 (1H, s), 7.46 (1H, s) |
| A-0283 | 400 MHz 1.50-1.60 (4H, m), 1.81-1.93 (4H, m), 3.39-3.49 (4H, m), 4.02 (2H, t), 7.13 (1H, s), 7.45 (1H, s) |
| A-0284 | 300 MHz 1.53 (4H, m), 1.70-2.03 (4H, m), 2.17 (3H, s), 2.38 (3H, s), 3.26-3.43 (4H, m), 3.94 (2H, t), 6.96 (1H, s), 6.99 (1H, s) |
| A-0292 | 300 MHz 2.49 (3H, s), 3.29 (2H, q), 3.97 (2H, t), 4.13 (2H, t), 6.98 (1H, d), 7.49 (1H, d) |

TABLE 65-continued

| Compound No. | Physical Property ($^1$H-NMR DATA, in CDCl$_3$/TMS δ (ppm)) |
|---|---|
| A-0317 | 300 MHz 1.54-1.81 (8H, m), 2.07-2.10 (2H, m), 2.41 (3H, s), 3.30 (2H, q), 3.94 (2H, d), 6.96 (1H, d), 7.16 (1H, d) |
| A-0328 | 400 MHz 1.23-1.40 (2H, m), 1.61-1.90 (7H, m), 2.04-2.16 (2H, m), 2.41 (3H, s), 3.29 (2H, q), 4.05 (2H, t), 6.97 (1H, d), 7.15 (1H, d) |
| A-0329 | 400 MHz 1.23-1.51 (2H, m), 1.60-1.88 (7H, m), 2.03-2.16 (2H, m), 3.41 (2H, q), 4.06 (2H, t), 7.21 (1H, d), 7.23 (1H, d) |
| A-0410 | 300 MHz 2.16-2.25 (5H, m), 2.39 (3H, s), 3.11 (2H, t), 3.31 (2H, q), 4.05 (2H, t), 6.97 (1H, s), 7.01 (1H, s) |

TABLE 66

| Compound No. | Physical Property ($^1$H-NMR DATA, in CDCl$_3$/TMS δ (ppm)) |
|---|---|
| A-0411 | 300 MHz 2.22-2.31 (8H, m), 3.12 (2H, t), 3.27-3.50 (2H, m), 4.16 (2H, m), 7.03 (1H, s), 7.38 (1H, s) |
| A-0412 | 300 MHz 2.21-2.29 (2H, m), 3.15 (2H, t), 3.45 (2H, q), 4.11 (2H, t), 7.15 (1H, s), 7.47 (1H, s) |
| A-0413 | 400 MHz 2.28 (2H, quint), 3.15 (2H, t), 3.32-3.44 (1H, m), 3.69-3.81 (1H, m), 4.25 (2H, t), 7.48 (1H, s), 7.50 (1H, s) |
| A-0416 | 300 MHz 1.90-2.04 (4H, m), 2.36 (3H, s), 2.97 (2H, t), 3.24-3.50 (2H, m), 4.13 (2H, t), 7.03 (1H, d), 7.54 (1H, d) |
| A-0424 | 400 MHz 1.90-2.02 (4H, m), 3.01 (2H, t), 3.45 (2H, q), 4.05 (2H, t), 7.13 (1H, s), 7.46 (1H, s) |
| A-0425 | 400 MHz 1.94-2.03 (4H, m), 3.01 (2H, t), 3.31-3.43 (1H, m), 3.68-3.81 (1H, m), 4.17 (2H, t), 7.18 (2H, s) |
| A-0432 | 400 MHz 1.62 (2H, m), 1.70-1.95 (4H, m), 2.31 (3H, s), 2.92 (2H, t), 3.32-3.48 (2H, m), 4.11 (2H, t), 6.98 (1H, d), 7.54 (1H, d) |
| A-0436 | 400 MHz 1.55-1.70 (2H, m), 1.75-1.93 (4H, m), 2.92 (2H, t), 3.51 (2H, q), 4.10 (2H, t), 7.25 (1H, d), 7.41 (1H, d) |
| A-0440 | 300 MHz 1.54-1.67 (2H, m), 1.70-1.95 (4H, m), 2.39 (3H, s), 2.92 (2H, t), 3.33 (2H, q), 4.01 (2H, t), 7.06 (1H, s), 7.24 (1H, s) |
| A-0480 | 400 MHz 1.49-1.53 (4H, m), 1.71-1.82 (4H, m), 2.17 (3H, s), 2.38 (3H, s), 2.90 (2H, t), 3.30 (2H, q), 3.94 (2H, t), 6.96 (1H, s), 6.70 (1H, s) |
| A-0511 | 300 MHz 1.40-1.56 (6H, m), 1.66-1.83 (4H, m), 2.17 (3H, s), 2.38 (3H, s), 2.88 (1H, t), 3.31 (2H, q), 3.93 (2H, t), 6.96 (1H, s), 7.00 (1H, s) |
| A-0512 | 300 MHz 1.41-1.52 (6H, m), 1.68-1.86 (4H, m), 2.28 (3H, s), 2.33 (3H, s), 2.89 (2H, t), 3.26-3.50 (2H, m), 4.03 (2H, t), 7.01 (1H, s), 7.36 (1H, s) |
| A-0544 | 300 MHz 1.81-2.01 (4H, m), 2.31 (3H, s), 2.90 (2H, t), 3.31-3.48 (2H, m), 4.13 (2H, t), 6.82 (1H, t), 6.99 (1H, d), 7.54 (1H, d) |

TABLE 67

| Compound No. | Physical Property ($^1$H-NMR DATA, in CDCl$_3$/TMS δ (ppm)) |
|---|---|
| A-0554 | 400 MHz 1.57-1.63 (2H, m), 1.75-1.89 (4H, m), 2.31 (3H, s), 2.84 (2H, t), 3.36-3.42 (2H, m), 4.10 (2H, t), 6.81 (1H, t), 7.00 (1H, d), 7.54 (1H, d) |
| A-0557 | 400 MHz 1.57-1.63 (2H, m), 1.72-1.84 (4H, m), 2.38 (3H, s), 2.84 (2H, t), 3.40 (2H, q), 3.94 (2H, t), 6.75 (1H, dd), 6.81 (1H, t), 7.00 (1H, s), 7.11 (1H, d) |
| A-0570 | 400 MHz 1.49-1.56 (4H, m), 1.70-1.81 (4H, m), 2.41 (3H, s), 2.81 (2H, t), 3.29 (2H, q), 4.00 (2H, t), 6.80 (1H, t), 6.96 (1H, d), 7.14 (1H, d) |
| A-0661 | 400 MHz 1.59-70 (2H, m), 1.79-1.92 (4H, m), 3.21 (2H, t), 3.41 (2H, q), 4.04 (2H, t), 7.21 (1H, d), 7.25 (2H, d) |
| A-0664 | 300 MHz 2.17 (3H, s), 2.34 (2H, quint), 2.39 (3H, s), 3.19 (2H, t), 3.32 (2H, q), 4.09 (2H, t), 6.98 (1H, s), 7.01 (1H, s) |
| A-0678 | 400 MHz 1.50-1.62 (4H, m), 1.83-1.92 (4H, m), 2.96 (2H, t), 3.45 (2H, q), 4.03 (2H, t), 7.13 (1H, s), 7.46 (1H, s) |
| A-0679 | 300 MHz 1.53-1.54 (4H, m), 1.82-1.87 (4H, m), 2.17 (3H, s), 2.38 (3H, s), 2.96 (2H, t), 3.31 (2H, q), 3.94 (2H, t), 6.96 (1H, s), 6.70 (1H, s) |
| A-0681 | 300 MHz 1.40-1.56 (6H, m), 1.75-1.88 (4H, m), 2.17 (3H, s), 2.38 (3H, s), 2.95 (2H, t), 3.31 (2H, q), 3.93 (2H, t), 6.96 (1H, s), 7.00 (1H, s) |
| A-0687 | 300 MHz 2.40 (3H, s), 3.23 (2H, q), 5.31 (2H, s), 6.99 (1H, d), 7.12 (1H, d), 7.46 (1H, t), 7.57 (1H, t), 7.63-7.80 (2H, m) |
| A-0745 | 300 MHz 2.42 (3H, s), 3.24 (2H, q), 5.14 (2H, s), 7.00 (1H, d), 7.15 (1H, d), 7.21-7.37 (2H, m), 7.62 (1H, dd) |
| A-0747 | 300 MHz 2.41 (3H, s), 3.21 (2H, q), 5.17 (2H, s), 7.00 (1H, d), 7.15 (1H, d), 7.57 (2H, d), 7.64 (2H, d) |

TABLE 67-continued

| Compound No. | Physical Property ($^1$H-NMR DATA, in CDCl$_3$/TMS δ (ppm)) |
|---|---|
| A-0822 | 300 MHz 2.41 (3H, s), 3.15 (2H, t), 3.27 (2H, q), 4.23 (2H, t), 6.96 (1H, d), 7.11 (1H, d), 7.11-7.19 (2H, m), 7.55 (1H, t) |
| A-0834 | 400 MHz 2.12 (2H, quint), 2.41 (3H, s), 2.82 (2H, t), 3.27 (2H, q), 4.01 (2H, t), 6.96 (1H, d), 7.11 (1H, d), 7.19-7.32 (5H, m) |

TABLE 68

| Compound No. | Physical Property ($^1$H-NMR DATA, in CDCl$_3$/TMS δ (ppm)) |
|---|---|
| A-0970 | 300 MHz 1.10 (9H, s), 2.16 (2H, t), 2.41 (3H, s), 3.29 (2H, q), 4.11-4.20 (4H, m), 6.95 (1H, d), 7.14 (1H, d), 7.32 (1H, s) |
| A-0971 | 400 MHz 1.09 (9H, s), 2.18 (2H, t), 2.31 (3H, s), 3.30-3.50 (2H, m), 4.16-4.20 (4H, m), 6.98 (1H, d), 7.32 (1H, s), 7.57 (1H, d) |
| A-0998 | 400 MHz 2.40 (3H, s), 3.26 (2H, q), 4.26 (2H, t), 4.51 (2H, t), 6.98 (1H, d), 7.25 (1H, dd), 7.33-7.40 (1H, m), 7.47 (1H, t), 7.55-7.65 (2H, m), 7.65 (1H, d), 8.13 (1H, s) |
| A-1032 | 400 MHz 2.42 (3H, s), 3.09 (3H, s), 3.29 (2H, q), 4.25-4.35 (2H, m), 4.56-4.61 (2H, m), 6.99 (1H, d), 7.18 (1H, d) |
| A-1044 | 400 MHz 2.10 (2H, quint), 2.01 (3H, s), 3.29 (2H, q), 3.87 (2H, t), 4.10 (2H, t), 5.40 (2H, bs), 6.96 (1H, d), 7.18 (1H, d) |
| A-1072 | 400 MHz 1.83-1.97 (4H, m), 2.85 (2H, t), 3.41 (2H, q), 4.05 (2H, t), 7.20 (1H, d), 7.23 (1H, d) |
| A-1101 | 300 MHz 1.40 (2H, bs), 1.59-1.70 (2H, m), 1.79-1.89 (2H, m), 2.41 (3H, s), 2.78 (2H, t), 3.29 (2H, q), 4.03 (2H, t), 6.95 (1H, d), 7.15 (1H, s) |
| A-1116 | 400 MHz 1.80-1.93 (4H, m), 2.42 (3H, s), 3.29 (2H, q), 3.43-3.54 (2H, m), 4.06 (2H, t), 6.62 (1H, bs), 6.98 (1H, d), 7.15 (1H, d) |
| A-1149 | 400 MHz 1.78-1.94 (4H, m), 2.41 (3H, s), 2.97 (3H, s), 3.24 (2H, t), 3.30 (2H, q), 4.05 (2H, t), 4.44 (1H, bs), 6.97 (1H, d), 7.15 (1H, d) |
| A-1156 | 300 MHz 1.80-1.99 (4H, m), 3.36-3.47 (4H, m), 4.07 (2H, t), 5.15 (1H, m), 7.23 (1H, d), 7.25 (1H, d) |
| A-1201 | 400 MHz 1.48-1.57 (2H, m), 1.75-1.88 (4H, m), 2.41 (3H, s), 3.29 (2H, q), 3.82 (2H, t), 3.92 (3H, s), 4.11 (2H, t), 6.96 (1H, s), 7.14 (1H, s) |

TABLE 69

| Compound No. | Physical Property ($^1$H-NMR DATA, in CDCl$_3$/TMS δ (ppm)) |
|---|---|
| B-0028 | 300 MHz 2.42 (3H, s), 3.24 (2H, q), 5.13 (2H, s), 7.01 (1H, d), 7.15 (1H, d), 7.30-7.38 (2H, m), 8.60-8.68 (2H, m) |
| B-0031 | 300 MHz 2.41 (3H, s), 3.19-3.37 (2H, m), 5.30 (2H, s), 7.00 (1H, d), 7.17 (1H, d), 7.71 (1H, d), 7.97 (1H, d), 8.86 (1H, s) |
| B-0057 | 300 MHz 2.15 (2H, quint), 2.42 (3H, s), 2.94 (2H, t), 3.31 (2H, q), 4.03 (2H, t), 6.98 (1H, d), 7.13 (1H, d), 7.62 (1H, d), 7.72 (1H, d), 8.60 (1H, s) |
| B-0060 | 300 MHz 2.32 (2H, quint), 2.41 (3H, s), 3.22 (2H, t), 3.28 (2H, q), 4.13 (2H, t), 6.95 (1H, d), 7.15 (1H, d), 7.88 (1H, s), 8.70 (1H, s) |
| B-0063 | 300 MHz 2.44 (3H, s), 3.29 (2H, q), 5.33 (2H, s), 7.04 (1H, d), 7.22 (1H, d), 9.26 (1H, s), 9.35 (1H, s) |

TABLE 70

| Compound No. | Physical Property ($^1$H-NMR DATA, in CDCl$_3$/TMS δ (ppm)) |
|---|---|
| C-0005 | 400 MHz 2.36 (3H, s), 3.38 (2H, q), 5.61 (1H, brs), 6.69 (1H, dd), 6.93 (1H, s), 7.03 (1H, d) |
| C-0006 | 400 MHz 2.28 (3H, s), 3.37-3.56 (2H, m), 6.96 (1H, dd), 7.12 (1H, d), 7.73 (1H, d), 8.04 (1H, bs) |
| C-0015 | 300 MHz 3.30-3.44 (1H, m), 3.66-3.80 (1H, m), 7.40 (1H, s), 7.61 (1H, s) |

TABLE 70-continued

| Compound No. | Physical Property ($^1$H-NMR DATA, in CDCl$_3$/TMS δ (ppm)) |
|---|---|
| C-0017 | 300 MHz 2.20 (3H, s), 2.36 (3H, s), 3.32 (2H, q), 4.59 (1H, s), 6.93 (1H, s), 6.98 (1H, s) |
| C-0018 | 300 MHz 2.25 (6H, s), 3.35-3.53 (2H, m), 6.98 (1H, s), 7.63 (1H, s), 7.69 (1H, s) |

TABLE 71

| Compound No. | Specific Rotation |
|---|---|
| (−)-A-0086 | −104.4 |
| (+)-A-0086 | +103.6 |
| (−)-A-0434 | −120.3 |
| (+)-A-0434 | +119.3 |
| (−)-A-0479 | −120.6 |
| (+)-A-0479 | +115.2 |
| (−)-A-0481 | −93.2 |
| (+)-A-0481 | +96.5 |
| (−)-A-0764 | −86.4 |
| (+)-A-0764 | +88.5 |

TABLE 71-continued

| Compound No. | Specific Rotation |
| --- | --- |
| (−)-A-0767 | −117.0 |
| (+)-A-0767 | +122.8 |
| (−)-A-1215 | −99.2 |
| (+)-A-1215 | +98.1 |
| (−)-A-1218 | −120.4 |
| (+)-A-1218 | +121.6 |

Next, there are specifically explained examples of formulating the present pest control agent by using the present alkyl phenyl sulfide derivative produced as above or the agriculturally acceptable salt thereof. The kinds and proportions of compounds and additives used in each formulation are not restricted to those shown in the following Formulation Examples and may be varied in a wide range. In the following explanation, "parts (part)" refer (refers) to mass parts (mass part).

Formulation Example 1

Emulsifiable Concentrate

| A compound described in Table 1 to Table 41 | 10 parts |
| --- | --- |
| Cyclohexanone | 30 parts |
| Polyoxyethylene alkyl aryl ether | 11 parts |
| Calcium alkylbenzenesulfonate | 4 parts |
| Methylnaphthalene | 45 parts |

The above materials were dissolved homogeneously to obtain an emulsifiable concentrate.

Formulation Example 2

Wettable Powder

| A compound described in Table 1 to Table 41 | 10 parts |
| --- | --- |
| Sodium salt of naphthalenesulfonic acid-formalin condensate | 0.5 part |
| Polyoxyethylene alkyl aryl ether | 0.5 part |
| Diatomaceous earth | 24 parts |
| Clay | 65 parts |

The above materials were mixed and ground to obtain a wettable powder.

Formulation Example 3

Dust Formulation

| A compound described in Table 1 to Table 41 | 2 parts |
| --- | --- |
| Diatomaceous earth | 5 parts |
| Clay | 93 parts |

The above materials were mixed and ground to obtain a dust formulation.

Formulation Example 4

Granule

| A compound described in Table 1 to table 41 | 5 parts |
| --- | --- |
| Sodium salt of lauryl alcohol sulfate | 2 parts |
| Sodium ligninsulfonate | 5 parts |
| Carboxymethyl cellulose | 2 parts |
| Clay | 86 parts |

The above materials were mixed homogeneously and ground. Thereto was added 20 parts of water, followed by kneading. The kneaded material was passed through an extrusion-granulator to obtain granules of 14 to 32 meshes. The granules were dried to obtain a granule.

Formulation Example 5

Flowable Concentrate

| A compound described in Table 1 to Table 41 | 20 parts |
| --- | --- |
| Polyoxyethylene styrenated phenyl ether sulfate | 4 parts |
| Ethylene glycol | 7 parts |
| Silicone AF-118N (produced by Asahi Chemical Industry Co., Ltd.) | 0.02 part |
| Water | 68.98 parts |

The above materials were mixed for 30 minutes using a high-speed stirrer and then ground using a wet grinder to obtain a flowable concentrate.

The next, the effect of the present pest control agent is shown by Test Examples.

Test Example 1

Control Effect Test for *Tetranychus urticae* Koch (Two Spotted Spider Mite)

A wettable powder prepared based on Formulation Example 2 was diluted with water into an active ingredient concentration of 4 ppm. In the solution were immersed soybean seedlings which had been inoculated with 35 female adults of two spotted spider mite. The soybean seedlings were dried in the air and placed in a thermostat of 25° C. After 13 days, the number of living female adults was examined and the control value of the active ingredient was determined using the calculation formula of the following Mathematical Expression 1. This test was conducted with no replication.

Control value=100−[(number of living female adults after 13 days, in treated seedlings)/(number of living female adults after 13 days, in non-treated seedlings)]×100    [Mathematical Expression 1]

Tests similar to the above were conducted using, as comparative compounds, compound Nos. 22 and 23 described in JP-A-1975-29744, compound Nos. 3, 4, 5, 6 described in JP-A-1976-19121 and compound Nos. 18, 19 and 36 described in JP-A-1988-41451. The structures of these comparative compounds are as follows.

[Formula 21]
JP-A-1975-29744

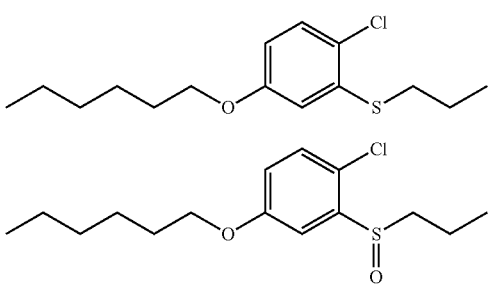

[Formula 22]
JP-A-1976-19121

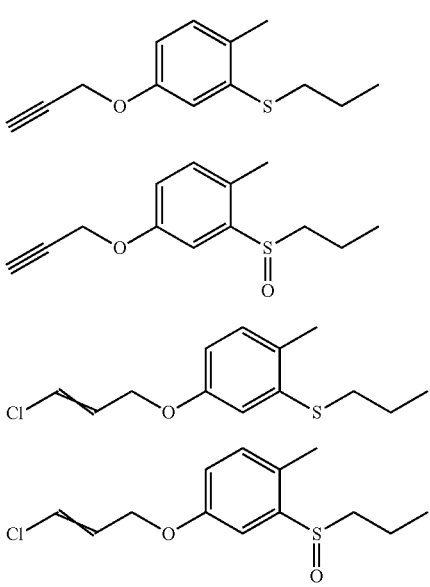

[Formula 23]
JP-A-1988-41451

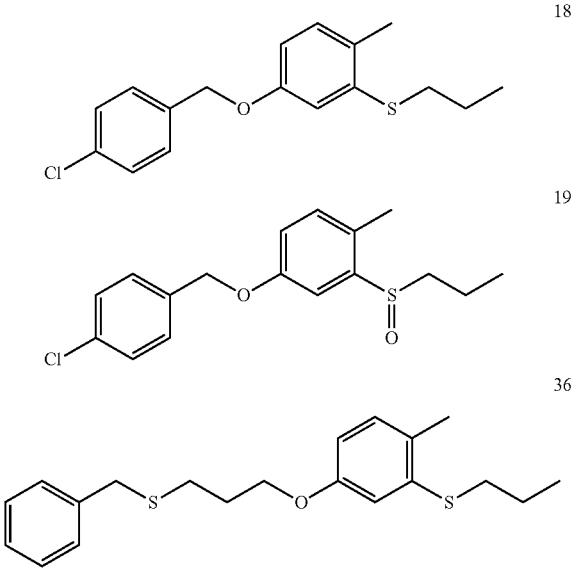

Compound Nos. of the compounds which gave, in the above test, a control value of 90 or above, are shown below.
A-0013, A-0017, A-0018, A-0024, A-0047, A-0052, A-0055, A-0056, A-0075, A-0077, A-0078, A-0079, A-0085, A-0086, A-0088, A-0089, A-0090, A-0092, A-0094, A-0108, A-0113, A-0115, A-0116, A-0117, A-0120, A-0123, A-0125, A-0126, A-0130, A-0133, A-0141, A-0144, A-0145, A-0147, A-0157, A-0160, A-0164, A-0168, A-0170, A-0175, A-0181, A-0185, A-0204, A-0212, A-0216, A-0220, A-0222, A-0223, A-0224, A-0244, A-0257, A-0262, A-0271, A-0277, A-0316, A-0318, A-0319, A-0320, A-0321, A-0322, A-0324, A-0325, A-0326, A-0327, A-0328, A-0329, A-0330, A-0331, A-0338, A-0339, A-0340, A-0341, A-0343, A-0346, A-0347, A-0352, A-0353, A-0356, A-0359, A-0360, A-0363, A-0365, A-0368, A-0369, A-0379, A-0387, A-0388, A-0391, A-0392, A-0393, A-0394, A-0396, A-0406, A-0416, A-0418, A-0432, A-0434, A-0438, A-0439, A-0440, A-0441, A-0443, A-0444, A-0445, A-0446, A-0447, A-0448, A-0449, A-0471, A-0472, A-0473, A-0474, A-0475, A-0476, A-0477, A-0478, A-0479, A-0481, A-0482, A-0483, A-0484, A-0485, A-0487, A-0489, A-0495, A-0502, A-0503, A-0504, A-0505, A-0507, A-0508, A-0510, A-0524, A-0525, A-0526, A-0533, A-0536, A-0539, A-0543, A-0544, A-0553, A-0554, A-0555, A-0556, A-0557, A-0558, A-0559, A-0560, A-0561, A-0562, A-0563, A-0570, A-0571, A-0573, A-0574, A-0575, A-0576, A-0577, A-0578, A-0587, A-0588, A-0589, A-0590, A-0591, A-0592, A-0594, A-0599, A-0605, A-0606, A-0610, A-0611, A-0616, A-0617, A-0618, A-0622, A-0623, A-0625, A-0626, A-0631, A-0632, A-0638, A-0640, A-0642, A-0644, A-0665, A-0674, A-0683, A-0684, A-0686, A-0690, A-0692, A-0693, A-0694, A-0695, A-0697, A-0698, A-0703, A-0709, A-0710, A-0711, A-0712, A-0713, A-0716, A-0717, A-0724, A-0728, A-0734, A-0735, A-0736, A-0741, A-0743, A-0744, A-0745, A-0746, A-0748, A-0751, A-0752, A-0753, A-0754, A-0755, A-0757, A-0758, A-0761, A-0762, A-0763, A-0764, A-0765, A-0766, A-0767, A-0768, A-0769, A-0772, A-0773, A-0774, A-0775, A-0776, A-0778, A-0779, A-0780, A-0781, A-0782, A-0783, A-0784, A-0786, A-0787, A-0788, A-0789, A-0790, A-0791, A-0792, A-0793, A-0797, A-0798, A-0799, A-0800, A-0802, A-0805, A-0806, A-0807, A-0808, A-0809, A-0810, A-0813, A-0814, A-0816, A-0817, A-0818, A-0819, A-0820, A-0821, A-0822, A-0823, A-0824, A-0825, A-0826, A-0827, A-0838, A-0839, A-0844, A-0845, A-0853, A-0855, A-0856, A-0857, A-0860, A-0869, A-0870, A-0878, A-0880, A-0881, A-0885, A-0902, A-0913, A-0914, A-0915, A-0916, A-0917, A-0918, A-0921, A-0923, A-0924, A-0936, A-0940, A-0941, A-0942, A-0948, A-0956, A-0957, A-0969, A-0971, A-0973, A-0978, A-0979, A-0980, A-0982, A-0983, A-0984, A-0985, A-0988, A-0989, A-0990, A-0991, A-0992, A-1011, A-1032, A-1033, A-1052, A-1081, A-1087, A-1088, A-1107, A-1108, A-1112, A-1113, A-1119, A-1125, A-1126, A-1127, A-1128, A-1132, A-1136, A-1138, A-1140, A-1142, A-1149, A-1150, A-1151, A-1152, A-1154, A-1155, A-1156, A-1157, A-1158, A-1159, A-1164, A-1165, A-1166, A-1167, A-1175, A-1177, A-1178, A-1180, A-1181, A-1183, A-1185, A-1188, A-1190, A-1192, A-1195, A-1196, A-1200, A-1201, A-1207, A-1210, A-1211, B-0005, B-0006, B-0007, B-0008, B-0009, B-0010, B-0011, B-0017, B-0018, B-0019, B-0022, B-0023, B-0029, B-0055, B-0060, B-0063, B-0068, B-0070, B-0072, B-0073, B-0074, B-0075, B-0076, B-0078, B-0079, B-0080, B-0082, B-0084, B-0086, B-0088, B-0090, B-0092, B-0094, B-0096, B-0099, B-0102, B-0104, B-0106, B-0108

Any of comparative compounds 22 and 23 (described in JP-A-1975-29744), 3, 4, 5 and 6 (described in JP-A-1976-19121) and 18, 19 and 36 (described in JP-A-1988-41451) showed no activity at a concentration of 4 ppm.

Test Example 2

Insecticidal Activity Test for *Nilaparvata lugens* Stål (Brown Rice Planthopper)

A wettable powder prepared based on Formulation Example 2 was diluted with water into an active ingredient concentration of 100 ppm. In the solution was immersed sprouting unhulled rice. They were placed in a 60-ml plastic cup. Thereinto were released 10 3-instar larvae of brown rice planthopper. The cup was covered with a lid and placed in a thermostat of 25° C. After 6 days, the number of living insects was counted and the mortality of insect was determined from the calculation formula of the following Mathematical Expression 2. This test was conducted with no replication.

Mortality (%)=100−[(number of living insects after 6 days)/(number of tested insects)]×100 [Mathematical Expression 2]

As in the case of Test Example 1, tests similar to the above were conducted using, as comparative compounds, compound Nos. 22 and 23 described in JP-A-1975-29744, compound Nos. 4, 5, 6 described in JP-A-1976-19121 and compound Nos. 18, 19 and 36 described in JP-A-1988-41451.

Compound Nos. of the compounds which gave, in the above test, a mortality of 90% or above, are shown below.
A-0001, A-0004, A-0005, A-0006, A-0007, A-0015, A-0018, A-0022, A-0023, A-0025, A-0032, A-0035, A-0037, A-0038, A-0039, A-0043, A-0044, A-0046, A-0047, A-0051, A-0052, A-0056, A-0070, A-0074, A-0075, A-0077, A-0078, A-0085, A-0086, A-0087, A-0088, A-0089, A-0090, A-0091, A-0092, A-0108, A-0122, A-0123, A-0125, A-0130, A-0133, A-0141, A-0144, A-0145, A-0147, A-0157, A-0159, A-0160, A-0163, A-0164, A-0167, A-0168, A-0169, A-0170, A-0172, A-0173, A-0175, A-0180, A-0181, A-0185, A-0186, A-0187, A-0188, A-0199, A-0200, A-0203, A-0205, A-0206, A-0208, A-0211, A-0212, A-0213, A-0214, A-0215, A-0216, A-0217, A-0218, A-0219, A-0220, A-0221, A-0222, A-0223, A-0224, A-0228, A-0229, A-0230, A-0243, A-0244, A-0253, A-0254, A-0256, A-0257, A-0259, A-0260, A-0262, A-0263, A-0266, A-0271, A-0277, A-0285, A-0307, A-0308, A-0311, A-0314, A-0317, A-0319, A-0324, A-0325, A-0328, A-0329, A-0338, A-0340, A-0341, A-0346, A-0360, A-0369, A-0379, A-0405, A-0406, A-0415, A-0416, A-0417, A-0418, A-0431, A-0432, A-0433, A-0434, A-0436, A-0437, A-0438, A-0439, A-0440, A-0446, A-0447, A-0448, A-0472, A-0473, A-0474, A-0475, A-0503, A-0504, A-0505, A-0535, A-0539, A-0543, A-0544, A-0553, A-0554, A-0556, A-0557, A-0570, A-0572, A-0574, A-0587, A-0610, A-0617, A-0625, A-0626, A-0631, A-0644, A-0683, A-0684, A-0703, A-0732, A-0734, A-0741, A-0743, A-0744, A-0745, A-0747, A-0751, A-0753, A-0755, A-0761, A-0763, A-0764, A-0765, A-0766, A-0772, A-0777, A-0778, A-0779, A-0780, A-0781, A-0786, A-0787, A-0788, A-0789, A-0797, A-0798, A-0809, A-0811, A-0813, A-0815, A-0821, A-0822, A-0823, A-0824, A-0825, A-0834, A-0838, A-0839, A-0844, A-0846, A-0847, A-0853, A-0855, A-0857, A-0877, A-0968, A-0969, A-0970, A-0971, A-0972, A-0973, A-0975, A-0976, A-0977, A-0978, A-0979, A-0981, A-0982, A-0983, A-0984, A-0985, A-0988, A-0991, A-0992, A-0998, A-1003, A-1004, A-1005, A-1006, A-1008, A-1009, A-1032, A-1033, A-1037, A-1044, A-1051, A-1087, A-1093, A-1094, A-1107, A-1125, A-1136, A-1140, A-1142, A-1158, A-1159, A-1177, A-1180, A-1185, A-1187, A-1188, A-1195, A-1210, A-1211, A-1212, A-1213, B-0003, B-0004, B-0005, B-0007, B-0012, B-0013, B-0022, B-0028, B-0029, B-0032, B-0033, B-0035, B-0051, B-0053, B-0055, B-0058, B-0059, B-0060, B-0063, B-0066, B-0086, B-0088, B-0093, B-0101, C-0001

Any of comparative compounds 22 and 23 (described in JP-A-1975-29744), 4, 5 and 6 (described in JP-A-1976-19121) and 18, 19 and 36 (described in JP-A-1988-41451) each showed no activity even at a concentration of 100 ppm.

The invention claimed is:
1. An alkyl phenyl sulfide derivative represented by the general formula [I] or an agriculturally acceptable salt thereof

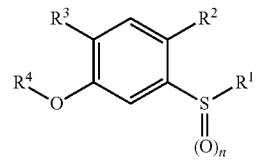

wherein n is an integer of 0, 1 or 2,
$R^1$ is a $C_1$-$C_6$ haloalkyl group (the group excludes 2-bromoethyl group), a $C_2$-$C_8$ alkenyl group (the group excludes allyl group), a $C_2$-$C_8$ haloalkenyl group, a $C_2$-$C_6$ alkynyl group, a $C_2$-$C_6$ haloalkynyl group, a branched $C_4$-$C_6$ alkyl group (the group excludes isobutyl group), a $C_3$-$C_6$ cycloalkyl $C_1$-$C_6$ alkyl group or a $C_3$-$C_6$ halocycloalkyl $C_1$-$C_6$ alkyl group,
$R^2$ is a halogen atom, a $C_1$-$C_6$ alkyl group, a $C_1$-$C_6$ haloalkyl group, a $C_3$-$C_6$ cycloalkyl group, a $C_3$-$C_6$ halocycloalkyl group, a $C_1$-$C_6$ haloalkoxy group, a cyano group or a nitro group,
$R^3$ is a hydrogen atom, a halogen atom, a $C_1$-$C_6$ alkyl group or a $C_1$-$C_6$ haloalkyl group,
$R_4$ is a $C_1$-$C_{12}$ alkyl group (the group may be mono- or poly-substituted with $R^5$), a $C_3$-$C_6$ cycloalkyl group (the group may be mono- or poly-substituted with $R^5$), a $C_2$-$C_8$ alkenyl group (the group may be mono- or poly-substituted with $R^5$), a $C_2$-$C_6$ alkynyl group (the group may be mono- or poly-substituted with $R^5$) or a benzoyl group (the group may be mono- or poly-substituted with $R^6$),
$R^5$ is a halogen atom, a $C_1$-$C_6$ alkyl group, a $C_1$-$C_6$ haloalkyl group, a $C_3$-$C_6$ cycloalkyl group (the group may be mono- or poly-substituted with $R^6$), a $C_3$-$C_6$ halocycloalkyl group, a hydroxyl group, a $C_1$-$C_6$ alkoxy group, a $C_1$-$C_6$ haloalkoxy group, a $C_3$-$C_6$ cycloalkoxy group, a $C_3$-$C_6$ halocycloalkoxy group, a $C_1$-$C_6$ alkoxy $C_1$-$C_6$ alkoxy group, a $C_1$-$C_6$ haloalkoxy $C_1$-$C_6$ alkoxy group, a $C_1$-$C_6$ haloalkoxy $C_1$-$C_6$ haloalkoxy group, a $C_1$-$C_6$ alkylsulfinyloxy group, a $C_1$-$C_6$ haloalkylsulfinyloxy group, a $C_3$-$C_6$ cycloalkylsulfinyloxy group, a $C_3$-$C_6$ halocycloalkylsulfinyloxy group, a $C_1$-$C_6$ alkylsulfonyloxy group, a $C_1$-$C_6$ haloalkylsulfonyloxy group, a $C_3$-$C_6$ cycloalkylsulfonyloxy group, a $C_3$-$C_6$ halocycloalkylsulfonyloxy group, a thiol group, a $C_1$-$C_6$ alkylthio group, a $C_1$-$C_6$ haloalkylthio group, a $C_2$-$C_6$ alkenylthio group, a $C_2$-$C_6$ haloalkenylthio group, a $C_3$-$C_6$ cycloalkylthio group, a $C_3$-$C_6$ halocycloalkylthio group, a $C_3$-$C_6$ cycloalkyl $C_1$-$C_6$ alkylthio group, a $C_3$-$C_6$ halocycloalkyl $C_1$-$C_6$ alkylthio group, a tri($C_1$-$C_6$ alkyl)silyl $C_1$-$C_6$ alkylthio group, a $C_1$-$C_6$ alkylsulfinyl group, a $C_1$-$C_6$ haloalkylsulfinyl group, a $C_3$-$C_6$ cycloalkylsulfinyl group, a $C_3$-$C_6$ halocycloalkylsulfinyl group, a $C_1$-$C_6$ alkylsulfonyl group, a $C_1$-$C_6$ haloalkylsulfonyl group, a $C_3$-$C_6$ cycloalkylsulfonyl group, a $C_3$-$C_6$ halocycloalkylsulfonyl group, a $C_1$-$C_6$ alkylcarbonyl group, a $C_1$-$C_6$ haloalkylcarbonyl group, a formyl group, a $C_1$-$C_6$ alkylcarbonyloxy group, a $C_1$-$C_6$ haloalkylcarbonyloxy group, a formyloxy group, an amino group, a $C_1$-$C_6$ alkylcarbonylamino group (the amino group may be substituted with $R^9$), a $C_1$-$C_6$ haloalkylcarbonylamino group (the amino group may be substituted with $R^9$), a phenylcarbonylamino group (the phenyl group may be mono- or poly-substituted with $R^6$, the amino group may be substituted with $R^9$), a $C_1$-$C_6$ alkoxycarbonylamino group (the amino group may be substituted with $R^9$), a $C_1$-$C_6$ haloalkoxycarbonylamino group (the amino group may be substituted with $R^9$), a $C_1$-$C_6$ alkylaminocarbonylamino group (the amino group may be substituted with $R^9$), a $C_1$-$C_6$ haloalkylaminocarbonylamino group (the amino group may be substituted with $R^9$), a $C_1$-$C_6$ alkylsulfonylamino group (the amino group may be substituted with $R^9$), a $C_1$-$C_6$ haloalkylsulfonylamino group (the amino group may be substituted with $R^9$), a phenylsulfonylamino group (the phenyl group may be substituted with $R^6$, the amino group may be substituted with $R^9$), a $C_1$-$C_6$ alkylamino group (the amino group may be substituted with $R^9$), a $C_1$-$C_6$ haloalkylamino group (the amino group may be substituted with $R^9$), a $C_1$-$C_6$ alkylaminocarbonylthio group (the amino group may be substituted with $R^9$), a $C_1$-$C_6$ haloalkylaminocarbonylthio group (the amino group may be substituted with $R^9$), a $C_1$-$C_6$ alkylaminocarbonyl group (the amino group may be substituted with $R^9$), a $C_1$-$C_6$ haloalkylaminocarbonyl group (the amino group may be substituted with $R^9$), a $C_1$-$C_6$ alkoxycarbonyl group, a $C_1$-$C_6$ haloalkoxycarbonyl group, a tri($C_1$-$C_6$ alkyl)silyl group, a phenyl group (the group may be mono- or poly-substituted with $R^6$), a pyridyloxyphenyl group (the pyridyl group may be mono- or poly-substituted with $R^6$), a phenoxy group (the group may be mono- or poly-substituted with $R^6$), a phenyl $C_1$-$C_6$ alkoxy group (the phenyl group may be mono- or poly-substituted with $R^6$), a phenylcarbonyloxy group (the phenyl group may be mono- or poly-substituted with $R^6$), a phenylcarbonyl group (the phenyl group may be mono- or poly-substituted with $R^6$), a benzoyl group (the group may be mono- or poly-substituted with $R^6$), a benzoyloxy group (the group may be mono- or poly-substituted with $R^6$), a phenylthio group (the group may be mono- or poly-substituted with $R^6$), a phenylsulfonyl group (the group may be mono- or poly-substituted with $R^6$), a phenylsulfinyl group (the group may be mono- or poly-substituted with $R^6$), a phenyl $C_1$-$C_6$ alkylthio group (the phenyl group may be mono- or poly-substituted with $R^6$), a phenyl $C_1$-$C_6$ alkylsulfinyl group (the phenyl group may be mono- or poly-substituted with $R^6$), a phenyl $C_1$-$C_6$ alkylsulfonyl group (the phenyl group may be mono- or poly-substituted with $R^6$), a —O—N=C($R^7$)($R^8$) group, an adamantyl group, a pyrrolyl group (the group may be mono- or poly-substituted with $R^6$), a pyrazolyl group (the group may be mono- or poly-substituted with $R^6$), an imidazolyl group (the group may be mono- or poly-substituted with $R^6$), a triazolyl group (the group may be mono- or poly-substituted with $R^6$), an oxazolyl group (the group may be mono- or poly-substituted with $R^6$), an isoxazolyl group (the group may be mono- or poly-substituted with $R^6$), a thiazolyl group (the group may be mono- or poly-substituted with $R^6$), an isothiazolyl group (the group may be mono- or poly-substituted with $R^6$), a pyridyl group (the group may be mono- or poly-substituted with $R^6$ and the nitrogen atom of the group may be oxidized to form N-oxide), a pyrimidinyl group (the group may be mono- or poly-substituted with $R^6$), a pyridyloxy group (the group may be mono- or poly-substituted with $R^6$), a tetrahydrofuranyl group (the group may be mono- or poly-substituted with $R^6$), 1,3-dioxoisoindolinyl group (the group may be mono- or poly-substituted with $R^6$), a cyano group, a nitro group, a carboxyl group, a thiocyanato group or an aminoxy group, $R^6$ is a halogen atom, a $C_1$-$C_6$ alkyl group, a $C_1$-$C_6$ haloalkyl group, a $C_3$-$C_6$ cycloalkyl group, a $C_3$-$C_6$ halocycloalkyl group, a $C_3$-$C_6$ cycloalkyl $C_1$-$C_6$ alkyl group, a $C_3$-$C_6$ halocycloalkyl $C_1$-$C_6$ alkyl group, a $C_1$-$C_6$ alkoxy group, a $C_1$-$C_6$ haloalkoxy group, a $C_1$-$C_6$ alkylthio group, a $C_1$-$C_6$ haloalkylthio group, a $C_1$-$C_6$ alkylsulfinyl group, a $C_1$-$C_6$ haloalkylsulfinyl group, a $C_1$-$C_6$ alkylsulfonyl group, a $C_1$-$C_6$ haloalkylsulfonyl group, a $C_1$-$C_6$ alkylthio $C_1$-$C_6$ alkyl group, a $C_1$-$C_6$ haloalkylthio $C_1$-$C_6$ alkyl group, a $C_1$-$C_6$ alkylsulfonyloxy group, a $C_1$-$C_6$ haloalkylsulfonyloxy group, a phenyl group (the group may be mono- or poly-substituted with halogen atom, alkyl group or haloalkyl group), a phenyl $C_1$-$C_6$ alkyl group, a phenyl $C_1$-$C_6$ alkoxy group, a cyano group or a nitro group, $R^7$ and $R^8$ may be the same or different, are each a hydrogen atom, a $C_1$-$C_6$ alkyl group, a $C_1$-$C_6$ haloalkyl group, a $C_3$-$C_6$ cycloalkyl group, a $C_3$-$C_6$ halocycloalkyl group or a phenyl group (the group may be mono- or poly-substituted with $R^6$), and may form a 3- to 6-membered ring together with the carbon atom to which they bond, and $R^9$ is a $C_1$-$C_6$ alkyl group, a $C_1$-$C_6$ haloalkyl group, a $C_3$-$C_6$ cycloalkyl group, a $C_3$-$C_6$ halocycloalkyl group, a $C_1$-$C_6$ alkylcarbonyl group, a $C_1$-$C_6$ haloalkylcarbonyl group, a $C_1$-$C_6$ alkoxycarbonyl group, a $C_1$-$C_6$ haloalkoxycarbonyl group, a $C_1$-$C_6$ alkylaminocarbonyl group, a $C_1$-$C_6$ haloalkylaminocarbonyl group or benzoyl group (the group may be mono- or poly-substituted with $R^6$.

2. An alkyl phenyl sulfide derivative or an agriculturally acceptable salt thereof, according to claim 1, wherein $R^1$ in the general formula [I] is a 2,2-difluoroethyl group, a 2,2,2-trifluoroethyl group, a 3,3,3-trifluoropropyl group, a pentafluoroethyl group, 1,2,2,2-tetrafluoroethyl group, 2-chloro-2,2-difluoroethyl group, a 2,2,3,3-tetrafluoropropyl group, a 2,2,3,3,3-pentafluoropropyl group, a 3,3-dichloroallyl group, a propargyl group, a cyclopropylmethyl group or a (2,2-difluorocyclopropyl)methyl group.

3. An alkyl phenyl sulfide derivative or an agriculturally acceptable salt thereof, according to claim 1, wherein $R^2$ in the general formula [I] is a halogen atom, a $C_1$-$C_6$ alkyl group, a $C_1$-$C_6$ haloalkyl group or a cyano group.

4. An alkyl phenyl sulfide derivative or an agriculturally acceptable salt thereof, according to claim 1, wherein $R^3$ in the general formula [I] is a hydrogen atom, a halogen atom or a $C_1$-$C_6$ alkyl group.

5. A pest control agent comprising an alkyl phenyl sulfide derivative or an agriculturally acceptable salt thereof, according to claim 1, as an active ingredient; and at least one additive component.

6. An alkyl phenyl sulfide derivative or an agriculturally acceptable salt thereof, according to claim 2, wherein $R^2$ in the general formula [I] is a halogen atom, a $C_1$-$C_6$ alkyl group, a $C_1$-$C_6$ haloalkyl group or a cyano group.

7. An alkyl phenyl sulfide derivative or an agriculturally acceptable salt thereof, according to claim 2, wherein $R^3$ in the general formula [I] is a hydrogen atom, a halogen atom or a $C_1$-$C_6$ alkyl group.

8. An alkyl phenyl sulfide derivative or an agriculturally acceptable salt thereof, according to claim 3, wherein $R^3$ in the general formula [I] is a hydrogen atom, a halogen atom or a $C_1$-$C_6$ alkyl group.

9. A pest control agent which contains, as an active ingredient, an alkyl phenyl sulfide derivative or an agriculturally acceptable salt thereof, according to claim 2.

10. A pest control agent which contains, as an active ingredient, an alkyl phenyl sulfide derivative or an agriculturally acceptable salt thereof, according to claim 3.

11. A pest control agent comprising an alkyl phenyl sulfide derivative or an agriculturally acceptable salt thereof, according to claim 4, as an active ingredient; and at least one additive component.

12. An alkyl phenyl sulfide derivative represented by the general formula [I] or an agriculturally acceptable salt thereof

wherein n is 1, $R^1$ is $CH_2CF_3$, $R^2$ is Cl, $R^3$ is F, and $R_4$ is $CH_2CH_2CH_2CH_2CH_2SCF_3$.

* * * * *